US012714676B2

(12) United States Patent
Li et al.

(10) Patent No.: US 12,714,676 B2
(45) Date of Patent: Aug. 25, 2026

(54) COMPOSITIONS AND METHODS FOR TARGETED DELIVERY OF THERAPEUTICS USING CARRIERS

(71) Applicant: VESSELON, INC., Norwalk, CT (US)

(72) Inventors: Rhodemann Li, Norwalk, CT (US); Clayton Larsen, Norwalk, CT (US); Ernest G. Schutt, Norwalk, CT (US); Llew Keltner, Norwalk, CT (US)

(73) Assignee: VESSELON, INC., Norwalk, CT (US)

( * ) Notice: Subject to any disclaimer, the term of this patent is extended or adjusted under 35 U.S.C. 154(b) by 0 days.

(21) Appl. No.: 18/457,915

(22) Filed: Aug. 29, 2023

(65) Prior Publication Data

US 2023/0414525 A1 Dec. 28, 2023

Related U.S. Application Data

(63) Continuation of application No. 17/743,056, filed on May 12, 2022, now abandoned, which is a (Continued)

(51) Int. Cl.
*A61K 9/50* (2006.01)
*A61B 8/08* (2006.01)
*A61K 9/00* (2006.01)

(52) U.S. Cl.
CPC ............ *A61K 9/5015* (2013.01); *A61B 8/085* (2013.01); *A61K 9/0009* (2013.01)

(58) Field of Classification Search
CPC .................................................... A61K 9/5015
See application file for complete search history.

(56) References Cited

U.S. PATENT DOCUMENTS 5,088,499 A 2/1992 Unger
5,123,414 A 6/1992 Unger
(Continued)

FOREIGN PATENT DOCUMENTS

CA 2037478 * 3/1991
CA 2 312 778 * 6/1999
(Continued)

OTHER PUBLICATIONS

Carson et al., Ultrasound-targeted microbubble destruction to deliver siRNA cancer therapy. Cancer Res. Dec. 1, 2012;72(23):6191-9.
(Continued)

*Primary Examiner* — Benjamin J Packard
(74) *Attorney, Agent, or Firm* — McCarter & English, LLP; Maria Laccotripe Zacharakis; Maneesh Gulati, Esq.

(57) ABSTRACT

The present invention provides novel compositions and methods for targeted delivery of therapeutics. In particular, the invention provides compositions comprising a plurality of carriers, such as microbubbles, wherein at least one active agent is associated or co-administered with the plurality of carriers for delivery to a target site, e.g., an organ, a tissue, or a tumor site, in a subject. The present invention also provides methods for treating a disease or condition, methods of targeted delivery of an active agent, e.g., to a target site, in a subject, using the carriers based compositions of the invention. The present invention further provides apparatus, devices and methods for preparing the compositions of the present invention.

36 Claims, 71 Drawing Sheets

Specification includes a Sequence Listing.

Related U.S. Application Data continuation-in-part of application No. PCT/US2021/057961, filed on Nov. 3, 2021.

(60) Provisional application No. 63/109,193, filed on Nov. 3, 2020.

(56) References Cited

U.S. PATENT DOCUMENTS

| | | | | |
|---|---|---|---|---|
| 5,639,443 | A | 6/1997 | Schutt et al. | |
| 5,695,741 | A | 12/1997 | Schutt et al. | |
| 5,798,091 | A | 8/1998 | Trevino et al. | |
| 6,264,917 | B1 | 7/2001 | Klaveness et al. | |
| 6,287,539 | B1 | 9/2001 | Schutt et al. | |
| 8,454,937 | B2 | 6/2013 | Claudio | |
| 9,302,124 | B2 | 4/2016 | Konofagou et al. | |
| 9,358,023 | B2 | 6/2016 | Konofagou et al. | |
| 2002/0102293 | A1* | 8/2002 | Sachse | A61K 9/1277 424/450 |
| 2003/0143161 | A1 | 7/2003 | Kawabata et al. | |
| 2003/0166043 | A1* | 9/2003 | Labrie | C07K 14/5759 435/7.1 |
| 2007/0078290 | A1* | 4/2007 | Esenaliev | A61N 7/00 600/1 |
| 2013/0090591 | A1 | 4/2013 | Ferrara et al. | |
| 2013/0261442 | A1* | 10/2013 | Yang | A61B 8/481 600/431 |
| 2014/0017323 | A1 | 1/2014 | Desai et al. | |
| 2023/0058977 | A1 | 2/2023 | Li et al. | |

FOREIGN PATENT DOCUMENTS

| | | | | |
|---|---|---|---|---|
| HU | 105391 | * | 2/1999 | |
| WO | 94/27640 | * | 12/1994 | |
| WO | WO-1999/39763 A1 | | 8/1999 | |
| WO | 2006/030534 A1 | | 3/2006 | |
| WO | 2008/058451 A2 | | 5/2008 | |
| WO | 2009/051712 | * | 4/2009 | |
| WO | WO-2017178954 A1 | * | 10/2017 | A61K 47/6925 |

OTHER PUBLICATIONS

Dauba et al., Recent Advances on Ultrasound Contrast Agents for Blood-Brain Barrier Opening with Focused Ultrasound. Pharmaceutics. Nov. 21, 2020;12(11):1125, 30 pages.

Hao et al., Proliferation inhibition and apoptosis enhancement of human cervical cancer cells by ultrasound-targeted microbubble destruction delivered double suicide genes. Int J Clin Exp Med. Dec. 15, 2014;7(12):5330-5.

Hernot et al., Microbubbles in ultrasound-triggered drug and gene delivery. Adv Drug Deliv Rev. Jun. 30, 2008;60(10):1153-66.

Jangjou et al., The promising shadow of microbubble over medical sciences: from fighting wide scope of prevalence disease to cancer eradication. J Biomed Sci. Jun. 21, 2021;28(1):49, 24 pages.

Liu et al., Ultrasound-mediated destruction of LHRHa-targeted and paclitaxel-loaded lipid microbubbles induces proliferation inhibition and apoptosis in ovarian cancer cells. Mol Pharm. Jan. 6, 2014;11(1):40-8.

Liu et al., Ultrasound-targeted microbubble destruction-mediated downregulation of CD133 inhibits epithelial-mesenchymal transition, stemness and migratory ability of liver cancer stem cells. Oncol Rep. Dec. 2015;34(6):2977-86.

Meng et al., Ultrasound-microbubbles-mediated microRNA-449a inhibits lung cancer cell growth via the regulation of Notch1. Onco Targets Ther. Sep. 13, 2019;12:7437-7450.

Pichon et al., Recent advances in gene delivery with ultrasound and microbubbles. Journal of Experimental Nanoscience. Mar. 2008;3(1):17-40.

Sorace et al., Ultrasound-stimulated drug delivery for treatment of residual disease after incomplete resection of head and neck cancer. Ultrasound Med Biol. Apr. 2014;40(4):755-64.

Ting et al., Concurrent blood-brain barrier opening and local drug delivery using drug-carrying microbubbles and focused ultrasound for brain glioma treatment. Biomaterials. Jan. 2012;33(2):704-12.

Tinkov et al., New doxorubicin-loaded phospholipid microbubbles for targeted tumor therapy: in-vivo characterization. J Control Release. Dec. 20, 2010;148(3):368-72.

Yan et al., Therapeutic ultrasonic microbubbles carrying paclitaxel and LyP-1 peptide: preparation, characterization and application to ultrasound-assisted chemotherapy in breast cancer cells. Ultrasound Med Biol. May 2011;37(5):768-79.

Zhu et al., GPC3-targeted and curcumin-loaded phospholipid microbubbles for sono-photodynamic therapy in liver cancer cells. Colloids Surf B Biointerfaces. Jan. 2021;197:111358.

U.S. Appl. No. 17/743,056, filed May 12, 2022, 2023-0058977, Published.

Delalande et al., Ultrasound and microbubble-assisted gene delivery: recent advances and ongoing challenges. Ther Deliv. Oct. 2012;3(10):1199-215.

Wang et al., Gene transfer with microbubble ultrasound and plasmid DNA into skeletal muscle of mice: comparison between commercially available microbubble contrast agents. Radiology. Oct. 2005;237(1):224-9.

European Office Action for Application No. 21890018.1, dated Aug. 28, 2024, 8 pages.

Howard et al., Ultrasound Guided Site Specific Gene Delivery System Using Adenoviral Vectors and Commercial Ultrasound Contrasts Agents. Journal of Cellular Physiology. 2006;209:413-421.

Iwanaga et al., Local delivery system of cytotoxic agents to tumors by focused sonoporation. Cancer Gene Therapy. 2007;14:354-363.

Muller et al., Augmentation of AAV-mediated cardiac gene transfer after systemic administration in adult rats. Gene Therapy. 2008;15:1558-1565.

Pitt et al., On Bubbles and Liposomes. J Control Release. Jan. 22, 2008;125(2):174-177.

Shroeder et al., Ultrasound, liposomes, and drug delivery: principles for using ultrasound to control the release of drugs from liposomes. Chemistry and Physics of Lipids. 2009;162:17 pages.

Howard et al., Using a Commercial Ultrasound Contrast Agent for Viral-Mediated Gene Transfer in Vitro and In Vivo. CP911, 6th International Symposium on Therapeutic Ultrasound. pp. 526-532, May 21, 2007.

Yang et al., Research Progress on Drug-Loaded Ultrasound Microbubbles. Chinese Journal of Imaging in Integrated Traditional Chinese and wester Medicine. Mar. 25, 2015;1:92-95.

Zhou et al., Ultrasound-mediated microbubble cavitation enhances gene transduction in rat pulmonary endothelial cells partially by affecting membrane fluidity and cytoskeleton structure. J South Med Univ. 2010;30(11):2505-2515.

Chinese Office Action for Application No. 202180089086.8, dated Apr. 22, 2026, 24 pages.

* cited by examiner

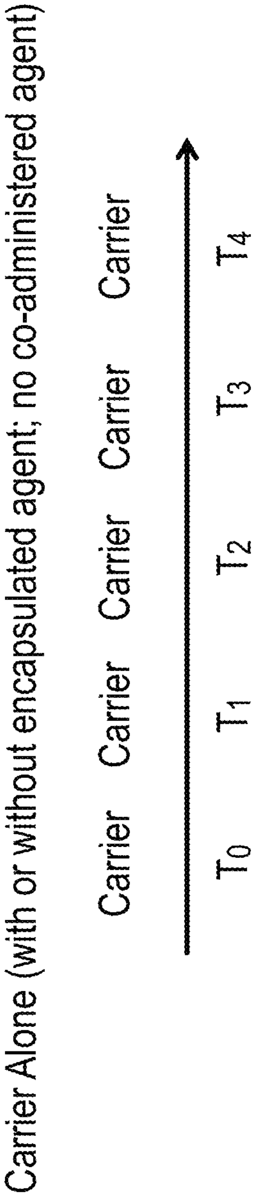

FIG. 6A

Carrier Alone (with or without encapsulated agent; no co-administered agent)

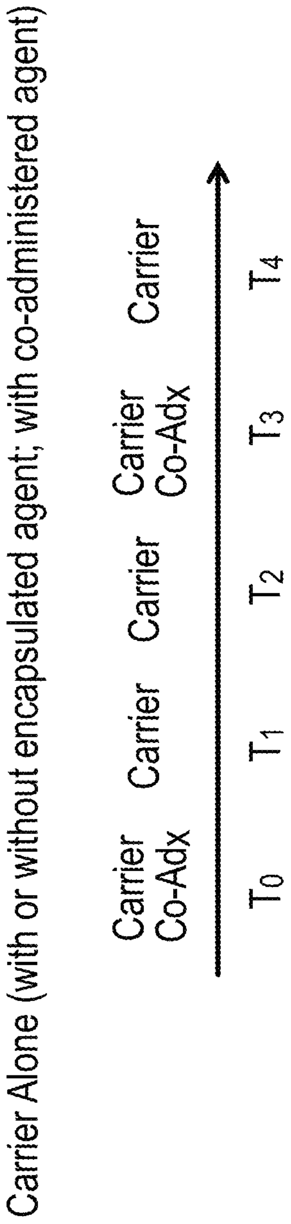

FIG. 6B

Carrier Alone (with or without encapsulated agent; with co-administered agent)

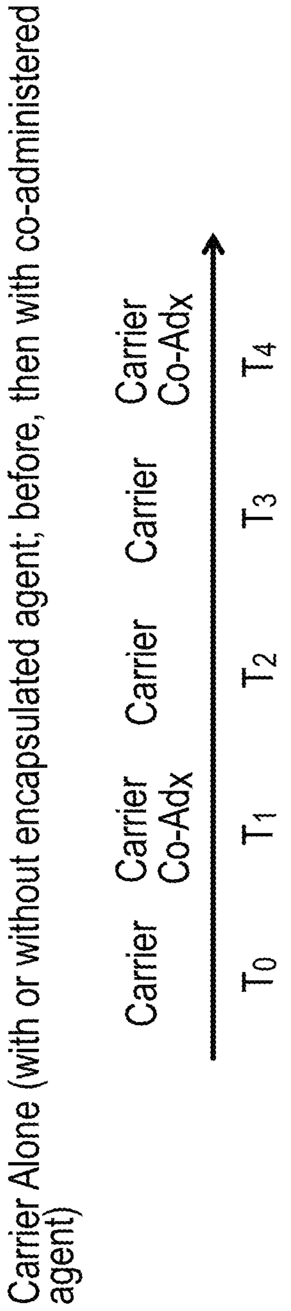

FIG. 6C

Carrier Alone (with or without encapsulated agent; before, then with co-administered agent)

Carrier | Carrier Co-Adx | Carrier | Carrier | Carrier Co-Adx $T_0$ $T_1$ $T_2$ $T_3$ $T_4$

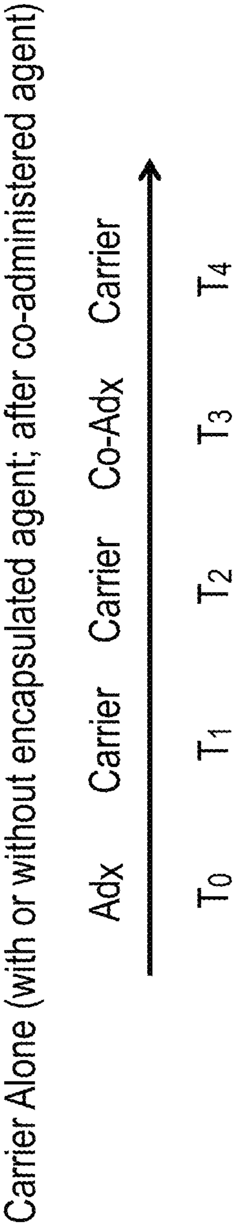

FIG. 6D

Carrier Alone (with or without encapsulated agent; after co-administered agent)

Adx | Carrier | Carrier | Co-Adx | Carrier $T_0$ $T_1$ $T_2$ $T_3$ $T_4$

FIG. 7

Human IL-2 Quantikine ELISA Assay Results

| Day/Group | Mean Result (Concentration pg/mL) | SD | CV | Mean Concentration in undiluted sample (pg/mL) | Mean Concentration in undiluted sample (ng/mL) |
|---|---|---|---|---|---|
| D1/G5 | 133.21 | 11.13 | 12.03 | 265248 | 265 |
| D4/G5 | 892.62 | 85.48 | 8.95 | 3520088 | 3520 |
| D8/G5 | 763.52 | 67.23 | 8.6 | 1437038 | 1437 |
| D1/G7 | 390.28 | 50.29 | 13.93 | 769993 | 770 |
| D4/G7 | 282.65 | 26.91 | 9.13 | 503580 | 504 |
| D8/G7 | 415.37 | 51.35 | 11.93 | 862103 | 862 |

FIG. 9

| | Day 0 | Day 2 | Day 4 | Day 6 | Day 8 | Day 12 |
|---|---|---|---|---|---|---|
| Group 1 | N.A. | N.A. | N.A. | N.A. | N.A. | N.A. |
| Group 2 | -3.87% | 39.24% | 42.39% | 38.20% | 35.60% | 30.28% |
| Group 3 | 0.12% | 35.82% | 53.30% | 34.81% | 37.18% | 39.04% |
| Group 4 | -5.39% | -21.05% | -5.97% | 0.18% | -0.83% | 8.97% |
| Group 5 | 3.62% | -30.30% | -19.47% | -7.79% | -5.06% | -2.06% |
| Group 6 | -4.14% | 38.12% | 58.18% | 54.55% | 56.92% | 39.49% |
| Group 7 | 7.23% | 49.45% | 62.28% | 68.09% | 69.20% | 62.04% |

FIG. 10

| | | Units: pg/mL | | | Units: pg/mL | | | Units: pg/mL | | | Units: pg/mL | | | Units: pg/mL | | |
|---|---|---|---|---|---|---|---|---|---|---|---|---|---|---|---|---|
| | | Eotaxin | | | G-CSF | | | GM-CSF | | | IFNγ | | | IL-1a | | |
| Description | Dilution | FI | Obs Conc. | Exp Conc. | FI | Obs Conc. | Exp Conc. | FI | Obs Conc. | Exp Conc. | FI | Obs Conc. | Exp Conc. | FI | Obs Conc. | Exp Conc. |
| **Standard 1** | 1 | 32 | 0.60 | 0.64 | ... | | 0.64 | ... | | 0.64 | 20 | 0.64 | 0.64 | ... | | 0.64 |
| **Standard 2** | 1 | 72 | 3.36 | 3.20 | 14 | 3.20 | 3.20 | 13 | 1.69 | 3.20 | 36 | 3.20 | 3.20 | ... | | 3.20 |
| **Standard 3** | 1 | 334 | 15.58 | 16.00 | 30 | 16.00 | 16.00 | 33 | 18.95 | 16.00 | 99 | 16.00 | 16.00 | 18 | 16.00 | 16.00 |
| **Standard 4** | 1 | 2189 | 80.78 | 80.00 | 104 | 80.00 | 80.00 | 189 | 75.30 | 80.00 | 412 | 80.00 | 80.00 | 30 | 80.00 | 80.00 |
| **Standard 5** | 1 | 8578 | 403.58 | 400.00 | 480 | 400.00 | 400.00 | 2390 | 412.35 | 400.00 | 2104 | 400.00 | 400.00 | 117 | 400.00 | 400.00 |
| **Standard 6** | 1 | 12761 | 1619.53 | 2000.00 | 2224 | 2000.00 | 2000.00 | 12495 | 1955.90 | 2000.00 | 8919 | 2000.00 | 2000.00 | 1025 | 2000.00 | 2000.00 |
| **Standard 7** | 1 | 14006 | OOR> | 10000.00 | 9212 | 10000.00 | 10000.00 | 18176 | 11470.18 | 10000.00 | 22290 | 10000.00 | 10000.00 | 5874 | 10000.00 | 10000.00 |
| 1 - Group 1 | 2 | 6677 | 538.88 | | 818 | 1382.38 | | 15 | 10.02 | | 24 | 2.58 | | 18 | **26.25** | |
| 2 - Group 1 | 2 | 4473 | 328.79 | | 1139 | 1953.30 | | 15 | 10.02 | | 28 | 3.73 | | 20 | 54.99 | |
| **3 - Group 1** | 2 | 6294 | 496.77 | | 862 | 1459.59 | | 15 | 10.02 | | 21 | 1.61 | | 18 | 32.00 | |
| **4 - Group 2** | 2 | 5663 | 433.36 | | 726 | 1221.13 | | 11 | OOR < | | 21 | 1.61 | | 16 | **9.01** | |
| **5 - Group 2** | 2 | 5808 | 447.37 | | 376 | 625.05 | | 15 | 10.02 | | 19 | **0.79** | | 20 | 54.99 | |
| 6 - Group 2 | 2 | 6215 | 488.50 | | 213 | 348.44 | | 43 | 49.53 | | 160 | 58.29 | | 20 | 49.25 | |
| 7 - Group 3 | 2 | 3651 | 264.96 | | 755 | 1272.40 | | 19 | 17.61 | | 22 | 1.93 | | 27 | 127.98 | |
| 8 - Group 3 | 2 | 6020 | 468.45 | | 427 | 710.94 | | 11 | OOR < | | 23 | 2.26 | | 22 | 77.82 | |
| **9 - Group 3** | 2 | 330 | 30.83 | | 117 | 183.63 | | 15 | 10.02 | | 72 | 20.30 | | 20 | 54.99 | |
| **10 - Group 4** | 2 | 5809 | 447.42 | | 555 | 927.83 | | 17 | 14.64 | | 28 | 3.73 | | 21 | 66.43 | |
| 11 - Group 4 | 2 | 6308 | 498.31 | | 473 | 788.58 | | 18 | 16.65 | | 28 | 3.89 | | 22 | 77.82 | |
| 12 - Group 4 | 2 | 9204 | 929.33 | | 372 | 618.32 | | 13 | 3.37 | | 15 | OOR | | 26 | 122.52 | |
| 13 - Group 5 | 2 | 3813 | 277.13 | | 143 | 228.01 | | 19 | 18.53 | | 27 | 3.40 | | 25 | 105.95 | |
| 14 - Group 5 | 2 | 4544 | 334.62 | | 119 | 187.12 | | 14 | 5.47 | | 27 | 3.40 | | 23 | 89.14 | |
| 15 - Group 5 | 2 | 7097 | 588.69 | | 805 | 1359.63 | | 13 | 3.37 | | 19 | **0.95** | | 20 | 54.99 | |
| 16 - Group 6 | 2 | 4188 | 306.05 | | 671 | 1126.83 | | 69 | 73.22 | | 92 | 28.92 | | 28 | 144.15 | |
| 17 - Group 6 | 2 | 1390 | 107.49 | | 220 | 361.25 | | 26 | 29.52 | | 63 | 16.61 | | 18 | 32.00 | |
| 19 - Group 7 | 2 | 3183 | 230.76 | | 986 | 1678.10 | | 82 | 83.50 | | 286 | 110.18 | | 39 | 248.48 | |
| 20 - Group 7 | 2 | 5144 | 385.67 | | 2784 | 5113.76 | | 17 | 14.64 | | 70 | 19.47 | | 31 | 175.50 | |
| 21 - Group 7 | 2 | 3441 | 249.41 | | 402 | 668.83 | | 55 | 61.13 | | 114 | 38.34 | | 26 | 122.52 | |

FIG. 10 continued

| | | Units: pg/mL | | | Units: pg/mL | | | Units: pg/mL | | | Units: pg/mL | | | Units: pg/mL | | |
|---|---|---|---|---|---|---|---|---|---|---|---|---|---|---|---|---|
| | | IL-1B | | | IL-2 | | | IL-3 | | | IL-4 | | | IL-5 | | |
| Description | Dilution | FI | Obs Conc. | Exp Conc. | FI | Obs Conc. | Exp Conc. | FI | Obs Conc. | Exp Conc. | FI | Obs Conc. | Exp Conc. | FI | Obs Conc. | Exp Conc. |
| **Standard 1** | 1 | 10 | 0.16 | 0.64 | ... | | 0.64 | 22 | 0.64 | 0.64 | 37 | 0.65 | 0.64 | 20 | 0.62 | 0.64 |
| **Standard 2** | 1 | 17 | 4.61 | 3.20 | 13 | 3.20 | 3.20 | 45 | 3.20 | 3.20 | 130 | 3.13 | 3.20 | 59 | 3.36 | 3.20 |
| **Standard 3** | 1 | 34 | 15.48 | 16.00 | 26 | 16.00 | 16.00 | 170 | 16.00 | 16.00 | 620 | 16.30 | 16.00 | 274 | 15.41 | 16.00 |
| **Standard 4** | 1 | 129 | 76.55 | 80.00 | 101 | 80.00 | 80.00 | 731 | 80.00 | 80.00 | 2943 | 80.14 | 80.00 | 1729 | 81.32 | 80.00 |
| **Standard 5** | 1 | 640 | 415.11 | 400.00 | 608 | 400.00 | 400.00 | 2836 | 400.00 | 400.00 | 11831 | 395.03 | 400.00 | 9016 | 398.55 | 400.00 |
| **Standard 6** | 1 | 2425 | 1976.75 | 2000.00 | 4657 | 2000.00 | 2000.00 | 8041 | 2000.00 | 2000.00 | 22976 | 2183.79 | 2000.00 | 19390 | 2033.11 | 2000.00 |
| **Standard 7** | 1 | 5187 | 10064.71 | 10000.00 | 17662 | 10000.00 | 10000.00 | 18099 | 10000.00 | 10000.00 | 24668 | 6525.28 | 10000.00 | 20789 | 8401.19 | 10000.00 |
| 1 - Group 1 | 2 | 13 | 4.30 | | 12 | **3.41** | | 16 | OOR | | 15 | **0.11** | | 31 | 2.91 | |
| 2 - Group 1 | 2 | 14 | 5.62 | | 17 | 14.36 | | 21 | **1.06** | | 15 | **0.08** | | 19 | **1.07** | |
| **3 - Group 1** | 2 | 14 | 5.62 | | 14 | 8.39 | | 14 | OOR | | 14 | **0.06** | | 31 | 2.91 | |
| **4 - Group 2** | 2 | 11 | 1.66 | | 10 | **0.43** | | 18 | **0.38** | | 13 | **0.00** | | 37 | 3.76 | |
| **5 - Group 2** | 2 | 12 | 2.98 | | 15 | 10.38 | | 15 | OOR | | 19 | **0.33** | | 34 | 3.34 | |
| 6 - Group 2 | 2 | 17 | 9.55 | | 216 | 328.05 | | 37 | 4.64 | | 25 | **0.65** | | 50 | 5.52 | |
| 7 - Group 3 | 2 | 16 | 8.24 | | 16 | 12.37 | | 22 | **1.17** | | 19 | **0.30** | | 41 | 4.31 | |
| 8 - Group 3 | 2 | 12 | 2.98 | | 14 | 8.39 | | 20 | **0.72** | | 21 | **0.43** | | 38 | 3.90 | |
| **9 - Group 3** | 2 | 14 | 4.96 | | 10 | **0.43** | | 19 | **0.61** | | 11 | OOR < | | 13 | OOR < | |
| **10 - Group 4** | 2 | 12 | 2.32 | | 9 | OOR | | 19 | **0.61** | | 18 | **0.27** | | 21 | 1.40 | |
| 11 - Group 4 | 2 | 13 | 4.30 | | 10 | **0.43** | | 18 | **0.38** | | 16 | **0.16** | | 27 | 2.32 | |
| 12 - Group 4 | 2 | 13 | 4.30 | | 11 | **2.42** | | 13 | OOR | | 15 | **0.11** | | 20 | **1.16** | |
| 13 - Group 5 | 2 | 14 | 5.62 | | 12 | **4.41** | | 15 | OOR | | 15 | **0.11** | | 26 | 2.10 | |
| 14 - Group 5 | 2 | 12 | 2.98 | | 13 | **5.40** | | 14 | OOR | | 13 | **0.00** | | 58 | 6.56 | |
| 15 - Group 5 | 2 | 15 | 6.93 | | 14 | 8.39 | | 15 | OOR | | 24 | **0.59** | | 41 | 4.31 | |
| 16 - Group 6 | 2 | 16 | 7.58 | | 127 | 200.14 | | 17 | **0.05** | | 28 | **0.81** | | 27 | 2.32 | |
| 17 - Group 6 | 2 | 16 | 8.24 | | 26 | 32.00 | | 15 | OOR | | 13 | **0.00** | | 17 | **0.73** | |
| 19 - Group 7 | 2 | 16 | 7.58 | | 61 | 94.11 | | 18 | **0.38** | | 22 | **0.46** | | 21 | 1.32 | |
| 20 - Group 7 | 2 | 14 | 5.62 | | 14 | 7.40 | | 19 | **0.61** | | 11 | OOR < | | 18 | **0.91** | |
| 21 - Group 7 | 2 | 49 | 50.96 | | 38 | 53.60 | | 45 | 6.40 | | 57 | 2.36 | | 38 | 3.90 | |

FIG. 10 continued

| | | Units: pg/mL IL-6 | | | Units: pg/mL IL-7 | | | Units: pg/mL IL-9 | | | Units: pg/mL IL-10 | | | Units: pg/mL IL-12 | | |
|---|---|---|---|---|---|---|---|---|---|---|---|---|---|---|---|---|
| Description | Dilution | FI | Obs Conc. | Exp Conc. | FI | Obs Conc. | Exp Conc. | FI | Obs Conc. | Exp Conc. | FI | Obs Conc. | Exp Conc. | FI | Obs Conc. | Exp Conc. |
| **Standard 1** | 1 | 20 | 0.64 | 0.64 | 22 | 0.68 | 0.64 | ... | | 0.64 | ... | | 0.64 | ... | | 0.64 |
| **Standard 2** | 1 | 51 | 3.20 | 3.20 | 28 | 2.90 | 3.20 | 17 | 3.20 | 3.20 | 20 | 3.20 | 3.20 | 20 | 3.20 | 3.20 |
| **Standard 3** | 1 | 201 | 16.00 | 16.00 | 61 | 17.52 | 16.00 | 23 | 16.00 | 16.00 | 40 | 16.00 | 16.00 | 29 | 16.00 | 16.00 |
| **Standard 4** | 1 | 878 | 80.00 | 80.00 | 181 | 75.61 | 80.00 | 78 | 80.00 | 80.00 | 125 | 80.00 | 80.00 | 99 | 80.00 | 80.00 |
| **Standard 5** | 1 | 3782 | 400.00 | 400.00 | 790 | 411.32 | 400.00 | 632 | 400.00 | 400.00 | 571 | 400.00 | 400.00 | 428 | 400.00 | 400.00 |
| **Standard 6** | 1 | 10976 | 2000.00 | 2000.00 | 2783 | 1984.15 | 2000.00 | 4464 | 2000.00 | 2000.00 | 2321 | 2000.00 | 2000.00 | 1829 | 2000.00 | 2000.00 |
| **Standard 7** | 1 | 22679 | 10000.00 | 10000.00 | 5826 | 10037.89 | 10000.00 | 16964 | 10000.00 | 10000.00 | 7823 | 10000.00 | 10000.00 | 6997 | 10000.00 | 10000.00 |
| 1 - Group 1 | 2 | 33 | 3.32 | | 21 | **0.60** | | 21 | 24.02 | | 21 | 7.68 | | 25 | 21.10 | |
| 2 - Group 1 | 2 | 34 | 3.57 | | 22 | 1.36 | | 15 | OOR | | 20 | 6.40 | | 25 | 19.67 | |
| **3 - Group 1** | 2 | 74 | 10.18 | | 22 | **0.98** | | 18 | 10.93 | | 16 | **1.28** | | 16 | OOR | |
| **4 - Group 2** | 2 | 40 | 4.55 | | 21 | **0.60** | | 15 | OOR | | 19 | **5.12** | | 18 | **0.44** | |
| **5 - Group 2** | 2 | 43 | 5.04 | | 21 | **0.60** | | 15 | OOR | | 21 | 7.68 | | 23 | 15.31 | |
| 6 - Group 2 | 2 | 68 | 9.18 | | 26 | 4.57 | | 156 | 282.69 | | 53 | 50.08 | | 32 | 38.28 | |
| 7 - Group 3 | 2 | 289 | 47.63 | | 35 | 12.20 | | 17 | 6.40 | | 20 | **5.76** | | 26 | 23.92 | |
| 8 - Group 3 | 2 | 28 | 2.59 | | 19 | OOR < | | 14 | OOR | | 20 | 6.40 | | 17 | OOR | |
| **9 - Group 3** | 2 | 31 | 3.08 | | 24 | 2.94 | | 20 | 17.60 | | 14 | OOR | | 22 | 12.36 | |
| **10 - Group 4** | 2 | 89 | 12.61 | | 23 | 2.14 | | 19 | 15.40 | | 19 | **5.12** | | 27 | 25.31 | |
| 11 - Group 4 | 2 | 37 | 4.06 | | 25 | 3.75 | | 22 | 28.09 | | 19 | **5.12** | | 29 | 32.00 | |
| 12 - Group 4 | 2 | 35 | 3.73 | | 34 | 11.33 | | 20 | 19.78 | | 14 | OOR | | 31 | 37.05 | |
| 13 - Group 5 | 2 | 36 | 3.90 | | 17 | OOR < | | 16 | **1.87** | | 17 | **2.56** | | 10 | OOR | |
| 14 - Group 5 | 2 | 29 | 2.75 | | 26 | 4.57 | | 19 | 13.17 | | 18 | **3.20** | | 21 | 9.39 | |
| 15 - Group 5 | 2 | 83 | 11.68 | | 22 | 1.36 | | 19 | 15.40 | | 19 | **4.48** | | 23 | 15.31 | |
| 16 - Group 6 | 2 | 68 | 9.18 | | 19 | OOR < | | 99 | 196.14 | | 20 | 6.40 | | 19 | **3.41** | |
| 17 - Group 6 | 2 | 36 | 3.90 | | 18 | OOR < | | 18 | 10.93 | | 18 | **3.84** | | 23 | 15.31 | |
| 19 - Group 7 | 2 | 55 | 7.02 | | 22 | **0.98** | | 126 | 238.86 | | 34 | 24.43 | | 27 | 26.68 | |
| 20 - Group 7 | 2 | 164 | 24.47 | | 21 | **0.24** | | 28 | 49.28 | | 19 | **5.12** | | 26 | 23.92 | |
| 21 - Group 7 | 2 | 64 | 8.43 | | 27 | 4.98 | | 65 | 135.89 | | 50 | 45.90 | | 98 | 158.37 | |

FIG. 10 continued

| | | IL-13 (Units: pg/mL) | | | IL-15 (Units: pg/mL) | | | IL-17 (Units: pg/mL) | | | IP-10 (Units: pg/mL) | | | KC (Units: pg/mL) | | |
|---|---|---|---|---|---|---|---|---|---|---|---|---|---|---|---|---|
| Description | Dilution | FI | Obs Conc. | Exp Conc. | FI | Obs Conc. | Exp Conc. | FI | Obs Conc. | Exp Conc. | FI | Obs Conc. | Exp Conc. | FI | Obs Conc. | Exp Conc. |
| **Standard 1** | 1 | ... | | 2.56 | ... | | 0.64 | 25 | 0.59 | 0.64 | 44 | 0.63 | 0.64 | 14 | 0.64 | 0.64 |
| **Standard 2** | 1 | 8 | 10.23 | 12.80 | 21 | OOR < | 3.20 | 68 | 3.49 | 3.20 | 147 | 3.27 | 3.20 | 22 | 3.20 | 3.20 |
| **Standard 3** | 1 | 24 | 81.93 | 64.00 | 27 | 32.04 | 16.00 | 273 | 15.65 | 16.00 | 609 | 15.76 | 16.00 | 44 | 16.00 | 16.00 |
| **Standard 4** | 1 | 79 | 304.15 | 320.00 | 34 | 77.74 | 80.00 | 1435 | 77.24 | 80.00 | 2602 | 79.11 | 80.00 | 157 | 80.00 | 80.00 |
| **Standard 5** | 1 | 376 | 1478.38 | 1600.00 | 86 | 394.86 | 400.00 | 7782 | 417.36 | 400.00 | 8055 | 427.54 | 400.00 | 1040 | 400.00 | 400.00 |
| **Standard 6** | 1 | 2002 | 8583.40 | 8000.00 | 372 | 2009.44 | 2000.00 | 19069 | 1843.54 | 2000.00 | 11791 | 1492.80 | 2000.00 | 5900 | 2000.00 | 2000.00 |
| **Standard 7** | 1 | 7757 | 39777.40 | 40000.00 | 1780 | 9999.99 | 10000.00 | 23377 | 57244.92 | 10000.00 | 14088 | OOR > | 10000.00 | 18925 | 10000.00 | 10000.00 |
| 1 - Group 1 | 2 | 22 | 146.98 | | 23 | 8.75 | | 15 | OOR < | | 2416 | 144.85 | | 421 | 377.77 | |
| 2 - Group 1 | 2 | 24 | 163.86 | | 21 | OOR < | | 20 | **0.51** | | 695 | 36.33 | | 38 | 21.97 | |
| **3 - Group 1** | 2 | 19 | 117.05 | | 20 | OOR < | | 16 | OOR < | | 2621 | 159.59 | | 428 | 383.02 | |
| **4 - Group 2** | 2 | 20 | 129.95 | | 18 | OOR < | | 15 | OOR < | | 2374 | 141.92 | | 546 | 468.89 | |
| **5 - Group 2** | 2 | 27 | 188.95 | | 21 | OOR < | | 21 | **0.66** | | 1701 | 96.73 | | 171 | 172.91 | |
| 6 - Group 2 | 2 | 163 | 1261.96 | | 29 | 90.61 | | 52 | 4.95 | | 2075 | 121.32 | | 885 | 698.91 | |
| 7 - Group 3 | 2 | 30 | 213.81 | | 26 | 50.62 | | 19 | **0.35** | | 2321 | 138.21 | | 418 | 375.90 | |
| 8 - Group 3 | 2 | 16 | 95.28 | | 25 | 43.83 | | 17 | **0.00** | | 2458 | 147.87 | | 399 | 361.54 | |
| **9 - Group 3** | 2 | 28 | 193.11 | | 28 | 84.02 | | 15 | OOR < | | 1476 | 82.53 | | 78 | 79.66 | |
| **10 - Group 4** | 2 | 18 | 112.73 | | 20 | OOR < | | 20 | **0.51** | | 1793 | 102.63 | | 138 | 142.57 | |
| 11 - Group 4 | 2 | 29 | 205.54 | | 29 | 97.18 | | 17 | **0.00** | | 2232 | 131.99 | | 539 | 464.27 | |
| 12 - Group 4 | 2 | 19 | 121.36 | | 53 | 398.96 | | 13 | OOR < | | 1845 | 106.05 | | 259 | 250.20 | |
| 13 - Group 5 | 2 | 25 | 172.25 | | 20 | OOR < | | 18 | **0.10** | | 1519 | 85.21 | | 570 | 486.20 | |
| 14 - Group 5 | 2 | 18 | 112.73 | | 20 | OOR < | | 14 | OOR < | | 1197 | 65.46 | | 61 | 57.98 | |
| 15 - Group 5 | 2 | 25 | 172.25 | | 19 | OOR < | | 22 | **0.82** | | 2685 | 164.31 | | 140 | 144.48 | |
| 16 - Group 6 | 2 | 152 | 1179.58 | | 36 | 181.03 | | 21 | **0.66** | | 1382 | 76.72 | | 346 | 320.24 | |
| 17 - Group 6 | 2 | 30 | 213.81 | | 32 | 136.20 | | 19 | **0.35** | | 2285 | 135.66 | | 457 | 404.92 | |
| 19 - Group 7 | 2 | 48 | 360.03 | | 33 | 149.07 | | 18 | **0.19** | | 702 | 36.69 | | 298 | 282.34 | |
| 20 - Group 7 | 2 | 32 | 230.28 | | 39 | 225.33 | | 16 | OOR < | | 1052 | 56.88 | | 69 | 68.56 | |
| 21 - Group 7 | 2 | 42 | 311.71 | | 44 | 287.91 | | 17 | **0.00** | | 1569 | 88.35 | | 413 | 372.13 | |

FIG. 10 continued

| | | LIF (Units: pg/mL) | | | LIX (Units: pg/mL) | | | MCP-1 (Units: pg/mL) | | | M-CSF (Units: pg/mL) | | | MIG (Units: pg/mL) | | |
|---|---|---|---|---|---|---|---|---|---|---|---|---|---|---|---|---|
| Description | Dilution | FI | Obs Conc. | Exp Conc. | FI | Obs Conc. | Exp Conc. | FI | Obs Conc. | Exp Conc. | FI | Obs Conc. | Exp Conc. | FI | Obs Conc. | Exp Conc. |
| **Standard 1** | 1 | 39 | 0.65 | 0.64 | ... | | 0.64 | ... | | 0.64 | ... | | 0.64 | 20 | 0.10 | 0.64 |
| **Standard 2** | 1 | 67 | 3.16 | 3.20 | ... | | 3.20 | 10 | 3.20 | 3.20 | 14 | 3.20 | 3.20 | 27 | 3.91 | 3.20 |
| **Standard 3** | 1 | 219 | 16.17 | 16.00 | 24 | 16.00 | 16.00 | 15 | 16.00 | 16.00 | 25 | 16.00 | 16.00 | 52 | 15.97 | 16.00 |
| **Standard 4** | 1 | 940 | 79.43 | 80.00 | 44 | 80.00 | 80.00 | 42 | 80.00 | 80.00 | 75 | 80.00 | 80.00 | 213 | 78.79 | 80.00 |
| **Standard 5** | 1 | 3820 | 401.79 | 400.00 | 158 | 400.00 | 400.00 | 360 | 400.00 | 400.00 | 381 | 400.00 | 400.00 | 1228 | 402.50 | 400.00 |
| **Standard 6** | 1 | 9898 | 1992.76 | 2000.00 | 1216 | 2000.00 | 2000.00 | 3203 | 2000.00 | 2000.00 | 2014 | 2000.00 | 2000.00 | 7329 | 2000.02 | 2000.00 |
| **Standard 7** | 1 | 14918 | 10033.73 | 10000.00 | 6498 | 10000.00 | 10000.00 | 13251 | 10000.00 | 10000.00 | 6207 | 10000.00 | 10000.00 | 13182 | 9993.20 | 10000.00 |
| 1 - Group 1 | 2 | 35 | **0.47** | | 168 | 843.92 | | 276 | 668.81 | | 23 | 27.78 | | 195 | 144.43 | |
| 2 - Group 1 | 2 | 25 | OOR < | | 258 | 1227.15 | | 80 | 279.53 | | 18 | 15.86 | | 171 | 126.68 | |
| **3 - Group 1** | 2 | 27 | OOR < | | 100 | 496.33 | | 169 | 480.54 | | 19 | 18.23 | | 170 | 125.94 | |
| **4 - Group 2** | 2 | 25 | OOR < | | 159 | 803.60 | | 219 | 572.54 | | 15 | 8.76 | | 248 | 182.74 | |
| **5 - Group 2** | 2 | 30 | OOR < | | 318 | 1453.97 | | 100 | 332.29 | | 17 | 13.49 | | 172 | 127.43 | |
| 6 - Group 2 | 2 | 28 | OOR < | | 76 | 354.15 | | 158 | 457.95 | | 17 | 13.49 | | 549 | 386.31 | |
| 7 - Group 3 | 2 | 28 | OOR < | | 149 | 754.96 | | 275 | 667.18 | | 27 | 36.25 | | 275 | 201.87 | |
| 8 - Group 3 | 2 | 27 | OOR < | | 1614 | 5053.11 | | 100 | 331.07 | | 19 | 18.23 | | 186 | 137.44 | |
| **9 - Group 3** | 2 | 26 | OOR < | | 311 | 1428.65 | | 21 | 62.80 | | 41 | 72.63 | | 28 | 9.39 | |
| **10 - Group 4** | 2 | 23 | OOR < | | 264 | 1252.46 | | 54 | 202.67 | | 20 | 19.42 | | 211 | 156.12 | |
| 11 - Group 4 | 2 | 25 | OOR < | | 249 | 1193.65 | | 85 | 292.97 | | 23 | 26.58 | | 212 | 156.85 | |
| 12 - Group 4 | 2 | 25 | OOR < | | 285 | 1332.60 | | 102 | 337.15 | | 21 | 22.99 | | 148 | 109.37 | |
| 13 - Group 5 | 2 | 25 | OOR < | | 928 | 3249.05 | | 133 | 407.41 | | 23 | 27.78 | | 74 | 50.39 | |
| 14 - Group 5 | 2 | 25 | OOR < | | 195 | 968.64 | | 18 | 47.43 | | 25 | 32.61 | | 39 | 20.13 | |
| 15 - Group 5 | 2 | 28 | OOR < | | 27 | 51.30 | | 353 | 790.08 | | 16 | 9.94 | | 274 | 201.16 | |
| 16 - Group 6 | 2 | 22 | OOR < | | 317 | 1450.37 | | 40 | 150.99 | | 21 | 21.80 | | 360 | 260.72 | |
| 17 - Group 6 | 2 | 24 | OOR < | | 1321 | 4276.04 | | 651 | 1213.59 | | 21 | 22.99 | | 73 | 49.97 | |
| 19 - Group 7 | 2 | 26 | OOR < | | 1600 | 5015.63 | | 52 | 194.11 | | 26 | 35.03 | | 100 | 72.03 | |
| 20 - Group 7 | 2 | 23 | OOR < | | 145 | 735.12 | | 17 | 42.29 | | 24 | 28.98 | | 119 | 87.04 | |
| 21 - Group 7 | 2 | 110 | 13.62 | | 454 | 1909.47 | | 103 | 339.56 | | 78 | 168.94 | | 792 | 540.72 | |

FIG. 10 continued

| | | MIP-1a (Units: pg/mL) | | | MIP-1B (Units: pg/mL) | | | MIP-2 (Units: pg/mL) | | | RANTES (Units: pg/mL) | | | TNFa (Units: pg/mL) | | | VEGF (Units: pg/mL) | | |
|---|---|---|---|---|---|---|---|---|---|---|---|---|---|---|---|---|---|---|---|
| Description | Dilution | FI | Obs Conc. | Exp Conc. | FI | Obs Conc. | Exp Conc. | FI | Obs Conc. | Exp Conc. | FI | Obs Conc. | Exp Conc. | FI | Obs Conc. | Exp Conc. | FI | Obs Conc. | Exp Conc. |
| **Standard 1** | 1 | ... | | 0.64 | ... | | 0.64 | ... | | 0.64 | ... | | 0.64 | 14 | OOR < | 0.64 | 42 | 0.62 | 0.64 |
| **Standard 2** | 1 | ... | | 3.26 | ... | | 3.20 | ... | | 3.20 | 20 | 3.20 | 3.20 | 19 | 4.26 | 3.20 | 180 | 3.09 | 3.20 |
| **Standard 3** | 1 | 14 | 19.74 | 16.00 | 22 | 16.00 | 16.00 | 25 | 16.00 | 16.00 | 39 | 16.00 | 16.00 | 44 | 15.29 | 16.00 | 861 | 17.43 | 16.00 |
| **Standard 4** | 1 | 35 | 75.00 | 80.00 | 47 | 80.00 | 80.00 | 30 | 80.00 | 80.00 | 185 | 80.00 | 80.00 | 309 | 81.64 | 80.00 | 3383 | 81.26 | 80.00 |
| **Standard 5** | 1 | 719 | 418.09 | 400.00 | 456 | 400.00 | 400.00 | 69 | 400.00 | 400.00 | 1550 | 400.00 | 400.00 | 1931 | 393.86 | 400.00 | 11029 | 366.51 | 400.00 |
| **Standard 6** | 1 | 9587 | 1939.92 | 2000.00 | 4647 | 2000.00 | 2000.00 | 876 | 2000.00 | 2000.00 | 6158 | 2000.00 | 2000.00 | 4070 | 2487.90 | 2000.00 | 23968 | 3470.59 | 2000.00 |
| **Standard 7** | 1 | 22772 | 11609.63 | 10000.00 | 11901 | 8984.34 | 10000.00 | 9657 | 8984.34 | 10000.00 | 11635 | 10000.00 | 10000.00 | 4193 | 4194.35 | 10000.00 | 24452 | 4384.21 | 10000.00 |
| 1 - Group 1 | 2 | 19 | 80.75 | | 33 | 96.40 | | 22 | OOR | | 454 | 319.31 | | 14 | OOR < | | 37 | **1.08** | |
| 2 - Group 1 | 2 | 17 | 70.97 | | 36 | 111.88 | | 28 | 109.61 | | 28 | 17.34 | | 15 | 2.02 | | 21 | **0.58** | |
| **3 - Group 1** | 2 | 19 | 83.75 | | 29 | 74.16 | | 19 | OOR | | 392 | 286.39 | | 16 | 3.91 | | 57 | 1.74 | |
| **4 - Group 2** | 2 | 19 | 83.75 | | 25 | 50.39 | | 28 | 122.35 | | 276 | 219.64 | | 20 | 8.82 | | 40 | **1.16** | |
| **5 - Group 2** | 2 | 14 | 45.36 | | 30 | 79.88 | | 25 | 45.01 | | 114 | 106.17 | | 18 | 6.21 | | 24 | **0.67** | |
| 6 - Group 2 | 2 | 233 | 464.83 | | 75 | 246.12 | | 27 | 96.80 | | 143 | 129.37 | | 24 | 13.83 | | 279 | 10.02 | |
| 7 - Group 3 | 2 | 19 | 83.75 | | 31 | 85.50 | | 28 | 109.61 | | 373 | 275.96 | | 26 | 15.34 | | 37 | **1.08** | |
| 8 - Group 3 | 2 | 23 | 104.68 | | 17 | **1.58** | | 18 | OOR | | 50 | 44.79 | | 15 | 2.02 | | 22 | **0.61** | |
| **9 - Group 3** | 2 | 17 | 70.97 | | 33 | 96.40 | | 26 | 70.99 | | 48 | 41.91 | | 18 | 6.90 | | 42 | 1.24 | |
| **10 - Group 4** | 2 | 20 | 89.45 | | 41 | 135.33 | | 26 | 70.99 | | 93 | 87.96 | | 19 | 8.20 | | 19 | **0.50** | |
| 11 - Group 4 | 2 | 18 | 77.63 | | 36 | 111.88 | | 30 | 172.33 | | 253 | 205.34 | | 17 | 5.49 | | 20 | **0.55** | |
| 12 - Group 4 | 2 | 14 | 39.47 | | 31 | 85.50 | | 22 | OOR | | 70 | 66.12 | | 17 | 5.49 | | 12 | **0.31** | |
| 13 - Group 5 | 2 | 21 | 94.81 | | 32 | 88.27 | | 32 | 208.60 | | 43 | 36.59 | | 17 | 5.49 | | 20 | **0.53** | |
| 14 - Group 5 | 2 | 16 | 63.61 | | 18 | **4.56** | | 24 | **5.99** | | 35 | 26.61 | | 14 | OOR < | | 107 | 3.49 | |
| 15 - Group 5 | 2 | 18 | 77.63 | | 30 | 79.88 | | 21 | OOR | | 192 | 165.06 | | 18 | 6.90 | | 26 | **0.72** | |
| 16 - Group 6 | 2 | 166 | 387.41 | | 86 | 273.22 | | 29 | 147.55 | | 34 | 25.31 | | 22 | 11.71 | | 91 | 2.92 | |
| 17 - Group 6 | 2 | 30 | 133.56 | | 33 | 96.40 | | 39 | 372.21 | | 97 | 91.54 | | 22 | 11.16 | | 25 | **0.70** | |
| 19 - Group 7 | 2 | 17 | 70.97 | | 63 | 213.15 | | 41 | 401.43 | | 59 | 54.73 | | 17 | 4.73 | | 253 | 9.01 | |
| 20 - Group 7 | 2 | 21 | 94.81 | | 31 | 85.50 | | 32 | 220.43 | | 32 | 22.03 | | 19 | 8.20 | | 31 | **0.89** | |
| 21 - Group 7 | 2 | 15 | 55.25 | | 51 | 174.70 | | 31 | 196.63 | | 62 | 57.91 | | 24 | 13.83 | | 54 | 1.64 | |

CD8+/Treg Ratio (as % of $CD_{45}$) on Day 12 (*n* = 6).

Drug X

MCC201a

MCC203 add Drug X solution to powder to reconstitute Imagent/Viral Complex

IMAGENT

Pre-Reconstituted Imagent®
MCC201

MCC202 drug encapsulated within microbubbles and free drug

FIG. 15

| Results: IL2 in PBS | | | | | | | | |
|---|---|---|---|---|---|---|---|---|
| | | | | Assay Range: | 31.25 to 2000.0 pg/mL | | | |
| Batch ID: IL2 Batch13 | | | | | | | | |
| Sample | Wells | OD | R | Mean Result (Concentration pg/mL) | SD | CV | Dilution Factor | Mean Concentration in undiluted sample (ng/mL) |
| AI1_250K | A4-A6 | 1.321 | | 787.01 | 12.33 | 1.6 | 250000 | 196753 |
| AI1_1000K | B4-B6 | 0.305 | | 186.59 | 1.46 | 0.8 | 1000000 | 186590 |
| BI1_250K | A7-A9 | 1.233 | | 731.60 | 13.84 | 1.9 | 250000 | 182900 |
| BI1_1000K | B7-B9 | 0.284 | | 174.45 | 4.95 | 2.8 | 1000000 | 174450 |
| CI1_250K | A10-A12 | 1.207 | | 715.87 | 7.47 | 1.0 | 250000 | 178968 |
| CI1_1000K | B10-B12 | 0.268 | | 165.39 | 4.01 | 2.4 | 1000000 | 156390 |
| AMB1_2500 | C4-C6 | 2.146 | | 1361.25 | 4.72 | 0.3 | 2500 | 3403 |
| AMB1_10000 | D4-D6 | 0.502 | | 299.60 | 5.74 | 1.9 | 10000 | 2996 |
| BMB1_2500 | C7-C9 | 1.075 | | 634.34 | 17.41 | 2.7 | 2500 | 1586 |
| BMB1_10000 | D7-D9 | 0.243 | | 150.74 | 4.85 | 3.2 | 10000 | 1507 |
| CMB1_2500 | C10-C12 | 2.250 | | 1443.41 | 47.49 | 3.3 | 2500 | 3609 |
| CMB1_10000 | D10-D12 | 0.531 | | 316.19 | 6.52 | 2.1 | 10000 | 3162 |
| AI2_2500 | E4-E6 | 1.878 | | 1162.59 | 9.79 | 0.8 | 2500 | 2906 |
| AI2_10000 | F4-F6 | 0.419 | | 252.12 | 2.74 | 1.1 | 10000 | 2521 |
| BI2-2500 | E7-E9 | 0.946 | | 557.09 | 10.65 | 1.9 | 2500 | 1393 |
| BI2_10000 | F7-F9 | 0.206 | | 128.92 | 2.52 | 2.0 | 10000 | 1289 |
| CI2_2500 | E10-E12 | 2.161 | | 1373.49 | 64.37 | 4.7 | 2500 | 3434 |
| CI2_10000 | F10-F12 | 0.485 | | 289.93 | 2.62 | 0.9 | 10000 | 2899 |
| AMB2_500 | G4-G6 | 2.473 | | 1625.5 | 16.67 | 1 | 500 | 813 |
| AMB2_2000 | H4-H6 | 0.620 | | 366.9 | 6.7 | 1.8 | 2000 | 734 |
| BMB2_500 | G7-G9 | 0.403 | | 242.8 | 35.12 | 14.5 | 500 | 121 |
| BMB2_2000 | H7-H9 | 0.081 | | 52.6 | 1.74 | 3.3 | 2000 | 105 |
| CMB2_500 | G10-G12 | 1.937 | | 1204.9 | 11.2 | 0.9 | 500 | 602 |
| CMB2_2000 | H10-H12 | 0.451 | | 270.37 | 6.42 | 2.4 | 2000 | 541 |

Patient 1a
Patient 1b
Patient 2
Patient 3...
data
First Device
FD101, FD102,
FD103...
data
Other Device OD101
Second Device
SD101
PACS
SD102
network
SD103
data
External Database
ED 101
data

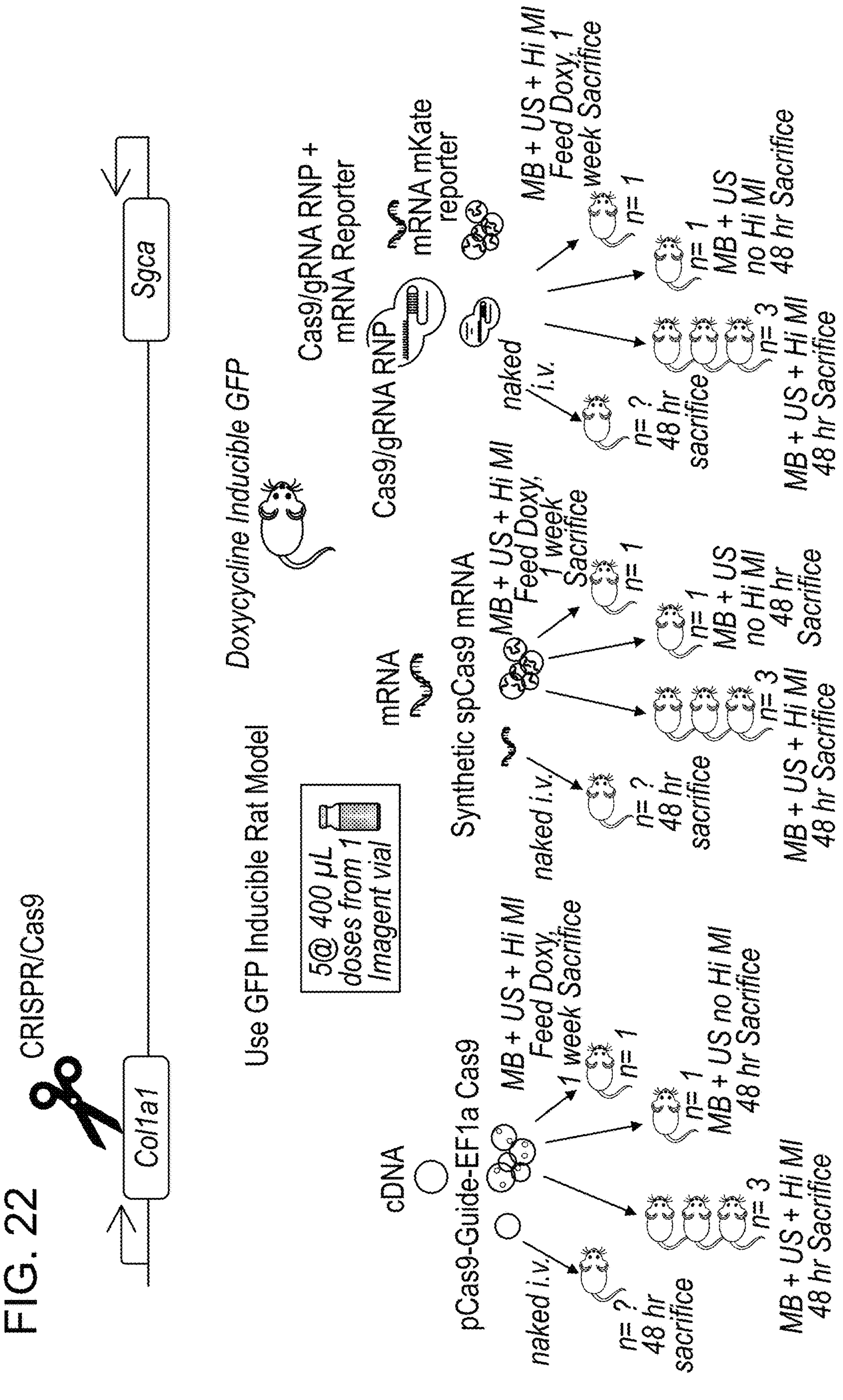

FIG. 22
CRISPR/Cas9
Col1a1
Sgca
Use GFP Inducible Rat Model
Doxycycline Inducible GFP
5@ 400 μL doses from 1 Imagent vial
cDNA
pCas9-Guide-EF1a Cas9
naked i.v.
n= ?
48 hr sacrifice
n= 3
MB + US + Hi MI 48 hr Sacrifice
n= 1
MB + US no Hi MI 48 hr Sacrifice
MB + US + Hi MI Feed Doxy, 1 week Sacrifice
n= 1
mRNA
Synthetic spCas9 mRNA
naked i.v.
n= ?
48 hr sacrifice
n= 3
MB + US + Hi MI 48 hr Sacrifice
n= 1
MB + US no Hi MI 48 hr Sacrifice
MB + US + Hi MI Feed Doxy, 1 week Sacrifice
n= 1
Cas9/gRNA RNP + mRNA Reporter
Cas9/gRNA RNP
mRNA mKate reporter
naked i.v.
n= ?
48 hr sacrifice
n= 3
MB + US + Hi MI 48 hr Sacrifice
n= 1
MB + US no Hi MI 48 hr Sacrifice
MB + US + Hi MI Feed Doxy, 1 week Sacrifice
n= 1

E

Intact Distant Tumor

A

Disrupted Distant Tumor

Intact Primary Tumor

F

Effector T Cell Migration

Ultrasound Transducer

B

D

Disrupted Primary Tumor

Permeabilized Vessel

C

Microstreaming

Oscillation

Vehicle
0.3mpk (x3)
1mpk (x3)
3mpk (x3)
0.3mpk (x1)
1mpk (x1)
3mpk (x1)
10mpk (x1)
Tumor volume (mm³)
Days on study
CR: 0/10
CR: 0/9
CR: 0/10
CR: 0/10
CR: 0/10
CR: 8/9
CR: 8/9
CR: 10/10

Percent survival
100
50
0
0
10
20
30
Days on study
Vehicle
Vehicle + US + MB
0.3mpk (x1)
0.3mpk (x1) + US + MB
1mpk (x1)
1mpk (x1) + US
1mpk (x1) + MB
1mpk (x1) + US + MB
****
**
*
*
**
****

% Body weight change
15
10
5
0
-5
0
10
20
30
Days on study

CD8+ T cells
% of CD45+
GranB+CD8+ T cells
% of CD45+
Ki67+CD8+ T cells
% of CD45+
NK cells
% of CD45+
GranB+NK cells
% of CD45+
Ki67+NK cells
% of CD45+

G-MDSC
% of CD45+
M-MDSC
% of CD45+
APC
% of CD45+
DC
% of CD45+
Mφ
% of CD45+
Monocytic cells
% of CD45+
Vehicle
Vehicle + US + MB
1mpk (x1)
1mpk (x1) + US
1mpk (x1) + US + MB Pretreatment Tumor Volume
Tumor Weight 48 Hrs Posttreatment
250
200
150
100
50
0
1.20
1.00
0.80
0.60
0.40
0.20
0.00
1.15
1.03
1.08
1.12
1.06
1.03
1.03
0.65
0.79
Group 1
Group 2
Group 3a
Group 3b
Group 3c
Group 3d
Group 4
Group 5
Group 6
Avg Pretreatment Tumor Volume
Avg Post Treatment Tumor Weight

3300

FOR SPIN SEPARATION

3440

3442 motor/rotor controller

TIME 20:00
TEMP 40 C

SPIN ON/
OFF

INCUBATOR/
ROCKER
ON/OFF

FOR INCUBATION & ROTATION

3450

3452

3458

3456

3454

3470 motor/rotor controller

TIME 20:00
TEMP 40 C

SPIN ON/
OFF

INCUBATOR/
ROCKER
ON/OFF 3400
3420
3410
3416
3412
3414
motor/rotor
controller
TIME 20:00
TEMP 40 C
SPIN ON/OFF
INCUBATOR/ROCKER ON/OFF
5 mL
4002
4004
4006
4008
4010
4012
4014
4016
4018
4020
4022

4100

Sterile Water for Injection 2.0 mL to Proleukin IL-2 Vial 1

2.0 mL to Proleukin IL-2 Vial 2

Step 4110

Add 3.5 mL IL-2 to Imagent Vial

Step 4120

Incubate SonoLeukin in Vial for 20 min. Withdraw 2.0 mL to Syringe with 3.0 mL SWFI Step 4130

Spin Separate Syringe for 6 min. Discard Infranatant, 0.3 mL Cream left in Syringe Step 4140

Add 2.0 mL Sterile Saline

Step 4150

SonoLeukin ready for i.v. injection

SWFI + Swabable 20mm Vial Adapter
One or Two @ vials Proleukin (provided separately) + Standard Vial Adapters
Luer Lock Syringe
Sterile Saline with Vented Vial Adapter
Imagent
Filter Hub
PhaSeal Vial Adapter & Connector
COMPONENTS
4006
4020
4012
4022
4210A
4210B
4222
3400
4220
4010
4016
4014
4002
4230
5 mL
A
B
1
2

FIG. 43B
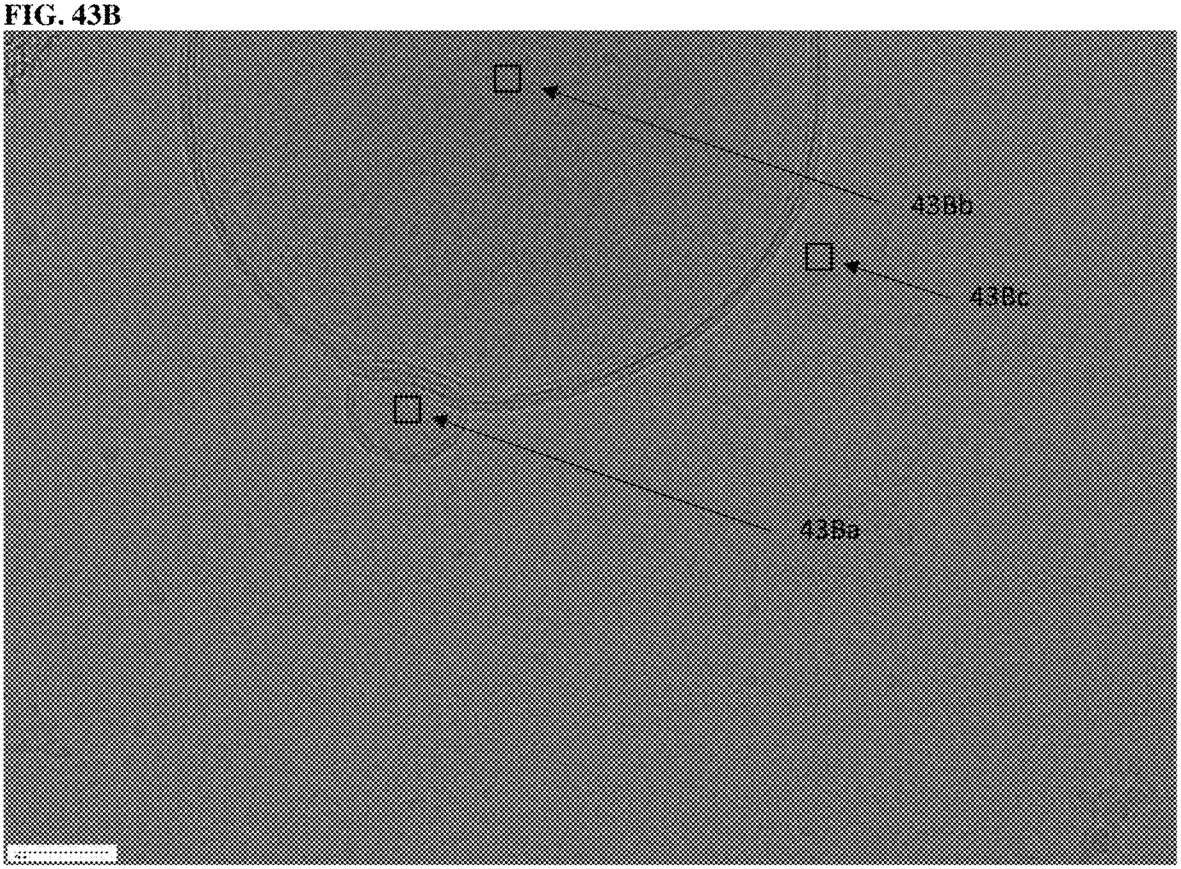
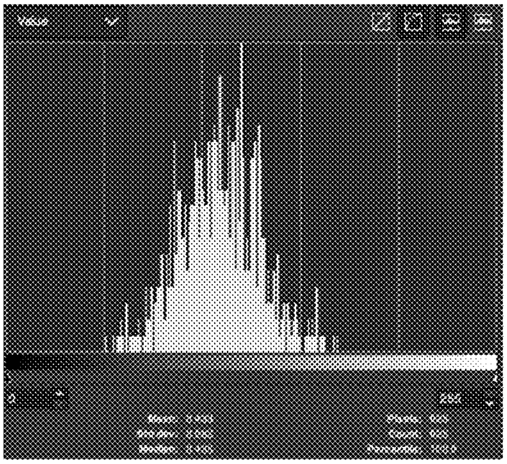
FIG. 43C: Histogram for 43Ba

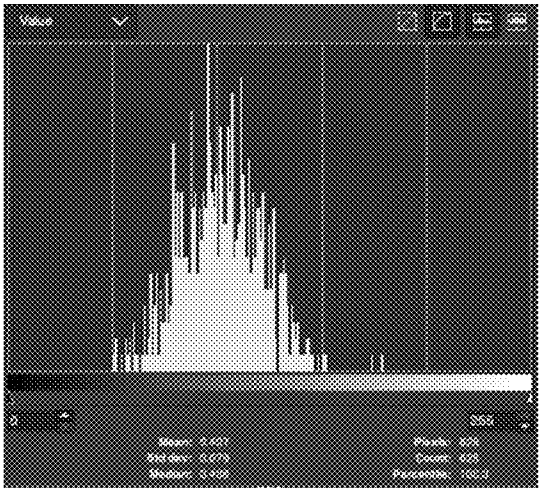
FIG. 43D: Histogram for 43Bb
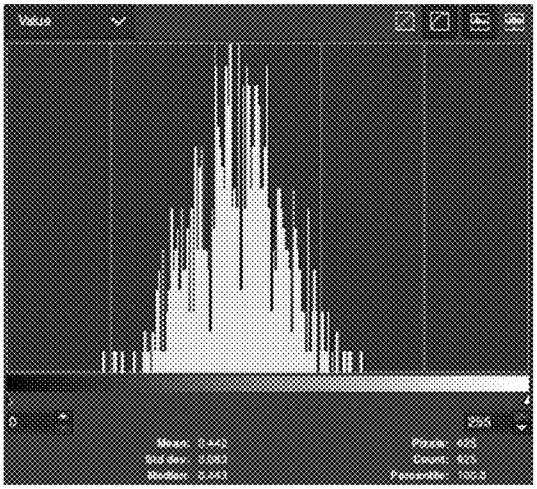
FIG. 43E: Histogram for 43Bc

FIG. 44A
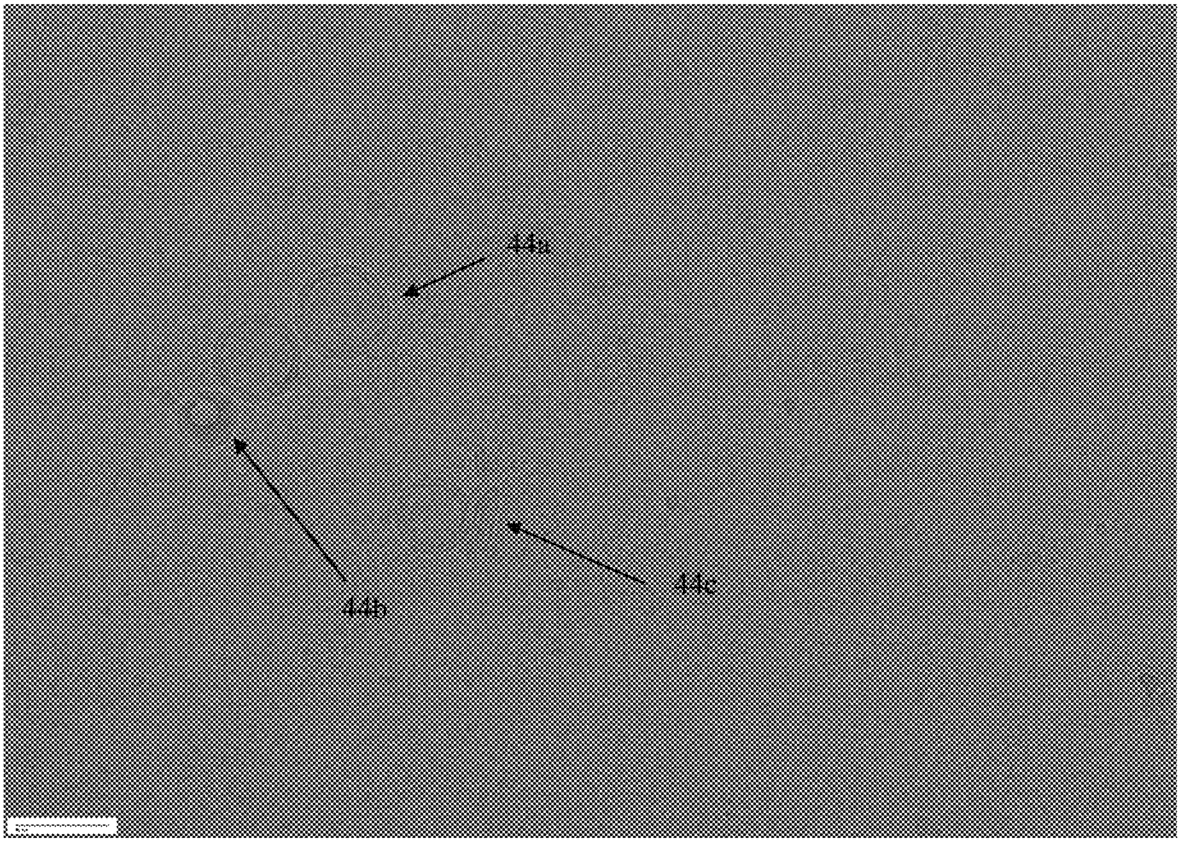
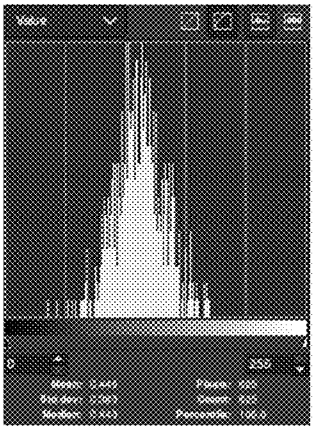
FIG. 44B: Histogram for 44a

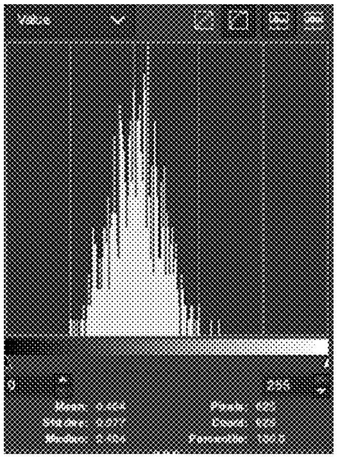
FIG: 44C: Histogram for 44b

Imagent with LNP Sample Preparation

COMPOSITIONS AND METHODS FOR TARGETED DELIVERY OF THERAPEUTICS USING CARRIERS

RELATED APPLICATION

This application is a continuation of U.S. patent application Ser. No. 17/743,056, filed May 12, 2022, which is a continuation in part of International Application No. PCT/US2021/057961, filed Nov. 3, 2021, which claims the benefit of priority to U.S. Provisional Application No. 63/109,193, filed on Nov. 3, 2020. The entire contents of the foregoing applications are incorporated herein by reference.

SEQUENCE LISTING

The instant application contains a Sequence Listing which has been submitted electronically in XML file format and is hereby incorporated by reference in its entirety. Said XML copy, created on Aug. 28, 2023, is named 132075-00102_SL.xml and is 11,360 bytes in size.

BACKGROUND

Currently, the administration of medicines to treat disease (particularly in cancer treatment) is typically a regimen where the dosage is based on such factors as patient weight or body surface area. This methodology leads to a treatment philosophy of administering the maximum tolerated dose of a therapeutic agent (or combination of agents), rather than taking into consideration relevant factors such as, but not limited to, how much of a therapeutic agent(s) is actually delivered to the target tissue (which may be a cell, e.g., tumor cell), or more relevantly what amount is required at the target in order to have a therapeutic effect. Even if the amount of an agent needed to have a therapeutic effect is known, there may be other factors that affect the ability to deliver said amount to the target, such as, but not limited to, anatomical, physiological, mechanical, chemical, biological, etc. For some agents (e.g., viruses, nucleic acids, etc.), the body's natural immune system may actually inhibit effective delivery. For some agents, mechanical or chemical processes (e.g., efflux pumps, interstitial fluid pressure, reactive oxygen species (ROS), bacteria, etc.) may inhibit effective therapy.

While drug discovery and development is beginning to adapt to new technologies, the actual treatment of cancer (and other diseases) itself is still stuck in an analog age. If a patient has a disease, one standard methodology is to prescribe a maximum tolerated dose of drug(s) that has been shown to have a clinical effect for 50 percent of treated patients from a clinical trial. The administration of many traditional or novel drugs is still performed in the same way since the 17th century, e.g., using a syringe to inject a specific dose of drugs intravenously, then waiting to see what clinical effect occurs in a specific patient, if any. Currently, dosage of drugs is typically either a fixed dose, or is determined by a patient's weight, body surface area, or other gross measures. Even when, in the case of cancer, the genetic profile of a patient's tumor has been identified and a specific mix of drugs is prescribed, the dosage remains fixed, or is based on some gross measure. Especially with systemically administered therapeutics, the amount of the therapeutic agent that actually reaches its intended target is a small fraction of the total injected dose, due in part because the therapeutic agents rely on the circulatory system to passively deliver the molecules to the target while the body's natural defense mechanisms may prevent or inhibit the process.

Pharmacokinetics (PK) describes how the body works on a particular drug. It is separated in time along four steps common to all drugs:

1. Absorption. How the drug gets into the systemic plasma (oral, IV, Infusion etc.)
2. Distribution. How the drug gets from systemic circulation into the target tissue.
3. Metabolism. How cells process the presence of the therapeutic.
4. Excretion. How tissue and the circulation remove the agent or its metabolites from the body.

Each drug has a therapeutic window defined by the range of concentration in plasma that provides safe and effective therapy. Too little drug and it will be ineffective. Too much drug in the system and adverse effects will be encountered, even if the underlying disease is treated.

The therapeutic window can be quantified in terms of a therapeutic index, represented by $TD_{50}/ED_{50}$, where $TD_{50}$ is the toxic dose where the plasma concentration causes 50% of patients to have adverse effects, and $ED_{50}$, where the plasma concentration is effective in 50% of patients.

This tradeoff in effective versus toxic levels is common in the field of chemotherapy, where cytotoxic agents take their toll on normal tissue in addition to cancer cells. Even with the latest immunotherapy approaches, sometimes the greater opportunity for curative effects comes with even more risks for serious and life threatening systemic immune responses to other organs not affected by the tumor that is being targeted. The wider the therapeutic window and higher the therapeutic index, the easier the drug is to safely administer and the higher likelihood that it will be effective for more patients.

Pharmacodynamics (PD), on the other hand, describes how a specific drug works on the body. Its steps are described by:

1. Affinity: A measure of how avidly a drug binds to a receptor.
2. Efficacy: Measure of the magnitude of effect once the drug is bound.
3. Potency: Measure of the quantity of drug needed to produce maximal effect.

If a drug can be delivered and maintained at its target for a longer period of time in higher concentrations, it improves its ability to bind receptors and to provide a longer duration of effect at the same plasma concentration.

Typically a drug has a PK profile well described during its drug discovery and development stages. This detailed experimental data is also critical to dosing selection for clinical trials and is a key component of regulatory agency submissions for approval. A key design goal of pharmaceutical developers is to maximize absorption and distribution of a therapeutic agent, as more active agent at the target tissue will increase potency and efficacy. There are pharmacological solutions to this optimization. One example is nab-paclitaxel, where the generic drug paclitaxel was made significantly more efficacious and less toxic by encapsulating it within an albumin bound nanoparticle.

There are also many drug delivery technologies that attempt to overcome distribution limitations of a drug's PK by direct injection into tumors, drug eluting beads or iontophoresis. Each of these approaches has limitations including the need to change the method of administration of a drug and requiring invasive procedures. These drug delivery methods are suboptimal with one drug, but are even more unwieldy for combination oncology therapy that requires coordination of drugs with different methods of administration at varying schedules. Treatment regimens may consist of a combination of daily oral tablets, weekly infusions or monthly monoclonal antibody (mAb) injections and are increasingly becoming more prevalent in cancer care.

If a drug, at a specific blood concentration, can be delivered more optimally to the target—and does not have limited binding sites—then the therapeutic window could be shifted to a lower blood concentration at which the minimum therapeutic effect can be achieved. This widens the therapeutic window at equal blood concentrations. If desired, the blood concentration can be reduced through a lower dose and achieve the same therapeutic window with fewer adverse events.

If, for a given blood concentration, the therapeutic effect can be improved for more patients due to better distribution pharmacokinetics, then the slope of the dose response curve for the therapeutic effect achieves a steeper slope, which in turn increases both the potency and efficacy of a drug.

Even with the advent of personalized medicine, clinicians are still administering therapeutic agents with doses that are standardized across all patients, with dosage typically dependent on patient weight or body mass. While the specific combination of agents may be based on, say a patient's tumor genetic profile, the dosage of each agent is generally not personalized to a particular patient. There is a need to change the paradigm of treatment instead to a specific patient, rather than relying on standard formulas that may or may not apply to an individual patient. For example, if it has been previously determined that a certain level of a therapeutic delivered to a target (e.g., tumor) has a clinical effect, then a major goal should be to deliver the required amount, versus delivering a maximum tolerated dose. This should be an improvement to current treatments, as administering a large amount results in much of the therapeutic agent being delivered off-target and presenting unintended effects.

There is a further need to provide a means to protect certain therapeutics while in circulation from degradation or from an immune response, to actively target the delivery of therapeutics to improve biodistribution to the target tissue, and to do so in a simple way, e.g., at the time of administration (rather than at the manufacturing stage to obviate the need to change manufacturing processes), all to improve the efficacy or the safety (or both) profile of therapeutic treatments.

There is also a further need to account for conditions where a patient has biological characteristics that may impede or inhibit effective treatment of a standard dose of a therapeutic. A major goal should be to adjust for the biological characteristics to allow for effective treatment rather than continuing to administer a dose based on, say just a patient's weight, body mass or surface area.

SUMMARY OF THE INVENTION

The present invention provides compositions comprising a plurality of carriers, e.g., microbubbles, wherein an at least one active agent is associated with the plurality of carriers, for example, encapsulated within the plurality of carriers (e.g., between the gas/shell interface and/or within the gas of the carriers), and/or bound to the surface (e.g., the exterior or interior surface, of the carriers) for delivery to a subject. In addition, the present invention provides compositions comprising a plurality of carriers, e.g., microbubbles, to be co-administered with compositions comprising at least one active agent to a subject. Furthermore, the present invention provides compositions comprising a plurality of carriers, e.g., microbubbles, wherein at least one active agent is associated with the plurality of carriers, for example, encapsulated within the plurality of carriers (e.g., between the gas/shell interface and/or within the gas of the carriers), and/or bound to the surface (e.g., the exterior or interior surface, of the carriers), to be co-administered with compositions comprising at least one free active agent, e.g., at least one active agent that is not associated with the plurality of carriers, to a subject.

The present invention also provides methods of treating a disease or condition, for example, cancer, and methods of targeted delivery of an active agent to, e.g., a target tissue, such as an organ, a tissue, or a tumor site, in a subject, using the carrier based compositions of the invention. The present invention further provides devices and methods for preparing the compositions of the present invention. In particular, the inventors of the present invention have surprisingly discovered that by associating or co-administering the active agent with the carriers, e.g., microbubbles, the level of the active agent required to achieve a therapeutic effect is substantially lower than the level of the active agent required to achieve a therapeutic effect when administered without being associated or co-administered with carriers such as microbubbles, e.g., by systemic administration without being associated or co-administered with carriers.

Accordingly, in one aspect, the present invention provides, a composition comprising a plurality of carriers, wherein at least one active agent is associated with the plurality of carriers for delivery to a subject, wherein the level of the at least one active agent associated with the plurality of carriers is lower than the level of the active agent required to achieve a therapeutic effect when administered without being associated with carriers.

In some embodiments, the level of the at least one active agent associated with the plurality of carriers is lower than the level of the active agent required to achieve a therapeutic effect when administered without being associated with carriers and by systemic administration.

In some embodiments, wherein the level of the at least one active agent associated with the plurality of carriers is lower than the level of the active agent required to achieve a substantially equivalent therapeutic effect when administered without being associated with carriers.

In some embodiments, the substantially equivalent therapeutic effect is about 50%, about 60%, about 70%, about 75%, about 80%, about 85%, about 90%, about 91%, about 92%, about 93%, about 94%, about 95%, about 96%, about 97%, about 98%, about 99% or about 100% of the therapeutic effect of the active agent when administered without being associated with carriers.

In some embodiments, wherein the carrier comprises a shell and a core.

In some embodiments, (i) the shell comprises a lipid, a polymer, a lipopolymer, a protein, or combination thereof; and/or (ii) the core comprises a gas.

In some embodiments, the lipid is selected from the group consisting of 1,2-dimyristoyl-sn-glycero-3-phosphocholine (DMPC), 4-dimethylaminochalcone (DMAC), dipalmitoylphosphatidylcholine (DPPC), 1,2-distearyol-sn-glycero-3-phosphocoline (DSPC), and 1,2-distearyol-sn-glycero-3-phosphoethanolamine-N-[methoxy(polyethylene glycol) 2000] (DSPE-PEG2000).

In some embodiments, the lipid is DMPC.

In some embodiments, the core comprises nitrogen, air, a perfluorocarbon gas, or combination thereof.

In some embodiments, the perfluorocarbon gas is selected from the group consisting of perfluorohexane, sulfur hexafluoride, perfluoromethane, perfluoroethane, perfluoropropane, perfluorobutane, and perfluoropentane.

In some embodiments, the perfluorocarbon gas is perfluorohexane.

In some embodiments, the core comprises a combination of perfluorohexane and nitrogen gas.

In one aspect, the present invention provides a composition comprising a plurality of carriers, wherein at least one active agent is associated with the plurality of carriers for delivery to a subject, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof.

In some embodiments, the level of the at least one active agent associated with the plurality of carriers is lower than the level of the active agent required to achieve a therapeutic effect when administered without being associated with carriers.

In some embodiments, the level of the at least one active agent associated with the plurality of carriers is lower than the level of the active agent required to achieve a therapeutic effect when administered without being associated with carriers and by systemic administration.

In some embodiments, the level of the at least one active agent associated with the plurality of carriers is lower than the level of the active agent required to achieve a substantially equivalent therapeutic effect when administered without being associated with carriers.

In some embodiments, the substantially equivalent therapeutic effect is about 50%, about 60%, about 70%, about 75%, about 80%, about 85%, about 90%, about 91%, about 92%, about 93%, about 94%, about 95%, about 96%, about 97%, about 98%, about 99% or about 100% of the therapeutic effect of the active agent when administered without being associated with carriers.

In some embodiments, the at least one active agent is associated with the plurality of carriers by being encapsulated within the plurality of carriers.

In some embodiments, the at least one active agent is associated with the plurality of carriers by binding to the interior or exterior surface of the plurality of carriers.

In some embodiments, the level of the at least one active agent associated with the plurality of carriers is about 0.001% to about 99%, about 0.001% to about 75%, about 0.001% to about 50%, about 0.005% to about 50%, about 0.005% to about 25%, or about 0.0001% to about 25% of the level of the active agent required to achieve a therapeutic effect, optionally, a substantially equivalent therapeutic effect, when administered without being associated with carriers.

In some embodiments, the level of the at least one active agent associated with the plurality of carriers is about 0.001% to about 0.005%, about 0.005% to about 0.1%, about 0.005% to about 10%, about 0.005% to about 20%, about 10% to about 50%, or about 50% to about 99% of the level of the active agent required to achieve a therapeutic effect, optionally a substantially equivalent therapeutic effect, when administered without being associated with carriers.

In some embodiments, the level of the active agent associated with the plurality of carriers is about 0.0001%, 0.001%, 0.005%, 0.01%, 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or about 99% of the level of the active agent required to achieve a therapeutic effect when administered without being associated with carriers, optionally, by systemic administration without being associated with carriers.

In some embodiments, administration of the composition results in a reduced systemic toxicity, as compared to administration of a composition of the same level of active agent without being associated with carriers.

In some embodiments, administration of the composition results in a reduced systemic toxicity, as compared to administration of a composition of the active agent without being associated with carriers required to achieve a substantially equivalent therapeutic effect.

In some embodiments, the level of the at least one active agent associated with the plurality of carriers elicits an immunostimulatory effect.

In some embodiments, the level of the at least one active agent associated with the plurality of carriers does not elicit an immunosuppressive effect.

In some embodiments, the at least one active agent is selected from the group consisting of a protein, an antibody, a small molecule, a virus, an antibiotic, a radionuclide, a peptide, a nucleic acid, a gene, a vector or a plasmid encoding a gene, and a component of a gene editing system.

In some embodiments, the at least one active agent comprises a cytokine, and/or a vector or plasmid encoding a gene encoding the cytokine.

In some embodiments, the cytokine is selected from a group consisting of IL-2, IL-7, IL-10, IL-12, IL-15, IL-18, IL-21, IL-23, IL-27, interferon, GM-CSF and TNF-alpha.

In some embodiments, the cytokine is IL-2.

In some embodiments, the level of IL-2 associated with the plurality of carriers is about 0.01 pg/mL to about 10 pg/mL, about 10 pg/mL to about 100 pg/mL, about 100 pg/mL to about 100 μg/mL, about 100 pg/mL to about 100 ng/mL, about 100 ng/mL to about 1 μg/mL, about 1 μg/ml to about 10 μg/mL, about 10 μg/mL to about 100 μg/mL, about 200 ng/mL to about 500 ng/mL, about 500 ng/mL to about 2 μg/mL, or about 2 μg/mL to about 5 μg/mL.

In some embodiments, the at least one active agent comprises a monoclonal antibody, and/or a vector or plasmid comprising a gene encoding the monoclonal antibody.

In some embodiments, the monoclonal antibody is selected from the group consisting of bevacizumab, pembrolizumab, nivolumab, cemiplimab, durvalumab, atezolizumab, avelumab, ipilimumab, rituximab, cetuximab and trastuzumab.

In some embodiments, the monoclonal antibody is bevacizumab.

In some embodiments, the level of bevacizumab associated with the plurality of carriers is about 0.01 pg/mL to about 10 pg/mL, about 1 pg/mL to about 25 mg/mL, about 1 ng/mL to about 25 mg/mL, about 1 μg/mL to about 25 mg/mL, about 1 pg/mL to about 100 pg/mL, about 100 pg/mL to about 500 pg/mL, about 500 pg/mL to about 1 ng/mL, about 1 ng/mL to about 100 ng/mL, about 100 ng/mL to about 500 ng/mL, about 500 ng/mL to about 1 μg/mL, about 1 μg/mL to about 100 μg/mL, about 100 μg/mL to about 500 μg/mL, about 500 μg/mL to about 1 mg/mL, about 1 mg/mL to about 5 mg/mL, about 5 mg/mL to about 10 mg/mL, about 10 mg/mL to about 25 mg/mL, about 100 μg/mL to about 250 μg/mL, about 250 μg/mL to about 2.5 mg/mL, or about 2.5 mg/mL to about 10 mg/mL.

In some embodiments, the monoclonal antibody is pembrolizumab.

In some embodiments, the level of pembrolizumab associated with the plurality of carriers is about 0.01 pg/mL to about 10 pg/mL, about 1 pg/mL to about 25 mg/mL, about 1 ng/mL to about 25 mg/mL, about 1 μg/mL to about 25 mg/mL, about 1 pg/mL to about 100 pg/mL, about 100 pg/mL to about 500 pg/mL, about 500 pg/mL to about 1 ng/mL, about 1 ng/mL to about 100 ng/mL, about 100 ng/mL to about 500 ng/mL, about 500 ng/mL to about 1 μg/mL, about 1 μg/mL to about 100 μg/mL, about 100 μg/mL to about 500 μg/mL, about 500 μg/mL to about 1 mg/mL, about 1 mg/mL to about 5 mg/mL, about 5 mg/mL to about 10 mg/mL, about 10 mg/mL to about 25 mg/mL, about 100 μg/mL to about 250 μg/mL, about 250 μg/mL to about 2.5 mg/mL, or about 2.5 mg/mL to about 10 mg/mL.

In some embodiments, the at least one active agent comprises one or more components of a gene editing system.

In some embodiments, the at least one active agent comprises one or more components of a CRISPR system.

In some embodiments, the at least one active agent comprises a cDNA and/or mRNA encoding a Cas9 protein, a guide RNA, and/or a ribonucleoprotein (RNP) complex.

In some embodiments, the composition comprises a virus that is an oncolytic virus, for example, wherein the oncolytic virus is encapsulated within the carrier.

In some embodiments, the oncolytic virus is selected from the group consisting of adenovirus, adeno-associated virus, herpes virus, poliovirus, measles virus, polioviruses, poxvirus, Newcastle disease virus, reovirus, coxsackievirus, vesicular stomatitis virus, Zika virus, RNA virus, and DNA virus.

In some embodiments, the composition comprises a viral vector comprising a gene encoding the active agent.

In some embodiments, the carrier is selected from the group consisting of a microbubble, a nanobubble, a nanoparticle, a nanodroplet, a micelle, a liposome, an exosome, a cell, and a virus.

In some embodiments, the carrier is a microbubble, optionally selected from the group consisting of Levovist™, Imagent®, Optison®, Sonazoid®, BR38, and SonoVue®.

In some embodiments, wherein the composition, or the preparation thereof, is free of an inactivation agent for the active agent.

In some embodiments, the composition, or the preparation thereof, is free of a viral inactivating agent.

In some embodiments, wherein the composition is free of a binding agent or a binding ligand.

In a particular embodiment, the present invention provides a composition comprising a conjugation, covalently or non-covalently, of an active agent and a carrier formulated from a combination of a lipid (e.g., 9.2 mg DMPC), a starch (e.g., 75 mg hydroxyethyl starch), a poloxamer (e.g., 2.1 mg poloxamer 288), sodium chloride (e.g., 75 mg), buffer (e.g., 36 mg sodium phosphate), at least one gas (e.g., 17% v/v perflexane vapor in nitrogen). In a preferred embodiment, the agent is a nucleic acid. DMPC, as a zwitterionic lipid (rather than a cationic lipid) with a net neutral charge, has a headgroup containing a positively charged choline group and negatively charged phosphate group.

In various embodiments of the foregoing aspects of the invention, the compositions further comprise free lipids. The free lipids may comprise at least 60%, 65%, 70%, 75%, 80%, 85%, 90% or 95% of the total lipid content in the composition. In a particular embodiment, the free lipids are in a high energy state before reconstitution of the carrier. "High energy" state of lipids can refer to a state in which the bonds of the lipids have been broken by high velocity, high temperature spray drying. Upon reconstitution in an aqueous diluent, the high energy state lipids immediately (in milliseconds) form lower energy structures such as sheets, rods and liposomes so that their hydrophobic tails are not exposed to water molecules.

Accordingly, in certain embodiments, the free lipids form a second plurality of carriers upon exposure to an aqueous solution. The second plurality of carriers may include a liposome, a lipid rod, a lipid disc and/or a lipid sheet. In a particular embodiment, the free lipids form a unilamellar liposome. In another embodiment, the free lipids form a multilamellar liposome. In certain embodiments the at least one active agent is encapsulated in, bound to, associated with or interacted with the second plurality of carriers.

In a further embodiment, the first plurality of carriers comprises microbubbles, for example, comprising (i) a shell comprising a lipid, a polymer, a lipopolymer, a protein, or combination thereof; and/or (ii) a core comprising a gas. In a particular embodiment, the shell comprises a lipid, and wherein the lipid is DMPC; and the core comprises at least one of perfluorohexane and nitrogen gas. In a particular embodiment, the plurality of free lipids comprises DMPC.

In another aspect, the present invention provides a composition wherein the carriers form fragments within the body upon inertial cavitation of the carrier. For example, the carrier is formed of a shell, e.g., at least one lipid, and a gas core, e.g., a perfluorohexane or perfluorocarbon gas with or without nitrogen, and upon inertial cavitation, breaks into fragments within the body. The active agent may be associated with or bound to the carriers prior to administration of the composition, or may bind or associate with the fragments of the carriers in vivo upon inertial cavitation. In various embodiments, (i) the shell may comprise (but is not limited to) at least one lipid comprising 1,2-dimyristoyl-sn-glycero-3-phosphocholine (DMPC), and the core may comprise a perfluorohexane gas with or without nitrogen or other gases; or (ii) the shell may comprise a lipid comprising 1,2-dimyristoyl-sn-glycero-3-phosphocholine (DMPC), and the core may comprise a gas comprising a perfluorocarbon gas, with or without nitrogen or other gases.

In this aspect, the compositions are a prodrug where active agent is encapsulated in a carrier, such that upon administration, a micrometer scale drug/carrier complex is converted to a nanometer scale drug suitable for lipid fusion, lipid mediated poration, or receptor-mediated endocytosis for release of the agent into the cytosol or nucleus of a targeted cell. Alternatively, the composition is a prodrug where administration of a carrier and a co-administered agent (i.e., unencapsulated) results in a micrometer scale carrier (e.g., microbubble) converted into nanometer scale particles (for example, as a result of inertial cavitation) which are subsequently complexed with the agent in vivo whether by affinity or self-assembly. The resulting nanoscale carrier/drug complex (e.g., microbubble fragment/agent complex) associates with the cellular membrane enabling the release or endocytosis of the agent into the cell. The effect of vascular permeabilization due to sonoporation during the micrometer scale (microbubble phase) combined with the creation of nanometer scale particles (post-inertial cavitation phase) complexed with at least one agent allows for increased local concentration of nanoscale lipid particles at the target tissue (including cells).

Alternatively in another aspect, the composition comprises (i) a plurality of carriers, e.g., microbubbles, wherein at least one active agent is associated with the plurality of carriers for delivery to a subject, and (ii) a plurality of free lipids (such as a free lipid in solution or a free lipid suspension of other structures). Active agent may be encapsulated within, bound to, associated with or interacted with the free lipids in the composition prior to administration and/or in vivo. In a particular embodiment, upon exposure to an aqueous solution, the free lipids may form a second plurality of carriers, to which the active agent may be encapsulated, bound to, associated with or interacted with. In one embodiment, the first plurality of carriers comprises microbubbles, for example, formed of a shell comprising a lipid, a polymer, a protein or combination thereof; and a core comprising a gas. In an exemplary embodiment, the shell is formed of the lipid DMPC and the core comprises at least one of a perfluorohexane and nitrogen gas. Alternatively or in combination, the free lipids are DMPC. The association of the active agent with the free lipids similarly serves as nanometer scale drug complexes enhancing the release or endocytosis of the agent into the cell, as described above.

In some embodiments, the level of active agent associated with the plurality of nanometer scale particle carriers/free lipids/fragments created after inertial cavitation (or from free lipids) is about 0.001 pg/mL to about 10 pg/mL, about 1 pg/mL to about 25 mg/mL, about 1 ng/mL to about 25 mg/mL, about 1 μg/mL to about 25 mg/mL, about 1 pg/mL to about 100 pg/mL, about 100 pg/mL to about 500 pg/mL, about 500 pg/mL to about 1 ng/mL, about 1 ng/mL to about 100 ng/mL, about 100 ng/mL to about 500 ng/mL, about 500 ng/mL to about 1 μg/mL, about 1 μg/mL to about 100 μg/mL, about 100 μg/mL to about 500 μg/mL, about 500 μg/mL to about 1 mg/mL, about 1 mg/mL to about 5 mg/mL, about 5 mg/mL to about 10 mg/mL, about 10 mg/mL to about 25 mg/mL, about 100 μg/mL to about 250 μg/mL, about 250 μg/mL to about 2.5 mg/mL, or about 2.5 mg/mL to about 10 mg/mL, as measured in target tissue by biopsy.

In some embodiments, the nanometer scale particles with an agent associated therewith formed are unilamellar complexes. In some embodiments, the nanometer scale particles with an agent associated therewith formed are multilamellar complexes. In a preferred embodiment, the particles are composed of at least one lipid. The lipid may be cationic, zwitterionic or anionic. The lipid may be a combination of at least two lipids, including but not limited to, a cationic lipid and a zwitterionic lipid. In the case where the active agent is a nucleic acid, for example DNA, mRNA, or ribonucleoprotein (RNP), the created nanometer scale particle may be a hexagonal structure with lipid elongated micelles arranged on a hexagonal lattice and DNA rods arranged on a honeycomb lattice in the interstices between the lipid micelles. The particle may be a lamellar structure with alternating lipid layers and DNA monolayers between the lipid layers. Alternatively, the particle may resemble an inverted hexagonal structure with lipid inverted micelles coating the DNA arranged on a hexagonal lattice (Gaspar 2020).

One advantage of the present invention is the extension of time in which the agent may be in circulation or present with the target (e.g., cell). In the case of a gas-filled microbubble carrier, the time in circulation for the microbubble is typically measured in minutes as eventually the gas core is diffused out, or when inertial cavitation is induced the gas is released instantaneously. In the present invention, the nanometer scale particles no longer contain gas thereby enabling the particles to remain in circulation beyond the typical time period of the original microbubbles. Furthermore, when the particle (along with its associated agent) reaches its target cell and binds with the cell membrane, at least one molecule of the associated agent may be released into the cytoplasm or nucleus. Upon particle fusion with the cellular membrane, cytosol enzymes may interact to release the active agent while avoiding endosomal or lysosomal elimination or degradation.

Another advantage of a preferred embodiment of the present invention is its principal constituent of 1,2-dimyristoyl-sn-glycero-3-phosphocholine (DMPC). DMPC is a zwitterionic lipid and is a chemical synthesis of phosphatidylcholine (PC). PC is present on the outer leaflet of all mammalian cell and intracellular membranes, compared to phosphatidylethanolamine or phosphatidylserine, which are present on the inner membrane leaflet. Accordingly, in embodiments of the present invention in which the carrier is formed of a PC, e.g., DMPC, or embodiments where the composition includes free PC lipids, e.g., DMPC, uptake of active agent across the cell membrane may be enhanced. Specifically, the use of DMPC may result in fusion of the DMPC lipid with the cell membrane to enable the agent to enter the cytosol or nucleus.

Another embodiment of the present invention includes the association of a DMPC lipid carrier with a conjugated cationic lipid and agent, and the resultant nanometer scale fragment comprised of DMPC/cationic lipid/agent created by inertial cavitation. Such a nanometer scale DMPC/cationic lipid/agent complex fragments migrate out of the vasculature to interact with the target tissue or cell, either through pores created by sonoporation or leaky vasculature.

In one aspect, the present invention provides a method of treating a disease or condition in a subject, the method comprising administering to the subject a composition comprising at least one active agent associated with a plurality of carriers, wherein the level of the at least one active agent associated with the plurality of carriers is lower than the level of the active agent required to achieve a therapeutic effect when administered without being associated with carriers, and applying an ultrasound energy to the subject, thereby treating the disease or condition in the subject.

In another aspect, the present invention provides a method of treating a disease or condition in a subject, the method comprising administering to the subject a composition comprising at least one active agent associated with a plurality of carriers, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof; and applying an ultrasound energy to the subject, thereby treating the disease or condition in the subject.

In another aspect, the present invention provides a method for treating a disease by administering a composition as described herein, wherein the carriers form fragments within the body upon inertial cavitation of the carrier. For example, the carrier is formed of a shell, e.g., at least one lipid, and a gas core, e.g., a perfluorohexane or perfluorocarbon gas with or without nitrogen, and upon inertial cavitation, breaks into fragments within the body. The active agent may be bound to, associated with or interacted with the fragments prior to administration of the composition, and/or may bind to, associate with or interacted with the fragments of the carriers in vivo upon inertial cavitation. In various embodiments, (i) the shell may comprise (but is not limited to) at least one lipid comprising 1,2-dimyristoyl-sn-glycero-3-phosphocholine (DMPC), and the core may comprise a perfluorohexane gas with or without nitrogen or other gases; or (ii) the shell may comprise a lipid comprising 1,2-dimyristoyl-sn-glycero-3-phosphocholine (DMPC), and the core may comprise a gas comprising a perfluorocarbon gas, with or without nitrogen or other gases.

In this aspect of the methods for treatment of a disease, the compositions are a prodrug where active agent is encapsulated in a carrier, such that upon administration, a micrometer scale drug/carrier complex is converted to a nanometer scale drug suitable for lipid fusion, lipid mediated poration, or receptor-mediated endocytosis for release of the agent into the cytosol or nucleus of a targeted cell. Alternatively, the composition is a prodrug where administration of a carrier and a co-administered agent (i.e., unencapsulated) results in a micrometer scale carrier (e.g., microbubble) converted into nanometer scale particles (for example, as a result of inertial cavitation) which are subsequently complexed with the active agent in vivo whether by affinity or self-assembly. The resulting nanoscale carrier/drug complex (e.g., microbubble fragment/agent complex) associates with the cellular membrane enabling the release or endocytosis of the active agent into the cell. The effect of vascular permeabilization due to sonoporation during the micrometer scale carrier (microbubble phase) combined with the creation of nanometer scale particles (upon inertial cavitation) complexed with at least one agent allows for increased local concentration of nanoscale lipid particles at the target tissue (including cells).

Alternatively, in another aspect, methods of treating a disease are providing, the method comprising administering a composition comprises (i) a plurality of carriers, e.g., microbubbles, wherein at least one active agent is associated with the plurality of carriers for delivery to a subject, and (ii) a plurality of free lipids (such as a free lipid in solution or a free lipid suspension of other structures). Active agent may be encapsulated within, bound to associated with or interacted with the free lipids in the composition prior to administration and/or in vivo. In a particular embodiment, upon exposure to an aqueous solution, the free lipids may form a second plurality of carriers, to which the active agent may be encapsulated, bound to, associated with or interacted with. In one embodiment of the method, the first plurality of carriers comprises microbubbles, for example, formed of a shell comprising a lipid, a polymer, a protein or combination thereof; and a core comprising a gas. In an exemplary embodiment, the shell is formed of the lipid DMPC and the core comprises at least one of a perfluorohexane and nitrogen gas. Alternatively or in combination, the free lipids are DMPC. The association of the active agent with the free lipids similarly serves as nanometer scale drug complexes enhancing the release or endocytosis of the agent into the cell, as described above. The effect of vascular permeabilization due to sonoporation during the micrometer scale (microbubble phase) carriers combined with (a) the creation of nanometer scale particles of such micrometer scale carriers (upon inertial cavitation) complexed with at least one agent, and (b) the co-administration of nanometer scale particles (e.g., from the free lipids) complexed with at least one agent allow for increased local concentration of nanoscale lipid particles at the target tissue (including cells).

In one aspect, the present invention provides a method of reducing tumor growth in a subject, the method comprising administering to the subject a composition comprising at least one active agent associated with a plurality of carriers, wherein the level of the at least one active agent associated with the plurality of carriers is lower than the level of the active agent required to achieve a therapeutic effect when administered without being associated with carriers, and applying an ultrasound energy to the subject, thereby reducing tumor growth in the subject.

In another aspect, the present invention provides a method of reducing tumor growth in a subject, the method comprising administering to the subject a composition comprising at least one active agent associated with a plurality of carriers, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof; and applying an ultrasound energy to the subject, thereby reducing tumor growth in the subject.

In one aspect, the present invention provides a method of delivering an active agent to a target site in a subject, the method comprising administering to the subject a composition comprising at least one active agent associated with a plurality of carriers, wherein the level of the at least one active agent associated with the plurality of carriers is lower than the level of the active agent required to achieve a therapeutic effect when administered without being associated with carriers, and applying an ultrasound energy at the target site in the subject, thereby delivering the active agent to the target site in the subject.

In another aspect, the present invention provides a method of delivering an active agent to a target site in a subject, the method comprising administering to the subject a composition comprising at least one active agent associated with a plurality of carriers, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof; and applying an ultrasound energy at the target site in the subject, thereby delivering the active agent to the target site in the subject.

The target site is an organ, a tissue, or a tumor site in the subject.

In some embodiments, the methods further comprise administering to the subject a composition comprising at least one free active agent, i.e., an active agent that will not be associated or encapsulated within a carrier, e.g., a microbubble.

In one aspect, the present invention provides a method of treating a disease or condition in a subject, the method comprising administering to the subject a first composition comprising a plurality of carriers, administering to the subject a second composition comprising at least one active agent, wherein the level of the at least one active agent co-administered with the plurality of carriers is lower than the level of the active agent required to achieve a therapeutic effect when administered without being co-administered with carriers, and applying an ultrasound energy to the subject, thereby treating the disease or condition in the subject.

In one aspect, the present invention provides a method of treating a disease or condition in a subject, the method comprising administering to the subject a first composition comprising a plurality of carriers, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof; administering to the subject a second composition comprising at least one active agent, and applying an ultrasound energy to the subject, thereby treating the disease or condition in the subject.

In one aspect, the present invention provides a method of reducing tumor growth in a subject, the method comprising administering to the subject a first composition comprising a plurality of carriers, administering to the subject a second composition comprising at least one free active agent, wherein the level of the at least one active agent co-administered with the plurality of carriers is lower than the level of the active agent required to achieve a therapeutic effect when administered without being co-administered with carriers, and applying an ultrasound energy to the subject, thereby reducing tumor growth in the subject.

In one aspect, the present invention provides a method of reducing tumor growth in a subject, the method comprising administering to the subject a first composition comprising a plurality of carriers, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof; administering to the subject a second composition comprising at least one active agent, and applying an ultrasound energy to the subject, thereby reducing tumor growth in the subject.

In one aspect, the present invention provides a method of delivering an active agent to a target site in a subject, the method comprising administering to the subject a first composition comprising a plurality of carriers, administering to the subject a second composition comprising at least one active agent, wherein the level of the at least one active agent co-administered with the plurality of carriers is lower than the level of the active agent required to achieve a therapeutic effect when administered without being co-administered with carriers, and applying an ultrasound energy at the target site in the subject, thereby delivering the active agent to the tumor site in the subject.

In one aspect, the present invention provides a method of delivering an active agent to a target site in a subject, the method comprising administering to the subject a first composition comprising a plurality of carriers, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof; administering to the subject a second composition comprising at least one active agent, and applying an ultrasound energy to the subject, thereby delivering an active agent to a target site in the subject.

In some embodiments, the target site is an organ, a tissue or a tumor site in the subject.

In some embodiments, the level of the at least one active agent co-administered with the plurality of carriers is lower than the level of the active agent required to achieve a therapeutic effect when administered without being co-administered with carriers.

In some embodiments, the level of the at least one active agent associated with the plurality of carriers is lower than the level of the active agent required to achieve a therapeutic effect when administered without being associated with carriers by systemic administration.

In some embodiments, the level of the at least one active agent associated with the plurality of carriers is lower than the level of the active agent required to achieve a substantially equivalent therapeutic effect when administered without being associated with carriers.

In some embodiments, the substantially equivalent therapeutic effect is about 50%, about 60%, about 70%, about 75%, about 80%, about 85%, about 90%, about 91%, about 92%, about 93%, about 94%, about 95%, about 96%, about 97%, about 98%, about 99% or about 100% of the therapeutic effect of the active agent when administered without being associated with carriers.

In some embodiments, applying the ultrasound energy induces cavitation of the carriers and/or enhances delivery of the active agent within the subject.

In some embodiments, the level of the at least one active agent associated or co-administered with the plurality of carriers is about 0.001% to about 99%, about 0.001% to about 75%, about 0.001% to about 50%, or about 0.001% to about 25% of the level of the active agent required to achieve a therapeutic effect, optionally, a substantially equivalent therapeutic effect, when administered without being associated or co-administered with carriers.

In some embodiments, the level of the at least one active agent associated with or co-administered with the plurality of carriers is about 0.001% to about 0.1%, about 0.1% to about 10%, about 0.1% to about 20%, about 10% to about 50%, or about 50% to about 99% of the level of the active agent required to achieve a therapeutic effect, optionally a substantially equivalent therapeutic effect, when administered without being associated or co-administered with carriers.

In some embodiments, the level of the active agent associated with the plurality of carriers is about 0.001%, 0.005%, 0.01%, 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or about 99% of the level of the active agent required to achieve a therapeutic effect when administered without being associated or co-administered with carriers, optionally, by systemic administration without being associated with carriers.

In some embodiments, administration of the composition results in a reduced systemic toxicity, as compared to administration of a composition of the same level of active agent without being associated with carriers.

In some embodiments, administration of the composition results in a reduced systemic toxicity, as compared to administration of a composition of the active agent without being associated with carriers required to achieve a substantially equivalent therapeutic effect.

In some embodiments, the level of the at least one active agent associated or co-administered with the plurality of carriers elicits an immunostimulatory effect.

In some embodiments, the level of the at least one active agent associated or co-administered with the plurality of carriers does not elicit an immunosuppressive effect.

In some embodiments, the at least one active agent is selected from the group consisting of a protein, an antibody, a small molecule, a virus, an antibiotic, a radionuclide, a peptide, a nucleic acid, a gene, a vector or a plasmid encoding a gene, and a component of a gene editing system.

In some embodiments, the at least one active agent comprises a cytokine, and/or a vector or plasmid encoding a gene encoding the cytokine.

In some embodiments, the cytokine is selected from a group consisting of IL-2, IL-7, IL-10, IL-12, IL-15, IL-18, IL-21, IL-23, IL-27, interferon, GM-CSF and TNF-alpha.

In some embodiments, the cytokine is IL-2.

In some embodiments, the level of IL-2 associated with the plurality of carriers is about 0.01 pg/mL to about 10 pg/mL, about 10 pg/mL to about 100 pg/mL, about 100 pg/mL to about 100 ug/mL, about 100 pg/mL to about 100 ng/mL, about 100 ng/mL to about 1 μg/mL, about 1 μg/ml to about 10 μg/mL, about 10 μg/mL to about 100 μg/mL, about 200 ng/mL to about 500 ng/mL, about 500 ng/mL to about 2 μg/mL, or about 2 μg/mL to about 5 μg/mL.

In some embodiments, the at least one active agent comprises a monoclonal antibody, and/or a vector or plasmid comprising a gene encoding the monoclonal antibody.

In some embodiments, the monoclonal antibody is selected from the group consisting of bevacizumab, pembrolizumab, nivolumab, cemiplimab, durvalumab, atezolizumab, avelumab, ipilimumab, rituximab, cetuximab and trastuzumab.

In some embodiments, the monoclonal antibody is bevacizumab.

In some embodiments, the level of bevacizumab associated with the plurality of carriers is about 0.01 pg/mL to about 10 pg/mL, about 1 pg/mL to about 25 mg/mL, about 1 ng/mL to about 25 mg/mL, about 1 μg/mL to about 25 mg/mL, about 1 pg/mL to about 100 pg/mL, about 100 pg/mL to about 500 pg/mL, about 500 pg/mL to about 1 ng/mL, about 1 ng/mL to about 100 ng/mL, about 100 ng/mL to about 500 ng/mL, about 500 ng/mL to about 1 μg/mL, about 1 μg/mL to about 100 μg/mL, about 100 μg/mL to about 500 μg/mL, about 500 μg/mL to about 1 mg/mL, about 1 mg/mL to about 5 mg/mL, about 5 mg/mL to about 10 mg/mL, about 10 mg/mL to about 25 mg/mL, about 100 μg/mL to about 250 μg/mL, about 250 μg/mL to about 2.5 mg/mL, or about 2.5 mg/mL to about 10 mg/mL.

In some embodiments, the monoclonal antibody is pembrolizumab.

In some embodiments, the level of pembrolizumab associated with the plurality of carriers is about 0.01 pg/mL to about 10 pg/mL, about 1 pg/mL to about 25 mg/mL, about 1 ng/mL to about 25 mg/mL, about 1 μg/mL to about 25 mg/mL, about 1 pg/mL to about 100 pg/mL, about 100 pg/mL to about 500 pg/mL, about 500 pg/mL to about 1 ng/mL, about 1 ng/mL to about 100 ng/mL, about 100 ng/mL to about 500 ng/mL, about 500 ng/mL to about 1 μg/mL, about 1 μg/mL to about 100 μg/mL, about 100 μg/mL to about 500 μg/mL, about 500 μg/mL to about 1 mg/mL, about 1 mg/mL to about 5 mg/mL, about 5 mg/mL to about mg/mL, about 10 mg/mL to about 25 mg/mL, about 100 μg/mL to about 250 μg/mL, about 250 μg/mL to about 2.5 mg/mL, or about 2.5 mg/mL to about 10 mg/mL.

In some embodiments, the at least one active agent comprises one or more components of a gene editing system.

In some embodiments, the at least one active agent comprises one or more components of a CRISPR system.

In some embodiments, the at least one active agent comprises a cDNA and/or mRNA encoding a Cas9 protein, a guide RNA, and/or a ribonucleoprotein (RNP) complex.

In some embodiments, the at least one active agent is an oncolytic virus, for example, encapsulated within the carrier. In some embodiments, the oncolytic virus is selected from the group consisting of adenovirus, adeno-associated virus, herpes virus, poliovirus, measles virus, polioviruses, poxvirus, Newcastle disease virus, reovirus, coxsackievirus, vesicular stomatitis virus, Zika virus, RNA virus, and DNA virus.

In some embodiments, the composition comprises a viral vector comprising a gene encoding the active agent.

In some embodiments, the carrier is selected from the group consisting of a microbubble, a nanobubble, a nanoparticle, a nanodroplet, a micelle, a liposome, an exosome, a cell, and a virus.

In some embodiments, the carrier is a microbubble, optionally selected from the group consisting of Levovist™, Imagent®, Optison®, Sonazoid®, BR38, and SonoVue®.

In some embodiments, the disease or condition is a non-cancer disease or condition.

In some embodiments, the disease or condition is cancer.

In some embodiments, the cancer is selected from a group consisting of pancreatic cancer, liver cancer, colorectal cancer, renal cancer, bladder cancer, prostate cancer, ovarian cancer, breast cancer and brain cancer.

In some embodiments, the method further comprises administering an additional therapeutic agent.

In some embodiments, the additional agent is an anti-PD-1 agent, anti-PD-L1 agent, or an anti-CTLA-4 agent.

In various embodiments of the foregoing methods of the invention, the compositions further comprise free lipids. The free lipids may comprise at least 60%, 65%, 70%, 75%, 80%, 85%, 90% or 95% of the total lipid content in the composition. In a particular embodiment, the free lipids are in a high energy state before reconstitution of the carrier. In certain embodiments, the free lipids form a second plurality of carriers upon exposure to an aqueous solution. The second plurality of carriers may include a liposome, a lipid rod, a lipid disc a lipid sheet and a combination thereof. In a particular embodiment, the free lipids form a unilamellar liposome. In another embodiment, the free lipids form a multilamellar liposome. In certain embodiments, the at least one active agent is encapsulated in, bound to, associated with or interacted with the second plurality of carriers.

In a further embodiment of the foregoing methods, the first plurality of carriers comprises microbubbles, for example, comprising (i) a shell comprising a lipid, a polymer, a lipopolymer, a protein, or combination thereof; and/or (ii) a core comprising a gas. In a particular embodiment, the shell comprises a lipid, and wherein the lipid is DMPC; and the core comprises at least one of perfluorohexane and nitrogen gas. In a particular embodiment, the plurality of free lipids comprises DMPC.

In one aspect, the present invention provides a method for reducing systemic toxicity of an active agent upon administration into a subject, the method comprising providing a composition comprising a plurality of carriers, associating the active agent with the plurality of carriers, administering the plurality of carriers associated with the active agent to the subject, and applying an ultrasound energy to the subject, thereby reducing the systemic toxicity of the active agent.

In one aspect, the present invention provides a method for reducing innate immune response against an active agent upon administration into a subject, the method comprising providing a composition comprising a plurality of carriers, associating the active agent with the plurality of carriers, administering the plurality of carriers associated with the active agent to the subject, and applying an ultrasound energy to the subject, thereby reducing the innate immune response against the active agent.

In one aspect, the present invention provides a method for reducing systemic toxicity of an active agent upon administration into a subject, the method comprising administering to the subject a first composition comprising a plurality of carriers, administering to the subject a second composition comprising the active agent, and applying an ultrasound energy to the subject, thereby reducing the systemic toxicity of the active agent.

In one aspect, the present invention provides a method for reducing innate immune response against an active agent upon administration into a subject, the method comprising administering to the subject a first composition comprising a plurality of carriers, administering to the subject a second composition comprising the active agent, and applying an ultrasound energy to the subject, thereby reducing the innate immune response against the active agent.

In some embodiments, the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof.

In some embodiments, associating the active agent with the plurality of carriers comprises encapsulating the active agent within the plurality of carriers.

In some embodiments, associating the active agent with the plurality of carriers comprises binding the active agent to the interior or exterior surface of the plurality of carriers.

In one aspect, the present invention provides a method of preparing a carrier-active agent complex, the method comprising reconstituting the carrier in a first solution, reconstituting the active agent in an at least second solution, and mixing the active agent in the first solution with the carrier in the second solution to create a carrier-active agent complex in a carrier-active agent complex solution, thereby preparing the carrier-active agent complex.

In one aspect, the present invention provides a method of preparing a carrier-active agent complex, the method comprising reconstituting the carrier in a solution comprising the active agent to create a carrier-active agent complex, thereby preparing the carrier-active agent complex.

In one aspect, the present invention provides a method of preparing a carrier-active agent complex, the method comprising reconstituting the carrier in a first solution, providing the active agent in a second solution, and mixing the carrier in the first solution with the active agent in the second solution to create a carrier-active agent complex in a carrier-active agent complex solution, thereby preparing the carrier-active agent complex.

In some embodiments, the method further comprises removing the free active agent from the carrier-active agent complex solution after preparation of the carrier-active agent complex.

In some embodiments, the active agent is encapsulated within the carrier to create the carrier-active agent complex.

In some embodiments, the active agent is bound to the interior or exterior surface of the carrier to create the carrier-active agent complex.

In some embodiments, the free active agent is removed from the carrier-active agent complex solution after preparation of the carrier-active agent complex by a separation method selected from a group consisting of centrifugation, flotation, filtration, chromatography, vortexing and precipitation.

In some embodiments, the carrier-active agent complex is prepared without modifying the surface of the carrier.

In some embodiments, the carrier-active agent complex is prepared in the absence of a binding agent.

In some embodiments, the carrier-active agent complex is prepared in the absence of an inactivating agent.

In some embodiments, the carrier is selected from the group consisting of a microbubble, a nanobubble, a nanoparticle, a nanodroplet, a micelle, a liposome, an exosome, a cell, and a virus.

In some embodiments, the carrier is a microbubble, optionally selected from the group consisting of Levovist™, Imagent®, Optison®, Sonazoid®, BR38, and SonoVue®.

In one aspect, the present invention provides a kit comprising (a) a plurality of microbubbles, (b) an active agent, and (c) a device for incubation of the plurality of microbubbles and the active agent.

In some embodiments, the plurality of microbubbles is present in a vial or a syringe in suspension, or in the form of lyophilized powder.

In some embodiments, the lyophilized powder of the plurality of microbubbles are reconstituted in a solution.

In some embodiments, the solution is a sterile water, a saline solution, or a solution comprising an active agent.

In some embodiments, the active agent is present in a vial or a syringe in suspension, or in the form of lyophilized powder.

In some embodiments, the lyophilized powder of the active agent is reconstituted in a solution.

In some embodiments, the solution is a sterile water, a saline solution, or a solution comprising a plurality of microbubbles.

In some embodiments, the device allows for isolation of microbubbles of different sizes.

In some embodiments, the device is an apparatus comprising: a housing having a base portion and an upper portion, the upper portion having a sealable access that allows placement and withdrawal of a fluid filed container; and a motor in the base portion having multiple modes of operation, a first mode operable to impart a first rotational motion to the container to mix two or more components held in the container, and a second mode operable to impart a second rotational motion to the container to generate a vortex therein to separate the first component from the second component.

In one aspect, the present invention provides an apparatus comprising: a housing having a base portion and an upper portion, the upper portion having a sealable access that allows placement and withdrawal of a fluid filed container; and a motor in the base portion having multiple modes of operation, a first mode operable to impart a first rotational motion to the container to mix two or more components held in the container, and a second mode operable to impart a second rotational motion to the container to generate a vortex therein to separate the first component from the second component.

In some embodiments, at least one of the two or more components comprises a plurality of microspheres.

In some embodiments, the plurality of microspheres comprise a plurality of carriers, wherein each of the plurality of carriers comprises a shell and a core.

In some embodiments, the vortex causes the plurality of microspheres to float inwardly away from walls of the container.

In some embodiments, the plurality of microspheres comprises a plurality of buoyant, pressure-sensitive particles, and wherein the liquid vortex causes the plurality of buoyant, pressure-sensitive particles to travel to the walls of the containers and precipitate.

In some embodiments, a spin speed of the motor is greater than 0 and less than 7,580 revolutions per minute (RPM).

In some embodiments, spin time to separate the first component from the second component is greater than 0 and less than 15 minutes.

In some embodiments, the motor is further configured such that the generated vortex is along a vertical axis of the container.

In some embodiments, the container is a syringe.

In some embodiments, the apparatus further comprise a connection collar to support the container, wherein the connection collar connects the container to the motor.

In some embodiments, the apparatus further comprises a holder to hold a second container for incubation and/or mixing, the holder includes a heater to heat a liquid mixture in the second container, and the motor is operable in the first mode to generate waves and/or gentle swirling in the liquid mixture via at least one of a seesaw motion, a back and forth rotating motion, a swing motion, a shaking motion, and a gentle rotation motion.

In some embodiments, the second container is a vial.

In some embodiments, the apparatus further comprises a controller configured to control the motor to switch between modes.

In some embodiments, the second container is placed in a horizontal position.

In one aspect, the present invention describes compositions of matter and methods that affect the therapeutic window of a drug, or combination of at least two drugs. As shown in FIG. 1, the present invention describes a drug (or combination of at least two drugs) that lowers the blood concentration at which a therapeutic effect can be achieved, thus widening the therapeutic window (Circled 1). The present invention allows a user to reduce blood concentration via a lower dose to reduce adverse effects without losing any therapeutic effect (Circled 2), thus providing the same therapeutic window with lower toxicity. By lowering the dose at which a threshold effect can be achieved, the duration of effect is increased which means the time during which a therapeutic agent concentration can be sustained at the target tissue is significantly widened (Circled 3).

In FIG. 2, the present invention enables incrementally higher doses to have more therapeutic effect for more people, thus rotating the top of the curve to the left (Circled 1), thereby increasing efficacy of a therapeutic agent. Also, incrementally lower doses can have increased therapeutic effect for more people, thus rotating the bottom of the curve to the right. The present invention lowers the dose at which for 50% of patients the agent will be effective, which shifts the ED curve left (Circled 2), thus widening the therapeutic index by increasing potency.

The present invention describes novel compositions comprising a plurality of osmotically stabilized, neutral charged, biphasic carriers, e.g., microbubbles, under specific and controllable sonication conditions, that can enable systemically delivery of therapeutic agents to cross targeted tissue barriers to achieve a therapeutic effect, even at doses and plasma concentrations that are at (or below) doses currently approved for clinical use or thought to be effective. The present invention is capable of fundamentally changing the pharmacokinetic profile of a drug and its distribution characteristics, thereby increasing potency and efficacy of drugs, while minimizing toxicity or adverse events.

The present invention includes delivering a clinically relevant level (which may include a microdose) of therapeutics into the target tissue of a body of a living being, gathering data about the therapeutic agent being administered, gathering data about devices used, gathering data about the patient (e.g., biological, physiological, anatomical, chemical, genetic or morphological conditions), and gathering data about events prior to, during or post-treatment, using machine learnings or artificial intelligence to adapt, modify or improve the diagnosis, treatment or theranosis of disease or condition.

The present invention further discloses a method and process of first determining the relevant amount of a therapeutic agent required to be delivered to a target (for example, but not limited to, cell, tumor, tissue, organ, area, volume, location, etc.) that has been previously determined to have a desired therapeutic effect, then delivering such desired therapeutic amount to the target. Distinct from present methods of delivering a dose of a therapeutic agent that is, for example, a maximum tolerated dose (MTD) of which a very small percentage actually reaches the intended target, the present invention administers the therapeutic level needed and delivers a significant amount to the target.

Furthermore, the present invention consists of novel therapeutic compositions, combinations, conjugates, or complexes that can be mixed onsite just prior to administration and are delivered in clinically relevant levels into the target tissue of a body of a living being. Such inventions may include therapeutics that are co-administered or encapsulated into a drug delivery vehicle (which may be, but not limited to, a microbubble, nanoparticle, nanodroplet, micelle, liposome, exosome, cell, virus, or other carrier). The invention discloses compositions that include therapeutic agents of various sizes, types, classes, or properties.

The present invention provides methods of combining two or more drugs at the time of administration (of which one may be a microbubble), the combination of which results in improved efficacy or biodistribution to a target compared to the administration of each drug alone. The present invention discloses various methods of encapsulation or binding of therapeutic agents into or onto a drug delivery vehicle at the time of administration as well as various methods of administering such compositions, combinations, conjugates, or complexes to improve a therapeutic agent's efficacy or safety profile.

Additionally, the present invention includes the use of devices, equipment, therapeutic complexes, software, and analytical tools, to improve the diagnosis, therapy or theranosis of disease or conditions. Such devices, equipment, therapeutic complexes, software, and analytical tools may be currently commercially available, added to those commercially available, or may be proprietary.

There is a need to improve upon the efficacy or safety (or both) of therapeutic agents. Although the present invention discloses improvements to the efficacy or safety of oncology agents, particularly immuno-oncology agents, the present invention discloses methods and compositions that are not intended to be limited to oncology, nor to chemical or biological agents.

BRIEF DESCRIPTION OF THE INVENTION

FIGS. 6A-F depict various methods of the present invention relating to the timing or sequence and use of a carrier in the presence or absence of an encapsulated agent.

FIG. 7 shows the amount of IL-2 encapsulated in Imagent microbubbles by Human IL-2 Quantikine ELISA assay.

Figure 8:
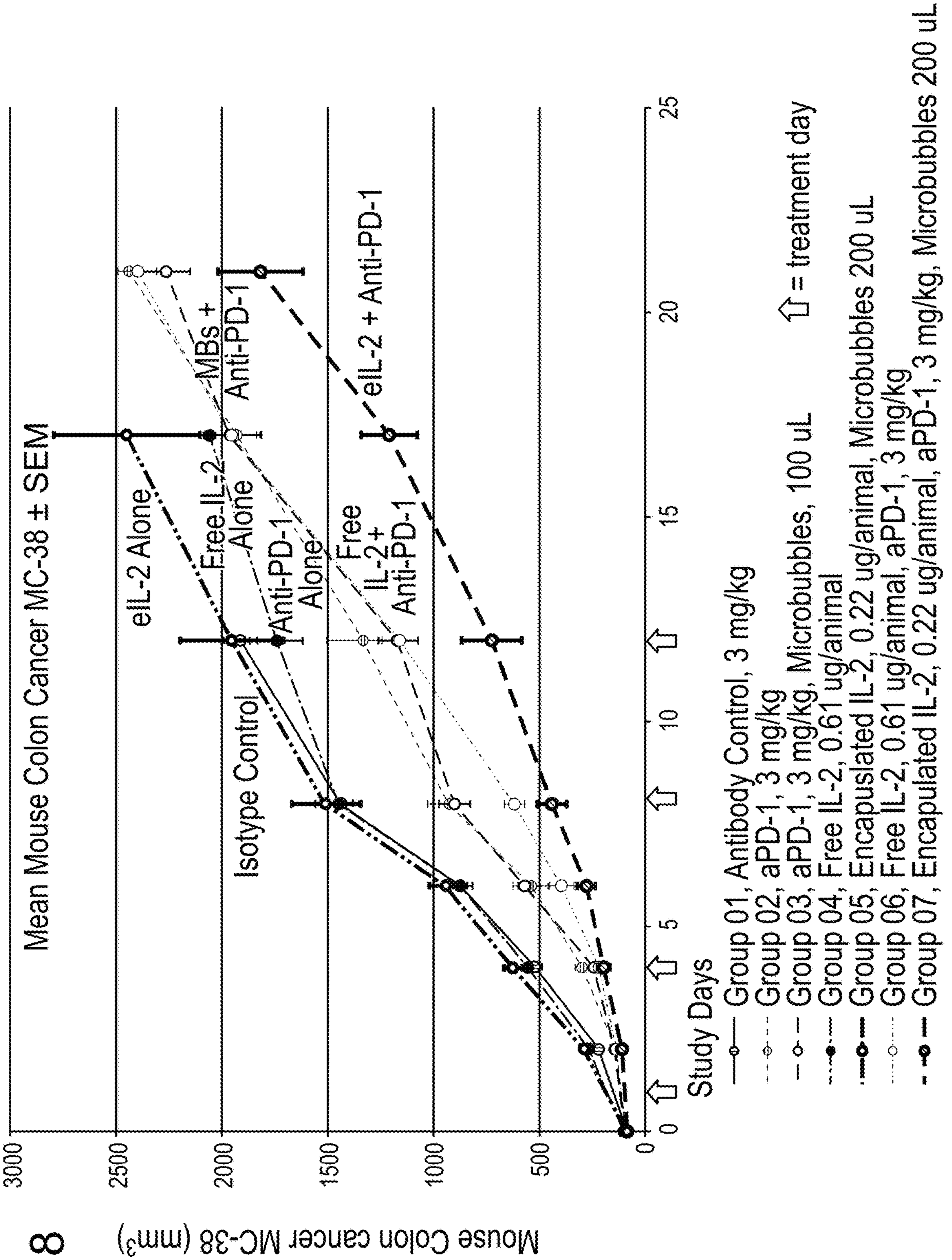

FIG. 8 depicts inhibition of tumor growth in MC38 mouse model of colon cancer using encapsulated IL-2 drug.

FIG. 9 shows the mean percentage inhibition data of FIG. 8.

FIG. 10 presents data from a human cytokine and chemokine analysis.

Figure 11:
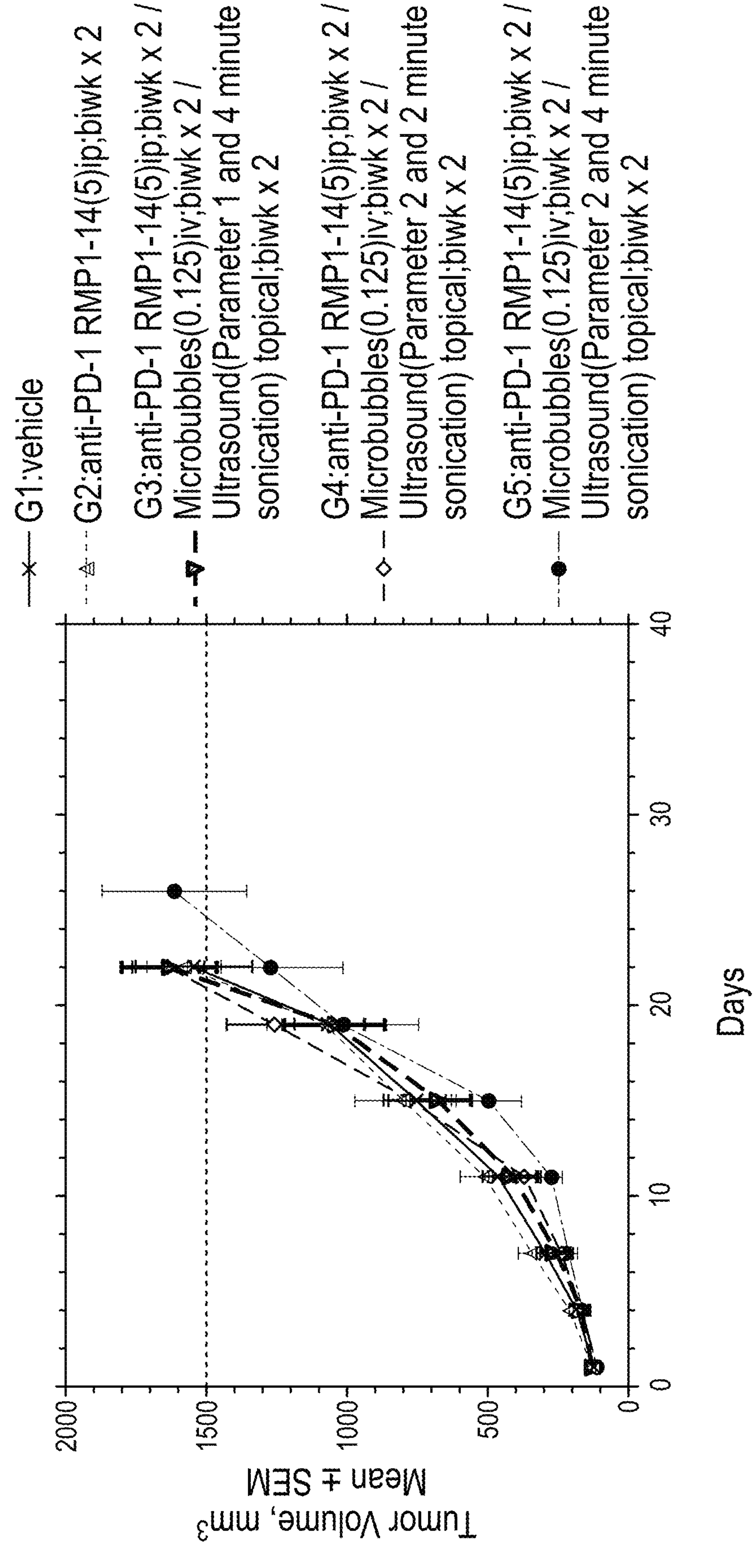

FIG. 11 depicts the tumor volume growth in mice treated with anti-PD-1 antibody.

Figure 12:
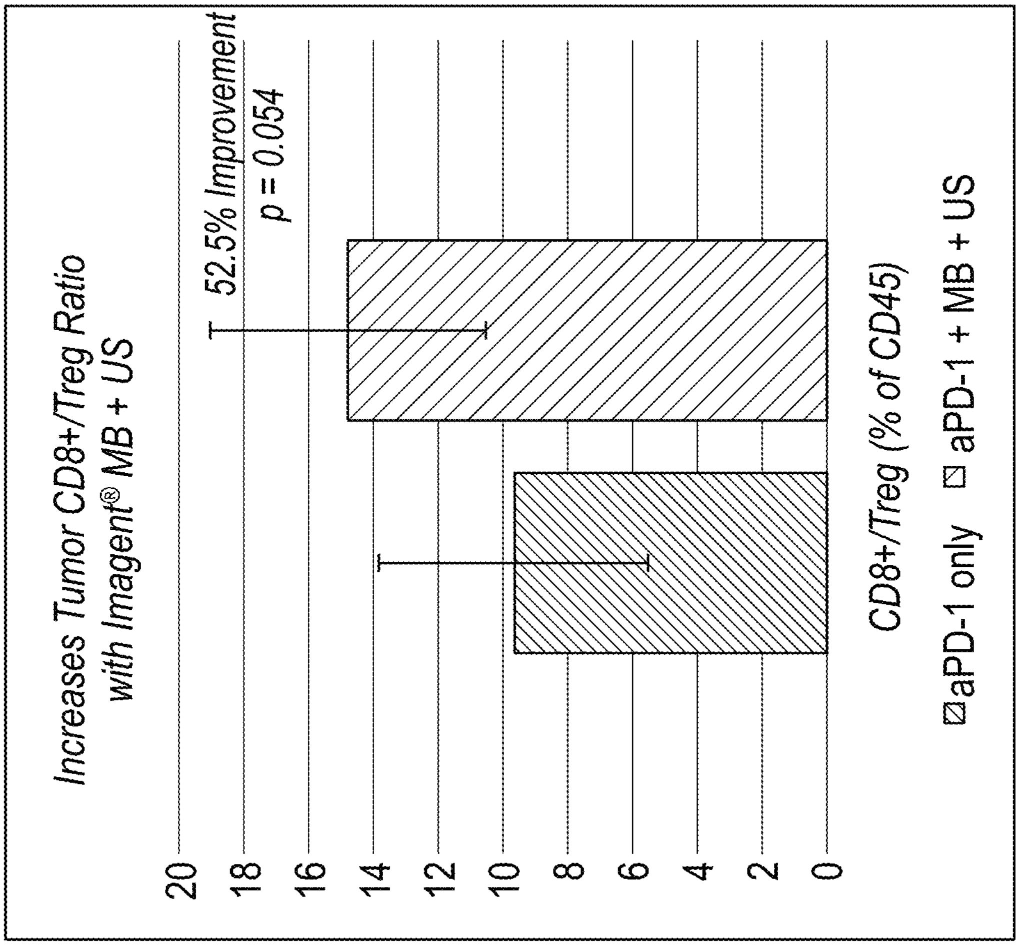

FIG. 12 depicts an increase in the tumor CD8+/Treg ratio in mice treated with microbubbles co-administered with anti-PD-1 antibody.

Figure 13:
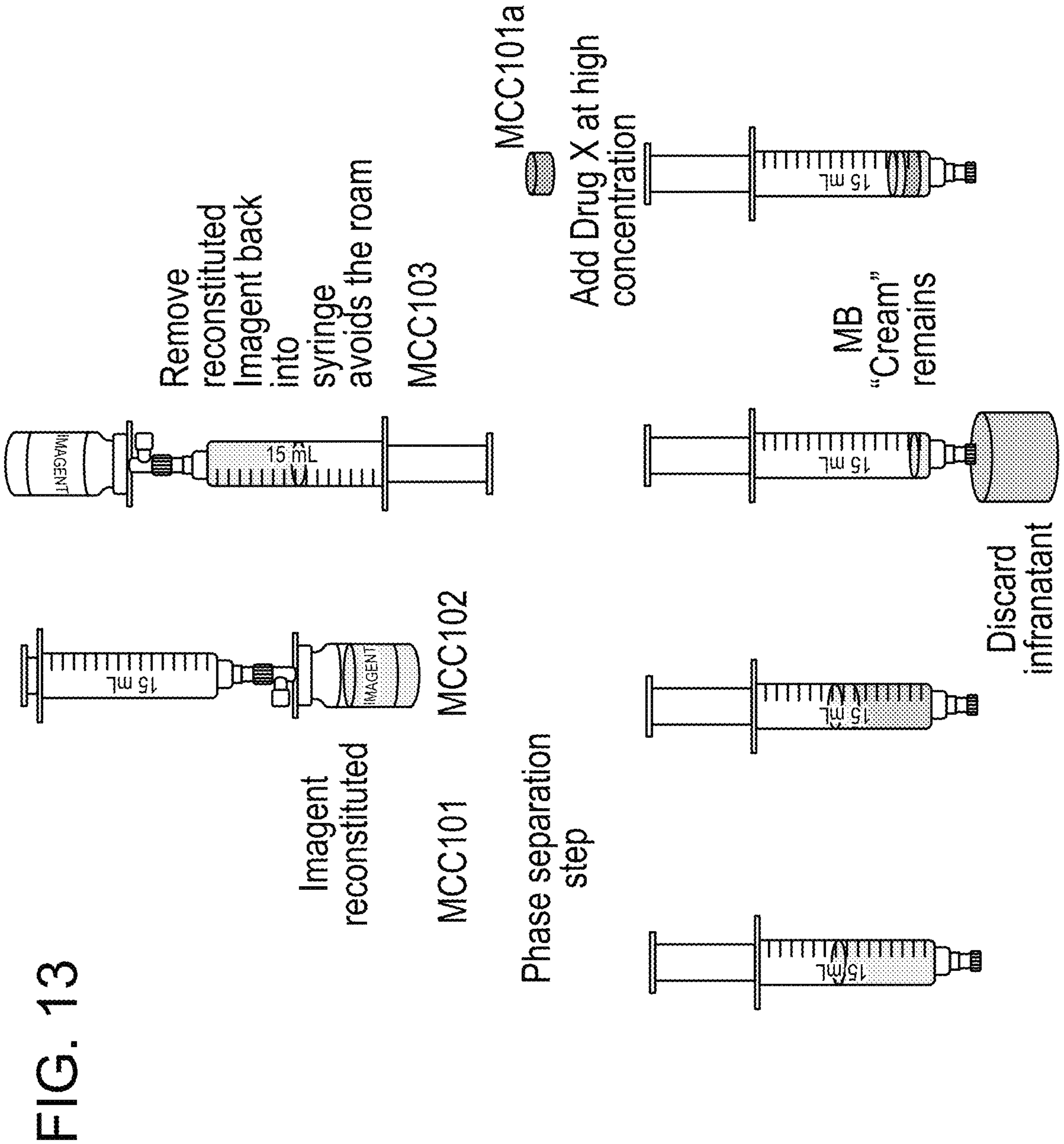

FIG. 13 is a schematic depicting the syringe method for making the compositions of the invention.

Figure 14:
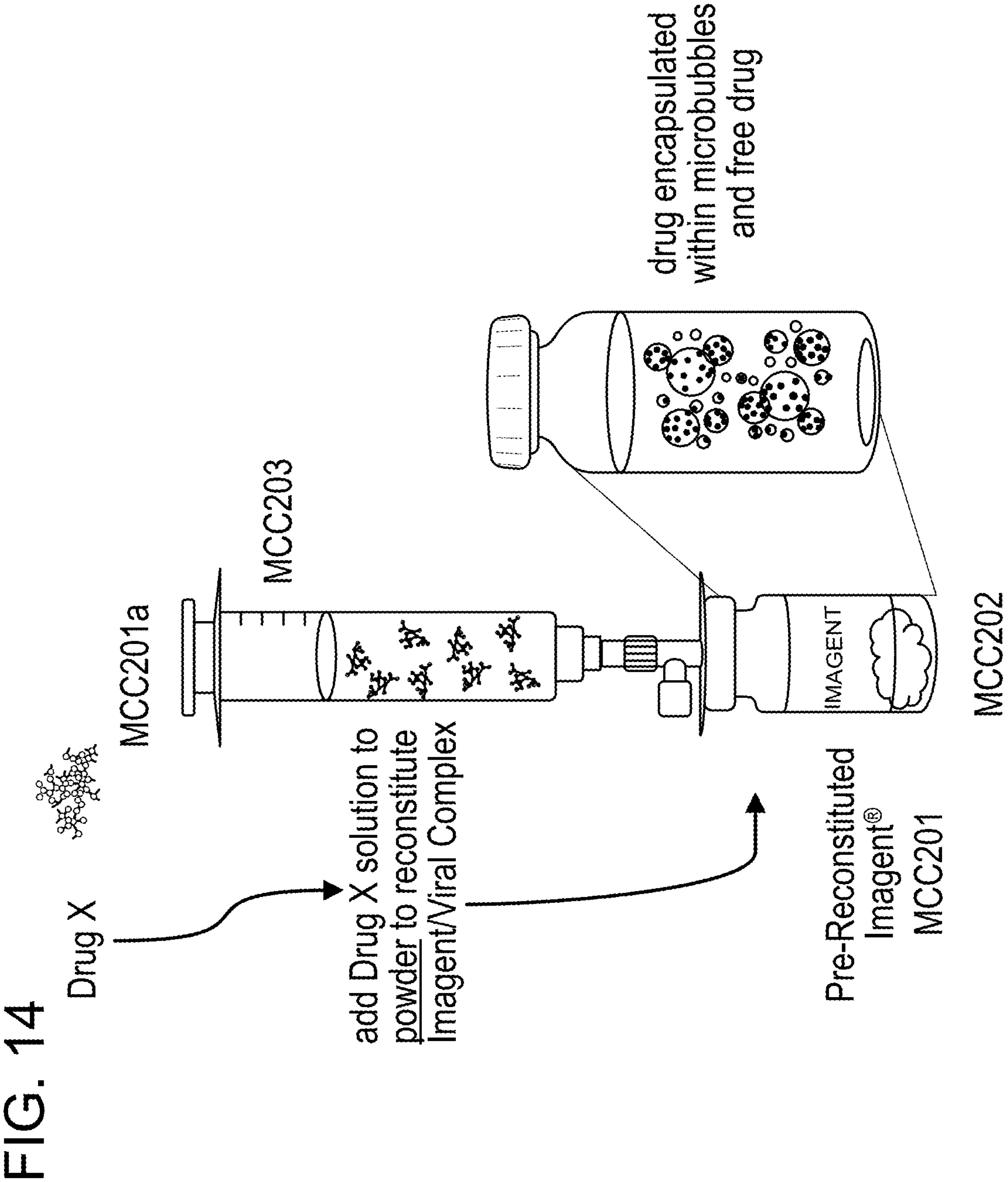

FIG. 14 is a schematic depicting the vial method for making the compositions of the invention.

FIG. 15 depicts the amount of IL-2 encapsulated within the Imagent microbubbles prepared using the syringe method.

Figure 16:
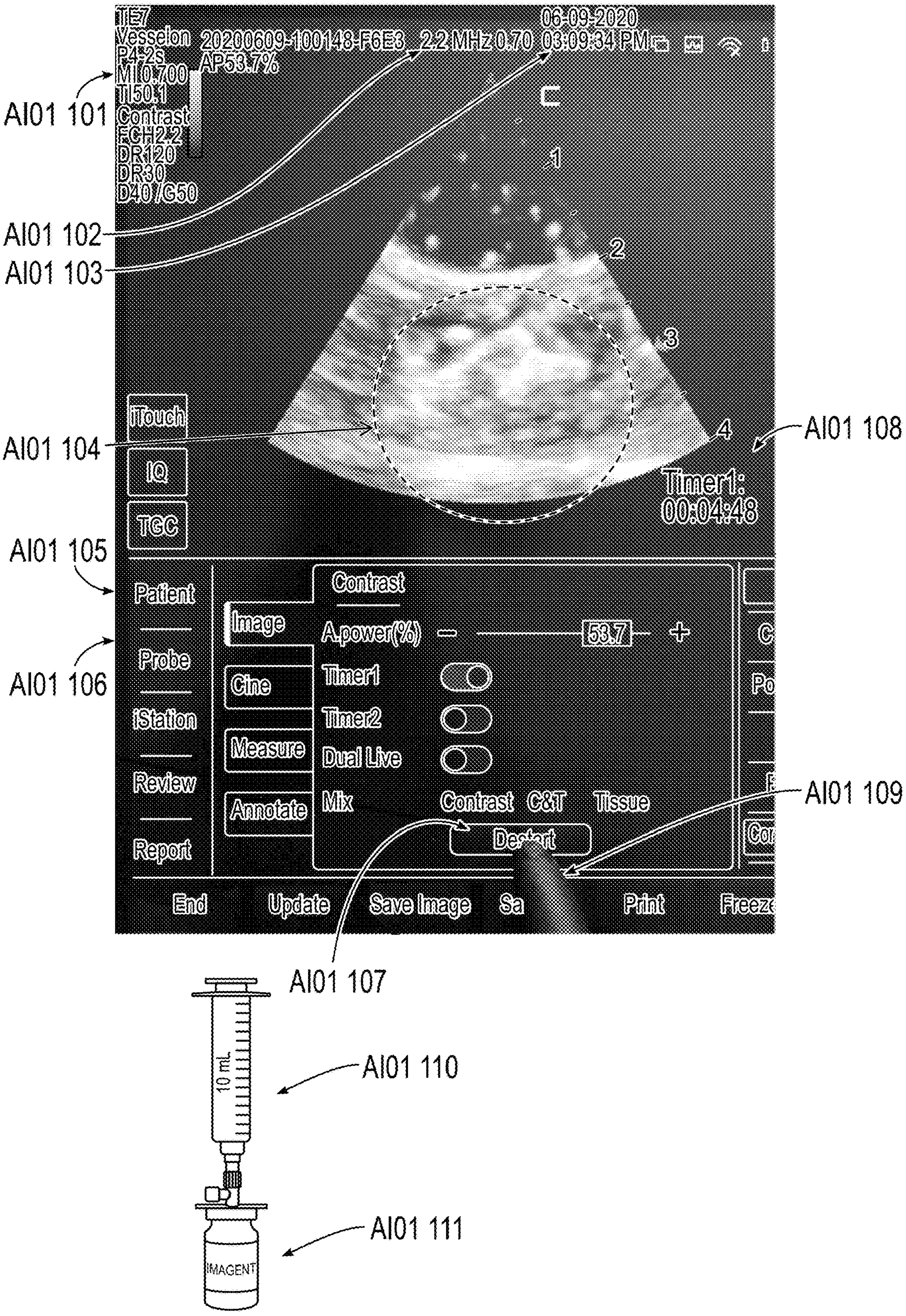

FIG. 16 depicts an exemplary ultrasound image for use in the methods of the invention.

Figure 17:
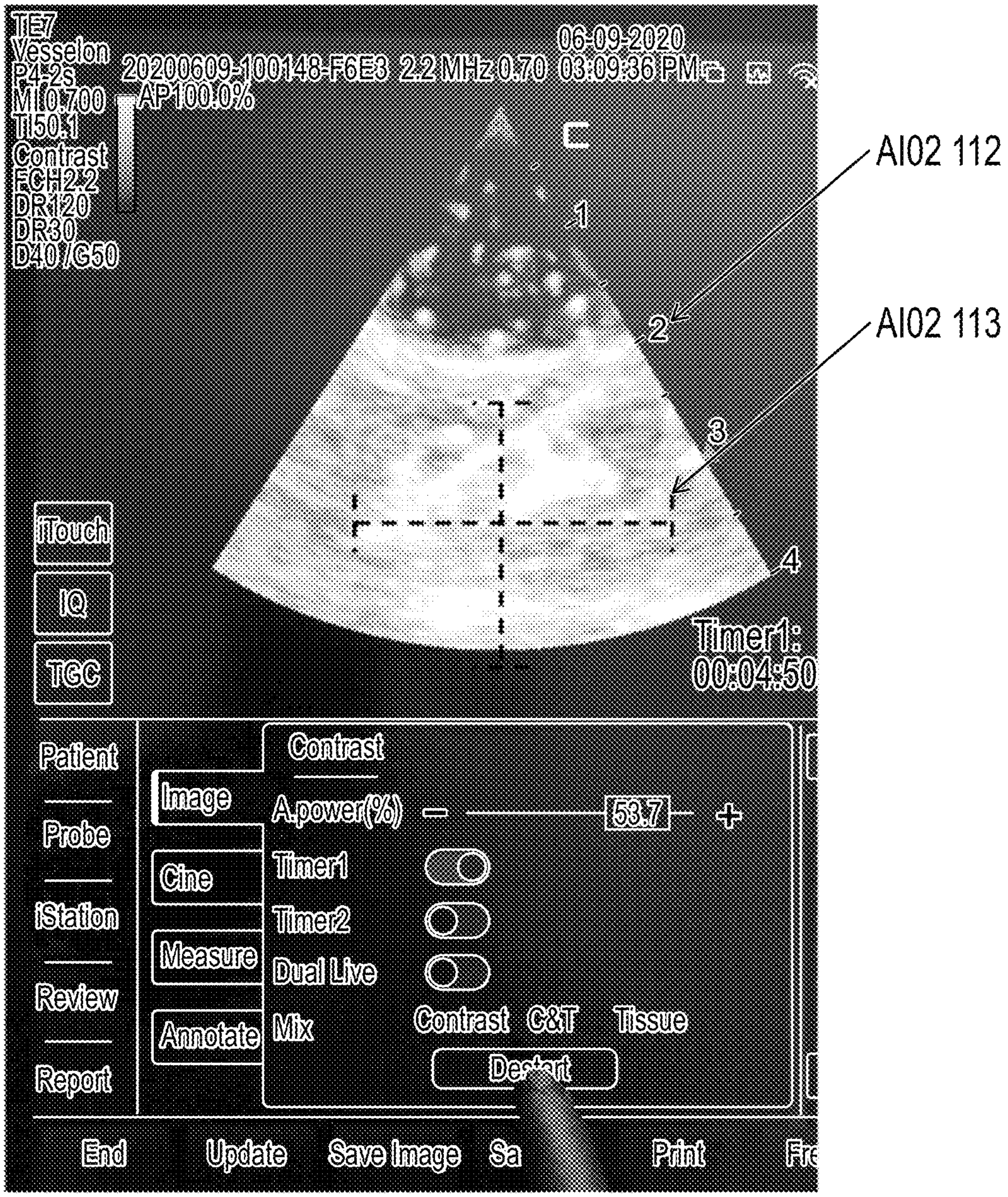

FIG. 17 depicts an exemplary ultrasound image for use in the methods of the invention.

Figure 18:
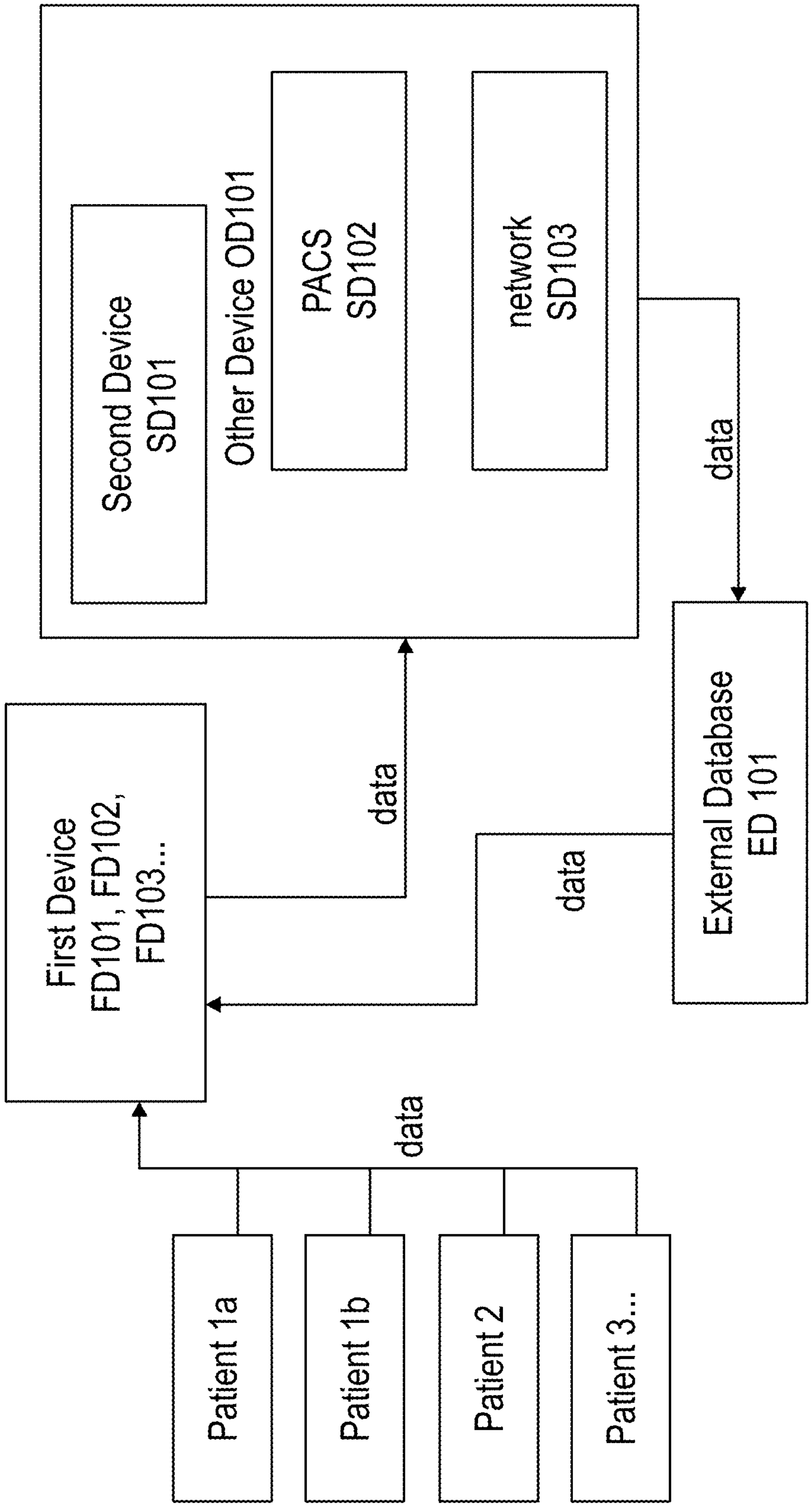

FIG. 18 depicts an exemplary data flow for use in the methods of the invention.

Figure 19:
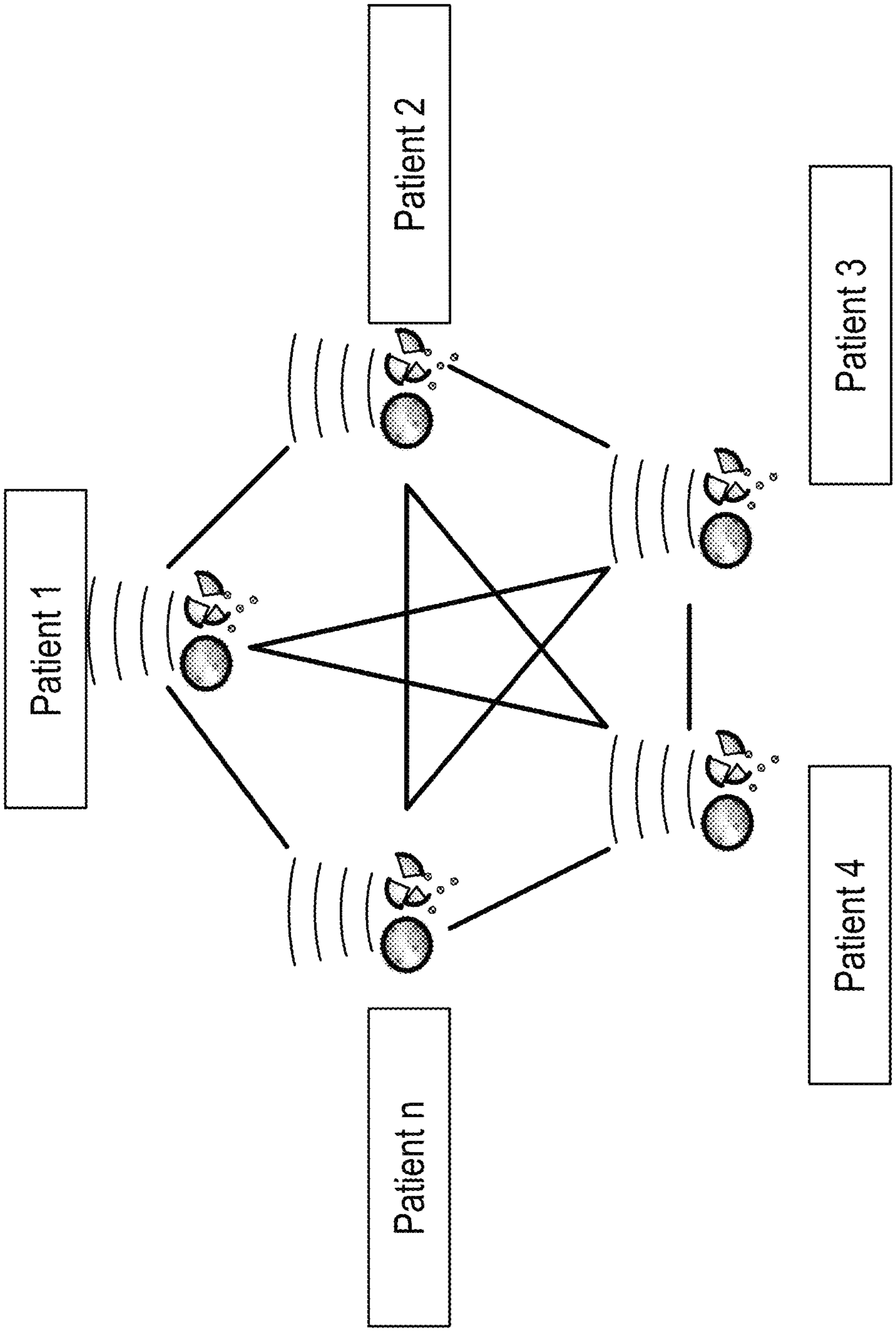

FIG. 19 is a schematic depicting a network effect of the methods of the invention.

Figure 20:
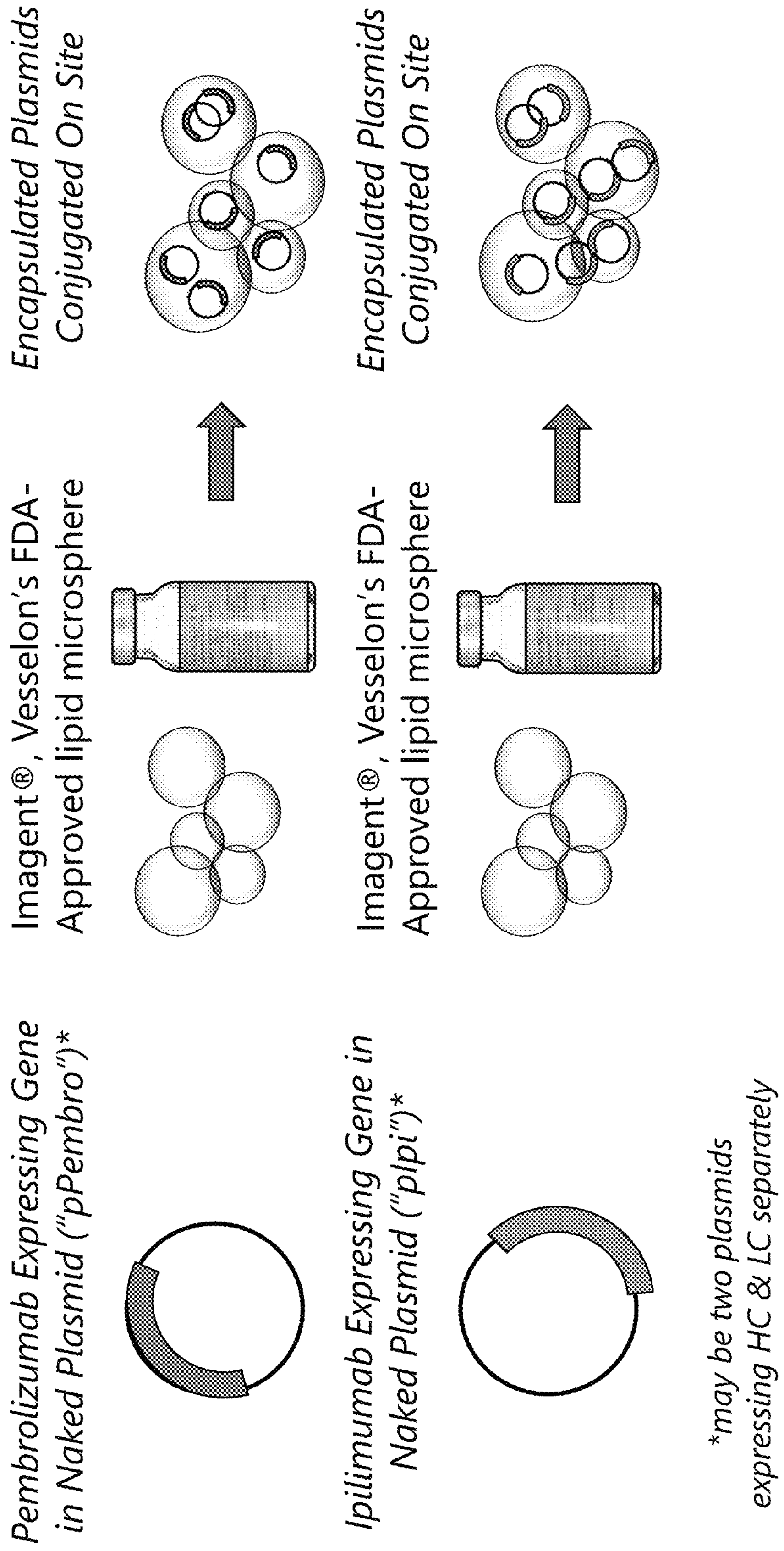

FIG. 20 depicts mAb-encoding plasmid DNA constructs in Imagent microbubbles.

Figure 21:
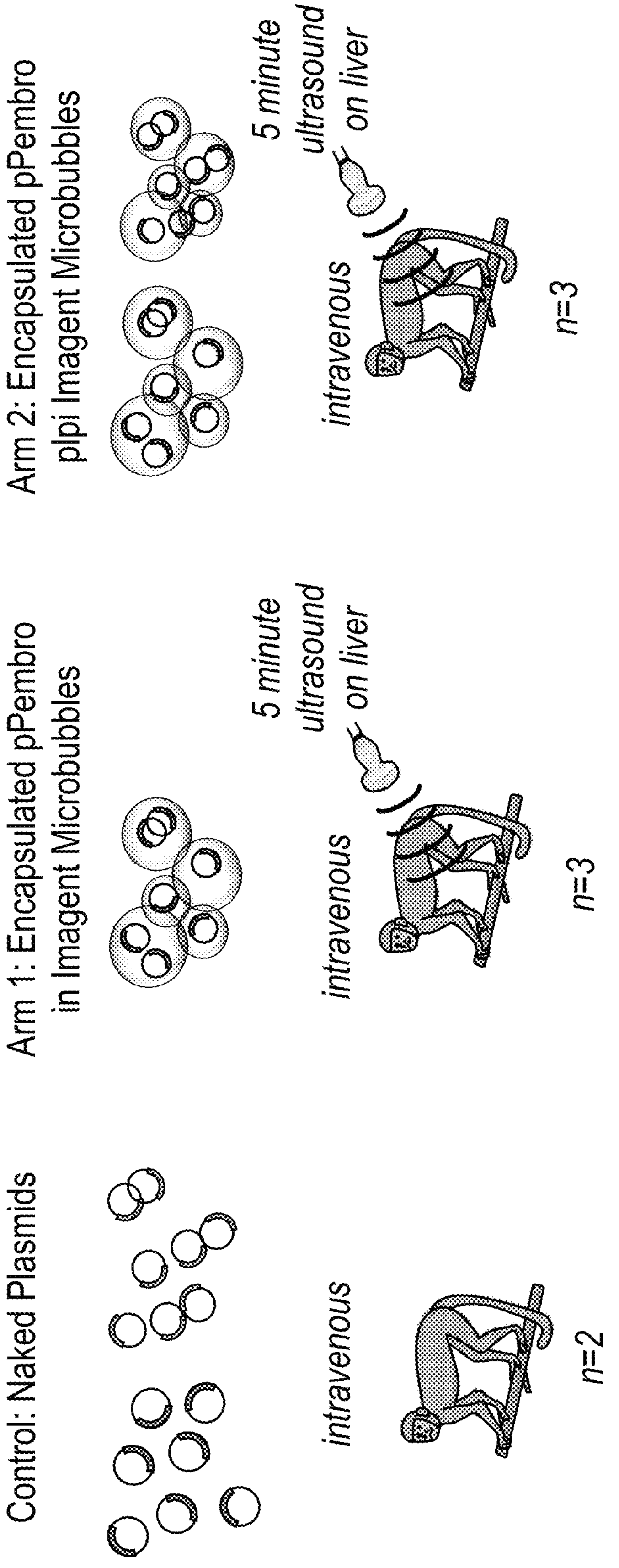

FIG. 21 depicts the overall protocol for cynomolgus monkey study.

FIG. 22 depicts the overall protocol for the delivery of Crisper/Cas9 DNA, mRNA, and ribonucleoprotein (RNP) targeting the Col1a1 locus by sonoporation.

Figure 23:
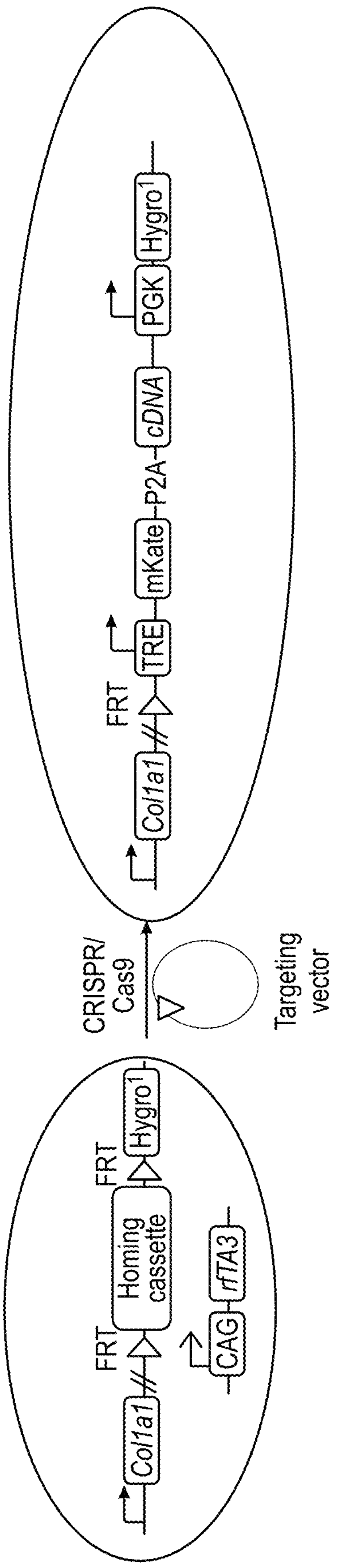

FIG. 23 depicts the knock-in model for overexpression of a gene from the Col1a1 locus.

Figure 24:
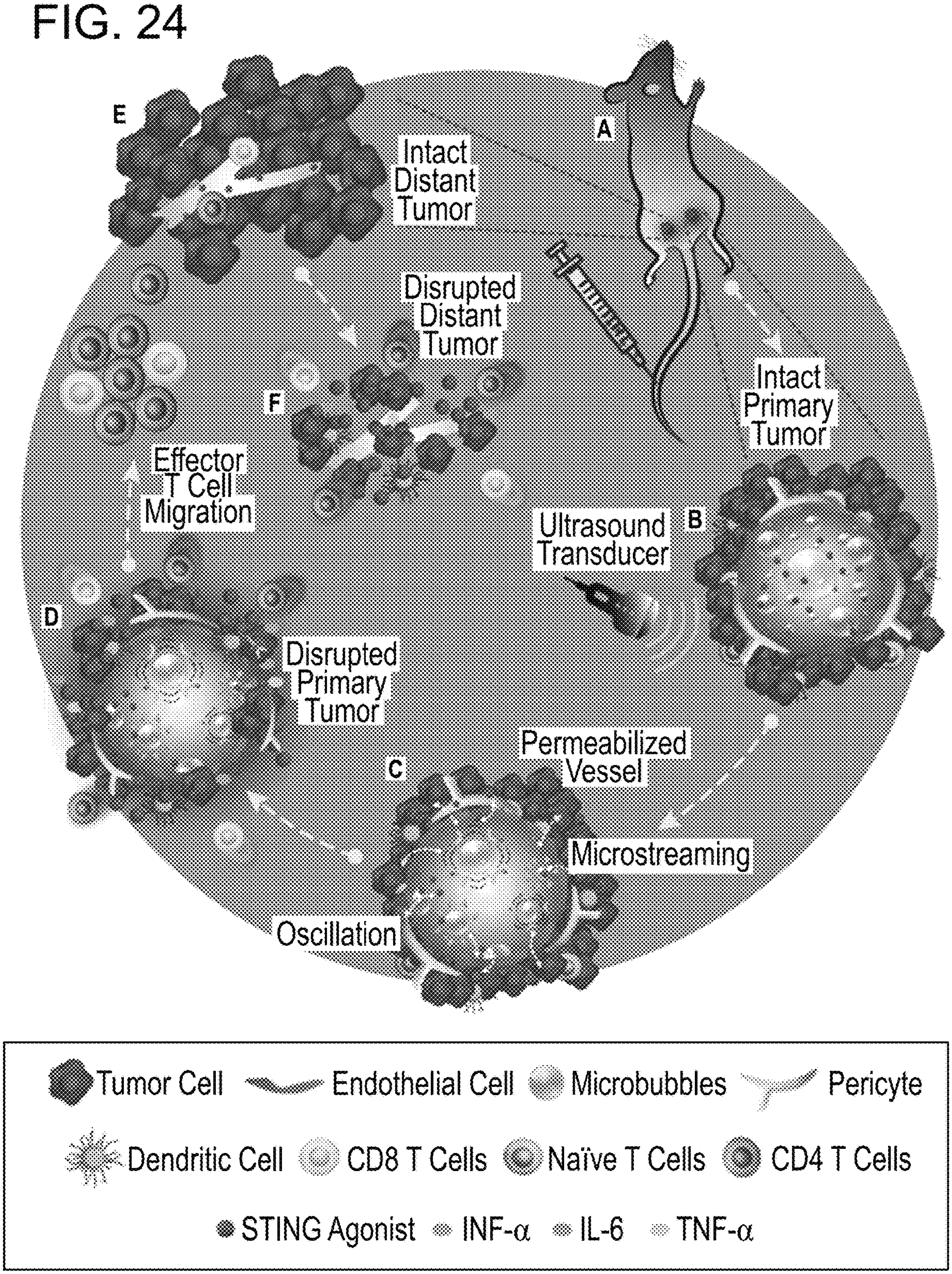

FIG. 24 is a schematic depicting that sonoporation-enhanced delivery of STING agonist, MSA-1, induced robust immune modulation and tumor regression.

Figure 25A:
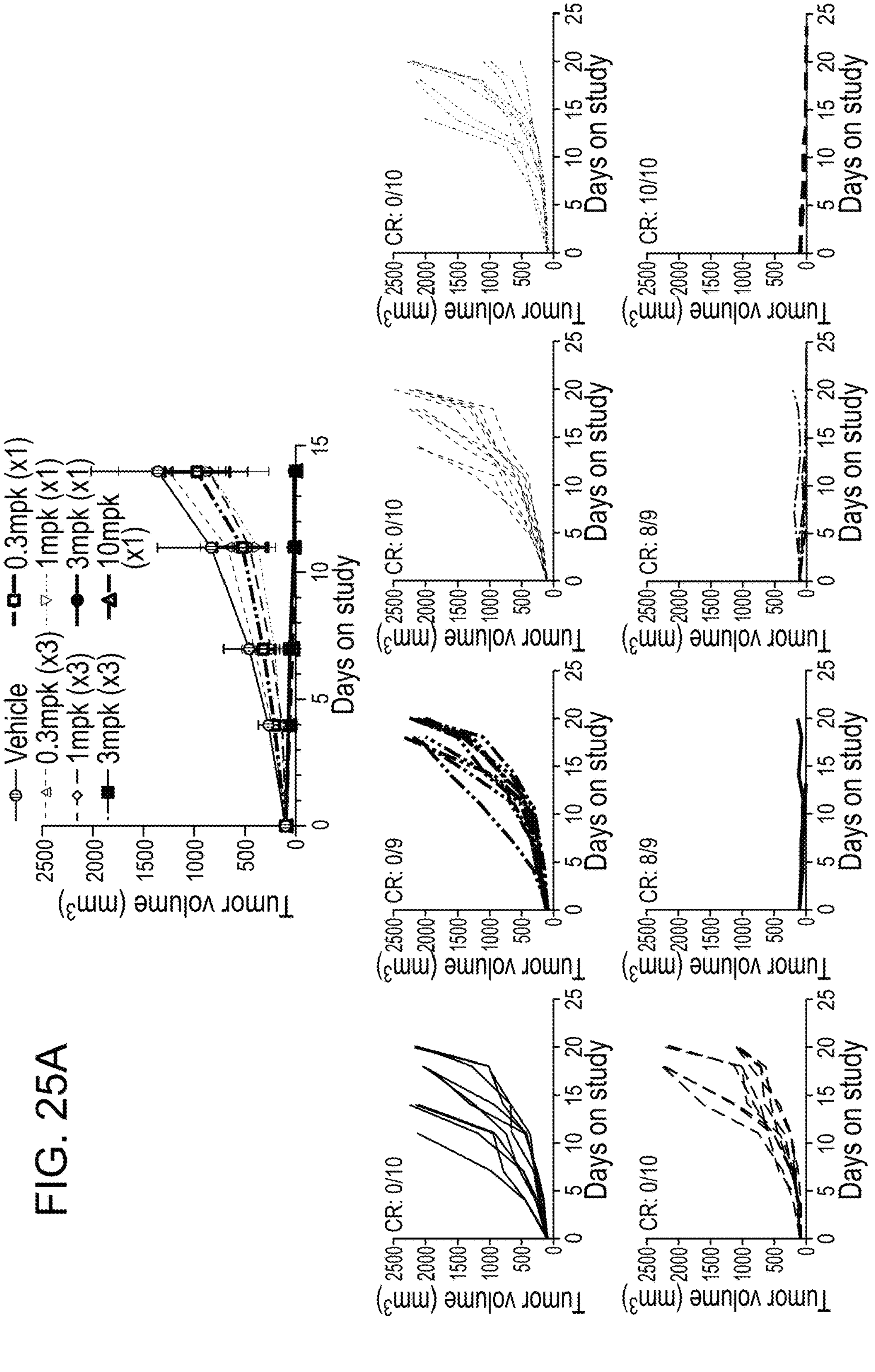
Figure 25B:
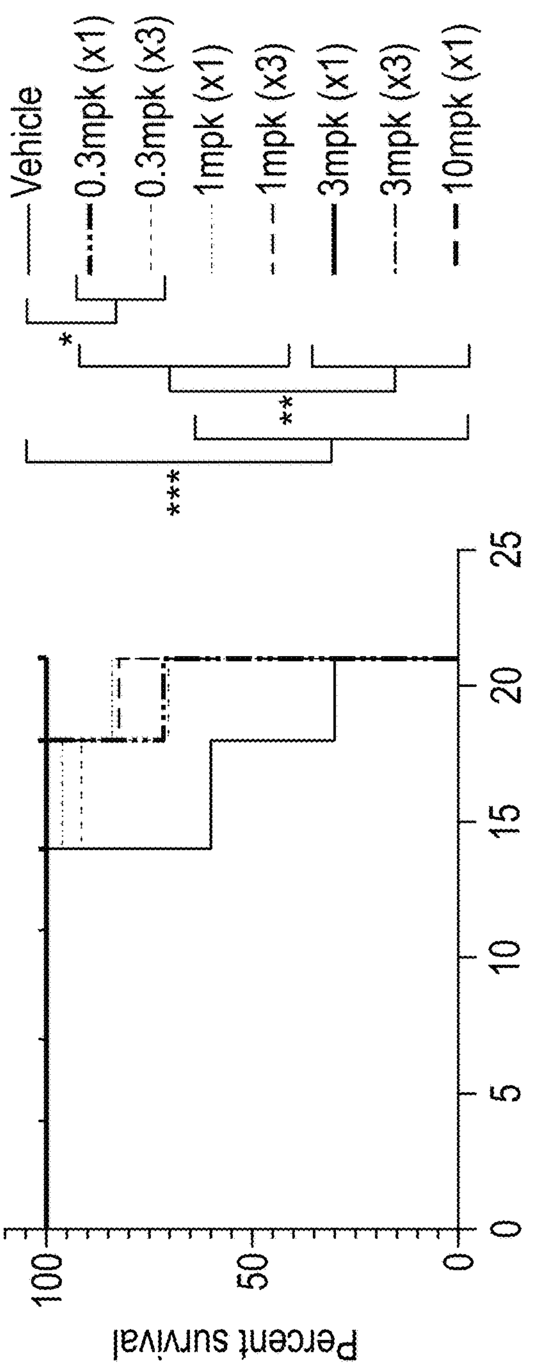
Figure 25C:
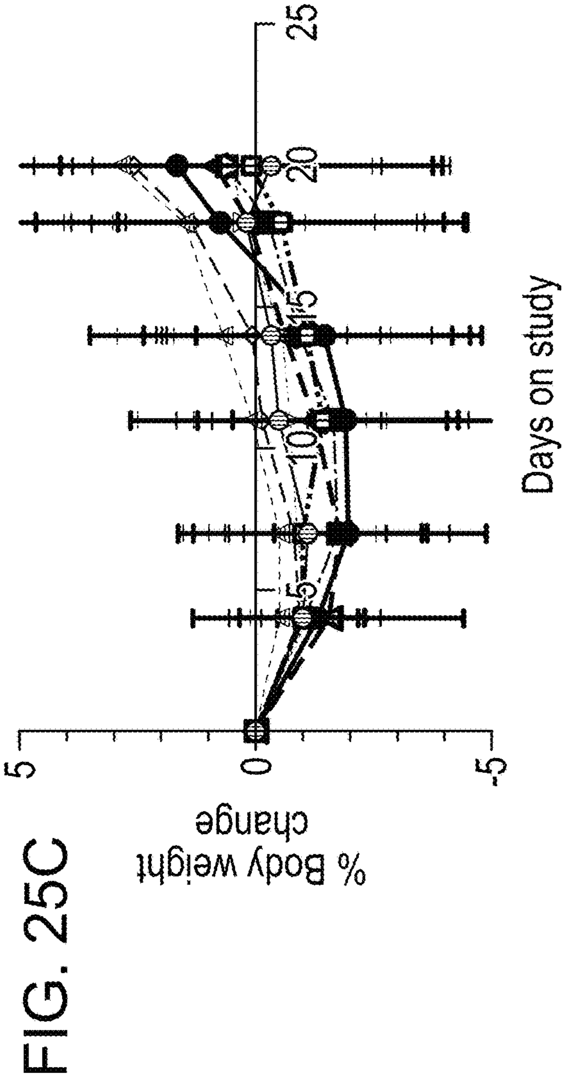

FIGS. 25A-C depict a dose-escalation study of IV administered MSA-1. C57BL/6 female mice were inoculated on the right flank with $0.5\times10^6$ MC38 mouse colon adenocarcinoma cells and when tumor volumes reached 100 $mm^3$, treatments of PBS (vehicle), 0.3, 1, 3, and 10 mpk of MSA-1 were administered. (×1) indicates single injection on day 1; (×3) indicates injections on day 1, 4, and 7. FIG. 25A depicts the tumor volume in mice receiving the indicated treatments. Tumor volumes were measured at indicated times until animals reached a tumor volume of 2000 $mm^3$. Volume measures are presented as mean tumor volume ±SEM. The number of mice that achieved CR is indicated. n=9-10 mice. FIG. 25B depicts the percent survival of mice receiving the indicated treatments. Log-rank (Mantel-Cox) test was used to compute statistical significance. *$p<0.05$; $p<0.01$; *$p<0.001$. FIG. 25C depicts the percentage body weight change in mice receiving the indicated treatments. Body weight measures are presented as mean percent body weight change ±SEM.

Figures 26A, 26B, 26C, 26D, 26E, 26F:
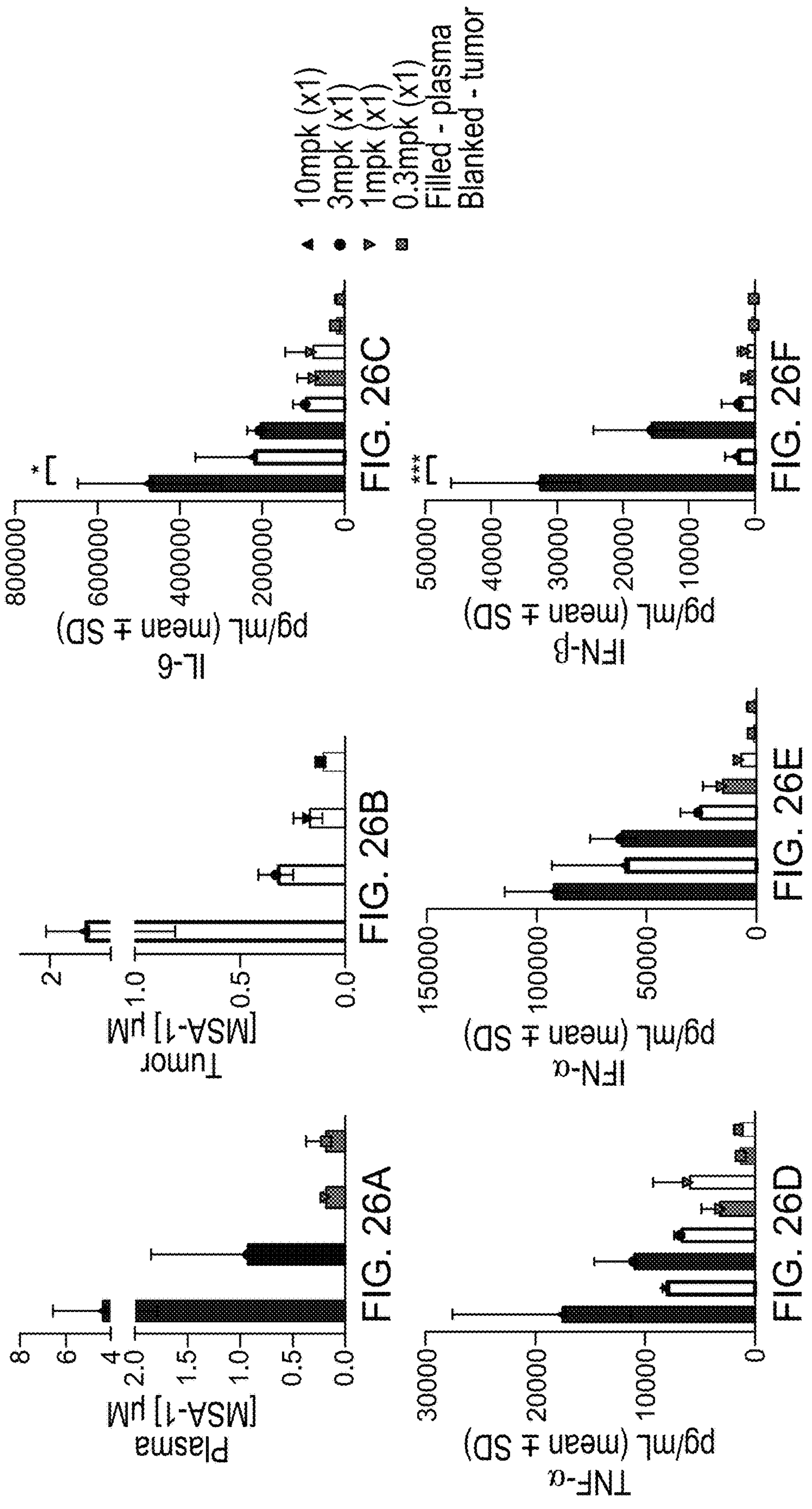

FIGS. 26A-F depict the correlation between the level of MSA-1 in the tumor and plasma with the anti-tumor efficacy of MSA-1. C57BL/6 mice were inoculated on the right flank with $0.5\times10^6$ MC38 mouse colon adenocarcinoma cells and when tumor volumes reached 100 $mm^3$, treatments of 0.3, 1, 3, and 10 mpk single dose of MSA-1 were administered. FIGS. 26A-B depict the tumor and plasma concentrations of MSA-1 10 min post-administration, shown as mean±SD. FIGS. 26C-F depict the tumor and plasma IL-6, TNF-α, IFN-α, and IFN-β cytokine levels 4 hr post-dosing, shown as mean±SD. Statistics calculated using one-way ANOVA followed by Tukey's test. *$p<0.05$; ***$p<0.001$. n=3 mice.

Figure 27A:
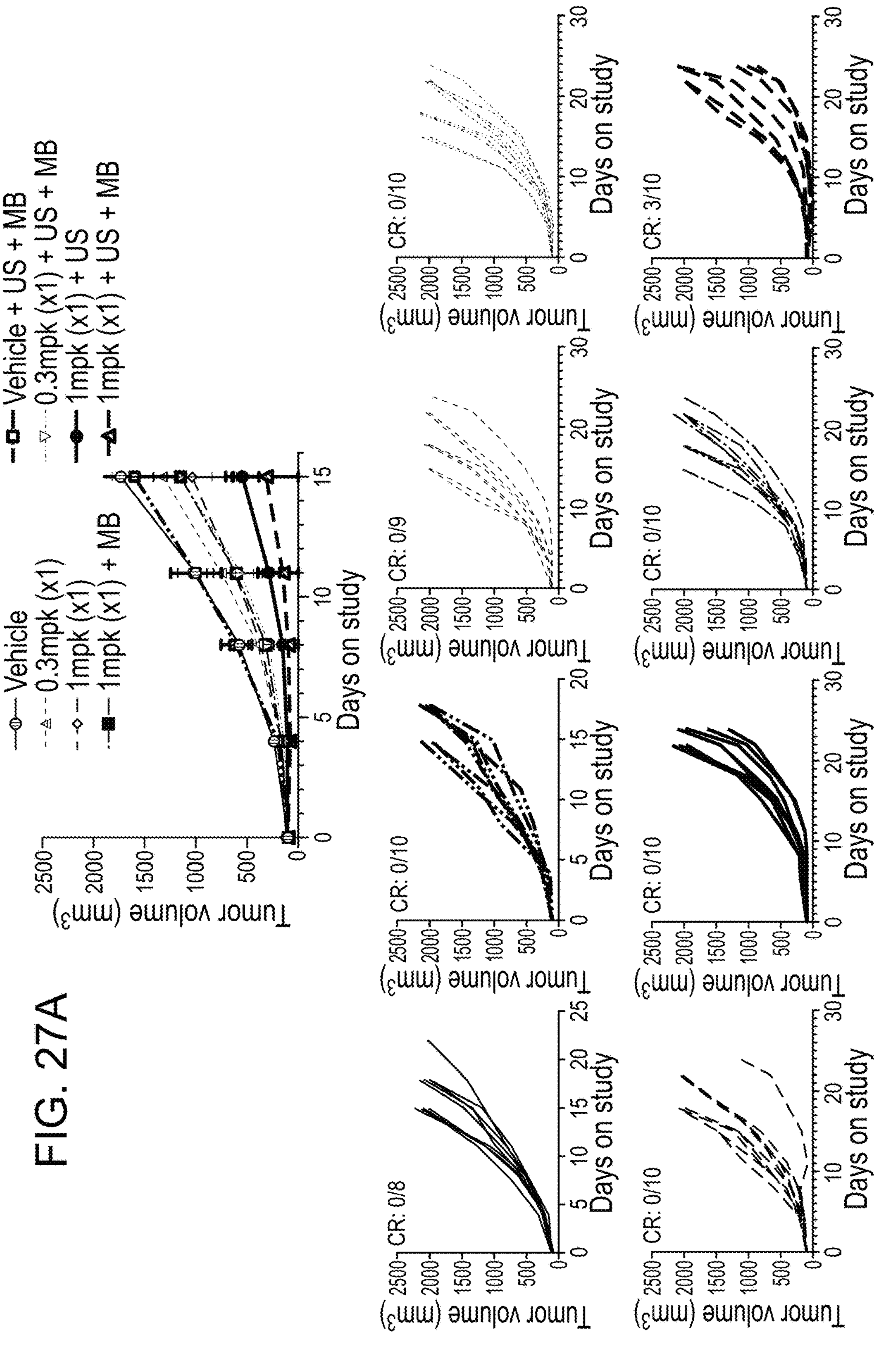
Figure 27B:
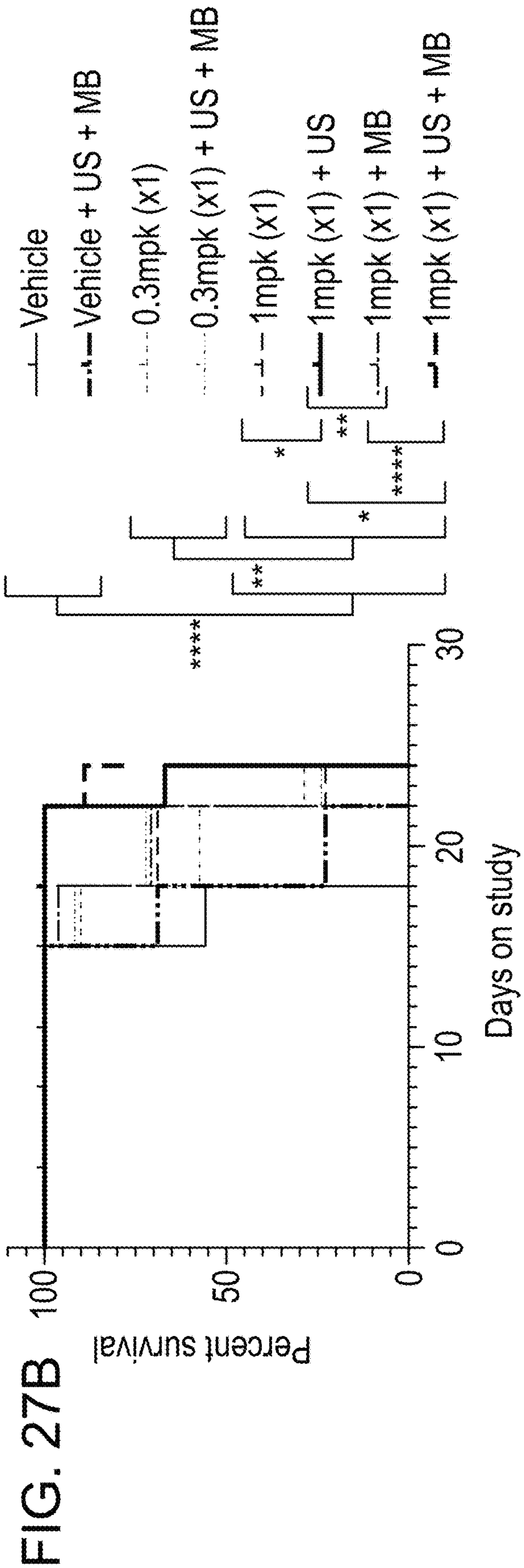
Figure 27C:
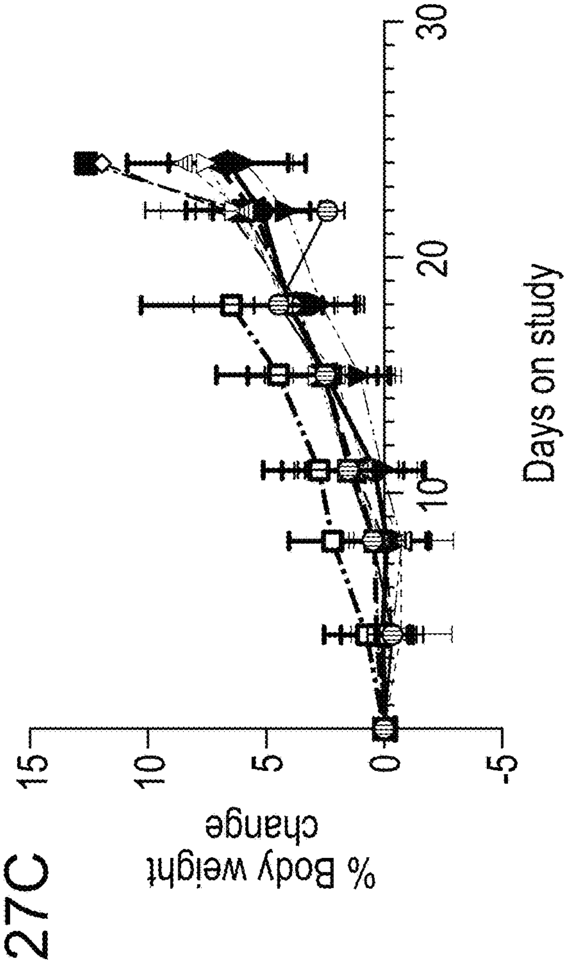

FIGS. 27A-C depict the anti-tumor efficacy behavior when combining MSA-1 at either 1 mpk or 0.3 mpk with sonoporation. C57BL/6 female mice were inoculated on the right flank with $0.5\times10^6$ MC38 mouse colon adenocarcinoma cells and when tumor volumes reached 100 $mm^3$, treatments were administered. FIG. 27A depicts the tumor volume in mice receiving the indicated treatments. Tumor volumes were measured at indicated times until animals reached a tumor volume of 2000 $mm^3$. Volume measures are presented as mean tumor volume ±SEM. The number of mice that achieved CR is indicated. n=8-10 mice. FIG. 27B depicts the percent survival of mice receiving the indicated treatments. Log-rank (Mantel-Cox) test was used to compute statistical significance. *$p<0.05$; $p<0.01$; $p<0.0001$. FIG. 27**C depicts the percentage body weight change in mice receiving the indicated treatments. Body weight measures are presented as mean percent body weight change ±SEM.

Figures 28A, 28B, 28C, 28D, 28E, 28F, 28G, 28H, 28I, 28J, 28K, 28L:
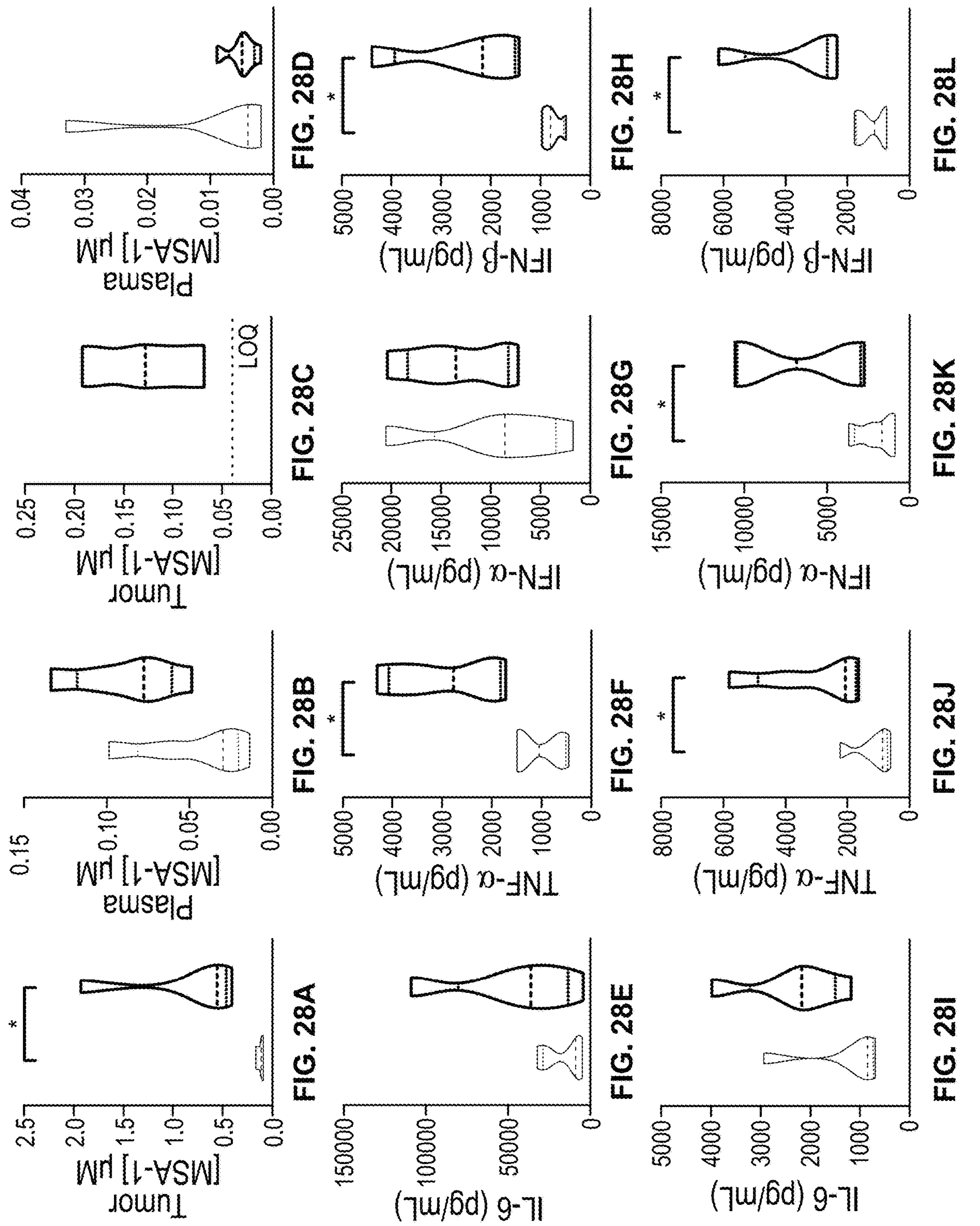

FIGS. 28A-L depict that sonoporation drastically enhanced tumor local concentration of MSA-1 and resulted in substantially elevated cytokine production. C57BL/6 female mice were inoculated on the right flank with $0.5\times10^6$ MC38 mouse colon adenocarcinoma cells and when tumor volumes reached 100 $mm^3$, treatments of 1 mpk MSA-1, color-coded orange, and 1 mpk MSA-1 plus sonoporation, color-coded blue, were administered. FIGS. 28A-B depict the violin plot of tumor and plasma concentrations of MSA-1 20 min post-administration. FIGS. 28C-D depict the Violin plot of tumor and plasma concentrations of MSA-1 60 min post-administration. FIGS. 28E-H depict the violin plot of plasma IL-6, TNF-α, IFN-α, and IFN-β cytokine levels 4 hr post-dosing. FIGS. 28I-L depict the violin plot of tumor IL-6, TNF-α, IFN-α, and IFN-β cytokine levels 4 hr post-dosing. Statistics calculated using a two-tailed t-test. *$p<0.05$. n=5 mice.

FIGS. 29A-L depict that sonoporation enhanced MSA-1's immune activation mechanisms while reduced its immune suppression mechanisms. C57BL/6 female mice were inoculated on the right flank with $0.5\times10^6$ MC38 mouse colon adenocarcinoma cells and when tumor volumes reached 100 $mm^3$, treatments of PBS (vehicle), PBS plus sonoporation, 1 mpk MSA-1, 1 mpk MSA-1 plus ultrasound, and 1 mpk MSA-1 plus sonoporation were administered. Five days post-treatment, mice were euthanized and tumors were collected for immunophenotyping. FIGS. 29A-F depict selective immune cells from the lymphoid lineage presented as a percentage of $CD45^+$ cells. FIGS. 29G-L depict selective immune cells from the myeloid lineage as a percentage of $CD45^+$ cells. Statistics calculated using a one-way ANOVA followed by Dunnett's test referencing the vehicle. *$p<0.05$. $p<0.01$; *$p<0.001$; ****$p<0.0001$. n=6 mice.

Figure 30A:
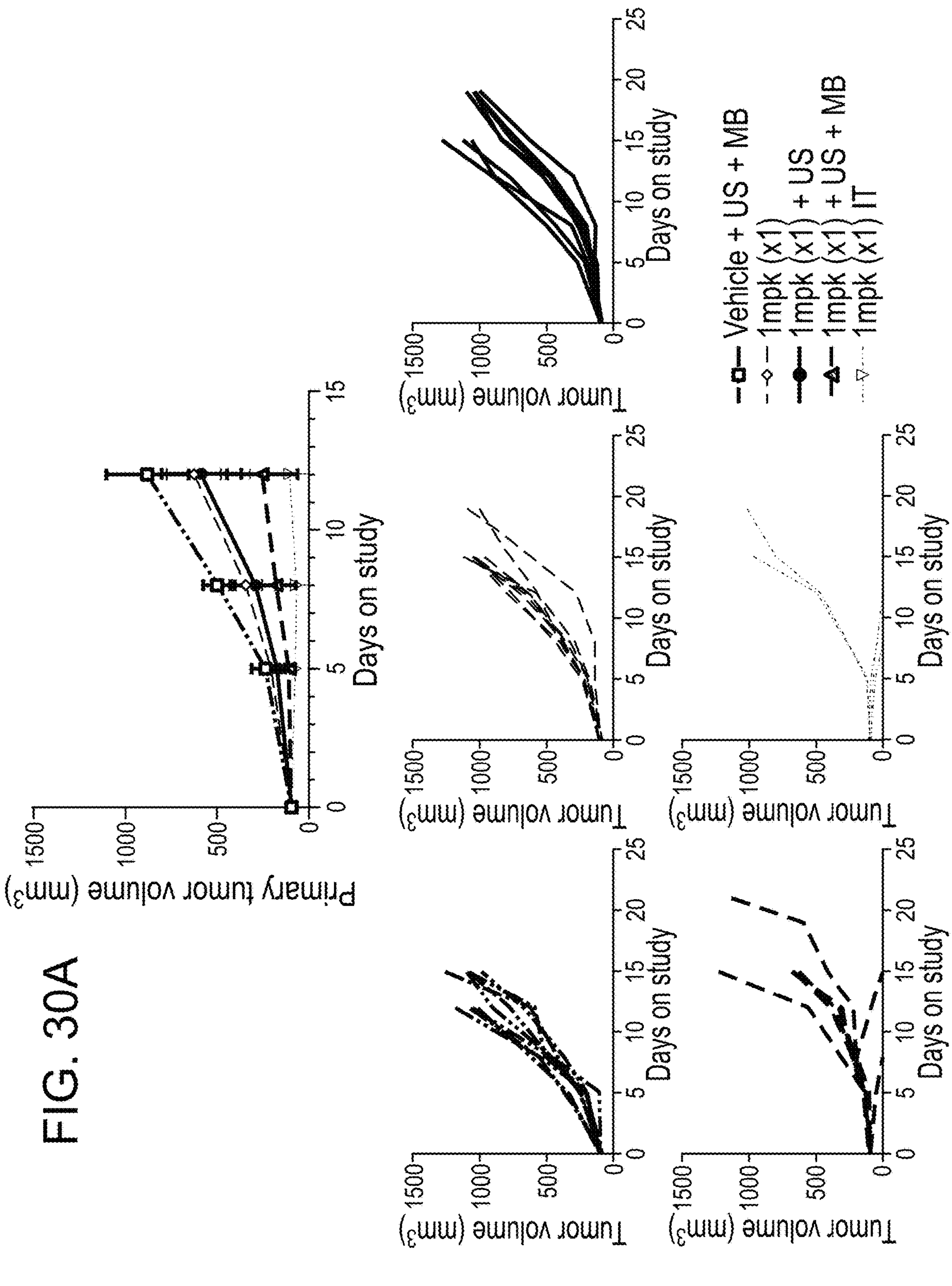
Figure 30B:
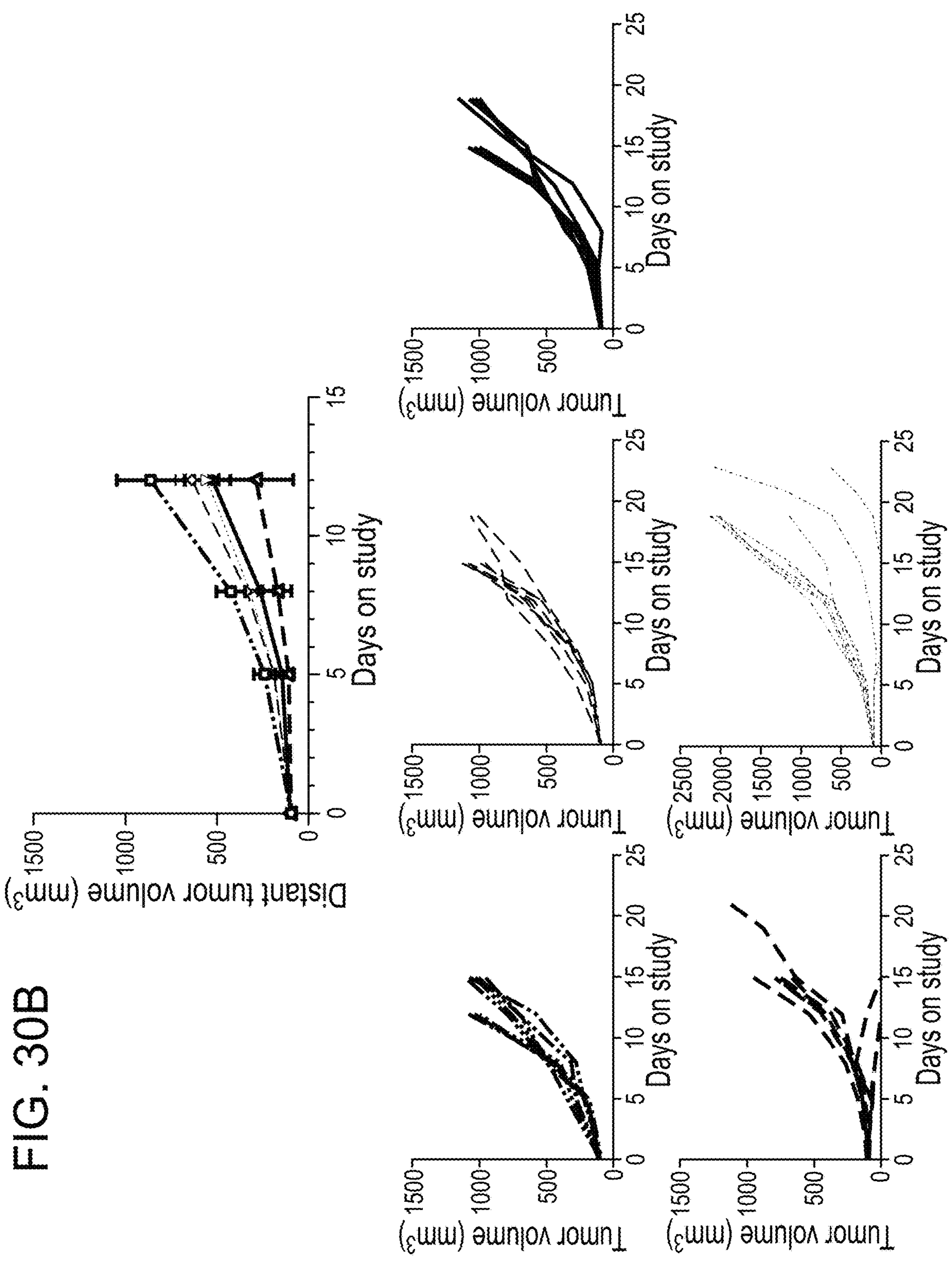

FIGS. 30A-B depict that MSA-1 in combination with sonoporation eradicated distantly located non-ultrasound-treated tumors. C57BL/6 female mice were inoculated on both the left and right flank with $0.5\times10^6$ MC38 mouse colon adenocarcinoma cells each and when both tumors reached an average of 100 $mm^3$, indicated treatments were administered. Ultrasound was only applied to the primary tumor. 1 mpk MSA-1 IT was injected into the primary tumor. FIG. 30A depicts the primary tumor volume in mice receiving the indicated treatments. Primary tumor volumes were measured at indicated times until animals reached a combined tumor volume of 2000 $mm^3$. Volume measures are presented as mean tumor volume ±SEM. FIG. 30B depicts the distant tumor volume in mice receiving the indicated treatments. Distant tumor volumes were measured at indicated times until animals reached a combined tumor volume of 2000 $mm^3$. Volume measures are presented as mean tumor volume ±SEM. n=9 mice.

Figure 31:
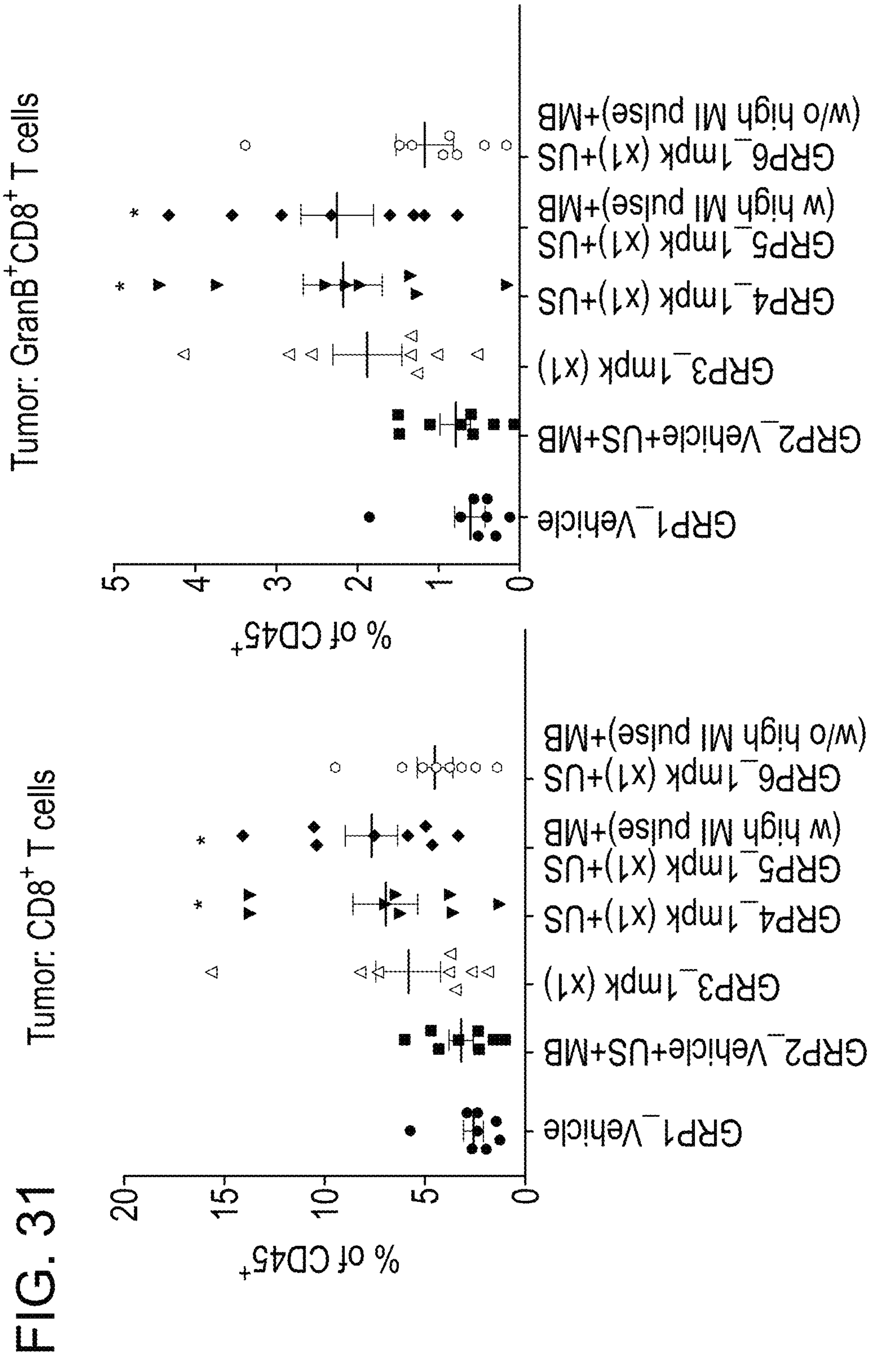

FIG. 31 depicts the number of $CD8^+$ and $GranB^+CD8^+$ T cells in MC38 in vivo tumor model upon receiving an intravenous dose of STING agonist and microbubbles. Animals were exposed to 0.531 MI ultrasound with or without the high 1.304 MI pulses.

Figure 32A:
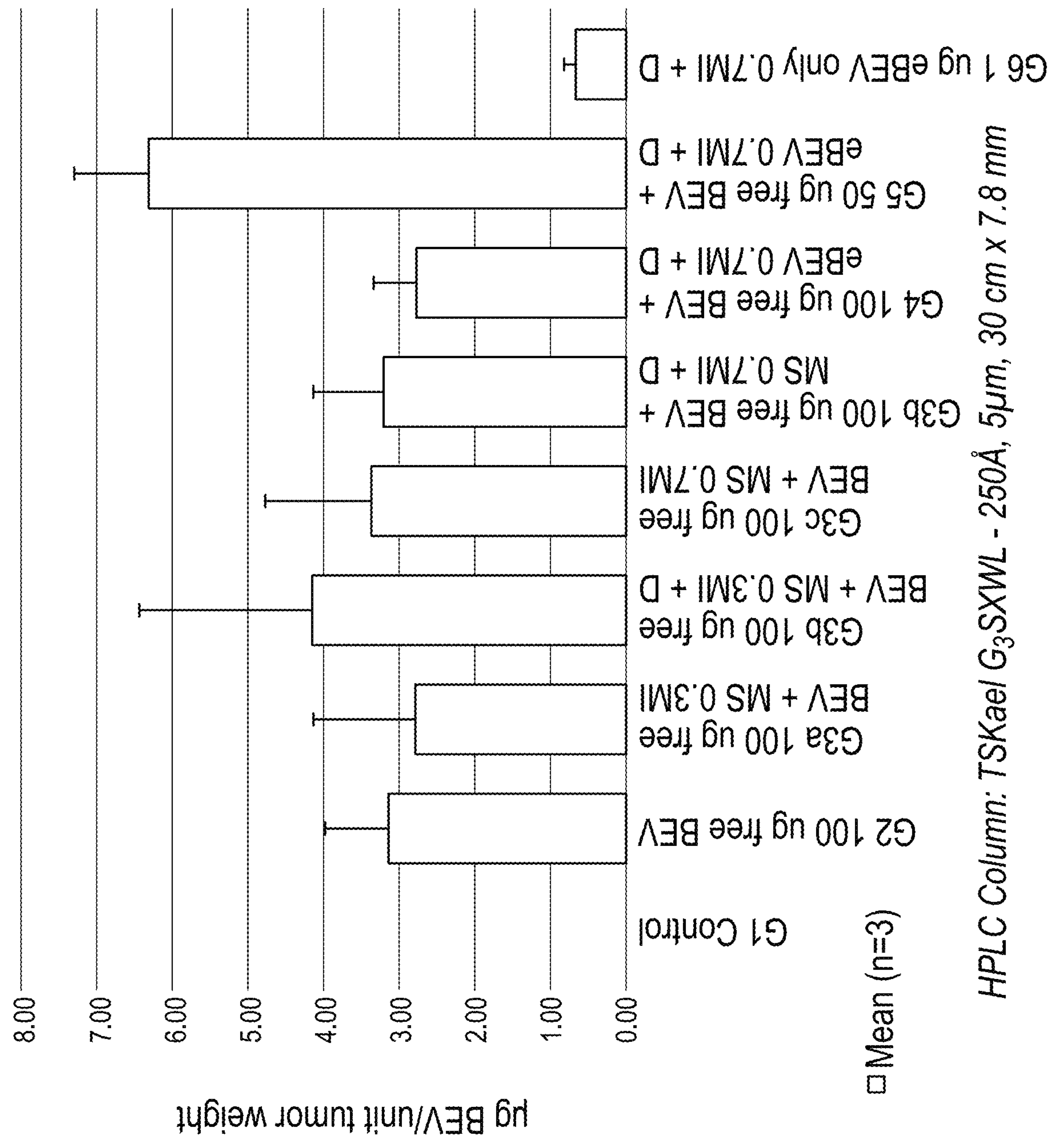
Figure 32B:
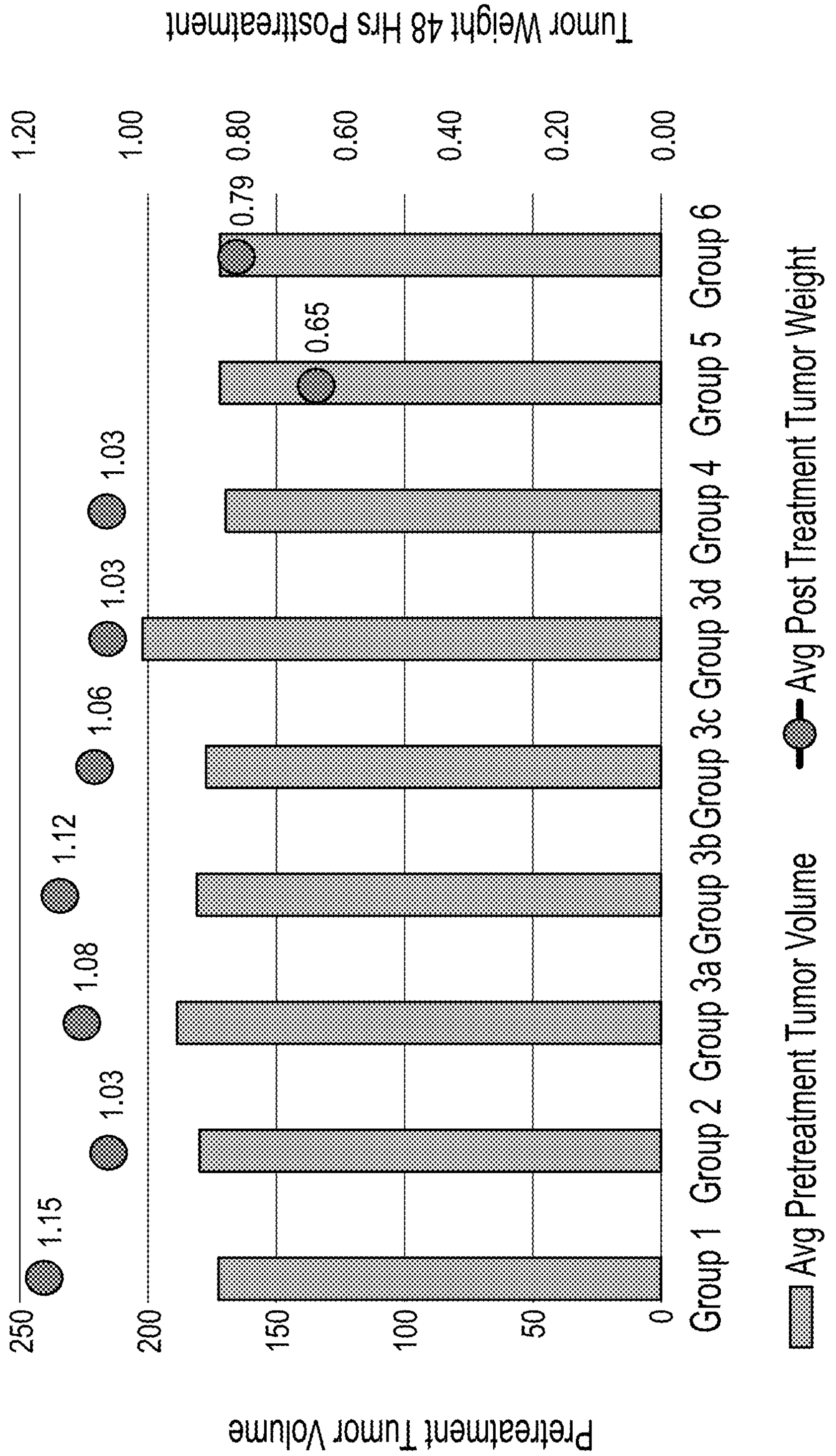

FIG. 32A depicts the mean concentration of bevacizumab-awwb as measured in the tumors upon receiving the indicated treatments. FIG. 32B depicts the tumor weights in animals receiving the indicated treatments.

Figure 33:
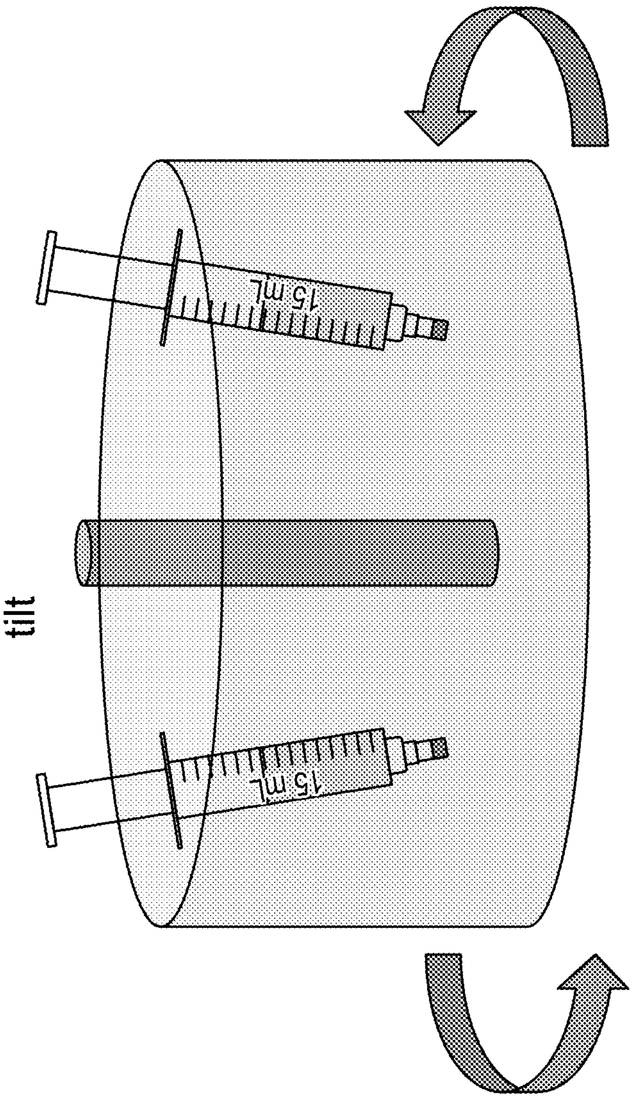

FIG. 33 depicts a reverse angle centrifuge rotor for use in the methods of the present disclosure.

Figure 34:
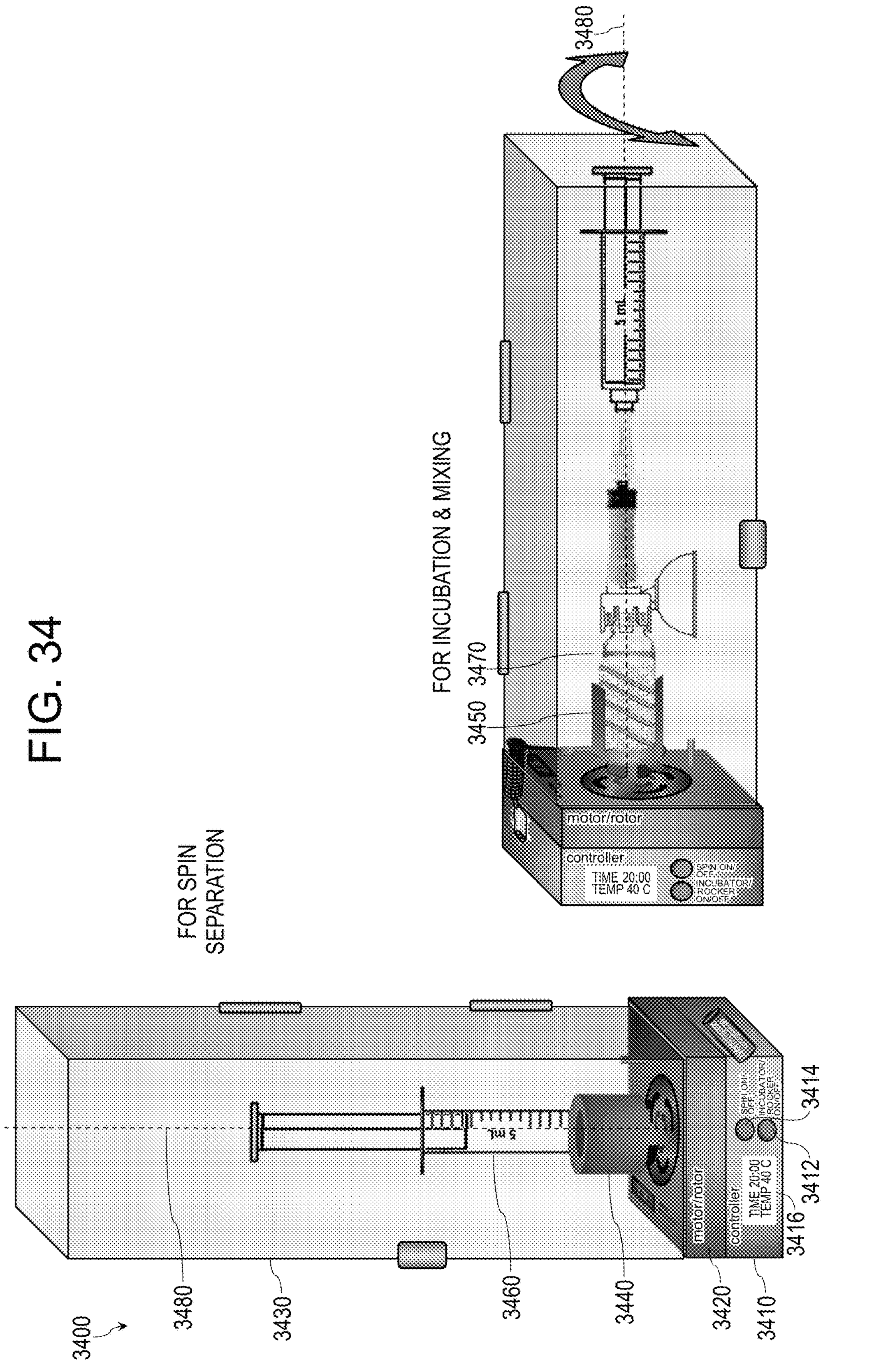

FIG. 34 illustrates an apparatus for performing incubation, spin separation, and mixing of the present disclosure.

Figure 35:
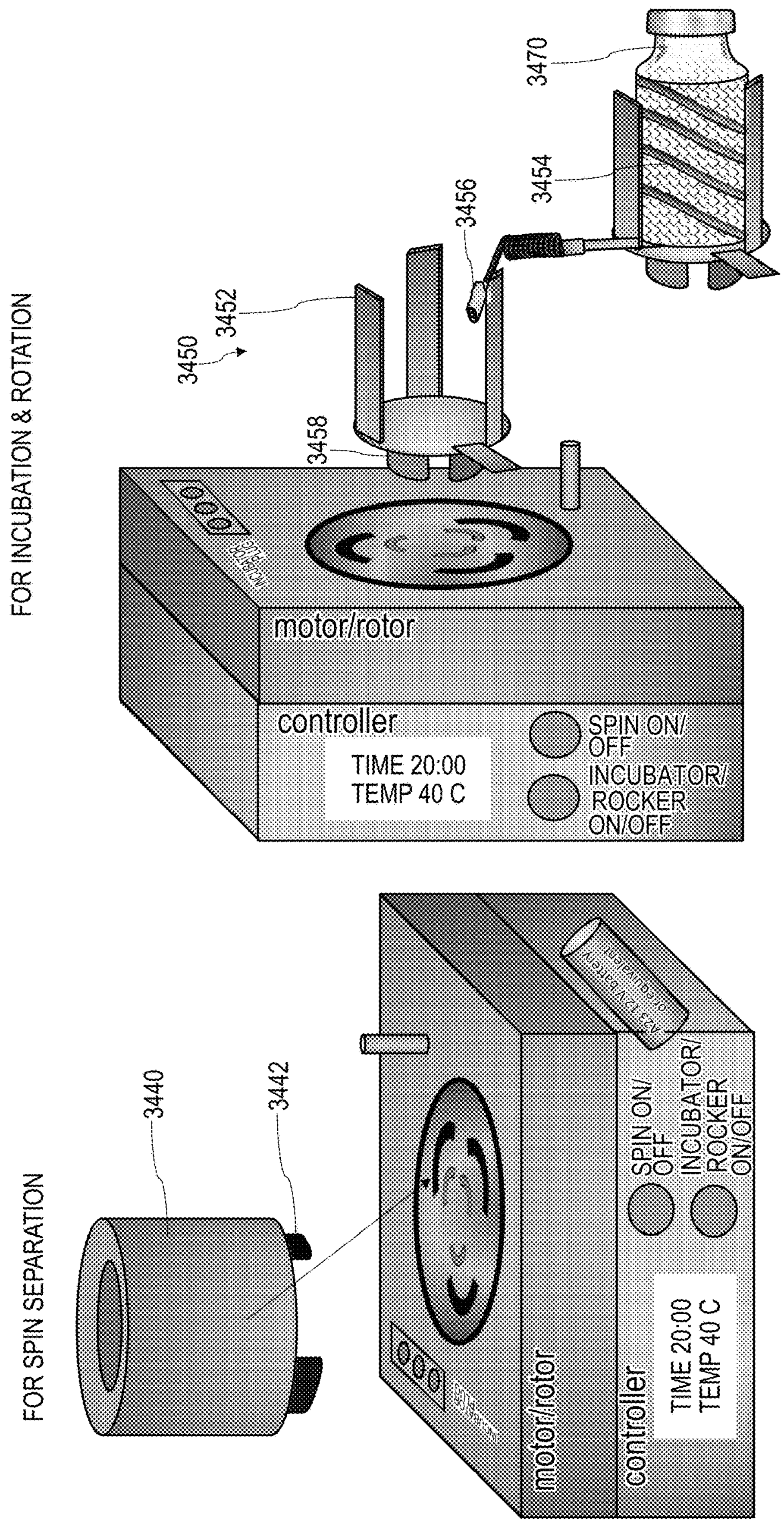

FIG. 35 illustrates an example connection collar and an example holder of the present disclosure.

Figure 36:
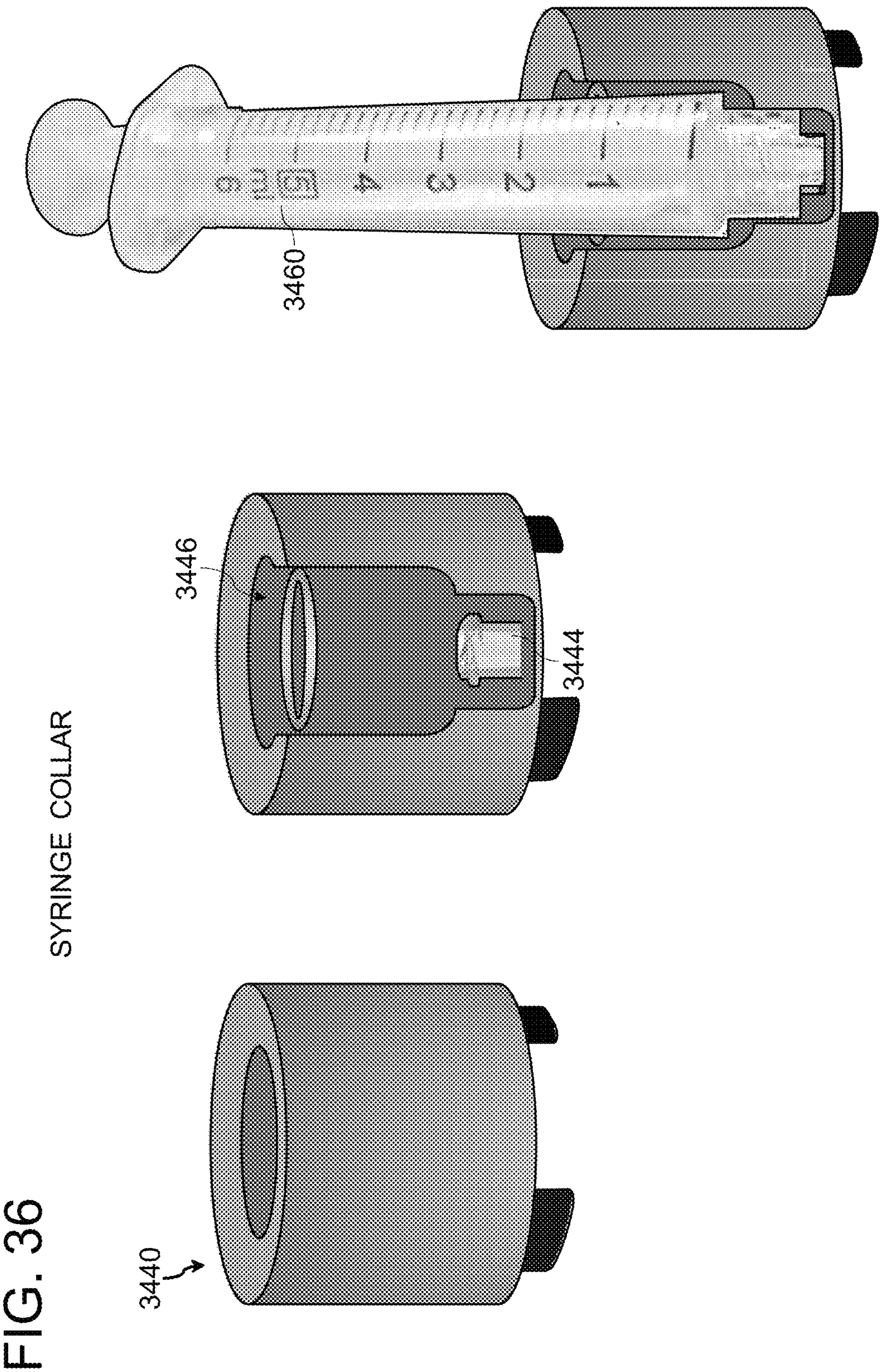

FIG. 36 illustrates an example connection collar in greater detail.

Figure 37:
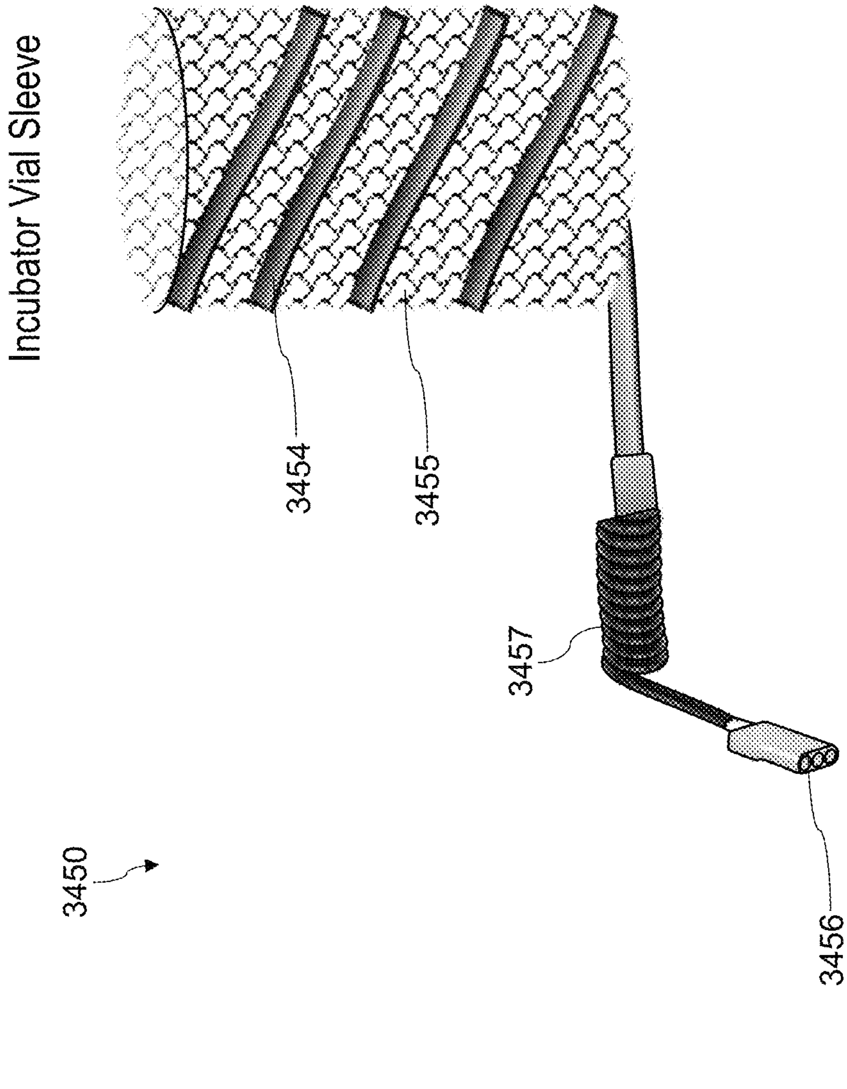

FIG. 37 illustrates an example holder in greater detail of the present disclosure.

Figure 38:
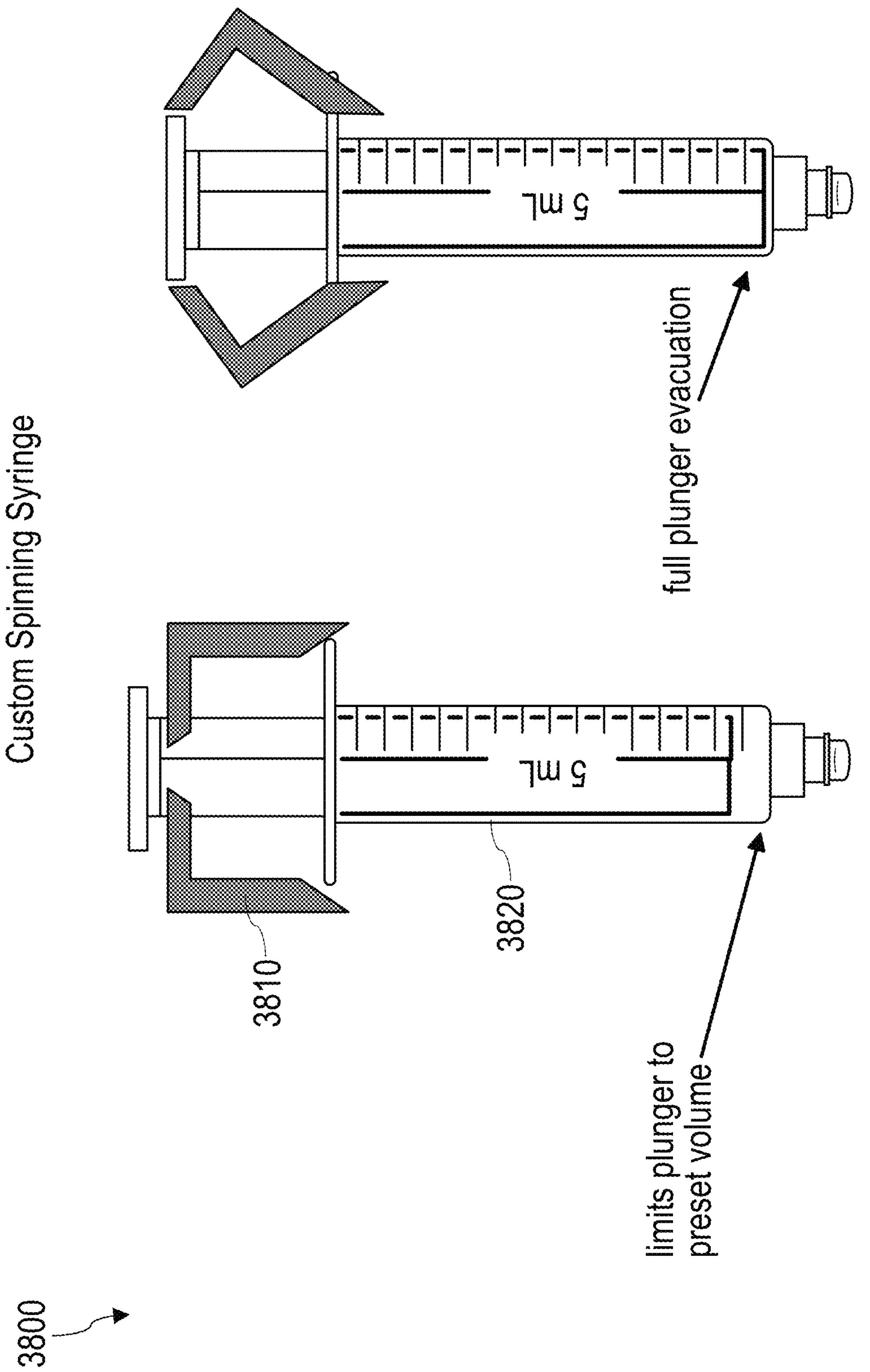

FIG. 38 illustrates an example spinning syringe of the present disclosure.

Figure 39:
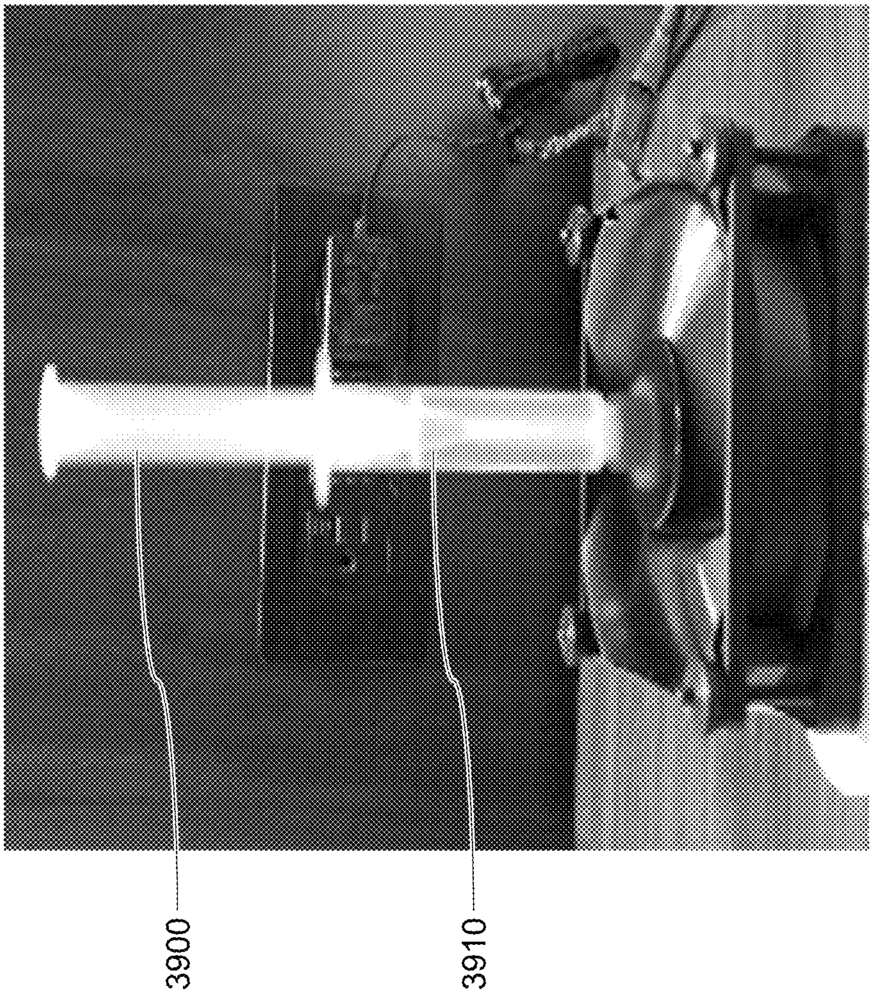

FIG. 39 depicts a device for use in the phase separation step of the microbubbles.

Figure 40:
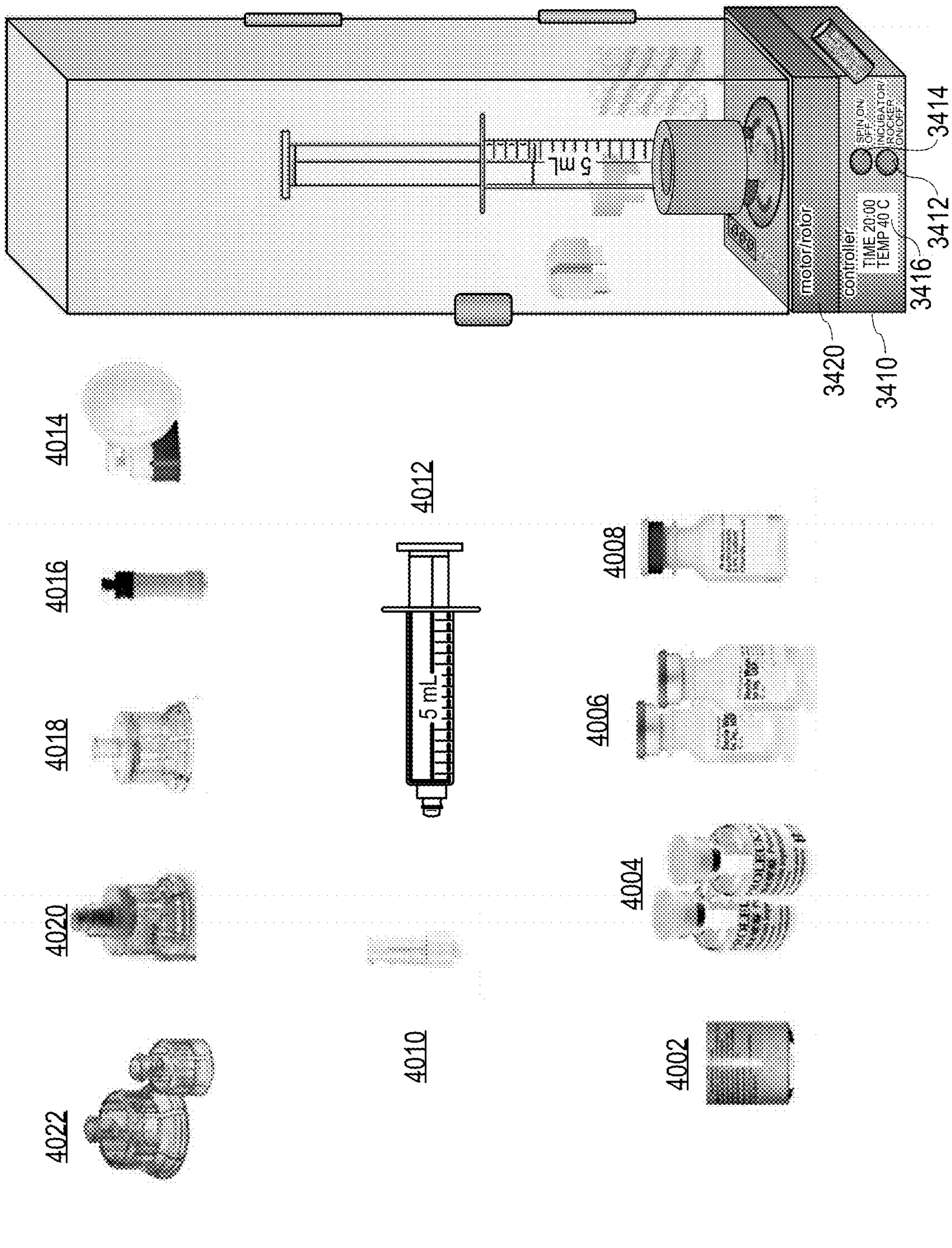

FIG. 40 illustrates example components of on-site eIL-2 preparation of the present disclosure.

Figure 41:
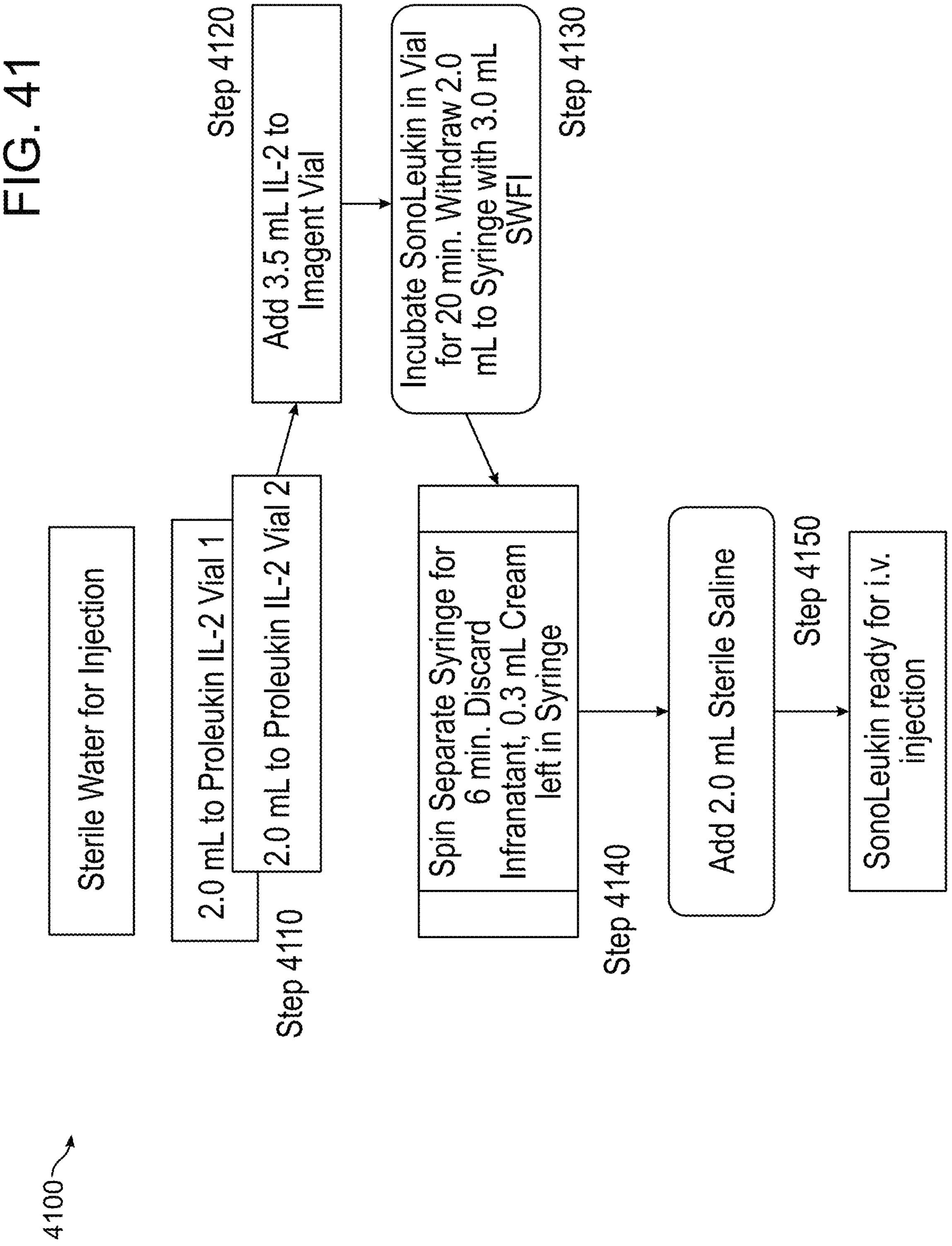

FIG. 41 illustrates a flowchart for an example method for on-site eIL-2 preparation using the components in FIG. 40.

Figure 42:
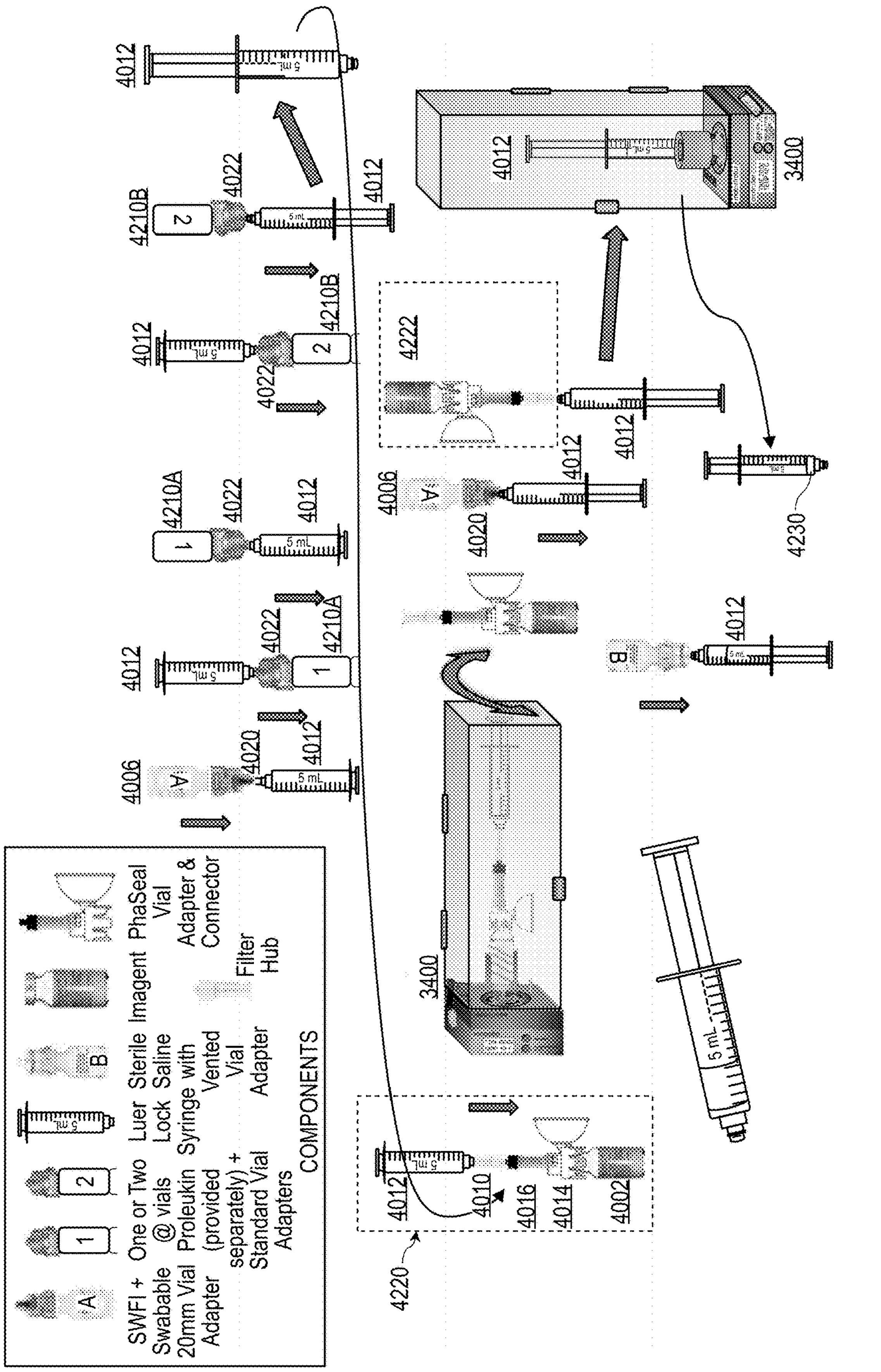

FIG. 42 illustrates a diagram for on-site eIL-2 preparation using the components in FIG. 40.

Figure 43A:
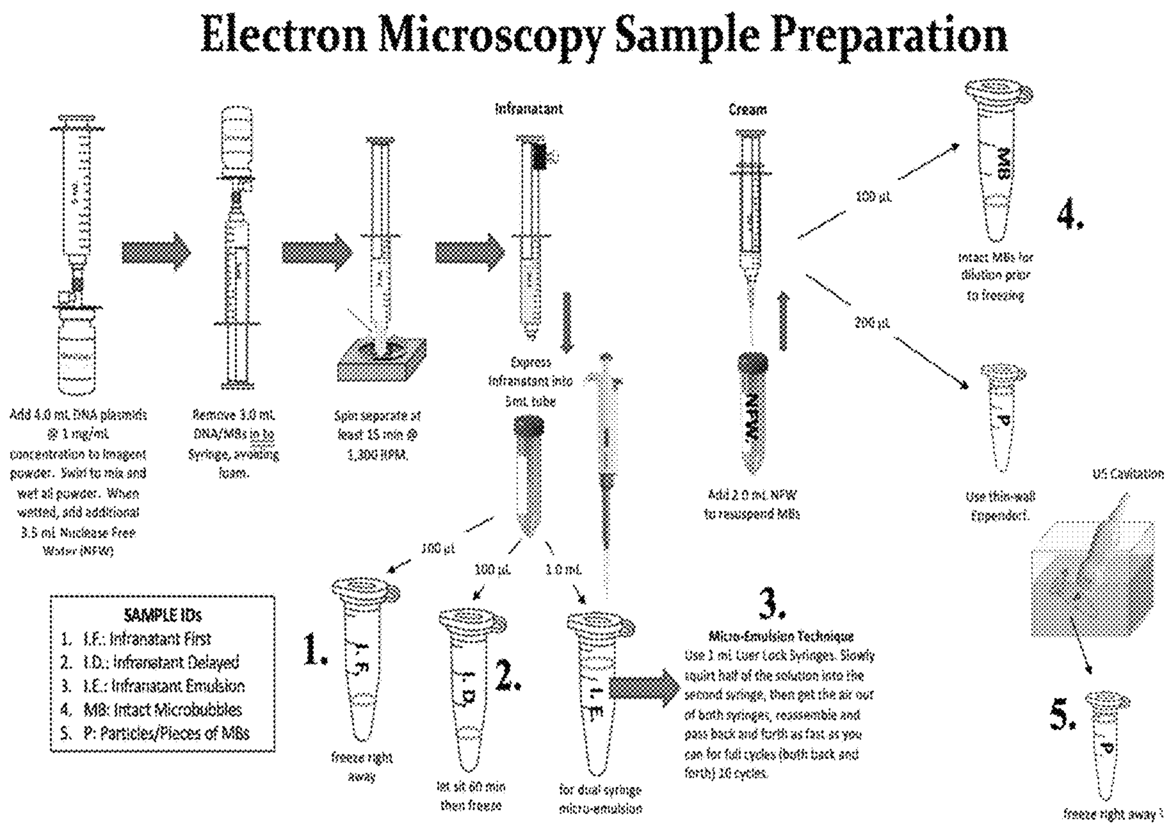

FIG. 43A is a schematic of a cryo TEM testing protocol. FIG. 43B is a cryo transmission election microscopy (TEM) image showing a nanoscale carrier of the present invention. FIG. 43C is a histogram for object 43Ba in FIG. 43B. FIG. 43D is a histogram for the object 43Bb in FIG. 43B. FIG. 43E is a histogram for object 43Bc in FIG. 43B.

FIG. 44A is a cryo TEM image showing various liposomal objects of the present invention after microbubble implosion. FIG. 44B is a histogram for object 44*a* in FIG. 44A. FIG. 44C is a histogram for object 44*b* in FIG. 44A.

Figure 45:
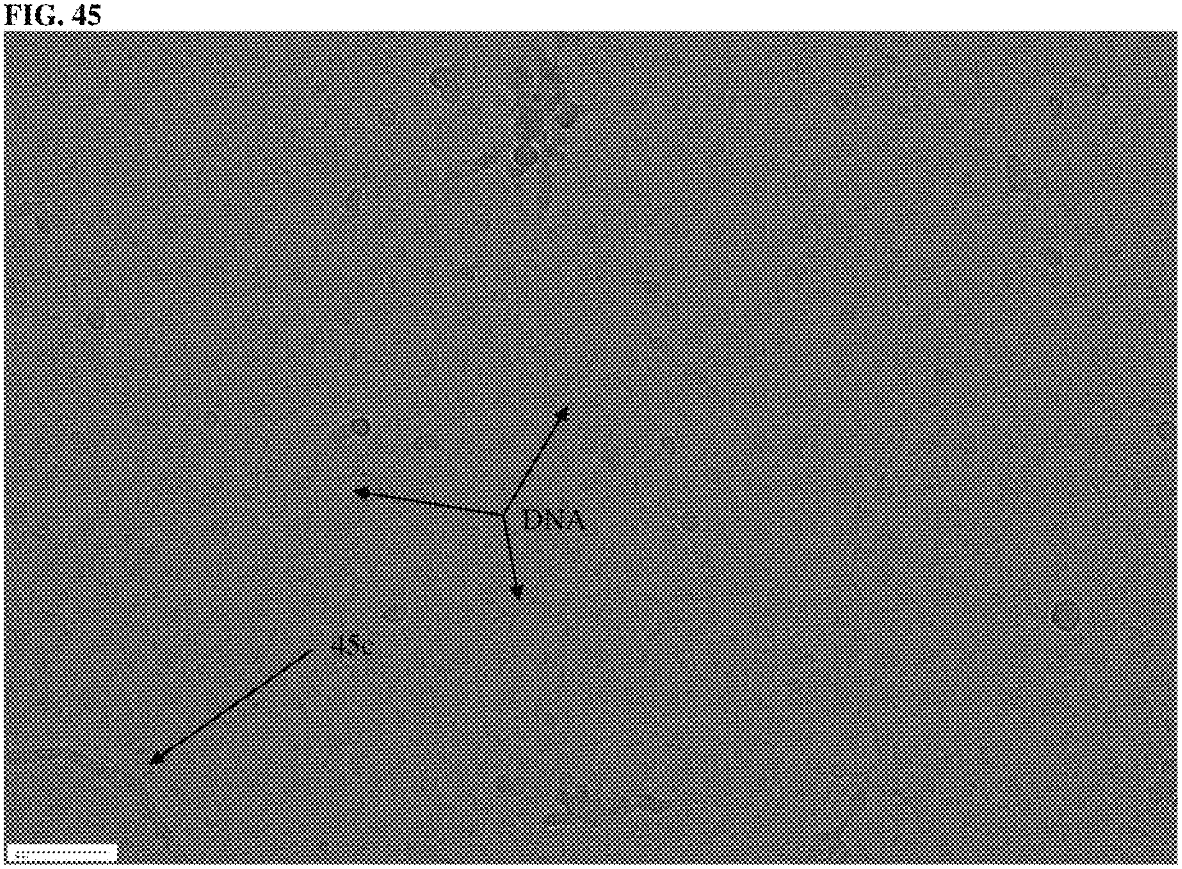

FIG. 45 is a cryo TEM image showing the presence of DNA and a liposome.

Figure 46:
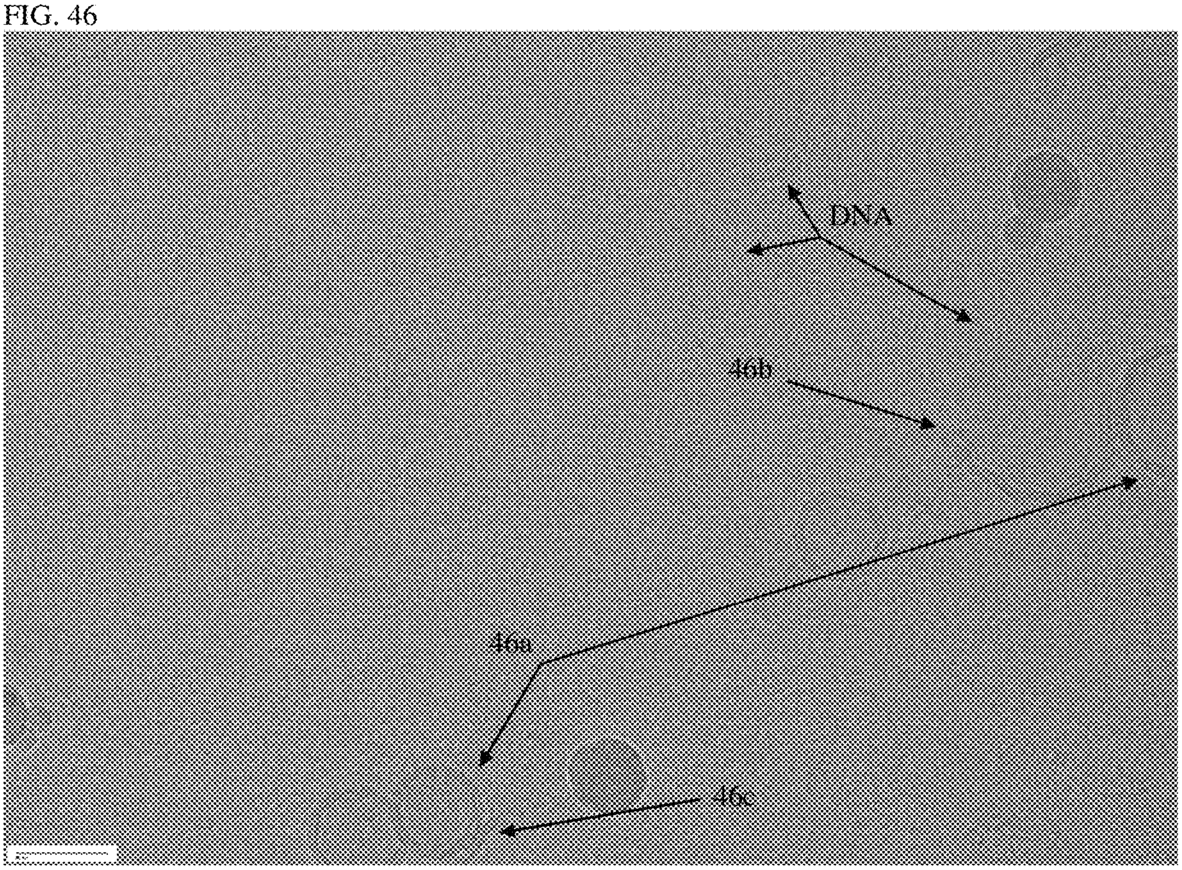

FIG. 46 is a cryo TEM image showing various lipid objects or structures after processing the microbubble infranatant using an emulsion technique.

Figure 47:
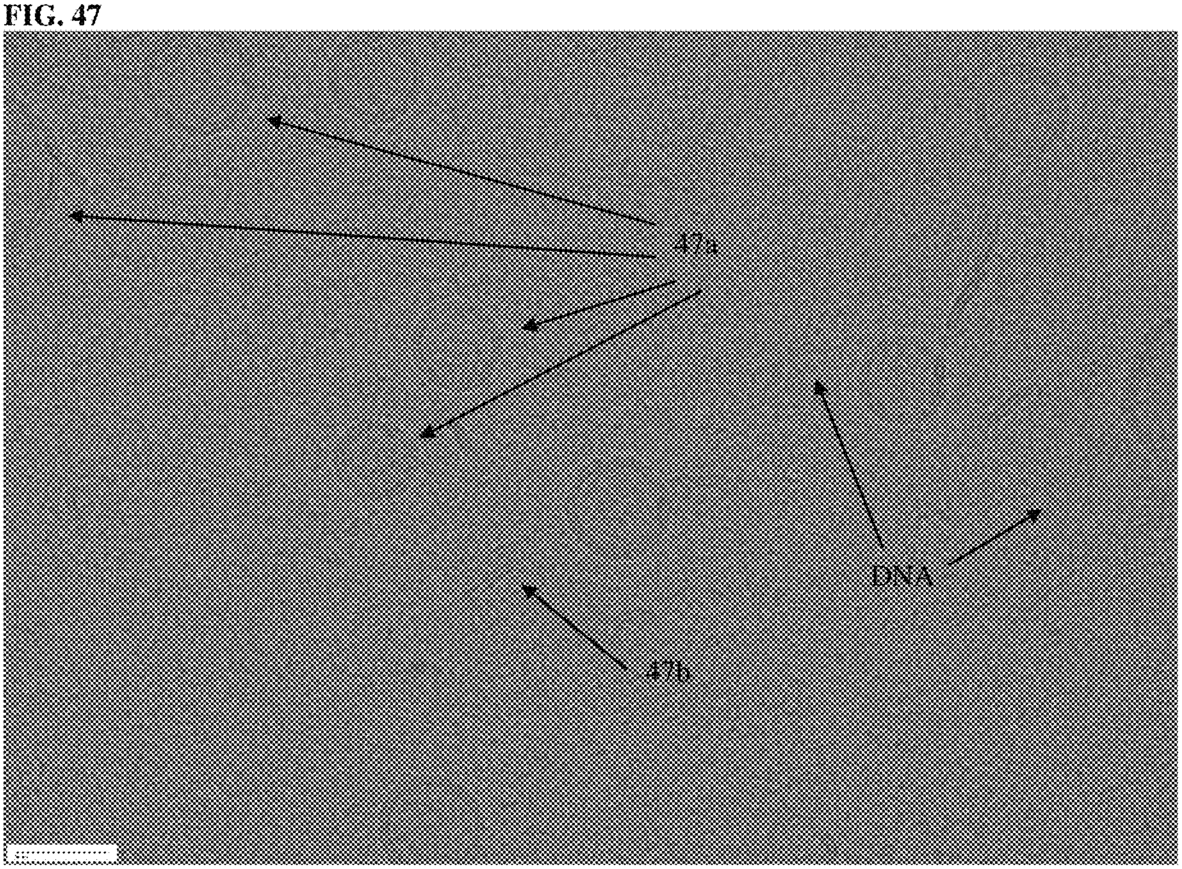

FIG. 47 is a cyro TEM image showing various lipid objects present in the carrier infranatant.

Figure 48A:
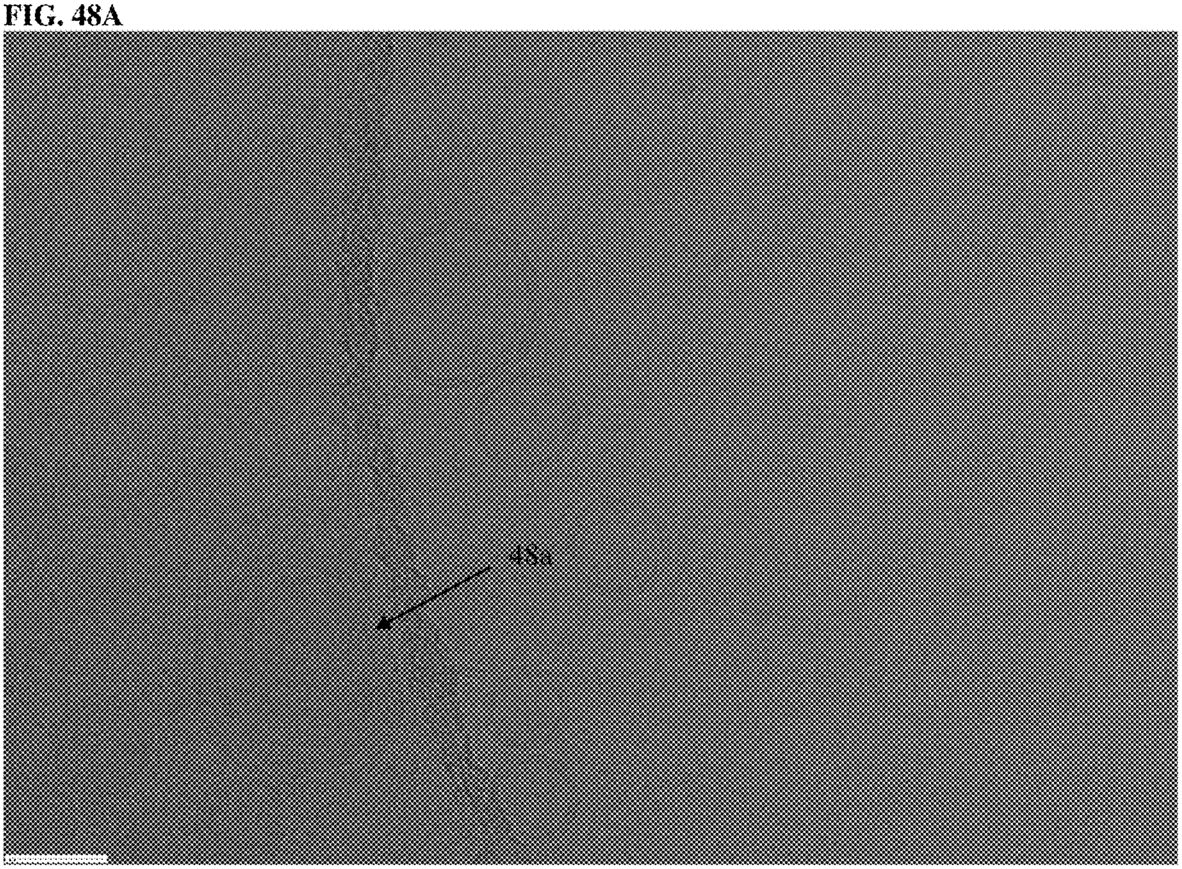
Figure 48B:
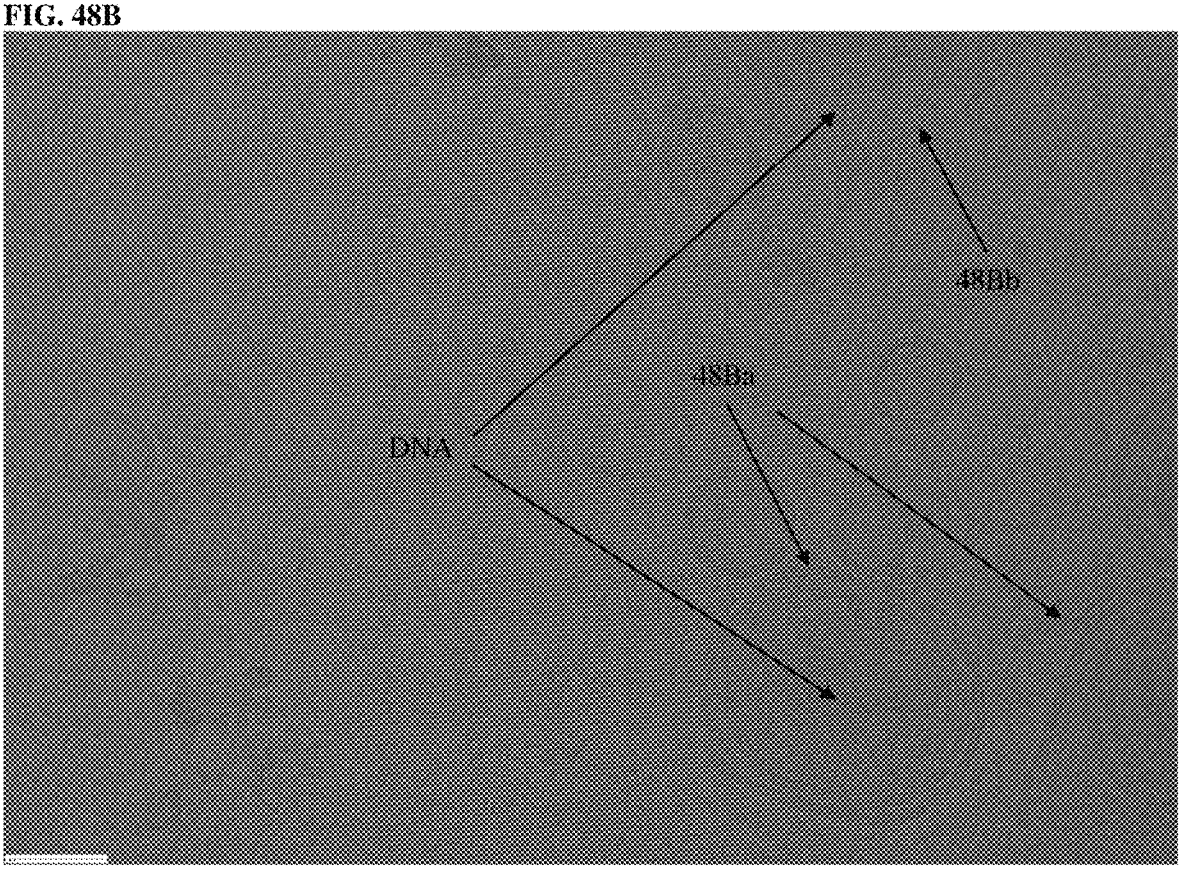
Figure 48C:
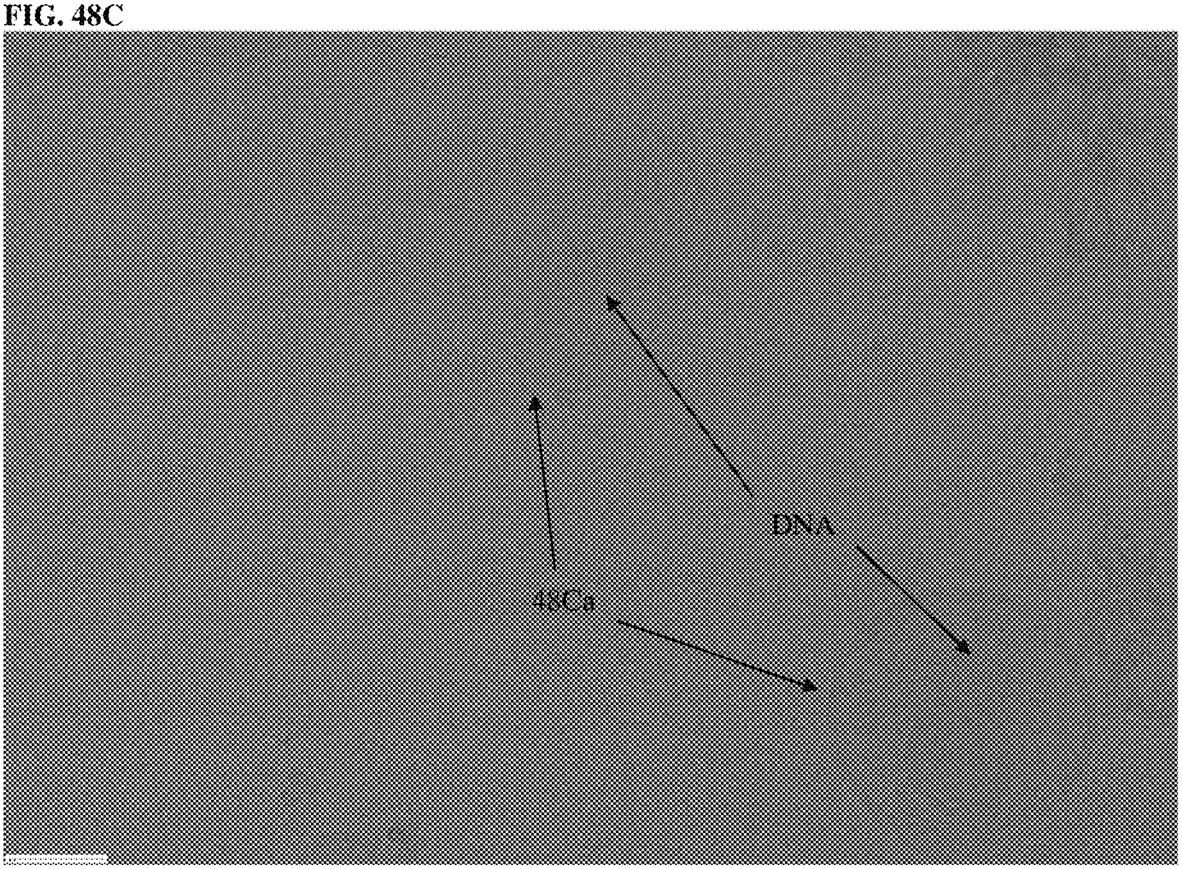

FIG. 48A-C are cryo TEM images showing various lipid objects present in the carrier infranatant.

Figure 49A:
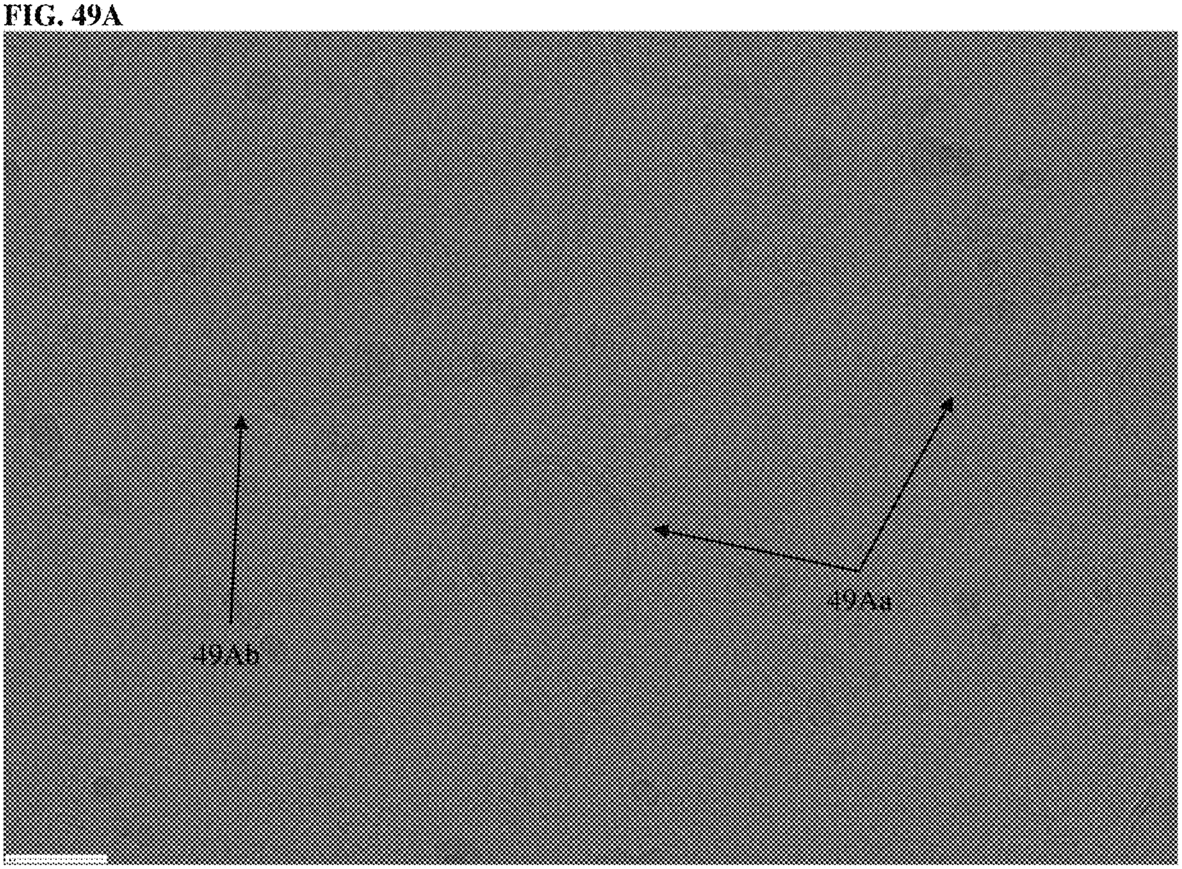
Figure 49B:
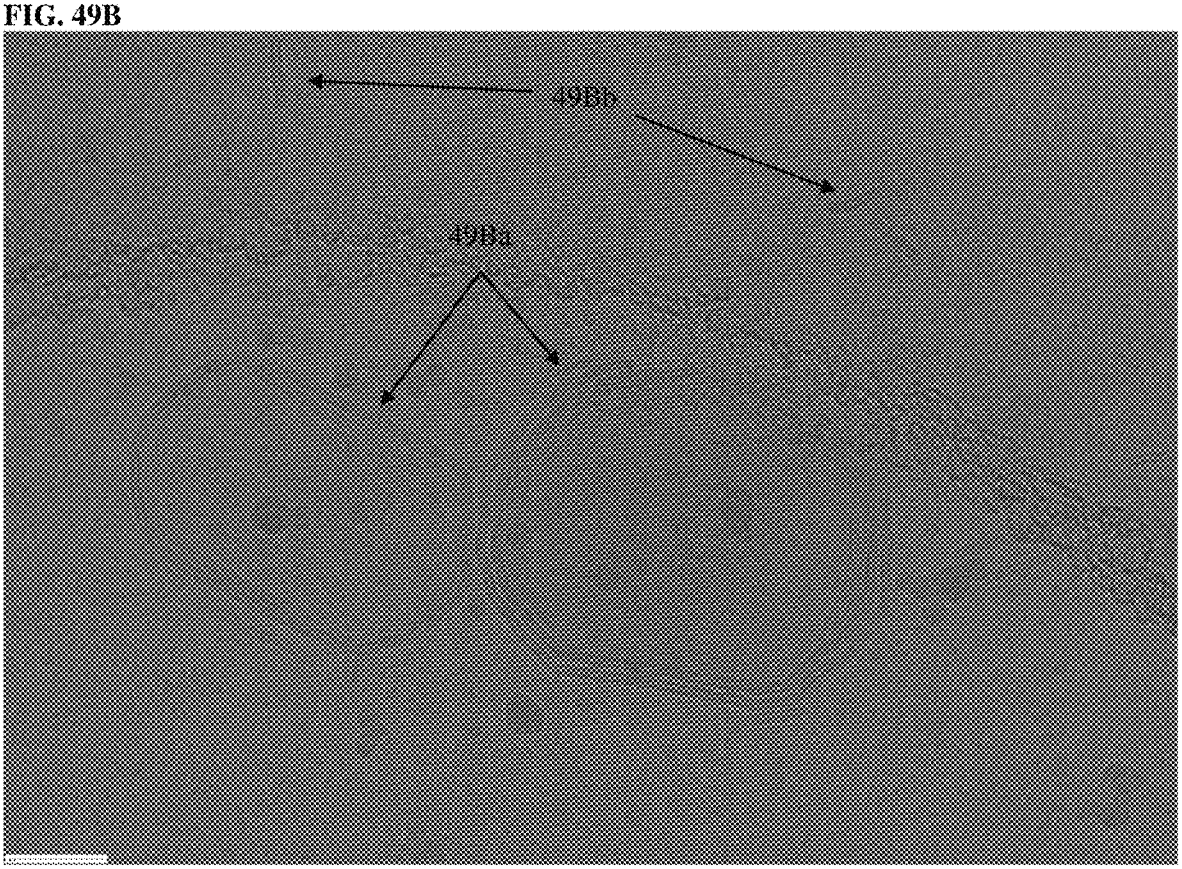

FIGS. 49A-B are cryo TEM images of the infranatant from the carrier reconstituted as per manufacturer's FDA labeling and instructions.

Figure 50A:
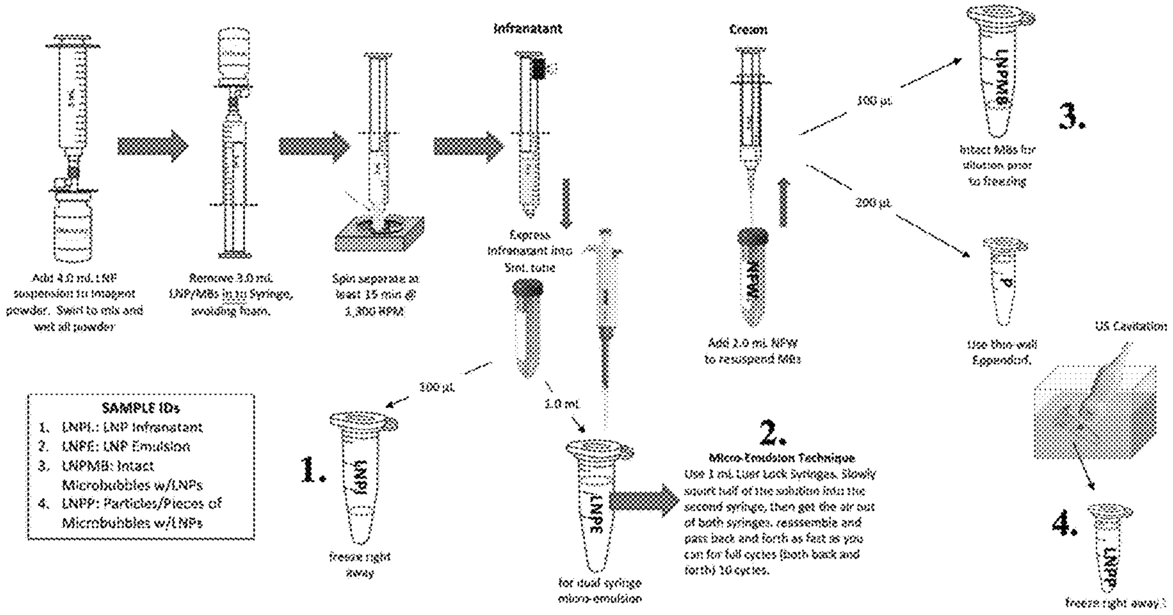

FIG. 50A is a schematic of a cryo TEM testing protocol. FIGS. 50B-E are cryo TEM images of the infranatant from the carrier reconstituted with a vaccine solution containing lipid nanoparticles (LNPs) encapsulating messenger RNA (mRNA).

DETAILED DESCRIPTION OF THE INVENTION

The present invention provides compositions comprising a plurality of carriers, e.g., microbubbles, wherein an at least one active agent is associated with the plurality of carriers, for example, encapsulated within the plurality of carriers (e.g., between the gas/shell interface and/or within the gas of the carriers), and/or bound to the surface (e.g., the exterior or interior surface, of the carriers) for delivery to a subject. In addition, the present invention provides compositions comprising a plurality of carriers, e.g., microbubbles, to be co-administered with compositions comprising at least one active agent to a subject. Furthermore, the present invention provides compositions comprising a plurality of carriers, e.g., microbubbles, wherein an at least one active agent is associated with the plurality of carriers, for example, encapsulated within the plurality of carriers (e.g., between the gas/shell interface and/or within the gas of the carriers), and/or bound to the surface (e.g., the exterior or interior surface, of the carriers), to be co-administered with compositions comprising an at least one free active agent, wherein the at least one active agent is not associated with the plurality of carriers, to a subject.

The present invention also provides methods of treating a disease or condition, and methods of targeted delivery of an active agent, e.g., to a target tissue, e.g., an organ, a tissue, a tumor site, in a subject, using the carrier based compositions of the invention. Furthermore, the present invention provides methods for improving efficacy of therapeutics, e.g., for treating a disease or disorder in a subject by identifying or determining or selecting a target characteristic, determining the amount of a therapeutic agent to be delivered to reach the target characteristic, and delivering the desired amount of active agent to reach the target characteristic.

In particular, the inventors of the present invention have surprisingly discovered that by associating or co-administering the active agent with carriers, the level of the active agent required to achieve a therapeutic effect is substantially lower than the level of the active agent required to achieve a therapeutic effect when administered without being associated or co-administered with carriers, e.g., by systemic administration without being associated or co-administered with carriers.

The compositions of the invention are protected and/or targeted. Creating the compositions just prior to administration allows for the rapid use of different combinations of active agents that could benefit from protection or targeting, or both, since the active agent (i.e., particularly an FDA approved agent) and the delivery vehicle, (i.e., particularly an FDA approved microbubble, such as Imagent) have known safety and toxicology profiles, are manufactured at scale, and able to be mixed into a complex just prior to or at the time of administration. This provides significant advantages when compared to reformulating an agent at the research and development or manufacturing stage to provide a means of protection in circulation or targeting, or both protection and targeting, such as by pegylation or through the use of nanoparticles, which may introduce issues related to manufacturing, biocompatibility, safety or efficacy of the carrier or the therapeutic agent.

The present invention also discloses devices and methods related to the preparation of the compositions of the invention after the manufacturing process and at the point of care (for example, but not limited to, in the hospital, outpatient center, medical office or facility, pharmacy, bedside, patient home, etc.), and methods for treating a disease or disorder in a subject using the compositions of the invention. The present invention further describes means to change the amount of active agent (e.g., concentration) that is attached or bound to said carrier. Additionally, the present invention relates to the creation of complexes consisting of multiple agents, or different classes of agents, with a carrier.

The section headings used herein are for organizational purposes only and are not to be construed as limiting the subject matter described. All references cited herein, including patent applications and publications, are incorporated herein by reference in their entireties for any purpose.

I. Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

The term "active moiety" as used herein refers to the molecule or ion, excluding those appended portions of the molecule that cause the drug to be an ester, salt (including a salt with hydrogen or coordination bonds), or other non-covalent derivative (such as a complex, chelate, or clathrate) of the molecule, responsible for the physiological or pharmacological action of the drug substrate.

The term "active pharmaceutical ingredient" or "API" as used herein refers to any substance or mixture of substances intended to be used in the manufacture of a drug product and that, when used in the production of a drug, becomes an active ingredient in the drug product. Such substances are intended to furnish pharmacological activity or other direct effect in the diagnosis, cure, mitigation, treatment or prevention of disease or to affect the structure and function of the body. Also see, e.g., International Conference on Harmonization of Technical Requirements for Registration of Pharmaceuticals for Human Use (ICH) Q7, Good Manufacturing Practice Guidance for Active Pharmaceutical Ingredients).

The term "administration" as used herein refers to any method or process of delivering a diagnostic, therapeutic or theranostic substance into a patient and may include, but is not limited to, parenteral and non-parenteral routes, such as intravenous, subcutaneous, intramuscular, intracranial, intranodal, intratumoral, intralesional, intraperitoneal, directly into an organ, transdermal, or oral.

The term "agent" as used herein refers to a therapeutic agent or an agent that is intended to create directly or indirectly a therapeutic effect, whether by itself or in combination with a delivery vehicle having, or intended to have a beneficial effect on a patient. The agent can be, but is not limited to, a small molecule, a protein, a peptide, a monoclonal or polyclonal antibody, a nucleic acid, a plasmid, RNA, DNA, or a cell, a gene, a vector or a plasmid encoding a gene, or a component of a gene editing system.

The term "free active agent", as used herein, refers an active agent that will not be associated or encapsulated within a carrier, e.g., a microbubble, upon contacting with a carrier, e.g., a microbubble.

The term "substantially equivalent therapeutic effect" of an active agent, as used herein, refers to an effect that is about 50%, about 60%, about 70%, about 75%, about 80%, about 85%, about 90%, about 91%, about 92%, about 93%, about 94%, about 95%, about 96%, about 97%, about 98%, about 99% or about 100% of the therapeutic effect of the active agent. The therapeutic effect may be assessed by a variety of art recognized techniques to assess, for example, efficacy, bioavailability, etc. For example, a therapeutic effect may be a reduction in tumor size or growth.

The term "subject" as used herein refers to an animal, such as a mammal, including a primate (such as a human, a non-human primate, e.g., a monkey, or a chimpanzee), or a non-primate (such as a cow, a pig, a horse, a goat, a rabbit, a sheep, a hamster, a guinea pig, a cat, a dog, a rat, or a mouse). In an embodiment, the subject is a human.

The term "carrier" as used herein refers to a structure either inside or outside of a cell consisting of a substance enclosed by an envelope or shell. The inside of the carrier may be a liquid, gas or solid, while the shell may be a lipid. An example of a carrier is a microbubble that contains a gas enclosed in a biocompatible shell. Other examples of a carrier are a nanoparticle, nanodroplet, vacuole, lysosome, exosome, endosome, micelle or cell, and may be constructed from of biological, chemical, or synthetic materials. The term "vehicle" as used herein is interchangeable or synonymous with the term "carrier."

The term "co-administered" or "co-administration" as used herein refers to administered at approximately the same time as another agent, or while another agent is in circulation (which may be hours to days to weeks after an agent is administered).

The term "complex" as used herein refers to the formation of a combination product using the active pharmaceutical ingredient (API) and companion delivery vehicle while preserving the integrity of the API.

The term "data" as used herein refers to information relating to a patient's gender, race, height, weight, age, condition, medication regimen, demographics, or genetic profile. Data may also be related to an organ, tissue, gas, solid, fluid, cell, particle, molecule, tumor, microenvironment, stroma, vasculature, treatment target, or non-treated organ, tissue, gas, solid, fluid, cell, particle, molecule, tumor, microenvironment, stroma, vasculature. Data on properties or characteristics of an organ, tissue gas, solid, fluid, cell, particle, molecule, tumor, microenvironment, stroma, vasculature, etc. may include location, proximity to other tissues, volume, area, dimensions, heterogeneity, fibrosis, chemical, electrical, biological, physical, anatomical, histological, pathological, genetic, genomic, proteomic, transcriptomic, spatial, volumetric, temperature, energy, bioeffect, reaction, stiffness, elasticity, density, permeability of tissue, vascularity, vascular density, size or duration of a vascular opening, viscosity, or flow rate. The data may be related to, but not limited to, the therapeutic agent, delivery vehicle, or drug/drug complex, such as PD, PK, AUC, MTD, molecular weight, chemical composition, event sequence, temporal patterns of the agent-target/disease/pathogen dynamics, flow rate, biodistribution, injected dose, drug interactions, date and time of administration, date and lot number of manufacture, name of manufacturer, amount of free agent, amount of therapeutic agent within or on delivery vehicle, amount of carrier, amount of microbubble. Data may include information on instrumentation, device or equipment used before, during, or after treatment, such as model number, serial number, lot number, manufacture information, measure of power, energy, mechanical index, peak negative pressure, radiation force, force, frequency, pulse length, duration, duty cycle, frame rate, transmission time, receive time, attenuation, displacement, action, reaction, mechanical, physical, effect, bioeffects, transmit or receive data, input or output data created as a result of the use of such instrument, device or equipment. Data may also include time of day, or duration of treatment, hospital or treatment location or setting information, or user or operator information (such as user name, age, title, number of times such user has used said device, etc.). The data may be related to, but not limited to, events that occurred prior to, during, or after the administration of an agent and may include clinical outcomes data.

The term "delivery vehicle" as used herein refers to a transporter that carries a therapeutic agent, whether attached to some element on the surface, attached directed to the surface, embedded onto the surface, or contained partially or completely within the surface, or within the interior of the vehicle.

The term "device" as used herein refers to a device, equipment, instrument, processor, sensor, externally or internally applied, emitting, transmitting or receiving a signal, energy or data and used as part of treatment of the present invention. The device may include, but is not limited to a, physical, mechanical, digital, ultrasonic, electrical, or magnetic instrument.

The term "associated" or "association" is used herein to mean the enclosure of an active agent within the interior of, or the attachment or binding onto the interior or exterior surface of a carrier or a delivery vehicle, e.g., a microbubble. Such association, e.g., encapsulation within the delivery vehicle or bound with the delivery vehicle, is intended either to protect the agent while in circulation within a body or to enable the active targeting of the delivery of said agent, or both protect and target.

The term "interacted" as used herein may refer to a temporary or transient binding of the active agent to the surface of the lipid.

The term "FDA" is used herein to mean the Food and Drug Administration of the United States Department of Health and Human Services or any successor agency thereof performing similar functions.

The term "Imagent®" or "Imagent" as used herein refers to that certain microbubble as listed in the NDA 21-191. Imagent also may be used herein interchangeably with carrier when referring to the use of microbubbles.

The term "microbubble" as used herein refers to a microsphere comprising a biocompatible shell surrounding at least one biocompatible gas.

The term "NDA" as used herein refers to a New Drug Application (as more fully described in 21 CFR 314.50 et seq. or its successor regulation), or any amendment or supplement thereto, with respect to NDA 21-191 approved by the FDA.

II. Compositions of the Invention

The present invention provides compositions comprising a plurality of carrier, e.g., microbubbles, wherein an at least one active agent is associated with the plurality of carriers, for example, encapsulated within the plurality of carriers (e.g., between the gas/shell interface and/or within the gas of the carriers) and/or bound to the surface (e.g., the exterior or interior surface, of the carriers) for delivery to a subject, e.g., a target site, e.g., an organ, a tissue, or a tumor site in the subject. In addition, the present invention provides compositions comprising a plurality of carriers, e.g., microbubbles, to be co-administered with compositions comprising at least one active agent to a subject, e.g., to a target tissue such as an organ, a tissue, a tumor site, in a subject. Furthermore, the present invention provides compositions comprising a plurality of carriers, e.g., microbubbles, wherein an at least one active agent is associated with the plurality of carriers, for example, encapsulated within the plurality of carriers (e.g., between the gas/shell interface and/or within the gas of the carriers), and/or bound to the surface (e.g., the exterior or interior surface, of the carriers), to be co-administered with compositions comprising an at least one free active agent, wherein the at least one active agent is not associated with the plurality of carriers, to a subject.

In particular, the inventors of the present invention have surprisingly discovered that by associating or co-administering the active agent with carriers, the level of the active agent required to achieve a therapeutic effect is substantially lower than the level of the active agent required to achieve a therapeutic effect when administered without being associated or co-administered with carriers, e.g., by systemic administration without being associated or co-administered with carriers.

Accordingly, in one aspect, the present invention provides a composition comprising a plurality of carriers, wherein an at least one active agent is associated with the plurality of carriers for delivery to a subject, wherein the level of the at least one active agent associated with the plurality of carriers is lower than the level of the active agent required to achieve a therapeutic effect when administered without being associated with carriers.

In some embodiments, the level of the at least one active agent associated with the plurality of carriers is lower than the level of the active agent required to achieve a therapeutic effect when administered without being associated with carriers and by systemic administration.

In some embodiments, the level of the at least one active agent associated with the plurality of carriers is lower than the level of the active agent required to achieve a substantially equivalent therapeutic effect when administered without being associated with carriers. As used herein, the substantially equivalent therapeutic effect is about 50%, about 60%, about 70%, about 75%, about 80%, about 85%, about 90%, about 91%, about 92%, about 93%, about 94%, about 95%, about 96%, about 97%, about 98%, about 99% or about 100% of the therapeutic effect of the active agent when administered without being associated with carriers. In another aspect, the present invention provides a composition comprising a plurality of carriers, wherein at least one active agent is associated with the plurality of carriers for delivery to a subject, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof.

In some embodiments, the carrier releases a nanoparticle, nanodroplet, vacuole, lysosome, exosome, endosome, micelle or cell that includes at least one active agent and a lipid. Non-limiting examples of a lipid include 1,2-dimyristoyl-sn-glycero-3-phosphocholine (DMPC), or 4-dimethylaminochalcone (DMAC), or dipalmitoyl phosphatidylcholine (DPPC), or 1,2-distearyol-sn-glycero-3-phosphocoline (DSPC), 1,2-distearyol-sn-glycero-3-phosphoethanolamine-N-[methoxy(polyethylene glycol)2000] (DSPE-PEG2000), lipofectamine, or any other cationic or helper lipids.

In some embodiments, the level of the at least one active agent associated with the plurality of carriers is lower than the level of the active agent required to achieve a therapeutic effect when administered without being associated with carriers.

In some embodiments, the level of the at least one active agent associated with the plurality of carriers is lower than the level of the active agent required to achieve a therapeutic effect when administered without being associated with carriers and by systemic administration.

In some embodiments, the level of the at least one active agent associated with the plurality of carriers is lower than the level of the active agent required to achieve a substantially equivalent therapeutic effect when administered without being associated with carriers. As used herein, the substantially equivalent therapeutic effect is about 50%, about 60%, about 70%, about 75%, about 80%, about 85%, about 90%, about 91%, about 92%, about 93%, about 94%, about 95%, about 96%, about 97%, about 98%, about 99% or about 100% of the therapeutic effect of the active agent when administered without being associated with carriers.

The at least one active agent may be associated with the plurality of carriers by being encapsulated within the plurality of carriers, or the at least one active agent is associated with the plurality of carriers by binding to the interior or exterior surface of the plurality of carriers.

In some embodiments, the level of the at least one active agent associated with the plurality of carriers is about 0.001% to about 99%, about 0.001% to about 75%, about 0.001% to about 50%, about 0.005% to about 50%, about 0.005% to about 25%, or about 0.0001% to about 25% of the level of the active agent required to achieve a therapeutic effect when administered without being associated with carriers, optionally, a substantially equivalent therapeutic effect, and optionally, by systemic administration without being associated with carriers.

In some embodiments, the level of the active agent associated with the plurality of carriers is about 0.001% to about 0.005%, about 0.005% to about 0.1%, about 0.005% to about 10%, about 0.005% to about 20%, about 10% to about 50%, or about 50% to about 99% of the level of the active agent required to achieve a therapeutic effect when administered without being associated with carriers, optionally, a substantially equivalent therapeutic effect, optionally, a substantially equivalent therapeutic effect, optionally, by systemic administration without being associated with carriers. In some embodiments, the level of the active agent associated with the plurality of carriers is about 0.001%, 0.005%, 0.01%, 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or about 99% of the level of the active agent required to achieve a therapeutic effect when administered without being associated with carriers, optionally, a substantially equivalent therapeutic effect, optionally, by systemic administration without being associated with carriers.

In some embodiments, administration of the composition results in a reduced systemic toxicity, as compared to administration of a composition of the same level of active agent without being associated with carriers.

In some embodiments, administration of the composition results in a reduced systemic toxicity, as compared to administration of a composition of the active agent without being associated with carriers required to achieve a substantially equivalent therapeutic effect.

In some embodiments, the level of the at least one active agent associated with the plurality of carriers elicits an immunostimulatory effect. In some embodiments, the level of the at least one active agent associated with the plurality of carriers does not elicit an immunosuppressive effect.

A. Carriers

In some embodiments, the carrier is selected from the group consisting of a microbubble, a nanobubble, a nanoparticle, a nanodroplet, a micelle, a liposome, an exosome, a cell, and a virus.

In some embodiments, the carrier is a microbubble. Any microbubbles known in the art may be used for the compositions and methods of the present invention. Exemplary commercially available, FDA-approved microbubbles include, but are not limited to, Levovist™ (Schering AG), Imagent® (Vesselon), Optison® (GE Healthcare), Sonazoid® (GE Healthcare), SonoVue® (GE Healthcare), Lumason® (GE Healthcare), and BR38 (Bracco Suisse SA).

In one embodiment, the microbubble comprises a shell and a core.

In one embodiment, the microbubble shell comprises a polymer. Polymers suitable for use in the microbubbles for use in the compositions and methods of the present invention include, but are not limited to polyvinyl alcohol (PVA), polyethylene glycol (PEG), poly(isobutylcyanoacrylate), and Poly(lactic-co-glycolic acid) (PLGA), poly(allylamine hydrochloride) (PAH) and poly(styrene sulfonate) (PSS).

In another embodiment, the microbubble shell comprises a lipid. In one embodiment, the lipid is a phospholipid. Examples of lipids useful in the microbubbles for use in the compositions and methods of the present invention include, but are not limited to, 1,2-dimyristoyl-sn-glycero-3-phosphocholine (DMPC), 4-dimethylaminochalcone (DMAC), dipalmitoyl phosphatidylcholine (DPPC), 1,2-distearyol-sn-glycero-3-phosphocoline (DSPC), and 1,2-distearyol-sn-glycero-3-phosphoethanolamine-N-[methoxy(polyethylene glycol)2000] (DSPE-PEG2000). In one embodiment, the microbubble shell comprises DMPC.

In one embodiment, the microbubble shell comprises a lipopolymer.

In another embodiment, the microbubble shell comprises a protein. Exemplary protein useful in the microbubbles for use in the compositions and methods of the present invention include, but are not limited to, albumin.

In another embodiment, the microbubble shell comprises a surfactant. Examples of surfactants useful in the microbubbles for use in the compositions and methods of the present invention include, but are not limited to, Span 60 and Tween 80.

In a further embodiment, the shell comprises one or more of the following: a polymer, a lipid, a lipopolymer, a protein, a surfactant, or a combination thereof.

The core of the microbubbles for use in the compositions and methods of the present invention comprises a gas. In one embodiment, the gas is an inert gas. In another embodiment, the gas is nitrogen. In another embodiment, the gas is air. In still another embodiment, the gas is a perfluorocarbon gas. Exemplary perfluorocarbon gases for use in the microbubbles for use in the compositions and methods of the present invention include, but are not limited to, perfluorohexane, sulfur hexafluoride, perfluoromethane, perfluoroethane, perfluoropropane, perfluorobutane, perfluoropentane, and octafluoropropane. In one embodiment, the gas is perfluorohexane. In some embodiments, the core comprises a combination of perfluorohexane and nitrogen gas.

In some embodiments, the carriers, e.g., the microbubbles, comprise a core comprising a perfluorocarbon gas and/or nitrogen, which are surrounded by a shell that comprises lipids. In some embodiments, the carriers, e.g., the microbubbles, comprise a core comprising a perfluorocarbon gas and/or nitrogen, which are surrounded by a shell that comprises DMPC. In another embodiment, the carriers, e.g., the microbubbles comprise a core comprising a perfluorohexane gas and/or nitrogen, which are surrounded by a shell that comprises DMPC (e.g., Imagent® perflexane microspheres, as described in NDA 21-191).

A preferred embodiment of the present invention describes the use of a carrier, such as a microbubble with the following properties: ultra-thin, flexible shell for low surface tension properties; highly insoluble inert gas to prevent dissolution and allow longer circulation times; nitrogen gas to osmotically stabilize the microbubble in the bloodstream; neutral charge so as not to activate the complement system or bind to charged branches of large therapeutic agents; and, biphasic size distribution that can be optimized for greater drug delivery efficiency. Ultrasound pulses generated by commercially available ultrasound systems (or specialized ultrasound system designs for certain clinical applications) deliver appropriate levels of ultrasound to a specific tissue to activate the microbubble, whether or not at least one therapeutic agent is encapsulated therein, for the purpose of permeabilizing vessel walls.

Research has suggested that the efficiency of permeabilization may be associated with the total volume of microbubbles rather than their specific average diameter. It has also been postulated that the concentration of microbubbles can affect drug delivery efficiency. The total efficiency factor, therefore, for a given ultrasound exposure, that may describe microbubble enabled drug delivery could be $$N \times V \times A \times T = \text{Efficiency}$$

where N=the number of microbubbles per unit dose, V=total volume of microbubbles per unit dose, A is the ultrasound energy absorption characteristics of the microbubble and T=the total time for circulation in the target vessel. If microbubbles are no longer present in the vessel, ultrasound alone, at safe, low intensity levels, may not benefit drug delivery to any significant degree.

The number of microbubbles available in a dose that can be administered will be dependent upon the body's ability to accommodate higher concentrations of microbubbles in circulation at any given time. A microbubble with a positive or negative charge is likely to be recognized by the body's immune system as a foreign body and the complement system would be activated to remove it. Microbubbles carrying a neutral charge, e.g., Imagent, have been shown experimentally to have little complement activation and to have zero absorption by Kupffer Cells in the liver, potentially allowing a much higher concentration of microbubbles to be infused with minimal adverse effects.

In some embodiments, for an optimal volume parameter, Imagent has a volume weighted average diameter of 6 microns so that a large percentage of the volume of gas will be made up of larger diameter microbubbles. This is achieved by the novel manufacturing process where preformed starch molds of the bubbles are created within the lyophilized powder which, when reconstituted, produced larger diameter microbubbles without the need for additional size isolation steps.

Increased acoustic absorption efficiency is provided for with the ultra-thin, ultra-low surface tension low carbon chain phospholipid DMPC shell that allows the microbubble to optimally absorb the maximum amount of ultrasound energy upon sonication that is far greater than comparable longer chain phospholipids, or stiffer albumin protein shells. Imagent microbubbles have a very thin (~3 nm) and malleable, 1,2-dimyristoyl-sn-glycero-3-phosphocholine (DMPC), lipid shell and contain a mixture of nitrogen and vapor perfluorohexane within the core. The soft-shelled microbubble has a malleable shell that stabilizes the core in vivo above its crystalline phase transition temperature (~24° C.). For a given input ultrasound energy, the Imagent microbubble will expand and contract with greater diameter distensions without incurring destruction or inertial cavitation. Osmotically stabilized microbubbles have a thinner shell that permits larger amplitude oscillations allowing them to be subject to greater radiation forces at their peak resonant frequency and for stable cavitation to incur maximal relaxation pressures on the vessel walls for increased sonoporation at a given acoustic input intensity. Additionally, the thin, flexible shell allows for larger Imagent microbubbles to be "squeezed" through smaller diameter capillaries and achieve more contact with vessel walls for maximal sonoporation closer to the targeted regions of interest. This large displacement stable cavitation may provide for more than 20% greater permeabilization for a given input of ultrasound energy compared to other carriers with more stiff shells. The absorption properties of the thin shell will enable stable cavitation at a lower mechanical index threshold so that a larger percentage of available microbubbles in circulation achieve a therapeutic stable cavitation level. When inertial cavitation is induced, Imagent's thin, low surface tension shell may have a lower microjet velocity than stiffer shell microbubbles, which may provide a greater safety profile for higher mechanical index sonications in a therapeutic context.

To extend circulation life, in addition to the neutral charge, the Imagent microbubble possesses other properties to substantially reduce the dissolution impact of the aqueous bloodstream. The interior gas used is a perfluorohexane that has a very low solubility index. For each $CF_2$ group added to a fluorocarbon gas, the solubility in water is decreased approximately by an order of 8.0. So microbubbles that use fluoropropanes (3 $CF_2$ groups) and fluorobutanes (4 $CF_2$ groups) will have a far faster dissolution time constant in blood than the Imagent perfluorohaexane (6 $CF_2$ groups). A benefit of the lengthened circulation time and neutral charge of Imagent would be its persistence in the liver and spleen. As increased numbers of Imagent microbubbles collect in the liver or spleen, additional sonication of those organs (or others in which Imagent persists) may provide benefits of priming T-Cells within those organs that would provide systemic benefits potentially well beyond the time of the sonoporation treatment.

The thin DMPC shell may permit larger amplitude oscillations when subjected to ultrasound, but could lack the ability to retain the core material driven out by the Laplace pressure (heightened internal pressure due to curvature and surface tension) of the microbubble. To avoid the dissolution of the Imagent microbubble, nitrogen is added to the gas core so that its partial pressure is equivalent to that of human tissue and blood. Imagent includes nitrogen to osmotically stabilize with the blood nitrogen gas concentration thus structurally reducing the blood pressure surface tension on the microbubble. Balancing the partial pressures of nitrogen within and outside of the microbubble creates an osmotically stabilized microbubble capable of retaining the perfluorohexane core for longer. An osmotically stabilized microbubble will persist in the blood stream longer as its original size distribution enables longer and multiple sonication treatments during a single bolus injection.

The microbubbles may be uniform in size or the plurality of microbubbles may comprise microbubbles of different sizes. In one embodiment, the microbubbles are from about 1 μm to about 10 μm in diameter. In one embodiment, the microbubbles are from about 2 μm to about 8 μm in diameter. In one embodiment, the microbubbles are from about 1 μm to about 5 μm in diameter. In another embodiment, the microbubbles are from 1 μm to about 4 μm in diameter. In another embodiment, the microbubbles are from about 1 μm to about 3 μm in diameter. In a further embodiment, the microbubbles are from about 1 μm to about 2 μm in diameter. In one embodiment, the microbubbles are about 1 μm in diameter. In another embodiment, the microbubbles are about 4.5 μm in diameter.

In one embodiment, the plurality of microbubbles has a diameter distribution having multiple peaks. In one embodiment, the microbubbles have two peaks in their diameter distribution. In one embodiment, the microbubbles, e.g., Imagent, have two peaks in its diameter distribution—one peak corresponding to a diameter of about 1 μm and a second peak corresponding to a diameter of about 4.5-5 μm. Although there are a large number of 1 μm bubbles in a given volume of Imagent, the vast majority of the volume of bubbles is represented by the 5 μm distribution. The efficiency of sonoporation is directly related to microbubble size and number present in the region of interest. An embodiment of the present invention may apply a bifrequency ultrasound pulse sequence to optimally stimulate the microbubbles to achieve stable cavitation. The smaller diameter microbubbles will more efficiently cavitate with an ultrasound frequency pulse range of 2.5 to 4.0 MHz whereas the larger diameter will more efficiently cavitate with an ultrasound frequency pulse range of 0.5 MHz to 2.0 MHz.

Due to their smaller gas volume, the smaller diameter microbubbles will circulate for the shortest period of time at which point there is insufficient gas volume to keep the bubble intact with the surface pressure from the bloodstream. Therefore, an embodiment of the present invention may use initial sonication pulses optimized for the smaller diameter microbubbles with a higher frequency sonication. After the initial higher frequency pulses are completed for a specified duration (for example, approximately 10 to 25% of the total sonication time), the remaining sonication time may be either automatically or manually switched to the lower frequency more optimized for the larger diameter microbubbles in the biphasic distribution. As an example, approximately 75% to 90% of the sonication time may be optimized for the larger diameter microbubbles that last longer in circulation and represent the largest volume weighted component to the microbubble dose.

Transient inertial cavitation may provide beneficial sonoporation capabilities. It may be a desired objective of the present invention to take advantage of this effect while minimizing risk for longer sonication exposures at peak negative pressures that induce widespread inertial cavitation. The present invention describes transient increases of acoustic intensity that initiate widespread microbubble destruction, for example on the order of a fraction of one second up to two or four seconds duration, can be periodically interposed during the sonication that otherwise predominantly activates stable cavitation. For example, during a five-minute sonication period, the ultrasound system can either manually or through automated software transiently increase the mechanical index of pulses above 1 MPa at minutes 1, 2, 3 and 4 that will ensure all microbubbles within the field will burst due to inertial cavitation. New circulating microbubbles will replace those that are destroyed within 5-10 seconds so that the continuing sonication at the lower acoustic intensity can continue to stably cavitate microbubbles in proximity to a target tissue and continue the sonoporation effect until the next inertial cavitation burst or until the sonication is complete. As the total sonication time is adjusted to optimize for specific tumor types or for a specific combination of agents, the intervals of high mechanical index bursts can be increased or decreased. For example, during a 5-minute total treatment time the bursts may be scheduled at intervals of 10 seconds, 30 seconds, 1 minute or 1.5 minutes. For a 10-minute total sonication time, the bursts may be scheduled at 2, 4, 6 and 8 minutes.

The combination of either stable or inertial cavitation of circulating microbubbles in a blood vessel has also been shown to activate an immune response to attract T Cell CD8+ cytotoxic T-lymphocytes (killer T Cells), CD4+ and or dendritic cells to adhere to the vessel wall at the point of sonoporation treatment and to be absorbed to the tissue in significantly higher concentrations. The larger diameter distensions allowed by the Imagent's thin shell, low solubility gas and osmotic stabilization with nitrogen may create a greater immune response for a given sonication energy and duration. In addition, the transient inertial cavitation pulses may increase this immune response.

In order to attract a greater T Cell immune response one preferred method would be to have intermittent high MI flashes where the ultrasound intensity would transiently reach a level to destroy microbubbles in the field of view. While high MI flashes have been used in diagnostic imaging for re-perfusion studies, in therapeutic drug delivery high MI flashes may preferentially activate an immune response at the site of tumor to attract the adhesion and absorption of more CD8+ cytotoxic T Cells, as well as create Reactive Oxygen Species that may be beneficial in a hypoxic tumor microenvironment.

In one embodiment, an MC38 in vivo colon tumor model was treated with an intravenous (IV) dose of STING agonist and Imagent microbubbles, and was exposed to 2.2 MHz ultrasound with only stable cavitation at 0.531 MI for 5 minutes. A separate arm of the animal was treated with the same 0.531 MI ultrasound for 5 minutes but with periodic 1100 ms ultrasound bursts of 1.304 MI administered every 10 s. FIG. 31 demonstrates that the increase of $CD8^+$ and $GranB^+CD8^+$ was significantly higher than the sonoporation arm without the high MI pulses. These cytotoxic lymphocytes are correlated with beneficial anti-tumor response mechanisms across many cancers.

By encapsulating an agent into or onto the carrier (e.g., a microbubble) and inducing cavitation of the carrier, the present invention describes a mixture of substances intended to be used in the manufacture (e.g., the mixing process) of a drug product and that, when used in the production of a drug, becomes an active ingredient in the drug product and is intended to furnish pharmacological activity or other direct effect in the diagnosis, cure, mitigation, treatment or prevention of disease or to affect the structure and function of the body. As a non-limiting example of the present invention, the encapsulation of IL-2 into or onto Imagent microbubbles describes a mixture of the two drugs that furnishes pharmacological activity and affects the structure and function of the body. In this case, the IL-2 when released from the Imagent (upon inertial cavitation) drug furnishes pharmacological activity while the Imagent drug (upon stable cavitation or inertial cavitation) affects the structure and function of the vascular or cellular membrane that is in contact or the vicinity of said Imagent microbubbles.

The use of experimental microbubbles in the clinic may be limited due to the addition of components that may elicit unintended biological effects or may involve significant or complicated processing steps that may introduce variability not conducive to achieving desired clinical results.

Figure 1:
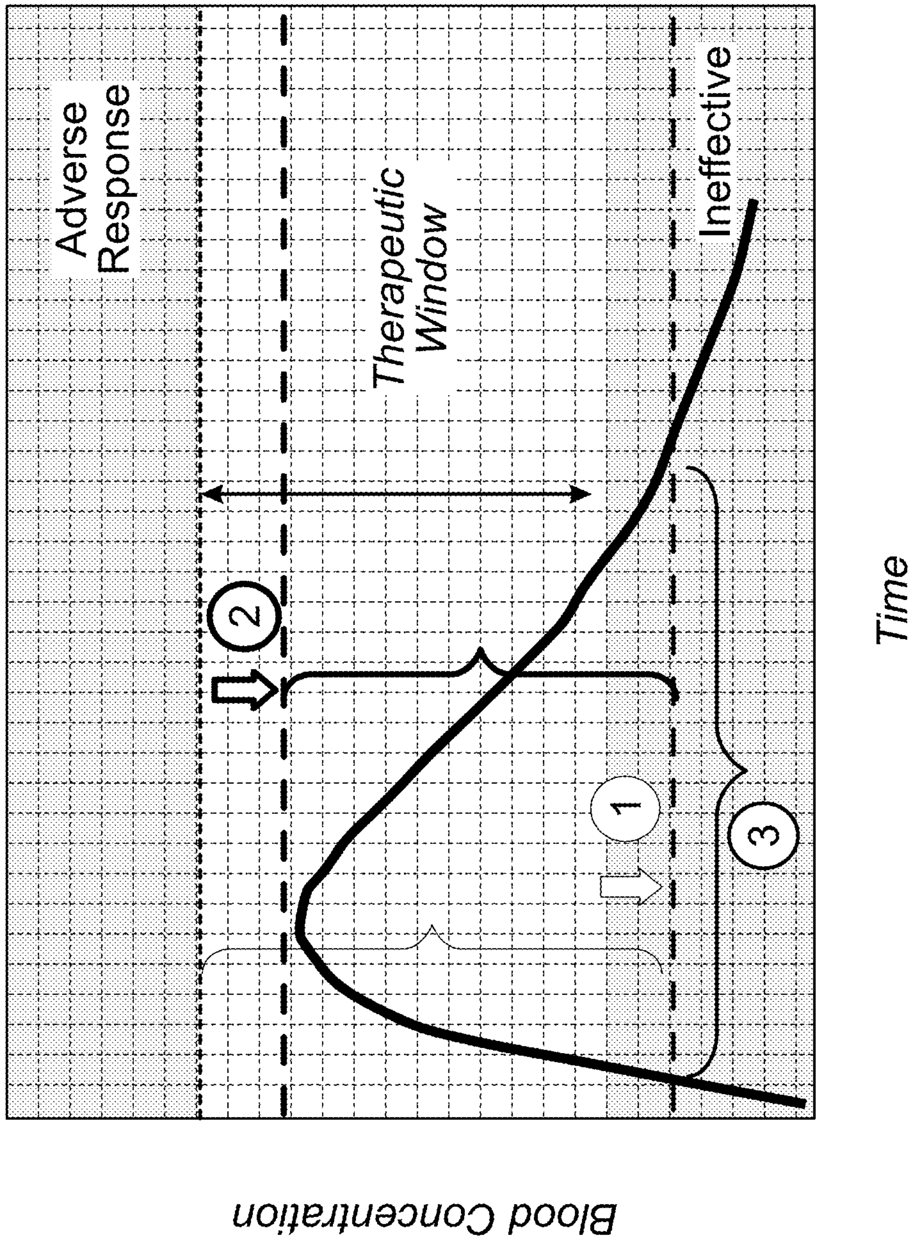
FIG. 1 depicts the change of a drug concentration in blood over time.
Figure 2:
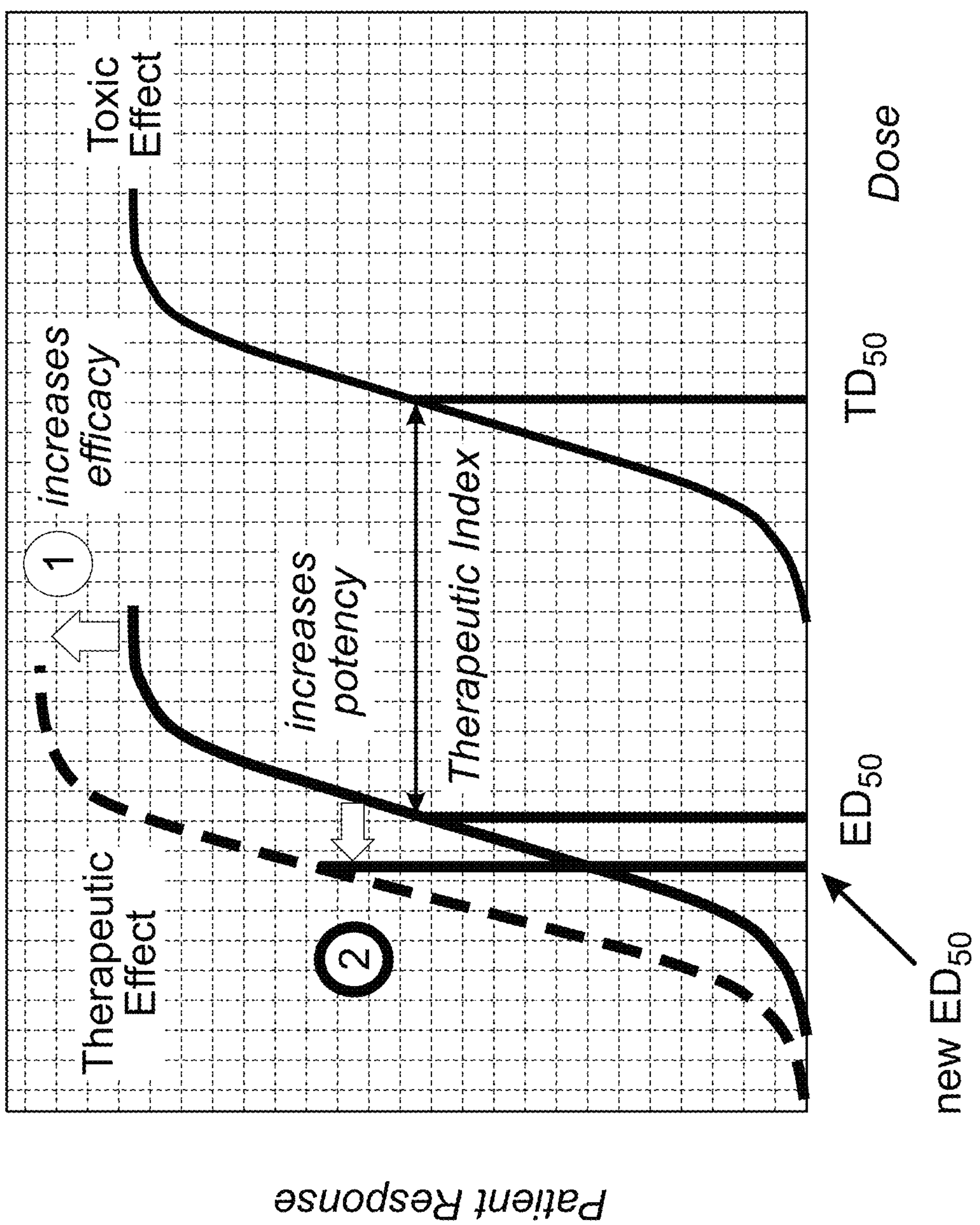
FIG. 2 depicts an exemplary dose response curve of a drug.
Figure 3:
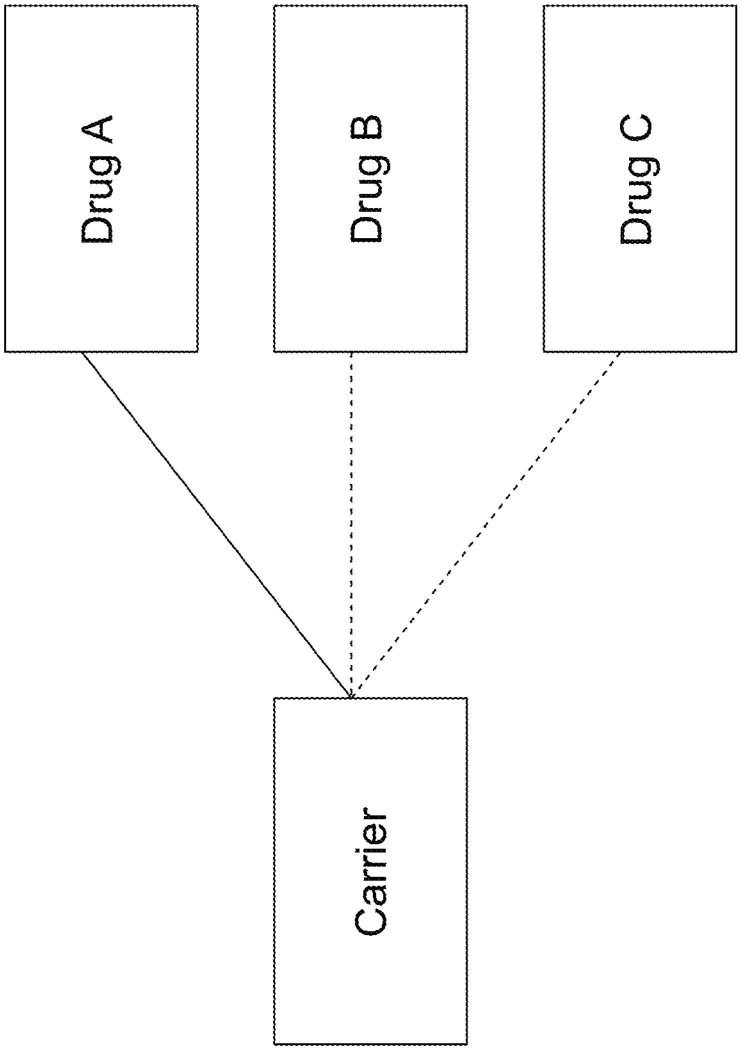
FIG. 3 is a schematic of the present invention where one or more agents 101*a*, 101*b*, 101*c*, etc., are associated with a carrier 100 to form a complex or combination.
Figure 4:
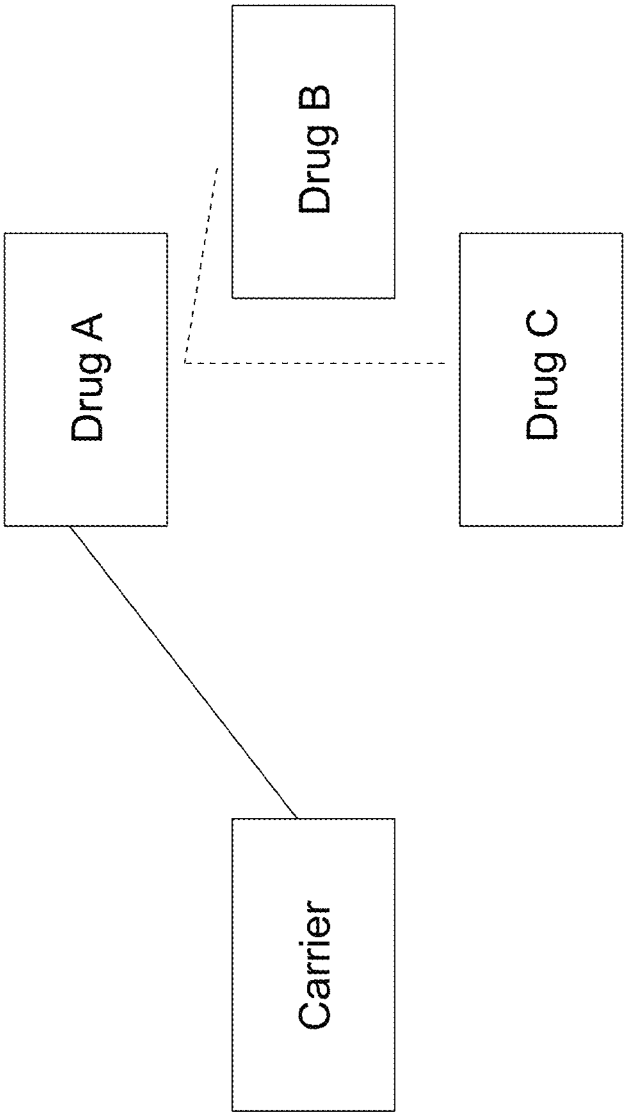
FIG. 4 is a schematic of the present invention where one or more agents 101*a*, 101*b*, 101*c*, etc., are associated with each other prior to being joined with a carrier 100 to form a complex or combination.

FIG. 3 illustrates a preferred embodiment of the present invention where one or more agent(s), etc., are combined with a carrier to form a complex, conjugate or combination. The agents may be used as a diagnostic, therapeutic, theranostic, mechanical, chemical, biological, genetic, synthetic, or other molecule. The agent may be a manufactured molecule, such as, but not limited to, a finished and packaged cancer drug that is ready to be administered to a patient, or may be a component used to aid in the formation of the complex (e.g., linker, ligand, etc.). As a non-limiting example of the present invention, an agent could consist of a solution of IL-2 that is mixed with a microbubble (carrier) to form a combination product. Such mixing could be performed using sterile products and closed fluid transfer processes just prior to administration, rather than at a manufacturing facility.

The present invention is particularly advantageous when the therapeutic molecule or compound has a safety or toxicity profile that could be improved to benefit a patient, has a low minimum inhibitory concentration measure, or has a low therapeutic index. Also, the present invention is particularly advantageous when, in order to improve clinical effect, greater concentrations of the therapeutic molecule or compound should be delivered to the desired target tissue.

The carriers, e.g., microbubbles, for use in the compositions and methods of the present invention can be modified at or near the time of administration without the addition of chemicals or ingredients (other than the solution containing the at least one active agent) during reconstitution or preparation to create a different version of the carrier. For example, during the phase separation step (e.g., flotation or centrifugation) since microbubbles having different sizes will float at different speeds, the infranatant (which may contain smaller microbubbles that take longer to float) may be expressed from the syringe of microbubbles, so that primarily larger microbubbles are present in the supernatant. Alternatively, the smaller microbubbles may be collected from the infranatant and used to deliver an encapsulated agent, as the smaller microbubbles collectively have greater surface area than the larger microbubbles and can therefore encapsulate more agent per a given volume of microbubbles, compared to the amount of agent per volume in the larger microbubbles. Using a differential centrifugation technique, larger diameter microbubbles float at different speeds (i.e., slower) compared to smaller diameter microbubbles (Feshitan 2009). Larger microbubbles may be more efficient at opening larger pores in tissues and therefore may be advantageous especially for the delivery of larger molecules, such as mAbs.

The present invention uses either the time period for a given method of phase separation, or a novel short axis syringe centrifugation method to create size isolated microbubbles at or near the time of administration. Centrifugation (or flotation) may be stopped at a certain point in time before substantially all of the microbubbles have floated to the supernatant layer. This would leave some smaller microbubbles still in the infranatant. As larger microbubbles (compared to smaller microbubbles) may be advantageous for sonoporation, the larger diameter microbubbles then could be isolated during the reconstitution or preparation phase by expressing the infranatant containing smaller microbubbles. Compared to the use of large and expensive centrifuge devices required to separate large microbubbles as described in Feshitan (2009), the use of a simple, low cost, single use device for the phase separation step and other processing steps in the present invention provides significant benefit. In the case of Imagent, the microsphere size distribution is noted in its package insert (https://www.accessdata.fda.gov/drugsatfda_docs/nda/2002/21-191_Imagent_Approv.pdf) where 78.8% are <3 μm, while 21.0% are between 3-10 μm in diameter. By isolating the larger Imagent microbubbles and expressing out many of the smaller microbubbles in the infranatant, the final administered dose of larger sized Imagent microbubbles may be injected and advantageous for sonoporation. Additionally, the larger microbubbles may be used to encapsulate a therapeutic agent or may be used without encapsulating an agent. In the case of Imagent, the number of larger microbubbles is less than the number of smaller microbubbles in each reconstituted suspension. Therefore, in order to ensure that a sufficient number of larger microbubbles is made available in the syringe for administration, multiple units of larger Imagent microbubbles (after using the processing steps as disclosed herein) may be combined into the final suspension, so that the target number of larger Imagent microbubbles is attained. Combining two or more units of larger microbubbles (or smaller microbubbles if desired) may be helpful also to increase the number of encapsulated drugs in the carrier.

Additional phase separation steps similar to the ones described above may be used to further isolate the smaller microbubbles in the infranatant layer. For example, after an initial phase separation step, once the infranatant has been expressed from the reconstituted or prepared microbubbles the infranatant layer, centrifugation or flotation may be used again to separate the smaller microbubbles from the infranatant. Additionally, the smaller microbubbles may be used to encapsulate a therapeutic agent or may be used without encapsulating an agent.

B. Active Agents

The compositions of the present invention comprise a plurality of carriers, wherein at least one active agent is associated with the plurality of carriers for delivery to a subject, wherein the level of the at least one active agent associated with the plurality of carriers is lower than the level of the active agent required to achieve a therapeutic effect when administered without being associated with carriers, optionally, by systemic administration without being associated with carriers.

Exemplary active agent may include, but are not limited to, a cytokine, e.g., interleukin-2 (IL-2); a monoclonal antibody, e.g., bevacizumab; an antibiotic, e.g., ciprofloxacin; a small molecule, e.g., gemcitabine; a nucleic acid, e.g., messenger ribonucleic acid (mRNA), a DNA, a gene, or a vector or plasmid comprising a gene, e.g., a gene encoding a protein, a cytokine, an antibody and/or a peptide; a gene editing or gene therapy system; an inhibitor, e.g., anti-PD-1, anti-PD-L1, or anti-CTLA-4; an agonist, e.g., a STING agonist or angiotensin II receptor agonist); a binding agent, e.g., a ligand, cross-linker; or immune receptor, e.g., T cell immunoglobulin and ITIM domain (TIGIT). In some embodiments, the composition further comprises a virus, e.g., an oncolytic virus (OV), e.g., a multitargeted OV.

As used herein, the term "association" or "associated with" refers to the enclosure or encapsulation of a therapeutic agent within the interior of, or the attachment or binding onto the interior or exterior surface of a delivery vehicle. In some embodiments, the active agent is encapsulated within the carriers, e.g., between the gas/shell interface and/or within the gas of the carriers. In other embodiments, the active agent is bound and/or attached to the interior or exterior surface of the carriers. Such association of active agents with the carriers provides several benefits, including protecting a molecule while in blood circulation from either degradation (e.g., a nucleic acid), metabolism, inactivation or immunogenicity (e.g., an oncolytic virus). Association with the carriers, e.g., encapsulated within the carriers, also can benefit the targeted deposition of a molecule to tissue, particularly when the encapsulated drug is released only at or near the intended tissue.

Encapsulation or attachment of at least one therapeutic agent into or onto a carrier, e.g., microbubble, creates a drug/drug combination, drug/drug conjugate, carrier/drug conjugate, or a drug/drug complex. Other classes of active agents or drugs or molecules (whether within a specific class or in combination with a different class) may also be encapsulated, including but not limited to, small molecules, proteins, DNA, RNA, genes, fragments of genes, interferons, poly(ADP-ribose) polymerase inhibitors, aptamers, polyclonal antibodies, antibody drug conjugates, bispecifics, nanoparticles, liposomes, micelles, silica particles, metallic particles, nanobots, antibiotics, molecules, repurposed agents, or compositions up to or exceeding approximately 4 megadaltons in molecular weight. The encapsulation process may be performed either at the time of administration (e.g., by the clinician, nurse, pharmacist or technician), or near the time of administration (e.g., at the pharmacy), or at any point prior to the time of administration (e.g., including but not necessarily at the manufacturing or distribution stage).

Cytokines

The active agent for use in the compositions and methods of the invention comprises a cytokine, and/or a vector or plasmid encoding the cytokine. Exemplary cytokines may include, but are not limited to, IL-2, IL-7, IL-10, IL-12, IL-15, IL-18, IL-21, IL-23, IL-27, interferon, GM-CSF or TNF-alpha.

Aldesleukin (brand name Proleukin®, Prometheus Laboratories Inc., San Diego, CA, USA) is a human recombinant interleukin-2 agent that is FDA approved to treat certain solid tumor cancer patients. Aldesleukin is a highly purified protein with an approximate molecular weight of 15.3 kDa. Aldesleukin has been shown to have a beneficial clinical effect for a subset of metastatic melanoma and renal cell carcinoma patients, but also is very toxic. It would be advantageous to be able to encapsulate into a microbubble carrier and to release therapeutically relevant amounts of aldesleukin in a controlled manner to allow such released aldesleukin to extravasate out of the vasculature into the desired target tissue. By encapsulating an amount (in a microbubble carrier) that is less than the clinical dose of 600,000 International Units (IU)/kg (0.037 mg/kg) of aldesleukin (https://www.proleukin.com), the present invention describes the delivery of therapeutically relevant rIL-2 doses at levels expected to have a lower toxicity profile.

In safety and efficacy studies leading to its eventual FDA approval and as described in its package insert, Proleukin was "given by 15-minute intravenous infusion every 8 hours for up to 5 days (maximum of 14 doses). No treatment was given on days 6 to 14 and then dosing was repeated for up to 5 days on days 15 to 19 (maximum of 14 doses). These 2 cycles constituted 1 course of therapy. Patients could receive a maximum of 28 doses during a course of therapy. In practice >90% of patients had doses withheld. Doses were withheld for specific toxicities . . . " Furthermore, the Proleukin package insert stated that there is a "Lack of efficacy with low dose [systemically administered] Proleukin regimens." In a 65-patient clinical study with metastatic renal cell carcinoma, it was determined that two low doses Proleukin regimens were ineffective. The Proleukin regimens administered 18,000,000 international units (IU) as a single subcutaneous injection, daily for 5 days during week 1; then $9\times10^6$ IU days 1-2, and $18\times10^6$ IU days 3-5, weekly for an additional 3 weeks (n=40) followed by a 2-week rest or 5 weeks (n=25) followed by a 3 week rest, for a maximum of 3 or 2 treatment cycles, respectively. (See https://www.proleukin.com/.)

Local delivery is generally considered as a more effective approach than systemic delivery for most therapeutic agents. In addition, given the complexities associated with intratumoral injections and the systemic toxicity of high dose IL-2, there is a clear need to deliver therapeutically relevant but low dose amounts of IL-2 systemically that can provide reduced systemic toxicity.

The present invention is a novel drug/drug complex of a cytokine (e.g., IL-2, or preferably a recombinant Human IL-2 (rIL-2)) and a carrier (e.g., a microbubble, or preferably Imagent). In summary, using the Syringe Method (as described below) and reconstituting vials of rIL-2 (1 mg) and Imagent separately, then after centrifugation to separate the microbubbles from the infranatant and expressing out the infranatant leaving the "cream" layer of microbubbles, rIL-2 was added to the syringe. The syringe containing rIL-2 and Imagent was then placed in an incubation bath, further centrifuged and the suspension washed to eliminate as much "free" or un-encapsulated rIL-2 from the syringe for injection of primarily only Imagent encapsulated rIL-2 creating a novel drug/drug complex herein referred to as SonoLeukin™, or "eIL-2". Clinically relevant levels of rIL-2 encapsulated in Imagent (after wash step) were confirmed using human IL-2 Quantikine ELISA Kits (R&D Systems, Minneapolis, MN, USA).

In the present invention, a surprising and unexpected in vivo result was the signal of efficacy with low dose systemically administered rIL-2 shown in an MC38 colon cancer tumor animal model. The present invention describes encapsulated low concentrations of rIL-2 (GenScript®, Piscataway, NJ, USA) in the Imagent microbubbles (the combination referred to as "SonoLeukin™"). Novel drug/drug complexes were formed and used in an MC38 colon cancer tumor model to show the effect of SonoLeukin on tumor volume growth in mice (C57BL/6J mice, Jackson Labs, Bar Harbor, ME, USA). In an in vivo study also was shown the effect of eIL-2 co-administered with an RMP1-14 monoclonal antibody (aPD-1) that reacts with mouse PD-1 (Bio X Cell, West Lebanon, NH, USA) (aPD-1).

Using separate sterile vials of rIL-2 and Imagent microbubbles, the present invention combines two drugs (by Vial Method, as described below) into a single vial for injection without requiring the addition of linkers, ligands, binders, additives, or other chemical means. While the relative amount of rIL-2 encapsulated in the Imagent microbubbles may be low (<50% of starting rIL-2 concentration, relative amount encapsulated in the present invention ranging preferably from 0.01-5.0% or more), of particular relevance is the absolute amount of rIL-2 molecules encapsulated in the microbubble carrier and how much of IL-2 is actually delivered to the target tissue (e.g., tumor).

An embodiment of the present invention consisting of microdoses of encapsulated IL-2 injected systemically alongside anti-PD-1 monoclonal antibody (Group 7) exhibited a benefit above and beyond either the monoclonal antibody or encapsulated IL-2 alone. Key measures such as, but not limited to, G-CSF, GM-CSF, IFNγ, IL-12 and IP-10 were unexpectedly shown to be affected, suggestive of a clinical benefit.

Additional cytokines for use in the compositions of the invention may include IL-10, IL-12, IL-15, or IL-23, or TNF-alpha.

In some embodiments, the carriers, e.g., microbubbles, e.g., Imagent, comprise a vector or a plasmid comprising a gene encoding any one of the cytokines, e.g., IL-2, IL-7, IL-10, IL-12, IL-15, IL-23, TNF-alpha, G-CSF, GM-CSF, IFNγ.

Monoclonal Antibodies (mAbs)

In one embodiment, the active agent for use in the compositions of the invention comprises antibodies, e.g., monoclonal antibodies, and/or a vector or plasmid comprising a gene encoding the antibody, e.g., a gene encoding the light chain of the antibody, a gene encoding the heavy chain of the antibody, and/or a gene encoding the heavy and light chain of the antibody. Exemplary antibodies may include, but are not limited to, bevacizumab, pembrolizumab, nivolumab, cemiplimab, durvalumab, atezolizumab, avelumab, ipilimumab, rituximab, cetuximab or trastuzumab. In some embodiments, the active agent for use in the compositions and methods of the present invention comprise Bevacizumab, or a vector or a plasmid encoding the light chain and heavy chain of Bevacizumab. In some embodiments, the active agent for use in the compositions and methods of the present invention comprise Pembrolizumab, or a vector or a plasmid encoding the light chain and heavy chain of Pembrolizumab.

Bevacizumab: Bevacizumab (brand name Avastin®, Genentech, Inc., South San Francisco, CA, USA) is a recombinant humanized monoclonal IgG1 antibody that acts as a vascular endothelial growth factor inhibitor and has an approximate molecular weight of 149 kDa. Per the manufacturer, bevacizumab binds VEGF and prevents the interaction of VEGF to its receptors (Flt1 and KDR) on the surface of endothelial cells, thereby acting to inhibit or prohibit angiogenesis. Avastin is administered as an intravenous infusion over 30-90 minutes and is dosed between 5-15 mg/kg every 2-3 weeks, either as a monotherapy or in combination with other therapeutic agents, depending on clinical indication.

According to the Avastin package insert (https://www.gene.com/download/pdf/avastin_prescribing.pdf), serious and sometimes fatal adverse events may occur when patients received Avastin, including but not limited to, gastrointestinal perforations (0.3-3.0%), Grade 3-5 hemorrhagic events (0.4-7.0%), serious or fatal pulmonary hemorrhage (4-31%), Grades 3-5 Arterial Thromboembolic Events (5%), Grades 3-4 Venous Thromboembolic Events (11%), Grades 3-4 hypertension (5-18%), proteinuria (20%), and ovarian failure (34%). Meanwhile, documentation provided by the manufacturer to the European Medicines Authority (https://www.ema.europa.eu/en/medicines/human/EPAR/avastin) stated "dose reduction for adverse reactions [of Avastin] is not recommended. If indicated, therapy should either be permanently discontinued or temporarily suspended." Given the high rate of adverse events associated with Avastin, there exists a clear need to improve the safety and efficacy profile of bevacizumab.

The present invention is a novel drug/drug complex of a monoclonal antibody (e.g., bevacizumab) and a carrier (e.g., a microbubble, or preferably Imagent). In summary, using the Syringe Method (as described below) and reconstituting vials of bevacizumab (100 mg) and Imagent separately, then after centrifugation to separate the microbubbles from the infranatant and expressing out the infranatant leaving the "cream" layer of microbubbles, bevacizumab was added to the syringe. The syringe containing bevacizumab and Imagent was then placed in an incubation bath, further centrifuged and the suspension washed to eliminate as much "free" or un-encapsulated bevacizumab from the syringe for injection of primarily only Imagent encapsulated bevacizumab creating a novel drug/drug complex herein referred to as "eBEV". Bevacizumab was encapsulated in Imagent (after wash step) as confirmed by using human VEGF Quantikine ELISA Kits (R&D Systems, Minneapolis, MN, USA).

In the present invention, a surprising and unexpected in vitro result was the ability to encapsulate clinically relevant levels of bevacizumab with commercially available carriers (e.g., microbubbles, such as, but not limited to, Imagent) without modifying the surface of carrier or adding binding agents or ligands. Testing in vivo was expected to demonstrate an increased delivery of bevacizumab to a tumor microenvironment using either eBEV alone or a combination of eBEV and free bevacizumab, compared to intravenous injection of bevacizumab alone.

The present invention uses a manufactured carrier, Imagent, and without adding any chemicals or molecules at the manufacturing stage, adding a monoclonal antibody to create a microbubble drug conjugate having sufficient therapeutic agent encapsulated onto the carrier and delivered to the tissue target to have a clinically meaningful beneficial effect. In some embodiments, the carriers, e.g., microbubbles, e.g., Imagent, comprise a vector or a plasmid comprising a gene encoding the antibody, e.g., Bevacizumab. In some embodiments, the carriers, e.g., microbubbles, e.g., Imagent, comprises a vector or a plasmid comprising a gene encoding the light chain of the antibody, a gene encoding the heavy chain of the antibody, and/or a gene encoding the heavy and light chain of the antibody, e.g., Bevacizumab.

Pembrolizumab: Pembrolizumab (brand name Keytruda®, Merck & Co., Kenilworth, NJ, USA) is a programmed death receptor-1 (PD 1)-blocking humanized monoclonal IgG4 kappa antibody and has an approximate weight of 149 kDa. Per the manufacturer, pembrolizumab binds to the PD-1 receptor and blocks the receptor's interaction with PD-L1 and PD-L2, releasing PD-1 pathway-mediated anti-tumor immune response. Pembrolizumab is administered as an intravenous infusion over 30 minutes and is dosed between 200 or 400 mg every 3 or 6 weeks, either as a monotherapy or in combination with other therapeutic agents, depending on clinical indication.

While immune checkpoint inhibitors (ICI) are approved for use in a number of solid tumors and patients, depending on the clinical indication, as many as 40-85% of treated patients do not respond to treatment. Certain patients may be more likely to respond to ICI treatment if more ICI molecules or ICI activated cells are present in the TME, for example those whose "cold" tumors are turned "hot". In the present invention, an ICI may be co-administered with a carrier or may be encapsulated within a carrier in order to improve the biodistribution of the ICI within the TME or to the tumor cells.

The present invention used Imagent with acoustic exposures from a standard diagnostic ultrasound system and was able to significantly benefit tumor inhibition and tumor immune environment by increasing the key measure of CD8+/Treg ratio in the tumor in combination with anti-PD-1 checkpoint inhibitor at standard doses. The fact that tumor inhibition with sonoporation was equivalent to and or better than checkpoint inhibition alone demonstrated that the sonoporation effect does not diminish the activity of the checkpoint inhibitor.

The present invention contemplates a carrier (e.g., Imagent) used to encapsulate antibodies (monoclonal or polyclonal) or vectors or plasmids encoding the antibodies, e.g., the light and heavy chains of the antibodies, such as, but not limited to, pembrolizumab, nivolumab, cemiplimab, durvalumab, atezolizumab, avelumab, ipilimumab, bevacizumab, rituximab, cetuximab, trastuzumab. Additionally, a microbubble may be used to cause sonoporation when co-administered with an antibody. Furthermore, a microbubble encapsulated drug (other than an antibody) may be used to cause sonoporation when co-administered with an agent different from the encapsulated agent.

An advantage of encapsulation would be a reduction in side effects as a smaller amount of the antibody would be delivered since the encapsulation efficiency of microbubbles is <100% of the agent being bound or encapsulated. In situations where the carrier (whether a drug is encapsulated or not into the carrier) is co-administered with an antibody, sonoporation would lead to greater biodistribution of the antibody to the target, thereby reducing the amount of antibody going off target and the toxicity related to antibody dose. In some embodiments, the carriers, e.g., microbubbles, e.g., Imagent, comprise a vector or a plasmid comprising a gene encoding the antibody, e.g., Pembrolizumab. In some embodiments, the carriers, e.g., microbubbles, e.g., Imagent, comprises a vector or a plasmid comprising a gene encoding the light chain of the antibody, a gene encoding the heavy chain of the antibody, and/or a gene encoding the heavy and light chain of the antibody, e.g., Pembrolizumab. In some embodiments, the carriers, e.g., microbubbles, e.g., Imagent, comprises a vector or a plasmid comprising a gene encoding the heavy chain of Pembrolizumab comprising the amino acid sequence of SEQ ID NO: 1. In some embodiments, the carriers, e.g., microbubbles, e.g., Imagent, comprises a vector or a plasmid comprising a gene encoding the light chain of Pembrolizumab comprising the amino acid sequence of SEQ ID NO: 2. In some embodiments, the carriers, e.g., microbubbles, e.g., Imagent, comprises a vector or a plasmid comprising a gene encoding the heavy chain of Pembrolizumab comprising the amino acid sequence of SEQ ID NO: 1, and a vector or a plasmid comprising a gene encoding the light chain of Pembrolizumab comprising the amino acid sequence of SEQ ID NO: 2. In some embodiments, the light chain and heavy chain of Pembrolizumab are encoded in a single plasmid or a single vector. In some embodiments, the light chain and heavy chain of Pembrolizumab comprises the amino acid sequence of SEQ ID NO: 5.

Ipilimumab: In some embodiments, the monoclonal antibody is Ipilimumab. In some embodiments, the carriers, e.g., microbubbles, e.g., Imagent, comprise a vector or a plasmid comprising a gene encoding the antibody, e.g., Ipilimumab. In some embodiments, the carriers, e.g., microbubbles, e.g., Imagent, comprises a vector or a plasmid comprising a gene encoding the light chain of the antibody, a gene encoding the heavy chain of the antibody, and/or a gene encoding the heavy and light chain of the antibody, e.g., Ipilimumab. In some embodiments, the carriers, e.g., microbubbles, e.g., Imagent, comprises a vector or a plasmid comprising a gene encoding the heavy chain of Ipilimumab comprising the amino acid sequence of SEQ ID NO: 3. In some embodiments, the carriers, e.g., microbubbles, e.g., Imagent, comprises a vector or a plasmid comprising a gene encoding the light chain of Ipilimumab comprising the amino acid sequence of SEQ ID NO: 4. In some embodiments, the carriers, e.g., microbubbles, e.g., Imagent, comprises a vector or a plasmid comprising a gene encoding the heavy chain of Ipilimumab comprising the amino acid sequence of SEQ ID NO: 3, and a vector or a plasmid comprising a gene encoding the light chain of Ipilimumab comprising the amino acid sequence of SEQ ID NO: 4. In some embodiments, the light chain and heavy chain of Ipilimumab are encoded in a single plasmid or a single vector. In some embodiments, the light chain and heavy chain of Ipilimumab comprises the amino acid sequence of SEQ ID NO: 6.

Gene Editing System

In some embodiments, the active agents for use in the compositions and methods of the present invention comprise one or more components of a gene editing system. Components of gene editing systems may be used in a variety of contexts including but not limited to gene editing. For example, such components may be used to target agents that physically modify, genetically modify, and/or epigenetically modify any gene sequences.

Exemplary gene editing systems include the clustered regulatory interspaced short palindromic repeat (CRISPR) system, zinc finger nucleases (ZFNs), and Transcription Activator-Like Effector-based Nucleases (TALEN). ZFNs, TALENs, and CRISPR-based methods are described, e.g., in Gaj et al. Trends Biotechnol. 31.7(2013):397-405; CRISPR methods of gene editing are described, e.g., in Guan et al, Application of CRISPR-Cas system in gene therapy: Pre-clinical progress in animal model. DNA Repair 2016 Jul. 30 [Epub ahead of print]; Zheng et al, Precise gene deletion and replacement using the CRISPR/Cas9 system in human cells. BioTechniques, Vol. 57, No. 3, September 2014, pp. 115-124.

CRISPR systems are adaptive defense systems originally discovered in bacteria and archaea. CRISPR systems use RNA-guided nucleases termed CRISPR-associated or "Cas" endonucleases (e. g., Cas9 or Cpf1) to cleave foreign DNA. In a typical CRISPR/Cas system, an endonuclease is directed to a target nucleotide sequence (e. g., a site in the genome that is to be sequence-edited) by sequence-specific, non-coding "guide RNAs" that target single- or double-stranded DNA sequences. Three classes (I-III) of CRISPR systems have been identified. The class II CRISPR systems use a single Cas endonuclease (rather than multiple Cas proteins). One class II CRISPR system includes a type II Cas endonuclease such as Cas9, a CRISPR RNA ("crRNA"), and a trans-activating crRNA ("tracrRNA"). The crRNA contains a "guide RNA", typically about 20-nucleotide RNA sequence that corresponds to a target DNA sequence. The crRNA also contains a region that binds to the tracrRNA to form a partially double-stranded structure which is cleaved by RNase III, resulting in a crRNA/tracrRNA hybrid. The crRNA/tracrRNA hybrid then directs the Cas9 endonuclease to recognize and cleave the target DNA sequence. The target DNA sequence must generally be adjacent to a "protospacer adjacent motif ("PAM") that is specific for a given Cas endonuclease; however, PAM sequences appear throughout a given genome. CRISPR endonucleases identified from various prokaryotic species have unique PAM sequence requirements; examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), and 5'-NNNGATT (*Neisseria meningiditis*). Some endonucleases, e. g., Cas9 endonucleases, are associated with G-rich PAM sites, e. g., 5'-NGG, and perform blunt-end cleaving of the target DNA at a location 3 nucleotides upstream from (5' from) the PAM site. Another class II CRISPR system includes the type V endonuclease Cpf1, which is smaller than Cas9; examples include AsCpf1 (from Acidaminococcus sp.) and LbCpf1 (from Lachnospiraceae sp.). Cpf1-associated CRISPR arrays are processed into mature crRNAs without the requirement of a tracrRNA; in other words, a Cpf1 system requires only the Cpf1 nuclease and a crRNA to cleave the target DNA sequence. Cpf1 endonucleases, are associated with T-rich PAM sites, e. g., 5'-TTN. Cpf1 can also recognize a 5'-CTA PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e. g., Zetsche et al. (2015) *Cell,* 163:759-771.

A variety of CRISPR associated (Cas) genes or proteins can be used in the present invention and the choice of Cas protein will depend upon the particular conditions of the method.

Specific examples of Cas proteins include class II systems including Cas1, Cas2, Cas3, Cas4, Cas5, Cas6, Cas7, Cas8, Cas9, Cas10, Cpf1, C2C1, or C2C3. In some embodiments, a Cas protein, e.g., a Cas9 protein, may be from any of a variety of prokaryotic species. In some embodiments a particular Cas protein, e.g., a particular Cas9 protein, is selected to recognize a particular protospacer-adjacent motif (PAM) sequence. In some embodiments, the site-specific targeting moiety includes a sequence targeting polypeptide, such as an enzyme, e.g., Cas9. In certain embodiments a Cas protein, e.g., a Cas9 protein, may be obtained from a bacteria or archaea or synthesized using known methods. In certain embodiments, a Cas protein may be from a gram positive bacteria or a gram negative bacteria. In certain embodiments, a Cas protein may be from a *Streptococcus*, (e.g., a *S. pyogenes*, a *S. thermophilus*) a *Cryptococcus*, a *Corynebacterium*, a *Haemophilus*, a *Eubacterium*, a *Pasteurella*, a *Prevotella*, a *Veillonella*, or a *Marinobacter*. In some embodiments nucleic acids encoding two or more different Cas proteins, or two or more Cas proteins, may be introduced into a cell, zygote, embryo, or animal, e.g., to allow for recognition and modification of sites comprising the same, similar or different PAM motifs. In some embodiments, the Cas protein is modified to deactivate the nuclease, e.g., nuclease-deficient Cas9, and to recruit transcription activators or repressors, e.g., the co-subunit of the *E. coli* Pol, VP64, the activation domain of p65, KRAB, or SID4X, to induce epigenetic modifications, e.g., histone acetyltransferase, histone methyltransferase and demethylase, DNA methyltransferase and enzyme with a role in DNA demethylation (e.g., the TET family enzymes catalyze oxidation of 5-methylcytosine to 5-hydroxymethylcytosine and higher oxidative derivatives).

For the purposes of gene editing, CRISPR arrays can be designed to contain one or multiple guide RNA sequences corresponding to a desired target DNA sequence; see, for example, Cong et al. (2013) *Science,* 339:819-823; Ran et al. (2013) *Nature Protocols,* 8:2281-2308. At least about 16 or 17 nucleotides of gRNA sequence are required by Cas9 for DNA cleavage to occur; for Cpf1 at least about 16 nucleotides of gRNA sequence is needed to achieve detectable DNA cleavage.

Whereas wild-type Cas9 generates double-strand breaks (DSBs) at specific DNA sequences targeted by a gRNA, a number of CRISPR endonucleases having modified functionalities are available, for example: a "nickase" version of Cas9 generates only a single-strand break; a catalytically inactive Cas9 ("dCas9") does not cut the target DNA but interferes with transcription by steric hindrance. dCas9 can further be fused with a heterologous effector to repress (CRISPRi) or activate (CRISPRa) expression of a target gene. For example, Cas9 can be fused to a transcriptional silencer (e.g., a KRAB domain) or a transcriptional activator (e.g., a dCas9-VP64 fusion). A catalytically inactive Cas9 (dCas9) fused to FokI nuclease ("dCas9-FokI") can be used to generate DSBs at target sequences homologous to two gRNAs. See, e. g., the numerous CRISPR/Cas9 plasmids disclosed in and publicly available from the Addgene repository (Addgene, 75 Sidney St., Suite 550A, Cambridge, MA 02139; addgene.org/crispr). A "double nickase" Cas9 that introduces two separate double-strand breaks, each directed by a separate guide RNA, is described as achieving more accurate genome editing by Ran et al. (2013) Cell, 154: 1380-1389.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1.

In some embodiments, the active agents for use in the compositions and methods of the present invention comprise one or more components of a CRISPR system described herein. In some embodiments, the active agent comprises a vector a plasmid comprising a cDNA encoding a Cas9 protein. In some embodiments, the active agent comprises a vector a plasmid comprising a guide RNA. In some embodiments, the active agent comprises a vector a plasmid comprising a cDNA encoding a gene of interest or fragment thereof. In some embodiments, the active agent comprises a vector a plasmid comprising a cDNA encoding a Cas9 protein, a guide RNA, and/or a gene of interest or fragment thereof. In some embodiments, the active agent comprises a synthetic mRNA encoding a Cas9 protein. In some embodiments, the active agent comprises a synthetic mRNA encoding a target protein. In some embodiments, the active agent comprises a synthetic mRNA encoding a Cas9 protein and a target protein. In some embodiments, the active agent comprises a Cas9/guide RNA ribonucleoprotein (RNP) complex.

In some embodiments, the active agents for use in the compositions and methods of the invention include, for example, nucleases, physical blockers, epigenetic recruiters, e.g., a transcriptional enhancer or a transcriptional repressor, and epigenetic CpG modifiers, e.g., a DNA methylase, a DNA demethylase, a histone modifying agent, or a histone deacetylase, and combinations of any of the foregoing.

In some embodiments, the one or more components of the gene editing system are included in an adenoviral or AAV vectors. In some embodiments, the active agents include an adenoviral or AAV vector encoding Cas9, a guide RNA and/or a template DNA.

Oncolytic Viruses

The compositions of the present invention may further comprise a virus, e.g., an oncolytic virus. Oncolytic viruses (OV) are modified to infect and replicate to kill cancer cells. Adenoviruses are used as an OV because of their high cell transduction and their safety profile. A multi-targeting conditionally replicating adenovirus that displays enhanced oncolysis while maintaining expression of immunotherapeutic agents has been shown to lyse tumor cells effectively at low titers (Dobbins 2015).

The present invention is a novel drug/drug complex of an OV (e.g., adenovirus, and preferably an Ad5/3-RGD-D24) and a carrier (e.g., a microbubble, or preferably Imagent). An advantage of encapsulating an Ad5/3-RGD-D24 into a microbubble is protecting the OV from immune response while in the vasculature until the application of ultrasound energy to induce cavitation and sonoporation, thereby releasing the OV into the TME. Via sonoporation, encapsulating the Ad5/3-RGD-D24 into Imagent and inactivating the free OV prior to administration, low amounts of virus particles would be delivered into the TME and given OV's effectiveness at low titers, the complex would still be effective against tumors. Efficacy of the Ad5/3-RGD-D24 OV in the present invention can be enhanced by loading certain transgenes (such as, but not limited to, p53, GM-CSF, immune checkpoint inhibitors, cytokines, other transgenes) into the OV prior to encapsulation by the microbubble.

Significant challenges to OV therapy may be overcome by the present invention of a drug/drug complex, namely enabling more efficient extravasation of the OV to the tumor microenvironment via sonoporation, reduced innate immune response from antiviral immunity, preexisting circulating antibodies, or complement proteins.

Other oncolytic virus complexes of the present invention include, but are not limited to, talimogene laherparepvec (T-VEC®), type 1 herpes simplex virus, poliovirus, measles virus, Newcastle disease virus, reovirus, coxsackievirus, vesicular stomatitis virus, Zika virus, RNA virus, DNA virus, etc.

C. eDrug+Co-Administered CAR T

Chimeric antigen receptor T cells (CAR T cells) are an emerging immunotherapy class of agents that have shown tremendous efficacy in hematological malignancies, but to date have shown limited efficacy against solid tumors. Exogenous IL-2 has been shown to enhance the survival and proliferation of adoptive T cells.

The present invention combines encapsulated agents, e.g., cytokines such as IL-2, to enhance CAR T therapy. By targeting the delivery of agents to modify the TME or to stimulate immune cells including T cells, natural killers or dendritic cells, the present invention provides important advantages to improve clinical outcomes. In the case of IL-2 or other potent but highly toxic agents, improving the safety profile or the biodistribution of such agents at the target tissue can not only provide single agent benefit, but also synergistic or additive benefit.

D. eDrug A+eDrug B, or e(Drug A+Drug B)

The present invention also provides compositions comprising a plurality of carriers, e.g., microbubbles, wherein at least one, e.g., two, three, four or more, active agents are associated with, e.g., encapsulated within the carriers, and/or bound to the surface of the carriers. In some embodiments, one of the active agents may comprise a therapeutic agent, e.g., chemotherapeutic, and the other active agent may comprise an antibiotic agent, e.g., ciprofloxacin. An example of the present invention combines different classes of agents either into, along with a carrier, or both within and along with a carrier. For example, a combination of separately administered chemotherapy (gemcitabine) and an antibiotic has been shown to have benefit in a mouse model of pancreatic cancer (Geller 2017). In the case of antibiotics, long-term treatment may lead to the emergence of antibiotic-resistant bacterial strains, and the use of antibiotics may also affect the response to cancer treatments (Bashiardes 2017).

Alternatively, the present invention describes a dosing of a patient using an encapsulated therapeutic agent and another separate encapsulated agent (both of which may be delivered through the same syringe, or through separate syringes).

The present invention describes the encapsulation of one or more agents, each of which may be in the same class of drug or may be in different classes of drugs (e.g., small molecules, proteins, antibodies, nucleic acids, viruses, etc.). For example, two chemotherapy agents may be encapsulated (e.g., gemcitabine and abraxane) into a carrier. Multiple agents of the same class may be encapsulated into a carrier, for example, oxaliplatin, folinic acid, irinotecan and fluorouracil (representing an encapsulated version of FOLFIRINOX). Or a chemotherapy agent (e.g., gemcitabine) and an antibiotic agent (e.g., ciprofloxacin) may be encapsulated into a carrier. Alternatively, for example, a TME modulating agent may be encapsulated along with an immunostimulatory agent. Additionally, for example, a monoclonal antibody and a small molecule, or a bispecific or multispecific drug may be encapsulated into a carrier with or without an additional agent.

The present invention also contemplates combining treatment of an encapsulated (or unencapsulated) carrier with a different agent. Such combination may be administered at or around the same time (generally within 24 hours of each other), may be administered on different schedules (for example, Drug A administered at time 0 (to) and eDrug B administered either before ($t_{-1}$) or after ($t_{+1}$) Drug A. Another dosing schedule may be Drug A and eDrug B are co-administered on day 0 ($d_0$), eDrug B is then administered on a subsequent day ($d_{+1}$), Drug A and eDrug B are again co-administered on yet another subsequent day ($d_{+2}$), and the dosing cycle is repeated (or amended). The drugs may be administered on the same day or on different days, or in any combination of days.

In certain embodiments of the present invention, an encapsulated agent(s) may be administered as often, more often, or less often than a different agent. Alternatively, in the present invention, a carrier (without an encapsulated agent) may be administered as often, more often, or less often than a different agent. A consideration of the present invention dictating the frequency and specific dosing days of either the encapsulated agent or the (unencapsulated) carrier may be the circulation time of the agent used in combination with either the encapsulated agent or the unencapsulated carrier. For example, a monoclonal antibody such as aPD-1 may stay in a patient's circulatory system for several weeks, while encapsulated IL-2 may stay in circulation for only a matter of minutes or hours. Even though the encapsulated IL-2 has a short circulatory duration, the sonoporation effect of the present invention will permeabilize the vasculature allowing any circulating aPD-1 (that may have been administered at a time pre-dating the administration of the encapsulated IL-2) to reach the target tumor tissue. Alternatively, an unencapsulated carrier (typically also having a short circulatory duration) may be administered as often, more often, or less often than a different agent, such as aPD-1.

E. Bioeffects

A carrier (e.g., microbubble) under the influence of an energy source (e.g., ultrasound) may elicit bioeffects leading to significant anticancer immune response and significantly suppressed tumor progression (Liu, 2012). In contrast, rather than observing the bioeffects, the present invention describes the use of a carrier under the influence of an energy source to create bioeffects, such as, but not limited to, ROS at desired levels. The measurement of the desired ROS levels in vivo may be conducted using imaging or the inclusion of protein-based indicators. For example, by administering a greater concentration of microbubbles and using certain ultrasound parameters to direct energy to the target area, an increase in ROS to a targeted level may be reached, thereby eliciting the desired bioeffect. For example, it may be beneficial for anti-tumor activity if reactive oxygen species levels could be manipulated to modify the TME (Weinberg 2019). Bioeffects, such as, but not limited to, ROS may be affected whether the carrier is delivered with or without a therapeutic agent. In the case of co-administration of the carrier with another drug, certain bioeffects can be attained or inhibited by manipulation of such factors as, but not limited to, type of carrier used, device operating parameters, amount of carrier introduced into the target area or vicinity, duration of treatment, etc.

A contributing factor to chemotherapy toxicity may be the generation of excess ROS production in normal tissue. The present invention describes a means to increase (or decrease) the level or range of desired bioeffects to both a target level and location. In other words, if for example, the desired level of ROS production within a TME is x, then providing certain ultrasound operating parameters along with the presence of microbubbles in the tumor vasculature would induce the target level of ROS in the TME.

If a target level or range of bioeffects such as, but not limited to, ROS, Heat-shock protein 60 (hsp60), calcium ions, CD8+ T cell recruitment, CD8+/Treg ratio is desired at a certain tissue target, then under the present invention certain carrier or ultrasound parameters may be used in combination to achieve such desired level or range at such location. In particular, conventional diagnostic ultrasound probes, e.g., sector arrays, linear arrays, curvilinear arrays, may be used to induce the level or range of bioeffects desired for a therapeutic use of a carrier or microbubble. The target bioeffects achieved at the desired tissue may result from such factors as, but not limited to, specific cavitation states at specific intervals, microbubble concentrations, ultrasound frequencies, duty cycles, pulse lengths, peak negative pressures, mechanical indices, etc.

Encapsulation of an agent provides several benefits, including protecting a molecule while in blood circulation from either degradation (e.g., a nucleic acid), metabolism, inactivation or immunogenicity (e.g., an oncolytic virus). Encapsulation also can benefit the targeted deposition of a molecule to tissue, particularly when the encapsulated drug is released only at or near the intended tissue.

Targeted deposition of the therapeutic agent may be enhanced through the use of an energy source that is both aimed at the target tissue and interacts with the carrier only when the carrier is present within the energy field. For example, when a therapeutic molecule is encapsulated in a carrier (e.g., a microbubble) and the carrier is activated (e.g., stable or inertial cavitation) using an energy source (e.g., ultrasound), certain barriers (e.g., vessel walls, cell membranes, etc.) may become permeable as a result of mechanical shear forces from cavitation imparted onto the barrier surfaces ("sonoporation"). Additionally, certain bioeffects also may occur as a result of sonoporation. In the case of encapsulated agents, the therapeutic agent is released from the microbubble upon inertial cavitation, and since either stable or inertial microbubble cavitation is known to cause sonoporation, the released agent can pass through the permeabilized tissue into either the cells or tissue. In the case of therapeutic agents co-administered (and not encapsulated in the microbubbles), stable and inertial cavitation of the microbubbles still cause sonoporation of the ultrasound targeted barriers thereby allowing the freely circulating therapeutic agents to have a pathway into the cells or tissues by virtue of the permeabilized barrier.

III. Devices and Methods for Producing the Compositions of the Invention

The present disclosure provides methods for producing the compositions taught herein. In some embodiments, a vial of a carrier (e.g., a microbubble, such as Imagent) is supplied or reconstituted (if necessary) as per its manufacturer's instructions (e.g., Imagent is reconstituted with SWFI) and at least one drug, Drug A, is mixed with the carrier in suspension (herein referred to as "Syringe Method"). Alternatively, a vial of a carrier (e.g., a microbubble, such as Imagent) is instead reconstituted with a sterile solution of at least one drug, Drug A, rather than with SWFI and mixed (herein referred to as "Vial Method"). Various processes of forming complexes and combinations are herein disclosed. In some embodiments of the present disclosure, a complex is formed through the combination of two or more drugs, one of which is a microbubble (e.g., but not limited to, a perflexane gas in a lipid microbubble shell such as the microbubble referenced in FDA NDA 21-191) acting as the carrier, while (at least one) therapeutic agent is another drug. Examples are described in FIGS. 13-15, and 40-42.

Syringe Method

FIG. 13 is a schematic depicting a syringe method for making the compositions of the present disclosure. As shown in FIG. 13, in the syringe method, carrier MCC101 (e.g., Imagent) is reconstituted or provided as per manufacturer's instructions or packaging. For example, if carrier MCC101 is Imagent, then sterile water for injection (SWFI) is injected into the vial MCC102 to reconstitute Imagent powder (not shown). Carrier MCC101 is withdrawn into a syringe MCC103. Once carrier MCC101 suspension is in the syringe MCC103, the microbubbles are separated using any of a variety of means, e.g., centrifugation, spinning, filtration, gravity, etc. after which infranatant is expressed out of syringe MCC103 leaving a layer of primarily carrier MCC101. In some embodiments, after the phase separation step, diluent (not shown) may be added into the syringe MCC103 to resuspend carrier MCC101. At least one drug, e.g., Drug X MCC101*a*, is drawn into syringe MCC103 so that Drug X MCC101*a* can be mixed with carrier MCC101 using any number of physical, mechanical, chemical, electrical means, e.g., incubation, stirring, agitation, shaking, rocking, rolling, amalgamation, linkers, binding agents, charges, etc. For example, the mix step using incubation may consist of placing the syringe in a water bath or incubation plate at 40° C. (or higher or lower) for up to 60 minutes (or more) with regular intervals of agitation.

The starting amount or concentration of Drug X MCC101*a*, Drug Y (not shown), Drug Z (not shown), etc. may be manipulated (e.g., higher, lower or the equal concentration of Drug X MCC101*a* than the amount that would be used as an agent separate from the present invention) such that, before drawing the diluent containing Drug X MCC101*a* into syringe MCC103, the desired concentration of Drug X MCC101*a* after the creation of the drug/drug complex is achieved. Differing amounts of carrier MCC101 and Drug X MCC101*a*, phase separation methods, mixing parameters all may influence the amount of agent encapsulated in the carrier.

Use of phase separation techniques provides the ability to express substantially all or a portion of infranatant, leaving desired levels of encapsulated drug (or the carrier without encapsulating any drug) remaining in microbubble suspension. One or more separation methods (e.g., centrifugation, flotation, filtration, chromatography, precipitation, spinning, vortexing, or other separation methods) may be utilized in one or more steps of the present disclosure as a means to separate the carrier (whether loaded with therapeutic agents or not) from the infranatant (or any "free" drug, i.e., drug not encapsulated or attached to the carrier). One advantage of separating the carrier (e.g., microbubble) is that, in the case of microbubbles, they will float to become the top layer ("supernatant") in a liquid solution, whereupon the supernatant becomes a high concentration with which to use to encapsulate a therapeutic agent (or to deliver a high concentration of non-drug loaded microbubbles (per milliliter). Another advantage of separating the supernatant of microbubbles is that the amount of therapeutic agent encapsulated into the microbubbles and the amount of free drug (i.e., therapeutic agent not encapsulated into the microbubbles) can be quantified using, for example, an ELISA kit as in the case of IL-2.

After phase separation and a wash or inactivation step, a higher concentration of the carrier (with or without encapsulated agents) could be injected to achieve the desired therapeutic effect. For example, after normal preparation of a microbubble, a phase separation step would create a layer of microbubbles in the supernatant. Once the desired amount of microbubbles has been separated, the infranatant could be discarded by, e.g., being expressed out of the syringe containing the phase separated microbubbles. Prior to injection into a patient, the microbubbles could be resuspended in an isotonic solution (such as sterile saline) in an amount less than the amount of diluent indicated in the normal reconstitution process. For example, Imagent is reconstituted from a powder with 10 mL of SWFI; in the present disclosure, after phase separation, it may be desirable to resuspend Imagent in the isotonic solution with less than 10 mL prior to injection. Furthermore, Imagent microbubbles in supernatant from more than one syringe may be combined together prior to adding a diluent, or with small amounts of isotonic solution in each syringe before combining multiple syringes prior to injection. In certain instances, free drug in the mixture solution may be inactivated, eradicated, filtered or expressed out, bound to non-carrier components, e.g., antibodies, free lipids, etc., or eliminated from the solution to leave only or primarily encapsulated drug. Alternatively, such free drug that may be bound to non-carrier components, e.g., antibodies, free lipids, etc., may be injected along with the encapsulated drug.

To increase the amount of therapeutic agent that could be encapsulated into a carrier, the present disclosure may use at least one portion of a therapeutic agent, but likely two or more portions, per portion of a carrier. In some embodiments, depending on the starting agent concentration, used a ratio of multiple vials (e.g., 2 vials) of a therapeutic agent (IL-2) per 1 vial of Imagent. The higher the starting concentration of a manufactured agent, the fewer finished vials needed to mix with each vial of Imagent. If the therapeutic agent needs reconstitution and the amount of diluent may be reduced (without affecting the safety profile of the agent), then the reduced diluent used would result in a higher starting concentration of the agent that could be combined with the carrier for encapsulation. As described below in the "Vial Method", to further increase the amount of IL-2 available for encapsulation into Imagent, each 1 mg vial of IL-2 (Genscript) was reconstituted with a small amount of SWFI, in this case 1.5 mL of SWFI was injected into each IL-2 vial and mixed. Then the contents of 2 vials of IL-2, each containing 1.5 mL of IL-2 in solution were withdrawn and injected into 1 vial of Imagent for a total solution of 3 mL for reconstitution of Imagent.

Vial Method

FIG. 14 is a schematic depicting a vial method for making the compositions of the present disclosure. As shown in FIG. 14, a method for encapsulating an agent into a carrier is herein referred to as the Vial Method. In this method, the carrier MCC201 is reconstituted using a solution containing Drug X MCC201*a* in the vial MCC202 substituting the agent solution for the fluid normally used to reconstitute the carrier MCC201. The amount and concentration of Drug X MCC201*a* used to reconstitute carrier MCC201 may be varied, depending on the desired amount of Drug X MCC201*a* to be delivered to the target tissue. Once the carrier MCC201 has been reconstituted using Drug X MCC201*a*, the solution is mixed by any of a variety of methods, including but not limited to such methods as described in the Syringe Method to enable Drug X MCC201*a* to bind or become encapsulated in the carrier MCC201. After the mix step, the encapsulated agent solution may be withdrawn using a syringe MCC203 so that a phase separation step is conducted (alternatively the phase separation step could be conducted in the vial MCC202). After the phase separation step is completed, the infranatant containing much of the free agent is expressed out of the syringe MCC203 leaving a layer of encapsulated Drug X MCC201*a* in the syringe MCC203 (any free drug not encapsulated in the reconstituted carrier may be further processed or concentrated and reintroduced into the syringe or vial containing the encapsulated carrier and mixed together to further increase the amount of drug encapsulated). With the layer of encapsulated Drug X MCC201*a* remaining in the syringe MCC203, an isotonic solution may be added into the syringe MCC203 prior to administration to assist in the injection of the encapsulated Drug X MCC201.

In the embodiment of encapsulated IL-2, the reconstituted vials of Imagent using a diluent containing IL-2 were then placed on an incubation shaker for a period of time, in this case for 60 minutes. After incubation, the vials were cooled in room temperature water for 5 minutes. After cooling, 2.0 mL of the Imagent/IL-2 drug/drug complex (SonoLeukin) were withdrawn into a syringe from the Imagent vial and the syringe was set at an approximately 75-degree angle for about 60-75 minutes to allow the microbubbles to float.

After the flotation phase separation step, the infranatant was expressed out of the SonoLeukin syringe, with roughly 100 μL injected into a separate, marked tube for assay (each tube marked "AI1", "BI1", or "CI1"). Then 4 mL of sterile saline was added to the SonoLeukin syringe to resuspend the microbubbles (and providing a "partial" wash), after which 100 μL was injected into a separate, marked tube for assay (each tube marked "AMB1", "BMB1", or "CMB1"). Then the SonoLeukin syringe was again set at an approximately 75-degree angle for 60 minutes to allow the SonoLeukin to float to the top of the syringe. The infranatant was expressed out of the SonoLeukin syringe, with roughly 100 μL injected into a separate, marked tube for assay (each tube marked "AI2", "BI2", or "CI2"). Finally, 1.0 mL of sterile saline was added to the SonoLeukin syringe (representing a full wash step) to prepare the complex for injection, of which 100 μL was injected into a separate, marked tube for assay (each tube marked "AMB2", "BMB2", or "CMB2"). The amount of a therapeutic agent, e.g., IL-2, encapsulated in a carrier (i.e., Imagent) using the Syringe Method were measured using an ELISA kit and tabulated in FIG. 15 (which depicts the amount of IL-2 encapsulated within the Imagent microbubbles prepared using the syringe method). As shown in FIG. 15, the target amount of IL-2 within the SonoLeukin complex had mean concentrations of 2710.5 ng/mL after the first partial wash (AMB1, BMB1, CMB1), and 486 ng/mL after the second wash step (AMB2, MBM2, CMB2), thereby exceeding a target concentration of 61 ng/mL of IL-2.

A similar process was used in a separate experiment to encapsulate bevacizumab into Imagent ("Sonovastin") and data on the amount of bevacizumab was collected.

Any free Drug X (not encapsulated in carrier MCC201) may need to be washed or inactivated prior to administration into a patient. For example, prior to administration, it may be desirous to have only or mostly encapsulated IL-2 or other highly toxic or immunogenic agents (e.g., chemotherapeutics, STING agonists, viruses, genes, etc.) remaining in the solution to limit systemic toxicity of or immune response to the administered agent. With certain therapeutic agents, like nucleic acid constructs or certain repurposed drugs, where systemic toxicity may be of less concern (e.g., compared to chemotherapeutics, STING agonists, or IL-2), a wash step may be omitted or modified as some amount of free drug in the carrier suspension may be acceptable or even desirable. A partial wash step may be acceptable to substantially reduce the amount of free drug, rather than eliminating substantially all the free drug prior to administration. Alternatively, any free drug not encapsulated in the microbubbles could instead be processed further and recaptured such that those free drug molecules could be reintroduced into the syringe containing the microbubbles (whether the microbubbles contain encapsulated drugs or not) and mixed together to increase the amount of drug ultimately encapsulated into the microbubbles. For example, in the case of negatively charged nucleic acids, those plasmids in the infranatant (not encapsulated in the carrier) may also be bound to the positively charged surfaces of any free lipids remaining after the reconstitution of Imagent. Those plasmids not encapsulated in the carrier, but bound and encapsulated by free lipids may also be either left in the syringe along with the carrier encapsulated drugs, expressed or washed out of the syringe, or further processed and reintroduced back into the syringe containing the carrier encapsulated drugs.

IV. Methods of Improving Efficacy of Therapeutics

The present invention further provides methods for improving efficacy of therapeutics, e.g., methods for treating a disease or disorder, e.g., cancer or non-cancer disease or disorder, methods for reducing tumor growth, and methods for delivering an active agent to a target site, in a subject.

The inventors of the present invention have surprisingly discovered that by associating or co-administering the active agent with carriers, the level of the active agent required to achieve a therapeutic effect is substantially lower than the level of the active agent required to achieve a therapeutic effect when administered without being associated or co-administered with carriers, e.g., by systemic administration without being associated or co-administered with carriers.

In one aspect, the present invention provides a method of treating a disease or condition in a subject, the method comprising administering to the subject a composition comprising at least one active agent associated with a plurality of carriers, wherein the level of the at least one active agent associated with the plurality of carriers is lower than the level of the active agent required to achieve a therapeutic effect when administered without being associated with carriers, and applying an ultrasound energy to the subject, thereby treating the disease or condition in the subject.

In another aspect, the present invention provides a method of treating a disease or condition in a subject, the method comprising administering to the subject a composition comprising at least one active agent associated with a plurality of carriers, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof; and applying an ultrasound energy to the subject, thereby treating the disease or condition in the subject.

In one aspect, the present invention provides a method of reducing tumor growth in a subject, the method comprising administering to the subject a composition comprising at least one active agent associated with a plurality of carriers, wherein the level of the at least one active agent associated with the plurality of carriers is lower than the level of the active agent required to achieve a therapeutic effect when administered without being associated with carriers, and applying an ultrasound energy to the subject, thereby reducing tumor growth in the subject.

In another aspect, the present invention provides a method of reducing tumor growth in a subject, the method comprising administering to the subject a composition comprising at least one active agent associated with a plurality of carriers, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof; and applying an ultrasound energy to the subject, thereby reducing tumor growth in the subject.

In one aspect, the present invention provides a method of delivering an active agent to a target site in a subject, the method comprising administering to the subject a composition comprising at least one active agent associated with a plurality of carriers, wherein the level of the at least one active agent associated with the plurality of carriers is lower than the level of the active agent required to achieve a therapeutic effect when administered without being associated with carriers, and applying an ultrasound energy at the target site in the subject, thereby delivering the active agent to the target site in the subject.

In another aspect, the present invention provides a method of delivering an active agent to a target site in a subject, the method comprising administering to the subject a composition comprising at least one active agent associated with a plurality of carriers, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof; and applying an ultrasound energy at the target site in the subject, thereby delivering the active agent to the target site in the subject.

The target site is an organ, a tissue, or a tumor site in the subject.

In some embodiments, the methods further comprise administering to the subject a composition comprising at least one free active agent, i.e., an active agent that will not be associated or encapsulated within a carrier, e.g., a microbubble.

In one aspect, the present invention provides a method of treating a disease or condition in a subject, the method comprising administering to the subject a first composition comprising a plurality of carriers, administering to the subject a second composition comprising at least one active agent, wherein the level of the at least one active agent co-administered with the plurality of carriers is lower than the level of the active agent required to achieve a therapeutic effect when administered without being co-administered with carriers, and applying an ultrasound energy to the subject, thereby treating the disease or condition in the subject.

In one aspect, the present invention provides a method of treating a disease or condition in a subject, the method comprising administering to the subject a first composition comprising a plurality of carriers, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof; administering to the subject a second composition comprising at least one active agent, and applying an ultrasound energy to the subject, thereby treating the disease or condition in the subject.

In one aspect, the present invention provides a method of reducing tumor growth in a subject, the method comprising administering to the subject a first composition comprising a plurality of carriers, administering to the subject a second composition comprising at least one free active agent, wherein the level of the at least one active agent co-administered with the plurality of carriers is lower than the level of the active agent required to achieve a therapeutic effect when administered without being co-administered with carriers, and applying an ultrasound energy to the subject, thereby reducing tumor growth in the subject.

In one aspect, the present invention provides a method of reducing tumor growth in a subject, the method comprising administering to the subject a first composition comprising a plurality of carriers, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof; administering to the subject a second composition comprising at least one active agent, and applying an ultrasound energy to the subject, thereby reducing tumor growth in the subject.

In one aspect, the present invention provides a method of delivering an active agent to a target site in a subject, the method comprising administering to the subject a first composition comprising a plurality of carriers, administering to the subject a second composition comprising at least one active agent, wherein the level of the at least one active agent co-administered with the plurality of carriers is lower than the level of the active agent required to achieve a therapeutic effect when administered without being co-administered with carriers, and applying an ultrasound energy at the target site in the subject, thereby delivering the active agent to the tumor site in the subject.

In one aspect, the present invention provides a method of delivering an active agent to a target site in a subject, the method comprising administering to the subject a first composition comprising a plurality of carriers, wherein the carriers comprise a shell and a core, wherein (i) the shell comprises a lipid comprising 1,2-dimyristoyl-sn-glycero-3-phosphocholine (DMPC); (ii) the core comprises a perfluorohexane gas and/or nitrogen; (iii) the shell comprises a lipid, and the core comprises a perfluorohexane gas and/or nitrogen; and/or (iv) the shell comprises a lipid comprising 1,2-dimyristoyl-sn-glycero-3-phosphocholine (DMPC), and the core comprises a gas comprising a perfluorocarbon gas, nitrogen, or combination thereof; administering to the subject a second composition comprising at least one active agent, and applying an ultrasound energy to the subject, thereby delivering an active agent to a target site in the subject.

In some embodiments, the target site is an organ, a tissue or a tumor site in the subject.

In some embodiments, the level of the at least one active agent co-administered with the plurality of carriers is lower than the level of the active agent required to achieve a therapeutic effect when administered without being co-administered with carriers.

In some embodiments, the level of the at least one active agent associated with the plurality of carriers is lower than the level of the active agent required to achieve a therapeutic effect when administered without being associated with carriers by systemic administration.

In some embodiments, the level of the at least one active agent associated with the plurality of carriers is lower than the level of the active agent required to achieve a substantially equivalent therapeutic effect when administered without being associated with carriers.

In some embodiments, the substantially equivalent therapeutic effect is about 50%, about 60%, about 70%, about 75%, about 80%, about 85%, about 90%, about 91%, about 92%, about 93%, about 94%, about 95%, about 96%, about 97%, about 98%, about 99% or about 100% of the therapeutic effect of the active agent when administered without being associated with carriers.

In some embodiments, applying the ultrasound energy induces cavitation of the carriers and/or enhances delivery of the active agent within the subject.

In some embodiments, the level of the at least one active agent associated or co-administered with the plurality of carriers is about 0.001% to about 99%, about 0.001% to about 75%, about 0.001% to about 50%, or about 0.001% to about 25% of the level of the active agent required to achieve a therapeutic effect, optionally, a substantially equivalent therapeutic effect, when administered without being associated or co-administered with carriers.

In some embodiments, the level of the at least one active agent associated with or co-administered with the plurality of carriers is about 0.001% to about 0.1%, about 0.1% to about 10%, about 0.1% to about 20%, about 10% to about 50%, or about 50% to about 99% of the level of the active agent required to achieve a therapeutic effect, optionally a substantially equivalent therapeutic effect, when administered without being associated or co-administered with carriers.

In some embodiments, administration of the composition results in a reduced systemic toxicity, as compared to administration of a composition of the same level of active agent without being associated with carriers.

In some embodiments, administration of the composition results in a reduced systemic toxicity, as compared to administration of a composition of the active agent without being associated with carriers required to achieve a substantially equivalent therapeutic effect.

In some embodiments, the level of the at least one active agent associated or co-administered with the plurality of carriers elicits an immunostimulatory effect.

In some embodiments, the level of the at least one active agent associated or co-administered with the plurality of carriers does not elicit an immunosuppressive effect.

Conventional therapeutic agents are typically administered either systemically or via direct injection. The dose of therapeutic agents, particularly cytotoxic drugs, is determined based on how much is circulating in the vasculature (Area Under the Curve, AUC), or on body surface area (BSA). AUC is dependent upon such factors as dose, schedule, patient age, gender, height, weight, genetics and clearance, and therefore subject to large variability from patient to patient. Historically, the dose is escalated until MTD is reached. Even when therapeutic levels of a drug are determined (using measures such as minimum inhibitory concentration (MIC) to determine minimum levels of antibiotics needed to inhibit growth of organisms), knowing how much of such drug actually reaches the desired cells or tissue is less understood. One way to improve the pharmacokinetics (PK), pharmacodynamics (PD), or biodistribution (BD) of an agent is to deliver greater concentrations of said agent directly to the target.

An agent used to treat a (non-intravascular) disease or condition, such as, but not limited to, cancer must enter the vascular system, extravasate out of the vasculature, and enter the target tissue. In diseased tissue, this process is compromised thereby limiting the effectiveness of therapeutic agents. Chauhan (2011) describes these abnormalities as "barriers to systemic drug delivery that exist in the form of variability avascular regions and sluggish blood flow leading to low and nonuniform perfusion rates in tumors, diminished transmural pressure gradients that limit transvascular transport to passive diffusion, highly viscoelastic interstitial components with tortuous paths and drug sequestration that hinder drug penetration by diffusion, and heterogeneity in the microenvironment that results in poor drug delivery." Uncontrolled tumor cell proliferation imparts solid stress on normal neighboring tissue that limits drug perfusion and penetration by compressing blood vessels and by slowing blood flow. Also, tumor cells generate abnormal pro-angiogenic factors, such as vascular endothelial growth factor (VEGF) creating disorderly, tortuous and leaky vessels contributing to localized slowing of blood flow. Additionally, interstitial fluid pressure increase is a result of a nonfunctioning lymphatic system and leaky blood vessels and contributes to poor drug delivery to the tumor cells. Finally, the stromal density of tumors comprised of fibrous tissue and high level of interstitial matrix molecules further inhibit the interstitial transport of drugs to tumor cells.

As a consequence of the above-mentioned abnormalities, in many cases of systemically administered agents including (but not limited to) injected agents, less than 1% of the agent actually reaches the target tissue. This leads to off-target effects or reduced therapeutic agent efficacy. Such low efficiency of biodistribution to the target may result from degradation or immunological responses to the delivered agents while in circulation, biological or physical barriers (as in the case of tumors or their microenvironments), or from poor targeting. Pharmaceutical companies seek to improve the pharmacokinetics and pharmacodynamics of agents to improve efficacy or reduce off-target effects through changes in formulations. Such formulation changes may result in changes in the properties of the underlying molecules that may compromise safety and efficacy.

In the case of local injection of agents, depending on the specific properties of the surrounding tissues, agents may either flow to limited areas, or worse, may flow to unintended areas. For some applications, local injection may not be feasible (e.g., tumors near critical biological structures), or may be impractical (e.g., large volume target tissues). Additionally, some molecules are not suitable for bolus injections and must be administered via an infusion, which is often a slow process. An additional advantage of the present invention is that low doses of encapsulated drugs onto a carrier may enable bolus or slow injection of drugs that currently need to be infused. Since many agents, whether due to the size of molecule, cytotoxic mechanisms, toxicity profile, half-life, or other factors, need to be slowly infused into patients, by encapsulating such agents into a microbubble and delivering a smaller quantity in a targeted manner, a bolus injection may be achieved. Non-limiting examples of such agents that could be injected via a bolus include monoclonal antibodies and chemotherapy, e.g., Oxaliplatin, an FDA approved agent used to treat solid tumors, such as bowel, stomach, pancreatic, esophageal and other cancers. Oxaliplatin is currently administered via an intravenous infusion over 2 to 6 hours and has a half-life of about 14 minutes in the human body.

The methods of the present invention differ from the basic concept of drug bioavailability relating to optimal plasma concentration of a drug to one of optimal deposition at the target.

Small molecules agents, such as, but not limited to, chemotherapy agents may be able to extravasate out of circulation and into a tumor, but are not generally very targeted, thereby requiring large administered doses as a very small percentage of the drug actually reaches its target. Some agents have been encapsulated to extend their circulation time so that more of those agents can ultimately reach the target, however, they still involve passive diffusion and may have off-target effects.

There is vast data relating to AUC factors and other physical, biological, chemical, or other factors that is not currently collected, and furthermore not acted upon when it comes to the delivery of therapeutic agents. For example, a chemotherapy agent can be infused into a patient over some period of time at a specific dose (whether a fixed dose or based on a BSA formula) over a number of cycles and courses. Treatment will be discontinued until the side effects can no longer be tolerated or disease has regressed or progressed. Given the number of factors involved in determining clinically relevant response to therapy, there is a need to take at least one of the factors into account in order to improve the safety or efficacy profile of the agent. Another way to improve the PK, PD or BD, is to identify, measure, or act upon at least one of the above-mentioned factors.

Even in the era of "personalized medicine," although a combination of therapeutic agents may take into account genetic mutations of a tumor, or T cells may be extracted from a particular patient and re-introduced back into that patient, the dosage of the agents may still be based on the factors above.

Rather than administering a MTD, the methods of the present invention disclose determining the amount (a therapeutically relevant or efficacious amount) of an agent to be delivered to a target, delivering approximately said amount of an agent to a target, using at least one device to apply an energy source, acquire, process or analyze data relating to the patient and to the treatment, providing for the ability to alter the treatment in real-time based on said data analysis. Instead of determining the dose of an agent based on generalized standards such as patient height, weight, age, etc. and applied across all or a group of patients, the present invention discloses determining the required dose based on evidence of clinical safety and efficacy (which is generally less than the MTD for systemically administered agents) and administering said required dose. The present invention also provides for a rationale to deliver said required dose (versus a MTD) by virtue of encapsulating or targeting (or both) the at least one agent in at least one carrier (e.g., a microbubble) such that, with the use of at least one device (e.g., ultrasound) the agent is protected in circulation or delivered directly to the intended tissue through an active targeting means (e.g., sonoporation or releasing the agent from the complex, or both) to enhance an agent's biodistribution into the intended target, safety or efficacy profile. As greater amounts of an active agent may be delivered directly to the target with the present invention (compared to conventional systemic administration), lower overall amounts of an active agent are required to be administered.

For example, the level of the at least one active agent associated or co-administered with the plurality of carriers is about 0.001% to about 99%, about 0.001% to about 75%, about 0.001% to about 50%, about 0.005% to about 50%, about 0.005% to about 25%, or about 0.001% to about 25% of the level of the active agent required to achieve a therapeutic effect when administered without being associated or co-administered with carriers. In some embodiments, the level of the at least one active agent associated with or co-administered with the plurality of carriers is about 0.001% to about 0.005%, about 0.005% to about 0.1%, about 0.005% to about 10%, about 0.005% to about 20%, about 10% to about 50%, or about 50% to about 99% of the level of the active agent required to achieve a therapeutic effect when administered without being associated or co-administered with carriers. In some embodiments, the level of the active agent associated with the plurality of carriers is about 0.001%, 0.005%, 0.01%, 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or about 99% of the level of the active agent required to achieve a therapeutic effect when administered without being associated with carriers, optionally, by systemic administration without being associated with carriers.

Exemplary routes of administration for therapeutic agents include, but are not limited to, systemic routes of administration, such as, parenteral, inhalation, nasal, sublingual, endoscopic, topical, or oral administration, or using direct injection routes, such as, intratumoral, intramuscular, intralymphatic, intraocular, direct injection, or convection-enhanced administration.

Figure 5:
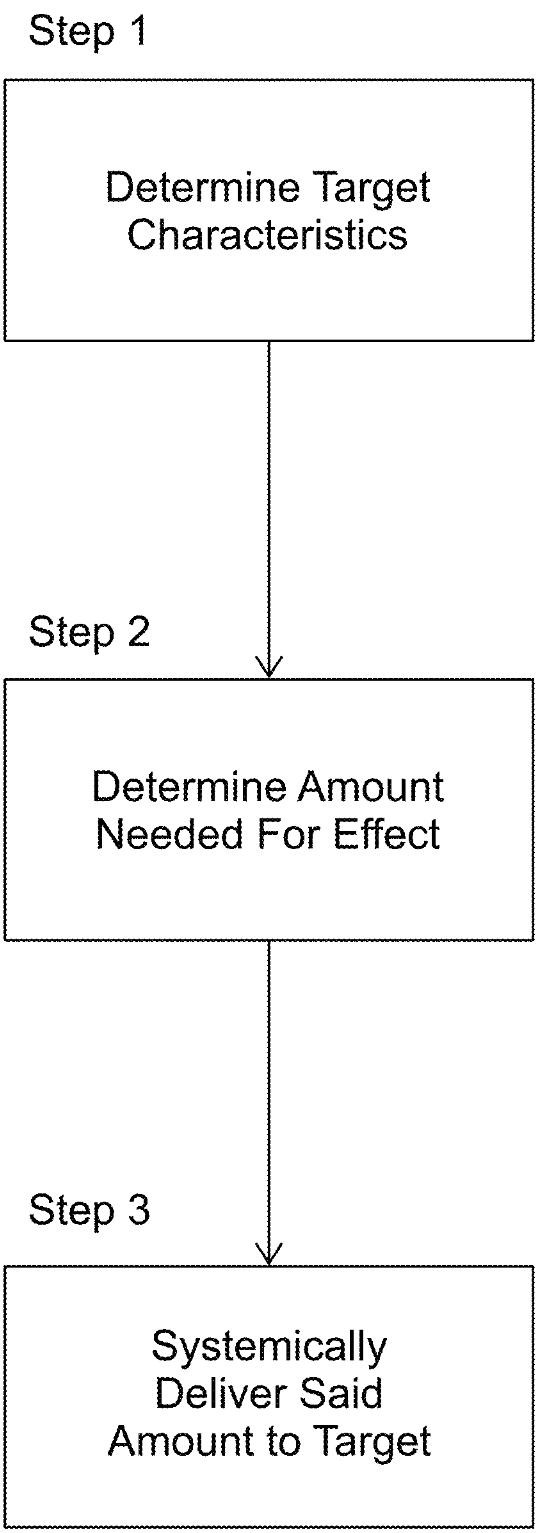
FIG. 5 is a schematic outlining the basic steps in the methods of the present invention.

The present invention further provides methods for improving efficacy of therapeutics. The methods comprise, first, identifying or determining a target characteristics using data (e.g., but not limited to, tumor volume, amount of a drug to be delivered at a target tissue, increasing therapeutic index, increasing therapeutic window, a bioeffect, etc); second, determining the amount of therapeutic agent desired to be delivered to said intended target; and third, delivering approximately said desired amount of therapeutic agent directly to the target site (see FIG. 5).

The target site may be, but is not limited to, an organ, a tissue, (e.g., brain, brain stem, skin, liver, spleen, thymus, kidney, pancreas, lung, prostate, bladder, ovary, uterus, breast, stomach, colon, rectum, esophagus, thyroid, lymph node, hippocampus, putamen, heart), vasculature, glioma, astrocytes, phagocytes, dendritic cells, B cells, T cells, antigen presenting cells, stroma, or a tumor site, e.g., a primary or metastatic tumor, or tumor microenvironment.

The term "cancer" is used herein to refer to a group of cells that exhibit abnormally high levels of proliferation and growth. A cancer may be benign (also referred to as a benign tumor), pre-malignant, or malignant. Cancer cells may be solid cancer cells or leukemic cancer cells. The term "cancer growth" is used herein to refer to proliferation or growth by a cell or cells that comprise a cancer that leads to a corresponding increase in the size or extent of the cancer.

Examples of cancer include but are not limited to, carcinoma, lymphoma, blastoma, sarcoma, myeloma and leukemia. In some embodiments, the cancer comprises a solid tumor cancer. In other embodiments, the cancer comprises a blood based cancer, e.g, leukemia, lymphoma or myeloma. More particular nonlimiting examples of such cancers include squamous cell cancer, small-cell lung cancer, pituitary cancer, esophageal cancer, astrocytoma, soft tissue sarcoma, non-small cell lung cancer (including squamous cell non-small cell lung cancer), adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cell carcinoma, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer (including squamous cell carcinoma of the head and neck).

In the case of cancer treatment, particularly solid tumors (and more specifically a localized tumor), such determined amount of therapeutic agent required to provide a desired effect may be based on estimated (or actual) tumor volume or weight, rather than patient weight or body area. Alternatively, as for the case of viral particles (e.g., oncolytic viruses) or nucleic acid constructs (e.g., messenger RNAs), the determined amount of therapeutic agent required to provide a desired effect may be based on estimated (or actual) number of cells (e.g., tumor cells) to be infected or treated.

Sonoporation has been shown to induce cellular bio-effects that are correlated to the cavitation dose (Lentacker 2014). Factors contributing to such bio-effects include a broad range of ultrasound and microbubble parameters, e.g., ultrasound pressure, exposure time, microbubble type and concentration.

Ultrasound Pressure. The peak negative pressures of commercial ultrasound systems are generally limited to 1.9 MI and are dictated by user adjustable settings of transducer frequency, depth of focus and acoustic output. These output limits set by the American Institute of Ultrasound in Medicine and FDA make therapeutic use of microbubbles for sonoporation relatively safe using commercial ultrasound system hardware or software. Stable cavitation is more predictable for closing of pores (Sun 2015) but inertial cavitation is better for greater volume opening, larger molecule delivery (Chen 2014) and longer permeability duration.

Exposure Time. Research has shown that longer ultrasound exposure led to increased permeability effect. But for clinical adoption, ultrasound operators cannot be expected to hold a transducer in place over a tumor for an extended period of time. A simple fixed transducer holder might not be able to accommodate patient motion (e.g., respiration) and the need to apply consistent pressure to the skin over a wide variety of anatomical positions for various tumors in different organs. Ultrasound exposure as used to induce stable and inertial microbubble cavitation is more complex than how long the ultrasound equipment is used. Pulse duration and duty cycles, for example, generally are not specifications that are displayed on ultrasound equipment.

Microbubble Concentration. The greater the number of microbubbles adjacent to a vessel wall, the greater the permeability that will be achieved. Clinically approved diagnostic microbubbles have a limited persistence in circulation of a few minutes. It would be advantageous to have the highest, safest dose that could be administered so that the maximum number of microbubbles will be within the tumor microenvironment during the period of circulation.

The present invention proposes to take advantage of both stable and inertial cavitation to provide improved drug delivery to target tissue within a clinically adoptable timeframe for a hand-held therapeutic ultrasound treatment. Low MI scanning (e.g., 0.3-0.7 MI) interspersed with intermittent high (e.g., >0.7 MI) pulses of short duration (e.g., 1 sec) would provide for the improved sonoporation effect during a single microbubble injection for a relatively short period of time (e.g., <10 minutes). The present invention uses a bolus injection (or a continuous infusion) of a carrier and a series of continuous pulses for stable cavitation and destruct pulses for inertial cavitation for sonoporation over a short period of time to be more advantageous in a clinical setting. The present invention describes a preferred amount of ultrasound sonication time over 5-10 minutes compared to Dimcevski (approximately 30 minutes), etc.

FIGS. 6A-F describe various sequences and timeframes of the present invention combining a carrier, encapsulated drug, and a co-administered agent. Time periods ($T_0$, $T_1$, $T_2$, etc.) may be seconds, days, weeks, months or years, or fractions or combinations thereof, e.g., $T_0$-$T_1$-$T_2$ may be $T_0$-$T_1$ interval of 1 hour, whereas $T_1$-$T_2$ may be 7 days. Carrier as used in FIGS. 6A-F is without an encapsulated agent, e.g., a microbubble. The subscript "A" represents an agent "A" encapsulated in the carrier; multiple drugs would therefore be subscript "AB", "ABC", etc. (not shown). Co-$Ad_X$ represents a co-administered agent X (may be more than one agent), whereas Adx represents an agent administered at a time different and distinct from the carrier injection time (e.g., may be hours or days apart).

FIG. 6A shows a regimen of carrier (with or without an encapsulated agent in the carrier) injections at different time points ($T_0$, $T_1$, $T_2$, etc.). Certain time points may have different energy sources or parameters to induce stable or inertial cavitation, or to induce different bio-effects. For example, treatment on $T_0$ may involve only inertial cavitation to cause desired level of inflammation at the target site, whereas treatment on $T_1$ may involve only stable cavitation, and on $T_2$ both stable and inertial cavitation would be induced.

FIG. 6B shows a combination where a carrier (with or without encapsulated agent) is co-administered with Drug X (Co-$Ad_X$) at $T_0$ and $T_3$. At subsequent time periods, e.g., $T_1$, $T_2$, $T_4$, the carrier is injected and energy is applied at the target to induce the desired sonoporation effect when Co-$Ad_X$ may still be in circulation (from its administration at $T_0$). In this scenario, the carrier would act to enhance the biodistribution of Co-$Ad_X$ upon initial administration of both drugs, and the carrier would enhance the biodistribution of Co-$Ad_X$ during the time when Drug X is still in circulation. This sonoporation effect would boost the delivery of Co-$Ad_X$ through additional sonoporation beyond the initial half-life of the carrier at $T_0$.

FIG. 6C shows a regimen where the carrier acts to "prime" the target tissue (e.g., endothelial layer, cell membrane) at $T_0$ before the administration of either the Co-$Ad_X$ or the carrier (or both the Co-$Ad_X$ and carrier) at $T_1$. At $T_0$, the carrier (with or without encapsulation of an agent) is used to sonoporate the target (e.g., the tumor vasculature) to induce desired bio-effects. At $T_1$, the carrier is co-administered and sonoporation is effected to enhance the targeted biodistribution of Co-$Ad_X$.

FIG. 6D shows a regimen where an agent $Ad_X$ is administered at $T_0$, and a carrier is administered at a distinctly different time period $T_1$ and sonoporation is induced to open the target vasculature to allow circulating $Ad_X$ to extravasate into the target. (Alternatively, the carrier may be administered at $T_0$, and an agent $Ad_X$ may be administered at a time $T_N$ distinct from the time of administration $T_{N-1}$ of the carrier.

Figure 6E:
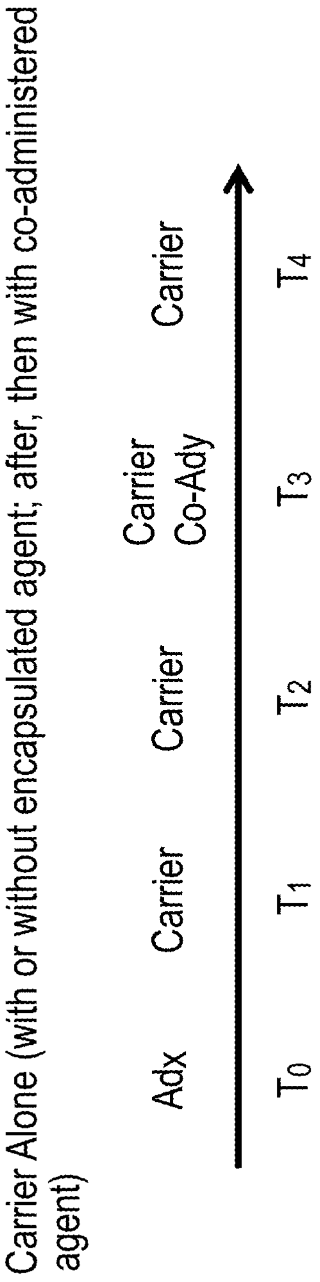

FIG. 6E shows a regimen where a combination of an agent $Ad_X$, carrier, and carrier plus co-administered agent Co-$Ad_X$ are administered at various time points.

Figure 6F:
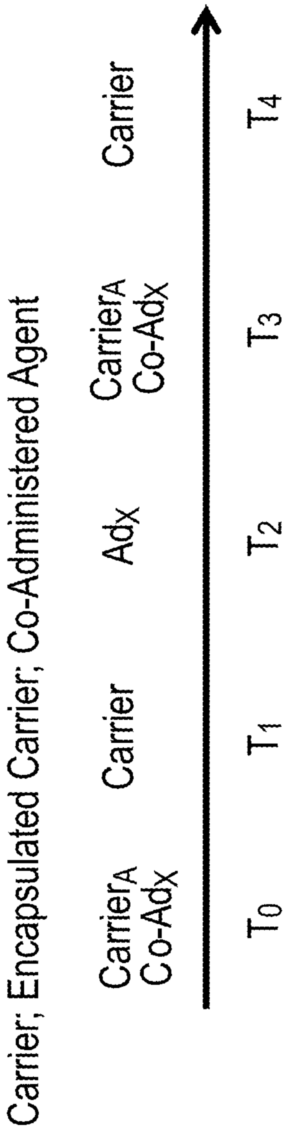

FIG. 6F shows a regimen of an encapsulated agent in a carrier $Carrier_A$, a carrier without any drug encapsulated within Carrier, a co-administered agent Co-$Ad_X$ and an administered agent $Ad_X$ at various time points.

The timing and sequence of each of the above regimens may be varied or changed as needed to deliver a target value of a drug, or effect desired clinical outcomes. Also, the carrier may be any type of carrier (e.g., microbubble, liposome, etc.) and may be for example a microbubble at $T_N$ and a different carrier at $T_{N+1}$. The encapsulated agent $Carrier_A$ may have any type of agent in the carrier (e.g., IL-2, adenovirus, antibody, gene etc.) and may be for example a cytokine at $T_N$ and an antibody at $T_{N+1}$. Administered agent AdX may be any type of agent (e.g., drug, ligand, etc.) and may be for example a checkpoint inhibitor at $T_N$ and a chemotherapeutic at $T_{N+1}$. The co-administered agent Co-AdX may be any type of agent (e.g., drug, ligand, etc.) and may be for example a checkpoint inhibitor at $T_N$ and a chemotherapeutic at $T_{N+1}$. For example, pembrolizumab may be administered every 3 weeks, the Carrier (with or without encapsulated agent) may be co-administered with pembrolizumab on $T_0$, but administered at some point on or before the next pembrolizumab administration.

Each of the therapeutic agents has its own molecular size, PK and PD. The present invention can be set to optimize each "sonication day" so that the respective drugs (whether oral, injected, or otherwise administered) can be optimally delivered just to the target tumor area, with no incremental systemic exposure. At days in which a large molecule (e.g., mAb) is being delivered, the sonication could be set for a higher mechanical index and longer pulse lengths and longer sonication time than those settings used for smaller molecule agents.

In another embodiment of the present invention, a fixed dose of a carrier, e.g., 160 mg/8 mL of Imagent may be used for injection, rather than a weight-based formula for injection.

AI, ML, Data Analysis

The present invention also describes a form of digitization of injected drugs (or other agents) by identifying, measuring, monitoring, or acting upon such factors through the use of instruments, equipment and devices in addition to the therapeutic molecule or method of delivery of such molecule.

The present invention identifies, measures, or acts upon factors or properties that include, but are not limited to, tissue, tumor, microenvironment, organ, vasculature, fluid, cellular, chemical, biological, physical, morphological, molecular, electrical, mechanical or genomic characteristics. As a non-limiting example, a therapeutic agent administered to the liver, e.g., for hepatocellular carcinoma (HCC), may have different PK/PD/BD compared to the pancreas, e.g., pancreatic ductal adenocarcinoma (PDAC), due in part to the differences in vascularization between the two organs, the fibrotic nature of the tumor microenvironment, or some other characteristics.

In a preferred embodiment of the present invention, certain data regarding a patient or tissue (for example, including, but not limited to, a tumor) is collected, at least one therapeutic agent is administered into the body of a patient, further data regarding such patient is collected, the treatment may be adjusted or augmented in real-time (i.e., during the administration of said at least on therapeutic agent) as a consequence of the analysis of the treatment data (including either acute or longitudinal data), with the objective of improving the biodistribution, safety or efficacy of the therapeutic agent for the benefit of a patient. The collection of such data may use software or hardware, may be collected via a combination of pre-, intra-, inter- or post-treatment timeframes, may be processed, analyzed or acted upon in real-time using machine learning or artificial intelligence to enable the immediate intra-treatment adjustment of the treatment. The collection of data may use distributed ledger technology to provide secure authoritative records and permanent unadulterated data for further transmission and analysis, which in turn may provide justification to modify the treatment including in real-time.

The present invention acquires data from at least one device, (for example, but not limited to, an ultrasound device such as a Shenzhen Mindray Bio-Medical Electronics Co., LTD, China, TE7 Diagnostic Ultrasound System (the "TE7")). As shown in FIGS. 16 and 17, such data from the ultrasound device may include (but not be limited to) MI AI01 101, frequency AI01 102, treatment date/time AI01 103, target tissue area AI01 104, patient information AI01 105, transducer settings AI01 106, alternate ultrasound settings, e.g., used to induce inertial cavitation AI01 107, duration of treatment AI01 108, operator data AI01 109, therapeutic agent data AI01 110, carrier data AI01 111, depth of target tissue AI02 112, and target tissue dimensions AI02 113. Data may be acquired in real time or at some post-treatment time directly from the device's hardware system, via the device's input/output port, such as a Universal Serial Bus (USB) or other hardware interface, or wirelessly from an external device containing such data (such as a cloud server). Data may be in the form using protocols such as, for example but not limited to, Digital Imaging and Communications in Medicine (DICOM), Health Level Seven (HL7), or Integrating the Healthcare Enterprise (IHE). The present invention contemplates, as an example, the storage of patient information, exam information, image files or reports into an external storage device for either real-time or post-treatment analysis. Image files may be any number of formats, including but not limited to, single-frame (e.g., BMP, JPG, TIFF, PNG, or DCM), multi-frame (e.g, AVI, DCM). Data may be exported from a device to an external memory device via a hardware connection, or transmitted wirelessly via, for example but not limited to, a DICOM or print server. Additionally, data may be captured or transmitted using voice, video, audio, image capture, video capture, photograph, barcode, QR code, RFID, or any other means whether or not such data is present in one device (e.g., ultrasound). For example, data relating to the treatment or patient may be transmitted by voice (or captured and transmitted by a video or audio device) to an external storage device, such as a server, for real-time or later processing and analysis.

As an example, the present invention describes the use of ultrasound equipment settings optimally determined to enable the steps described herein to improve therapy. For example, it is well known that the MI concept reflects a threshold for inertial cavitation, rather than the severity of effects (J Ultrasound Med 2000 February). Other factors affecting either MI or severity of effects relating to cavitation include certain aspects of waveform shape or pulse polarity. Also, ultrasound pressures in tissue may be underestimated when measurements are conducted in water then derated (e.g., at 0.3 dB $cm^{-1}$ $MHz^{-1}$). Carstensen et al (1998) showed that a "6 dB underestimate of negative pressures from water compared with those in liver . . . for a 3 MHz, 2 cm diameter, 8 cm focal length circular transducer." Therefore, merely setting and using an MI level on a particular ultrasound device (or transducer, or carrier) may not yield desired effects using the same MI on a different ultrasound manufacturer's device and could lead to variation in clinical outcomes from patient to patient. Human errors may be eliminated or minimized using data from such activities as, but not limited to, the angle, rotation, sliding, rocking, sweeping, fanning, pressure, compression force, or positioning of the ultrasound probe to ensure that the sonoporation can be repeatably performed, or optimized as needed.

The present invention discloses a means to create a positive feedback loop whereby treatments utilizing an electronic device and a carrier capable of changing the PK or PD of an agent can be continually improved by taking into account data (from a particular patient or from other patients, or both) acquired prior to, during or after agent administration and applying learnings from the data in real-time—the more patients treated and data acquired, the better the analytics that can be derived from the treatment. For example, based on data gathered during a treatment of a patient (Patient A) and comparing the data to that data collected from at least one other patient (Patient B) before, during or after Patient B's treatments, the operating parameters of the ultrasound device may be adjusted in real-time to account for differences (or similarities) in tissue elasticity that would impact the amount, magnitude or duration of the sonoporation effect. The advantage of the present invention is that treatment can be adjusted if necessary, based on data collected before, during or after a therapeutic agent has been administered (e.g., injected or infused) with the goal of improving patient outcomes. This compares to the current standard of care where an agent is administered and there is not a means to account for, say, tissue specific conditions that may have an impact on the biodistribution, safety or efficacy of an agent.

Furthermore, the present invention discloses the use of data from sources distinct from the episode of care (e.g., during the administration of the agent). Externally generated data may be gathered from sources such as, but not limited to, clinical research or clinical study data repositories or registries; real-world evidence from sources such as administrative/claims sources, electronic medical records (EMR), claims and billing data, product and disease registries; patient-generated/reported data gathered by sensors, personal devices, social media and health applications; and cross-industry collaborations, such as datasets from public-sector organizations, not-for-profit organizations, and commercial entities. Data may be collected from sources such as, but not limited to, medical imaging, including ultrasound, PET, MRI, or CAT scans. Such externally generated data (which may include a patient's own data) may be used for comparative purposes to assist in the real-time adaptation or change of treatment, resulting in the improvement of the agent biodistribution, safety or efficacy profile.

As an example, the present invention provides for the administration of at least one therapeutic agent (whether such agent is encapsulated or not within the carrier) and a carrier (e.g., a microbubble), the use of an energy source (e.g., ultrasound) capable of measuring data and interacting with said therapeutic agent or microbubble, the real-time capture of data, the analysis of said data, if needed, then the adjustment to and of said device to effect the biodistribution, safety or efficacy of said therapeutic agent. The present invention further describes the use of a microbubble to be administered either a) as a monotherapy, b) co-administered with a therapeutic agent, or c) as a delivery vehicle to be administered with a therapeutic agent as part of a drug/drug complex. In either case, the ultrasound device is used to deliver energy into body of a patient to interact with said microbubble, complex or target tissue, to generate, capture and analyze data in real-time, and if desired to adjust the operating parameters of said device to enhance the biodistribution, safety or efficacy of said therapeutic agent.

An energy source may be from a conventional or custom ultrasound system or probe. Such device (a "First Device") would provide energy that would be aimed at a target (e.g., a tumor, tumor microenvironment, tumor vasculature, or any combination thereof). The targeted ultrasound energy would cause the carrier complex (or the carrier without any drug loaded onto it) to be in either a stable or inertial cavitation state (or both), causing the targeted tissue barrier to open temporarily to allow a therapeutic agent that is in circulation or released from the complex near such opening. This provides a pathway out of the vasculature into the intended tissue, e.g., the tumor microenvironment, or preferably the tumor cells. Alternatively, an unloaded carrier, such as a microbubble (without any drugs loaded or co-administered) may elicit desirable bioeffects as a result of the induced cavitation. Such First Device would measure, record, or analyze data generated during the treatment, then would transmit such data to a separate device ("Second Device" or "Other Devices") that would collect data from the First Device, compare the data to data collected from other patients having undergone similar procedures using either the same First Device or Other Devices. Second Device or Other Devices may be physically or wirelessly connected to First Device. Second Device may be used to further transmit data to Other Devices. Data analysis may be performed by First Device, Second Device or Other Devices.

As a non-limiting example, FIG. 18 shows First Device FD101 may consist of an ultrasound transducer probe connected to an ultrasound signal generator used to treat a patient (e.g., Patient 1a, Patient 1b). (A different First Device FD102 may treat a different Patient 2; while yet another First Device FD103 may be used to treat another Patient 3, and so on.) Second Device SD101 may be an external memory card or other data collection device or data transmitter or transmission device (which may or may not be connected to First Device FD101 via a physical connection or wirelessly). Alternatively, Second Device SD101 may be a picture archiving and communication system (PACS) SD102 or network SD103 (connected to First Device FD101) capable of transmitting such data from First Device FD101 to an external database ("External Database" ED101). Based on the analysis of such data, operating parameters for the First Device FD101 may be adapted, changed, or maintained to improve the biodistribution, safety or efficacy profile of the administered agent for a given patient treated using the First Device FD101. The First Device FD101 or Second Device SD101 may use an algorithm that enables said First Device FD101 to automatically or manually adapt or change operating parameters in real-time, if desired. Such comparative data and analysis may be performed by Other Devices OD101 that transmit data or analysis back to the First Device FD101 being used to treat a particular patient or to a Second Device SD101 connected to First Device FD101 in order to allow for the adaptation or change of treatment of said patient based on data collected and analyzed from other patients. The result would be an improvement in patient outcomes due to the collection and analysis of data from many patients, some of whom would share similar data or data characteristics.

As shown in FIG. 19, a "network effect" would ensue where each additional treatment of a patient (Patient 1, Patient 2, Patient 3, . . . , Patient n) using the present invention would have data uploaded to External Database ED101 containing data from previous treatments. Patients being treated or about to be treated could benefit by comparing their data to the External Database ED101, use an algorithm to propose (or automatically) modify treatment protocols according to data in the External Database ED101 from patients successfully treated using the present invention. The External Database ED101 may be analyzed to provide, for example, operating ultrasound settings shown to treat successfully patients who share similar data to other previously treated patients. For example, a female patient, aged A years, with a breast cancer lesion measuring B cm3, at a depth of C cm, tumor consisting of D genetic profile, with tumor stiffness of E, having previously been treated with F drug(s) G weeks ago, etc. could be treated using similar ultrasound parameters to a previously treated female patient with similar data characteristics who was successfully treated using the present invention at another treatment center using a different First Device FD101. With each successive patient treated using the present invention and having his/her data transmitted to the External Database ED101, the more data is available to be analyzed to determine what set of data has been shown to have certain outcomes for patients with similar data characteristics, and the more value is derived as future patient treatments may be adjusted accordingly.

The analysis may be performed using artificial intelligence or machine learning techniques or processes to detect, recognize, or decipher such data as, but not limited to, acoustic signature patterns. Acoustic signature patterns may be derived from ultrasound, tissue or vehicle interactions to reflect status or changes of such data as, but not limited to, tumor, microenvironment or tissue stiffness, vasculature permeability, microbubble shell flexibility, number or characteristics of microbubbles, and other data that could have an impact on an agent's biodistribution, safety or efficacy profile. Data collected from a particular patient may be indicative of differences that are relevant or meaningful compared to other patients and may require different operating parameters of devices or dosing schedules or amounts in order to improve clinical outcomes for that patient. To the extent that operating parameters of the devices can be adapted or changed to account for the specific tissue properties (or based on other data) present at the time of treatment for a specific patient, then the effect of the treatment may be improved thereby also improving clinical outcomes.

V. Kits

In certain aspects, the instant disclosure provides kits that include a suitable container containing a plurality of microbubbles, The microbubbles may be in a vial or a pre-filled syringe in suspension, or in the form of lyophilized powder which can be reconstituted in a solution, e.g., sterile water, or a saline solution. The lyophilized microbubble powder may also be reconstituted in a solution comprising an active agent.

The kits also include a suitable container containing an active agent. The microbubbles may be in a vial or a pre-filled syringe in suspension or in the form of lyophilized powder which can be reconstituted in a solution, e.g., a sterile water, or a saline solution. The lyophilized active agent powder may also be reconstituted in a solution comprising a plurality of microbubbles.

Such kits also include a device, e.g., a syringe, to allow for incubation of the microbubbles and the active agents and to isolate microbubbles of desired sizes, and instructions for use. The kits may optionally further comprise means for administering the microbubbles and the active agents (e.g., an injection device, such as a pre-filled syringe), or means for measuring the concentration of the active agents. The kits of the invention may optionally further comprise means for determining the therapeutically effective or prophylactically effective amount.

In certain embodiments the individual components of the kits may be provided in one container, e.g., a vial or a pre-filled syringe. Alternatively, it may be desirable to provide the components of the kits separately in two or more containers, e.g., one container for the microbubble preparation, and at least another for an active agent. The kit may be packaged in a number of different configurations such as one or more containers in a single box. The different components can be combined, e.g., according to instructions provided with the kit. The components can be combined according to a method described herein, e.g., to prepare and administer a composition. The kit can also include a delivery device.

VI. Apparatuses

The present disclosure further provides apparatuses for carrying out the methods of the present disclosure. In some embodiments, the present disclosure combines the use of low cost, portable ultrasound devices, for example, but not limited to, Butterfly iQ®, Butterfly Networks (Guilford, CT); Lumify®, Koninklijke Philips N.V. (Amsterdam, Netherlands); SonoSite iViz®, Sonosite (Bothell, WA); Kosmos®, EchoNous (Redmond, WA); Clarius HD®, Clarius (Burnaby BC, Canada) in combination with a carrier (whether an agent is encapsulated or whether the carrier without an encapsulated agent). As long as such portable ultrasound equipment is capable of generating acoustic energy and operating at desired parameters to induce carrier cavitation sufficient to enable agents to extravasate into the target extravascular space, then such portable equipment could be used in the present disclosure for therapeutic purposes. In the case where a portable ultrasound device may not be able to generate sufficient acoustic energy or operate at desired parameters to induce carrier cavitation, then such portable ultrasound devices may benefit from the addition of another device, e.g., a power amplifier or other device.

In some embodiments, a portable ultrasound system having a single transducer according to the present disclosure, may be used to accommodate different tissue targets, rather than having to use a separate cardiac, or abdominal probe for example. For a non-limiting example, a single programmable probe, such as the Butterfly IQ, may be used for different depth targets, ranging from superficial (e.g., skin, or head and neck tumors) to deep (e.g., abdominal, or pancreas) when used with a carrier (either with or without encapsulated agents) to deliver agents out of the vasculature and into the target tissue.

The present disclosure provides one or more apparatuses that can spin (separate), mix and incubate a single or multiple syringes or vials to prepare the drug combination complexes, for example, in a non-manufacturing facility, such as a hospital, outpatient center, drug infusion clinic, physician office, home, or other location. For example, one or more apparatuses as taught herein may include a housing unit into which one or more vials or syringes containing at least one drug is inserted (including the carrier). In turn, the drug(s) are reconstituted, mixed, incubated, phase separated, size isolated, washed or inactivated, encapsulated or free drug amount analyzed, diluted, free drug or lipid encapsulated drug not bound to carrier reintroduced into the mixing process, or otherwise prepared for patient delivery (with any or all of these steps in any order incorporated into the apparatus(s).

In some embodiments, one or more apparatuses taught herein may have a component enabling the testing and determination of the amount or concentration of encapsulated drug within the carrier, such as a rapid assay.

In some embodiments, a kit is provided. The kit can include the fixture to hold the syringe, the heating component (e.g., for incubation), Carrier, fluid (e.g., sterile water for injection) for reconstituting the Carrier, a spike/filter hub to allow the fluid to be injected into the Carrier vial, needle and syringe cap and the apparatus 3400. In some embodiments, the kit can include a cooling means (e.g., a cool gel pack, freezer pack, etc.), at least one vial of therapeutic agent, fluid for reconstituting the agent, needle and syringe.

In some embodiments of the present disclosure, at least one Imagent vial may be removably coupled to an apparatus as disclosed herein. The fluid (whether or not such fluid contains a therapeutic agent) used to reconstitute Imagent is then injected into said Imagent vial(s). In some embodiments, the apparatus provides an automated means to mix the Imagent with the fluid (e.g., by rotation for a period of time period, for example, by a rocking motion, or gentle agitation) within the apparatus. If a therapeutic agent solution is used to reconstitute Imagent (in lieu of sterile water for injection SWFI), a separate compartment may be used to house and reconstitute the agent. The Imagent vial may be set at a desired angle, for example, horizontally along its longitudinal axis during the reconstitution step to facilitate thorough mixing, and may be set at the same (or different) angle, for example, vertically along its longitudinal axis for phase separation of the Imagent microbubbles from the infranatant. In some embodiments, a phase separation may enable mixing of an agent with the carrier at high concentrations or may create high concentrations of carrier. Various means of phase separation of the carrier from the infranatant as described herein may be used within the apparatus. In some embodiments, incubation or the use of linkers or other means may enhance encapsulation of an agent within the carrier. Either an incubation module or means to introduce such linkers, etc. may be used within the apparatus. If phase separation includes the expression of infranatant from the carrier, such process may be used within the apparatus. If additional diluent is used to prepare the carrier (whether or not an agent is encapsulated), such means may be included within the apparatus. After the steps to reconstitute the carrier (whether or not an agent is encapsulated), the suspension is ejected from the apparatus to allow administration of the product. As taught herein, in the syringe or vial methods discussed above to constitute, reconstitute the carrier, or the carrier and at least one agent may be contained within the apparatus to increase repeatability of such process using automation or precise measurements (e.g., time, volume, temperature, speed, etc.).

The present disclosure describes various methods to reduce on-site encapsulation preparation time or to increase the amount of agent encapsulated within the carrier. For example, in some embodiments a reverse angle centrifuge rotor 3300 as shown in FIG. 33 (which depicts a reverse angle centrifuge rotor 3300 for use in the methods of the present disclosure) may be used for separation. In such embodiments, the syringe or vial is vertically offset from a vertical axis of the centrifuge by about 10° during operation of the centrifuge. Phase separation techniques using centrifuges position a tube containing material to be separated such that precipitates are forced outwardly. In the case of a carrier such as a microbubble (whether encapsulating an agent or not), it may have the bubbles float towards the plunger of the syringe so that the infranatant may be expressed out of the syringe leaving only the layer of microbubbles. By positioning the syringe in a reverse angle (e.g., at least 10° from vertical) or a low angle fixed rotor in a centrifuge, microbubbles can float towards the plunger in less time than if the syringe were positioned in a swing bucket.

FIG. 34 illustrates an apparatus 3400 for performing incubation, spin separation (in some embodiments referred to as phase separation), and mixing of the present disclosure. The apparatus 3400 can include a controller 3410 or can be coupled to an external controller, a motor/rotor 3420, a housing 3430, one or more connection collars 3440, one or more holders 3450, and one or more hardware components supporting operations associated with incubation, spin separation and mixing. The apparatus 3400 can be placed horizontally along its longitudinal axis 3480 during incubation and/or mixing, and can be placed vertically along its longitudinal axis 3480 during spin separation. In some embodiments (not shown), the apparatus 3400 can be placed at the same angle (e.g., horizontally or vertically along its longitudinal axis 3480, or having a tilt angle relative to the longitudinal axis 3480) during incubation, mixing, and spin separation.

The controller 3410 receives user inputs and performs operations associated with incubation, mixing and spin separation. The controller 3410 can perform operations associated with a particular step (e.g., incubation, mixing, and spin separation) based on a user selection or input from a controller. For example, a user can turn on or turn off a particular step by pressing a corresponding button 3412 or 3414 on the controller 3410 or by inputting a selection via a user interface displayed to the user (not shown). The controller 3410 can control the motor/rotor 3420 to rotate a container 3460 (e.g., syringe and/or a vial) with one or more predetermined or user selected setting parameters associated with the motor/rotor 3420 (e.g., various angles and speeds for spinning, various tilt angles and speeds for incubation and/or mixing, etc.). The controller 3410 can obtain data from the one or more hardware components to present obtained data (e.g., elapsed time, temperature, or the like) for a particular step, for example, via a digital display 3416 to the user.

The motor/rotor 3420 has multiple modes of operation. A first mode of the motor is operable to impart a first rotational motion to the fluid filed container to mix two or more components held in the container, and a second mode of the motor is operable to impart a second rotational motion to the container to generate a vortex therein to separate a first component from a second component. In some embodiments, the motor/rotor 342 can be used as a spinner and a rocker. During incubation and/or mixing, the rocker motor function is activated. The motor/rotor 3420 can be used as rocker to create waves and/or gentle swirling in the content (e.g., a mixture) of a container 3470 (e.g., a syringe and/or a vial) via a seesaw motion by pivoting at a pivot point along the longitudinal axis of the syringe or vial, a back and forth rotating motion (e.g., 180° back and forth motion relative to the longitudinal axis of the syringe or vial in a horizontal position with a speed at a fixed alternating time of 1 revolution per minute before it reverses), a swing motion, a shaking motion, and/or a gentle rotation motion. In some embodiments (not shown), the motor/rotor 3420 can hold the container at an angle (e.g., between 45-90° from a vertical axis) to reduce the time for flotation of the microbubbles compared to a vertical syringe.

During spin separation, the motor/rotor 3420 can be used as a spinner to spin the container 3460 to create a vortex in the content of the container 3460 along a longitudinal axis of the container 3460 while in a vertical position. In some embodiments, the motor/rotor 3420 can provide a spinning separation having a spinning speed in a range of 0-7,580 revolutions per minute (RPM). Time for spinning separation depends on the spinning speed. For example, fully separating the microsphere layer from the infranatant is in approximately 15 minutes at 1,300 RPMs. A 2,000 RPM speed can reduce the separation step to 6 minutes. In some embodiments, the user can set and/or select setting parameters of the motor/rotor 3420 by pressing a corresponding button on the motor/rotor 3420 or by inputting a selectin via a user interface displayed to the user (not shown). In some embodiments, the motor/rotor 3420 can be integrated with the controller 3410. In some embodiments, the container 3460 can be syringe (or vial) containing a reconstituted microbubble suspension (whether containing an encapsulated drug or not). The motor/rotor 3420 can spin the container 3460 around the short axis of the container 3460 using any power source (e.g., battery or alternating current). By spinning the container 3460 in such a manner, a vortex can be created allowing the microbubbles to float inwardly away from the container walls, without high pressures compromising the microbubble stability, thereby facilitating and accelerating the separation process from the infranatant.

The housing 3430 can have a base portion and an upper portion, the upper portion have a sealable access that allows placement and withdrawal of a fluid filed container. The motor/rotor 3430 can be in the base portion. In some embodiments, the housing 3430 can be integrated with the peripheral of the motor/rotor 3420. The housing 3430 is sealable to avoid spilling and leaking during incubation, spin separation and mixing, which is suitable for viruses and toxic drugs. The housing 3430 can open to place or take out a container (e.g., a syringe and/or a vial) and can be closed and sealed during incubation, spin separation and mixing. The housing 3430 can be made of plastic material or other suitable material.

The one or more connection collars 3440 are connected with the motor/rotor 3420 to support a container 3460 during spin separation. For example, FIG. 35 illustrates an example connection collar of the present disclosure. As shown in FIG. 35, the connection collar 3440 can be inserted into the motor/rotor 3420 via multiple connectors 3442.

FIG. 36 illustrates an example connection collar in greater detail. As shown in FIG. 36, the connection collar 3440 holds a portion of the container 3460 and has a lock 3444 (e.g., a female luer lock) at the bottom of the connection collar 3440 to prevent the container 3460 from moving away from the connection collar 3440. For example, the container 3460 (e.g., a syringe) can have a luer lock connector (e.g., a male luer lock). In some embodiments, the connection collar 3440 can have an interior rubber gasket 3446 to support a snug fit. In some embodiments, the apparatus 3400 can include multiple connection collars based on various sizes/shapes of the container 3460. For example, if a container has a larger size or volume, a larger connection collar 3440 can be used.

Referring back to FIG. 34, the one or more holders 3450 can be connected with the motor/rotor 3420 to hold and/or heat a container 3470 during incubation and/or mixing. For example, FIG. 35 illustrates an example holder of the present disclosure. As shown in FIG. 35, the holder 3450 can include a limiter 3452 to support and fix the container 3470, a heater 3454 to heat the content of the container 3470, a heater connector 3456, and one or more connectors 3458 to connect the holder 3450 to the motor/rotor 3420. The limiter 3452 can have multiple separate pieces to hold the container 3470. In some embodiments (not shown), the limiter can have a cylinder shape to hold the container 3470. The limiter 3452 can connect with the motor/rotor 3420 and can prevent longer rotations before the motor/rotor 3420 switches directions, which reduces complexity of motor timing reversal and cabling needs. The heater 3454 can include one or more heating tapes or elements, one or more thermistors, and/or one or more other suitable heating elements to heat the content of the container 3470.

FIG. 37 illustrates an example holder 3450 in greater detail of the present disclosure. The holder 3450 can include mesh material 3455 to wrap the container 3470 for additional support and heat transfer. The heat tape and thermistor 3454 can be coupled directly or indirectly to the container wall. The holder 3450 includes coiled cable 3457 to allow 180 (or more) degree alternating mixing rotation. The heater connector 3456 can be a 3-pin molex connector, which is some embodiments plugs into the base of the motor/rotor 3420 or the controller 3410 or other fixture for heating and thermostat connection (e.g., for power supply and/or temperature control).

The apparatus 3400 further includes one or more hardware components. The one or more hardware components can include a power supply and/or a battery, one or more time clocks, and one or more sensors to detect various physical parameters (e.g., temperature, motion, pressure, or the like) associated with other components of the device. For example, a time clock (e.g., an elapsed time clock) can measure a time value for determining whether elapse time has been reached. A temperature sensor (e.g., a temperature gauge or the like) can measure a temperature provided by the heater, an incubation temperature (e.g., a temperature of an interior of the housing), a temperature of the content of the container, and/or other suitable temperature associated with the device.

In some embodiments, containers for incubation, mixing, and spin separation are different. For example, containers for incubation and mixing can be vials. Containers for spin separations can be syringes, or vice versa. In some embodiments, containers for incubation, mixing, and spin separation can be the same.

In some embodiments, the apparatus can further include other components such that other steps may be automated or at least set in a way to minimize manual effort, such as using fixtures in the apparatus that assist in regulating the amount of infranatant expressed out of the syringe, or limiting the travel distance of the syringe plunger to maintain internal pressures.

In some embodiments, the entire apparatus 3400 or some components of the apparatus 3400 can be disposable. For example, the one or more connection collars 3440, and the one or more holders 3450 can be disposable. In some embodiments, the entire apparatus 3400 or some components of the apparatus 3400 can be reused. For example, the controller 3410, the motor/rotor 3420, the housing 3430, the one or more connection collars 3440, the one or more holders 3450, and/or the one or more hardware components can be reused.

In some embodiments, the apparatus 3400 can be used to separate a plurality of buoyant, pressure-sensitive particles. For example, the motor/rotor 3420 creates a liquid vortex to cause the plurality of buoyant, pressure-sensitive particles to travel to the walls of the containers and precipitate.

FIG. 38 illustrates an example spinning syringe 3800 of the present disclosure. The spinning syringe 3800 can have a weight balanced collar 3810 built into a syringe component 3820 for balanced spinning. The weight balanced collar 3810 can limit a plunger to a specific volume for microbubble cream only (e.g., 300 microliters). When the weight balanced collar 3810 is opened, it allows full plunger movement to evacuate entire volume of syringe component 3820. The spinning syringe 3800 can be made of polypropylene material for smooth sliding (e.g., the same material as syringe barrel material).

FIG. 39 illustrates an example spinning of a syringe 3900 (e.g., the syringe 3460 of FIG. 34 or the syringe 3800 of FIG. 38) to illustrate a vortex 3910 produced within the syringe 3900 during spinning to separate the microbubble from the infranatant. FIG. 39 shows a syringe spinning at 1,300

RPMs. Such a device may utilize a high-speed spinning technique to float the microbubbles toward the center of the syringe creating a separation from the infranatant.

Apparatus for Phase Separation Step

In order to separate the lipid microspheres (with or without an encapsulated agent, e.g., IL-2) from the infranatant containing any free drug, a technique was used that would preserve the integrity and size distribution of the Imagent lipid microspheres as well as be practicable for clinical adoption, particularly in an outpatient environment. The standard lab method for microbubble separation has been the centrifuge. However, the thin, flexible DMPC shells of Imagent need a very low centrifuge g-force to avoid the column of water in the syringe adding weight and thus pressure to the microsphere layer as the Imagent microspheres are being separated from the infranatant. Also, use of a 5 mL syringe with 5.0 mL of solution in it creates a tall clearance that includes the height of the extended plunger that would need large centrifuge machines. Therefore, the apparatus 3400 taught herein provides a portable, single-use device containing at least one component used to separate the carrier (e.g., lipid microbubbles or microspheres), which would be advantageous by eliminating the need for a large centrifuge machine.

Imagent microspheres will collapse when the external (hydrostatic) pressure reaches the vapor pressure of perfluorohexane (PFH) which is 183 torr or 249 cm of water (at 70° F. or 21° C.). At this threshold pressure, in water saturated with air at one atmosphere, enough of the non-PFH gasses leave the bubble to cause the PFH to condense to a liquid causing the bubble to collapse. This collapse is fairly rapid. It can happen at a lower pressure if surface tension is considered or the aqueous solution is less than saturated with air or if the temperature drops below 70° F. A safety margin of at least 20% below threshold pressure is recommended.

This pressure is proportional to the g-force, and the depth (height of water column above bubble, height measured as distance along the g-acceleration field). This pressure linearly goes to zero at the top of the water column and linearly increases to the calculated maximum pressure at the bottom of the water column (i.e., the syringe exit end where the needle is attached). A maximum pressure 40% above the threshold pressure will eradicate 40% of the bubbles in the syringe cylinder if it were well mixed at startup (e.g., using a swinging bucket rotor).

The apparatus 3400 enables a syringe to be spun vertically along its long axis. The spinning syringe directs the vortex or "water column" in the direction of the acceleration field that is only half the internal diameter (i.e., radius) of the 5 mL syringe (compared to the length of the syringe column when using a conventional centrifuge). This allows the microspheres to withstand a very high g-force (or to be accurate, a high acceleration field). In addition, the microspheres only have to travel a short distance (radius=6 mm) to the center of the syringe cylinder. Once collected into the center of the syringe cylinder, the microspheres float more rapidly to the top of the column without hindrance of the medium fluid, further decreasing the time to separate microspheres from the infranatant.

The apparatus 3400 allows for fully separating the microsphere layer from the infranatant in approximately 15 minutes at 1,300 RPMs. A 2,000 RPM speed would reduce the separation step to 6 minutes. The threshold pressure for microsphere collapse can occur at about 7,580 RPMs, so a 2,000 RPM target for an apparatus as taught herein can alleviate risk of damage to any microspheres during the spin separation step.

VII. On-Site eIL-2 (SonoLeukin™) Preparation

Referring back to Section III, in some embodiments, the compositions can be produced using an apparatus described in FIG. 34 to avoid spilling and leaking (e.g., for viruses and toxic drugs) and to reduce manual operations for on-site eIL-2 preparation, as described below.

FIG. 40 illustrates example components of on-site eIL-2 preparation of the present disclosure. The example components include one vial of 200 mg Imagent 4002, one or two 1.3 mg vials of IL-2 4004 (e.g., Proleukin®), two vials of 10 mL of sterile water for injection 4006, one 10 mL vial of 0.9% sterile saline 4008, one 5 mL Norm-Ject syringe 4012, one 0.5 micron filter hub 4010, one BD PhaSeal™ vial adapter P20-O 4014 for closed reconstitution and pressure equalization, one BD PhaSeal™ Optima Injector N35-O 4016, one WEST PHARMA swabable 20 mm vial adapter 4020 one or two WEST PHARMA vial adapters/vial connectors 4022 (e.g., vial adapter/vial connector 20 mm), one WEST PHARMA vented 20 mm vial adapter 4018, and the apparatus 3400 for incubation, spin separation and mixing. Those skilled in the art will appreciate that the example components identified are for illustrative purposes and other suitable devices may be substituted in place from other manufacturers.

FIG. 41 illustrates a flowchart for an example method 4100 for on-site eIL-2 preparation using the components in FIG. 40.

At step 4110, Proleukin reconstitution is prepared using the vial method described in FIG. 14. Proleukin® (aldesleukin) is a sterile, white to off-white, preservative-free, lyophilized powder suitable for IV infusion upon reconstitution and dilution. Each vial contains 22 million International Units (1.3 mg) of Proleukin. For encapsulation of aldesleukin in a carrier (SonoLeukin), each Proleukin vial will be reconstituted with 2 mL SWFI and a net total of 3.5 mL of reconstituted Proleukin can be withdrawn and used as a diluent for one Imagent vial.

At step 4120, Imagent reconstitution with Proleukin solution is prepared. 1.75 mL of reconstituted Proleukin is removed from each vial into 5 mL syringe. The 3.5 mL Proleukin is added to one Imagent vial through a filter hub/vial adapter to produce SonoLeukin base suspension. The SonoLeukin base suspension is gently rocked to wet all powder.

At step 4130, incubation is performed using the apparatus 3400. The SonoLeukin base suspension vial is placed into incubation and rocker component (e.g., a sleeve) of the apparatus 3400 and is mixed for 20 minutes at 40° C. The SonoLeukin base suspension vial is removed from rocker and incubation sleeve and inverted. 2.0 mL SonoLeukin base suspension is withdrawn into 5 mL syringe along with 3.0 mL SWFI to produce a suspension of 5.0 mL in the syringe.

At step 4140, spin separation is preformed using the apparatus 3400. 3 mL SWFI is added to a syringe for a total volume of 5.0 mL and is mixed gently to suspend microspheres. Any air pockets are removed from the syringe cylinder. To enable repeatable expression of the infranatant, a plunger stabilizer may be used to limit the travel distance of the syringe barrel/plunger. The syringe is then placed in the apparatus 3400 for spinning separation for a certain amount of time (e.g., 6 minutes). When the separation cycle has been completed, the microspheres are collected in a cream layer on top of the clear infranatant containing the Proleukin solution. The syringe is kept vertical so as not to disturb the cream layer. The infranatant is expressed out of the syringe slowly until the plunger has reached the desired travel limit, leaving approximately 0.3 mL cream layer of drug encapsulated carriers.

In some embodiments, the step 4140 can further include a wash step (e.g., to reduce amount of free drug). Approximately 4.7 mL SWFI can be added to cream layer in the syringe to a total volume of 5.0 mL. Microspheres can be resuspended. This wash step further dilutes any unencapsulated IL-2. Any air pockets can be removed from the syringe cylinder. The plunger stabilizer can be added to the syringe barrel/plunger and the syringe can be placed in the apparatus 3400 served as the spin separator. The syringe can be spun for a time of 6 minutes. When complete, microspheres are collected in a cream layer on top of the clear infranatant containing the diluted residual Proleukin solution. The syringe can be kept vertical and infranatant can be discarded slowly until plunger reaches the limit of the plunger stabilizer. This leaves approximately 0.3 mL cream undisturbed.

At step 4150, suspension for injection is prepared. 2.0 mL sterile saline is added to 0.3 mL cream in a syringe. SonoLeukin microspheres are resuspended into an opaque off-white suspension. The dose is prepared for injection. To maintain microsphere solution, the syringe should be gently rocked every 3 minutes until the time of administration into a patient.

FIG. 42 illustrates a diagram for on-site eIL-2 preparation using the components in FIG. 40. 4 mL SWFI is withdrawn from the 10 mL SWFI 4006 into the 5 mL syringe 4012 via the vial adapter 4020. The 5 mL syringe 4012 is then used to inject the 4 mL SWFI into a 1.1 mg vial 4210A of Proleukin via the via adapter 4022 and the 4 mL SWFI is mixed with 1.1 mg Proleukin to create a mixture SWFI/IL-2. The vial 4210A is inverted to withdraw at least 3.75 mL of the mixture SWFI/IL-2 into the syringe 4012. The syringe 4012 is then used to inject the 3.75 mL mixture SWFI/IL-2 into a 1.1 mg vial 4210B of Proleukin via the vial adapter 4022. The 4 mL SWFI is mixed with 1.1 mg Proleukin to create a mixture SWFI/IL-2. The vial 4210B is inverted to withdraw at least 3.5 mL of the mixture SWFI/L-2 into the syringe 4012 via the vial adapter 4022, resulting in 3.5 mL IL-2 at 0.5 mg/mL in SWFI. The syringe 4220 then injects the 3.5 mL the mixture SWFI/IL-2 into the Imagent 4002 via the filter hub 4010, the syringe injector 4016 and the P20-0 vial adapter 4014. The whole assembly 4220 is placed into the apparatus 3400 for incubation mixing for 20 minutes at 40° C. The apparatus 3400 is placed in a horizontal direction to provide 180° back and forth motion for incubation and mixing. The assembly 4220 is taken out from the apparatus 3400. The syringe 4012 is taken out from the assembly 4220 and draws 3 mL SWFI from the 10 mL SWFI 4006. The syringe 4012 then draws out 2 mL SonoLeukin base suspension from the remainder 4222 of the assembly 4220. The syringe 4012 is placed in the apparatus 200 that is placed in a vertical direction for spin separation. 5 mL of suspension is spun at 2,000 revolutions per minute (RPM) for 6 minutes. After spin separation, 300 μL cream 4230 of concentrated microspheres are collected, and 4.7 mL of infranatant is expressed out. The syringe 4012 with the cream 4230 withdraws 2 mL sterile saline to resuspend microspheres. The dose is prepared for injection.

It should be understood that those skilled in the art will appreciate that the example components, the examples numerical values (e.g., volumes, concentrations, or the like) identified in exemplary embodiments described above are for illustrative purposes and other suitable devices and numerical values may be substituted in place from other manufacturers without departing from the spirit or scope of the present disclosure.

Unless otherwise defined, all technical and scientific terms used herein have the same meaning as commonly understood by one of ordinary skill in the art to which this invention be-longs. Although methods and materials similar or equivalent to those described herein can be used, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The present invention is further illustrated by the following examples, which are not intended to be limiting in any way. The entire contents of all references, patents and published patent applications cited throughout this application, as well as the Figures, are hereby incorporated herein by reference.

EXAMPLES

Example 1. In Vivo Study of the Efficacy of Microbubbles Associated with Cytokines Using MC38 Colon Cancer Tumor Model To determine the efficacy of the compositions of the invention, a bolus injection of SonoLeukin (compared to an infusion of rIL-2, e.g., Proleukin), either as a monotherapy or in combination with co-administered aPD-1 was tested for efficacy against tumor growth. Quantities of IL-2 used were provided in a 1 mg sterile sealed vial. For the SonoLeukin, the starting concentration of 1 mg IL-2 was reconstituted using only 0.25 mL of sterile water for injection (SWFI). Imagent microbubbles were reconstituted as per its package insert. Jugular catheters were surgically implanted in a total of 56 animals (8 animals per arm) prior to tumor xenograft inoculation. Treated animals were dosed on Day 1, Day 4, Day 8 and Day 12. Ultrasound (US) device used was a TE7 and P4-2S probe (Mindray North America, New Jersey, USA); settings used were 2.2 MHz frequency, 0.34 mechanical index (MI) during insonation, once every 10 seconds, a microbubble destruct pulse of 1.3 MI lasting 1,100 milliseconds was applied. Total insonation time of 5 minutes per animal was used.

The MC38 study tested Group 1: no treatment; Group 2: aPD-1, 3 mg/kg; Group 3: aPD-1, 3 mg/kg, Imagent+US; Group 4: rIL-2 (non-microbubble), 10,000 IU (0.6 μg)/animal; Group 5: SonoLeukin, 10,000 IU (approximately 0.2 μg)/animal+US; Group 6: rIL-2 (not encapsulated in microbubbles), 10,000 IU (0.6 μg)/animal, aPD-1, 3 mg/kg; Group 7: SonoLeukin, 10,000 IU (approximately 0.2 μg)/animal+US, aPD-1, 3 mg/kg. Each animal in Group 1 received 50 μL IgG2a isotope control. Each animal in Group 2 received 50 μL saline, 50 μL aPD-1, then 50 μL heparin to keep the jugular vein catheter clear. Each animal in Group 3 received 50 μL saline, 50 μL aPD-1, 100 μL Imagent microbubbles, then 50 μL heparin. Each animal in Group 4 received 50 μL saline, 100 μL IL-2, then 50 μL heparin. Each animal in Group 5 received 50 μL saline, 200 μL SonoLeukin, then 50 μL heparin. Each animal in Group 6 received 50 μL saline, 100 μL IL-2, 50 μL aPD-1, then 50 μL heparin. Each animal in Group 7 received 50 μL saline, 200 μL SonoLeukin, 50 μL aPD-1, then 50 μL heparin.

The amount of IL-2 encapsulated in Imagent microbubbles is shown in FIG. 7. On each treatment day (e.g., Day 1, Day 4, Day 8, Day 12), prior to injection of SonoLeukin in either Groups 5 or 7, samples were saved to analyze the amount of IL-2 encapsulated in the Imagent microbubbles using enzyme-linked immunosorbent assay (ELISA) techniques. For instance, on Day 1, Group 5 had a mean concentration in the undiluted sample of 265 ng/mL, while Group 7 had a mean concentration in the undiluted sample of 770 ng/mL. A low intratumoral injection of IL-2 ($10^3$-$10^5$ IU) was sufficient to induce good therapeutic effects. According to its package insert, Proleukin, when reconstituted, contains 18,000,000 IU (1.1 mg) per mL. At $10^5$ IU, it would be equivalent to approximately 6,111 ng/mL; at $10^3$ IU, it would be equivalent to approximately 61 ng/mL. In this experiment, the Group 5 mean concentration ranged from 265-3520 ng/mL, while Group 7 had a range of 504-770 ng/mL in the three days sampled. Although there is variability in the encapsulation rates shown, likely due to manual processes involved in the preparation, the range of variability should be narrower based on other aspects of the present invention, particularly the methods to automate the encapsulation processing steps.

Tumor growth inhibition curves are shown in FIG. 8. The Mean % Inhibition data (versus Group 1) is shown in FIG. 9.

As shown in the data above, the MC38 tumors were moderately responsive to aPD-1 alone treatment (Group 2) with a mean 30.28% tumor growth inhibition rate (versus control Group 1). The addition of Imagent microbubbles (without encapsulating IL-2) (Group 3) provided an incremental 30% benefit (versus control Group 1) in tumor growth inhibition with a mean 39.04% rate. Free IL-2 (i.e., non-encapsulated) provided relatively modest benefit with a mean 8.97% tumor growth inhibition rate (Group 4). Low dose eIL-2 appeared to have either no effect or be slightly immunosuppressive with a mean −2.06% tumor growth inhibition rate (Group 5). Free IL-2 combined with aPD-1 had a mean 39.49% tumor growth inhibition rate (similar to Group 3) (Group 6).

Surprisingly, when a micro dose (i.e., a dose even lower than what is generally considered "low dose") eIL-2 was combined with co-administered aPD-1 (Group 7), the mean 62.04% tumor growth inhibition rate was more than double the rate of aPD-1 alone and more than 50% greater than aPD-1 co-administered with Imagent microbubbles (no IL-2 encapsulated or co-administered). Given the apparent immunosuppressive nature of the low dose eIL-2, it was surprising that micodoses of IL-2 encapsulated in eIL-2 and in combination with aPD-1 actually improved tumor response (compared to Group 3, aPD-1 and Imagent). As IL-2 (and other cytokines and molecules) is pleiotropic, meaning it can either act as an immunostimulatory or immunosuppressive agent, it is important to regulate the amount of IL-2 administered. For reference, low dose IL-2 is typically represented by 1.5-2.5 million units/day. It is postulated that the immunosuppressive condition of low dose eIL-2 may have been overcome by increasing the number of microbubbles in the region of interest causing beneficial bioeffects leading to enhanced combination eIL-2/aPD-1 effects. It is also plausible that the low dose eIL-2 monotherapy arm did not provide a therapeutic effect due to dosing schedule and that more frequent dosing, e.g., Days 1-5, may provide enough targeted IL-2 to be immunostimulatory.

A human cytokine and chemokine analysis was performed using the Mouse Cytokine Array/Chemokine Array 44-Plex (MD44, Eve Technologies, Calgary, Canada). Analysis using the mouse serum samples showed at day 12 after initial treatment a number of unexpected results.

As shown in FIG. 10, Group 7 (aPD-1 and low dose eIL-2) Fluorescent Intensity (FI) and Observed Concentrations (Obs Conc) exhibited G-CSF mean levels of 1391 and 2487 respectively that exceeded those in Group 2 (aPD-1 alone) 438 and 732 respectively and Group 1 (control) 940 and 1398 respectively. Group 7 exhibited granulocyte-macrophage colony-stimulating factors (GM-CSF) mean levels of 51 FI and 53 Obs Conc that exceeded those in Group 2 (aPD-1 alone) 23 FI and 20 Obs Conc and Group 1 (control) 15 FI and 10 Obs Conc Interestingly, an increased level of GM-CSF in serum is considered a potential diagnostic and prognostic marker indicating poor prognosis in colorectal cancer patients (Taghipour Fard Ardekani 2014), yet unexpectedly Group 7 animals had better tumor growth inhibition relative to all other groups.

Again from FIG. 10, Group 7 exhibited a distinctly different level of interferon-gamma (IFNγ) with mean 157 FI and 56 Obs Conc, versus Group 2 mean 67 FI and 20 Obs Conc and Group 1 mean 24 FI and 3 Obs Conc. Even when aPD-1 was co-administered with IL-2 (Group 6), the IFNγ was only mean 78 FI and 23 Obs Conc while eIL-2 alone (Group 5) had mean 24 FI and 3 Obs Conc which was similar to control animals.

Immunomodulatory cytokines, including tumor necrosis factor (TNF) alpha, type I or type II Interferons (IFNs), Interleukins (IL)-2, IL-12, IL-15, IL-18, IL-21, IL-23 and IL-27 are either known or thought to be potent effectors of anti-tumor activity. IL-12 is thought to complement IL-2 with respect to immunoregulatory signals and preclinical tumor models have shown that the combination of IL-12 and IL-2 mediate synergistic anti-tumor activity. FIG. 10 showed again that Group 7 had an unusually large mean 50 FI and 70 Obs Conc, while Groups 2 (aPD-1 alone) and 5 (eIL-2 alone) had mean 24 FI and 18 FI, respectively and mean 18 Obs Conc and 8 Obs Conc, respectively.

FIG. 9 showed Group 7 having the lowest IP-10 serum levels of mean 1108 FI and 61 Obs Conc, while Group 2 had mean 2050 FI and 120 Obs Conc, Group 5 (eIL-2) had mean 1800 FI and 105 Obs Conc, and Group 6 (aPD-1+IL-2) had mean 1833 FI and 106 Obs Conc. Group 1 (Control) had 1910 FI and 114 Obs Conc.

Example 2. In Vivo Study of the Efficacy of Microbubbles Associated with Antibodies Using MC38 Colon Cancer Tumor Model A non-GLP study was conducted (Charles River Labs, Morrisville, NC, USA) using Imagent microbubbles and ultrasound with color Doppler in combination with the murine pembrolizumab equivalent anti-PD-1 RMP-1-14 (BioXcell, Lebanon, NH, USA) in MC38 syngeneic colon carcinoma model using female C57BL/6 mice (Charles River Labs).

Fifty mice were randomized into 5 groups of 10 mice and once tumor volumes reached 100-150 $mm^3$, the mice were treated biweekly for 2 weeks on a dosing schedule of days 1, 4, 7 and 11. Tumors were measured twice per week, and animals were euthanized when its tumor reached the endpoint volume of 1500 $mm^3$ or Day 45, whichever came first. The anti-PD-1 dose was 5 mg/kg, adjusted for body weight, via intraperitoneal administration (i.p.). Imagent microbubbles were injected intravenously (i.v.) and ultrasound treatment proceeded immediately after anti-PD-1 injection. It is likely that the Imagent and ultrasound treatment of sonoporation occurred before the anti-PD-1 absorption into circulation as the estimated time for i.p. administered antibodies to enter circulation is >20 minutes, by which time the IMB and ultrasound treatment was completed (which may have limited the efficacy of the sonoporation in this test).

Groups 1 & 6: vehicle.

Groups 2 & 7: anti-PD-1 only.

Groups 3, 4, 5, 8, 9, 10: anti-PD-1+Imagent+ultrasound.

Groups 1-5 were used for tumor growth and inhibition study.

Groups 6-10 were sacrificed at Day 12 and used for tumor infiltrating lymphocytes (TIL) analysis.

Imagent dose of 0.125 mg/kg (0.125 μL/20 g mouse) was used. Volume was adjusted accordingly for body weight and was administered i.v. via tail vein injection immediately after i.p. anti-PD-1 dose.

Ultrasound doses of 4.0 MHz B-Mode, 2.5 MHz Color Flow were used according to the following: Group 3 & 7: 4 minutes, B-Mode 0.5-0.6 MI, Color Flow 0.3-0.4 MI, Group 4 & 9: 2 minutes, B-Mode 0.8-1.0 MI, Color Flow 0.7-0.8 MI, Group 5 & 10: 4 minutes, B-Mode 0.8-1.0 MI, Color Flow 0.7-0.8 MI.

Tumor Inhibition Results

Tumor volume growth was measured at regular intervals for Groups 1-5. FIG. 11 showed that Group 5 provided significant tumor inhibition days 7-15 despite having i.p. administration of anti-PD-1. Since sonoporation was induced over 5 minutes and at least 15-20 minutes prior to the anti-PD-1 reaching optimal blood concentration levels, it was surprising to see tumor growth delay in this experiment. One inference may be that the duration of the sonoporation effect was at least 15-20 minutes allowing the anti-PD-1 to extravasate into the TME even after ultrasound insonation ceased or that bioeffects emanating from sonoporation were beneficial and lasted beyond the time of insonation.

Tumor TIL Analysis Results

On Day 12 (24 hours after fourth and final anti-PD-1+Imagent+ultrasound treatment), tumors in Groups 6-10 were sacrificed and analyzed via flow cytometry. Group 10 (same treatment regimen as Group 5) demonstrated a significant increase in CD8+/Treg ratio as a % of CD45) which is indicative of an immune stimulating and tumor suppression response benefit (FIG. 12).

Example 3. Sonoporation-Enhanced Delivery of STING Agonist Induced Robust Immune Modulation and Tumor Regression This Example demonstrated that a 5 min clinically translatable sonoporation procedure using FDA-approved microbubbles and commercially available diagnostic ultrasound enabled the systemic delivery of CDN-based STING agonist, MSA-1, and regressed both unilaterally and bilaterally inoculated syngeneic tumors as a result of improved PK/PD and immune modulation.

Immune regulatory checkpoint inhibition with monoclonal antibodies against targets such as cytotoxic T lymphocyte antigen-4 (CTLA-4), and programmed cell death protein 1 (PD-1) has demonstrated unprecedented efficacy in treating various human cancers, including melanoma, renal cell carcinoma (RCC), and non-small cell lung cancer (NSCLC) (T. Powles, et al., *Lancet Oncol.* 2045, 1-11 (2020); C. Robert, et al., *Lancet Oncol.* 20, 1239-1251 (2019); S. B. Goldberg, et al. *Lancet Oncol.* 21, 655-663 (2020)). Despite this, the response rate remains relatively poor in most cases (P. Sharma, et al., *Cell.* 168, 707-723 (2017); N. Riaz, et al., *Cell.* 171, 934-949.e15 (2017); F. Meric-bernstam, et al., *Lancet.* 6736 (2020), doi:10.1016/S0140-6736(20)32598-8). Additionally, severe autoimmune-like adverse effects limit the use of this new class of cancer treatments (F. Martins, et al., *Nat. Rev. Clin. Oncol.* 16, 563-580 (2019).). Therefore, there is still a pressing need to extend cancer immunotherapy further to benefit broader patient populations. Various efforts to study the "cancer immunogram" have highlighted complex biology that necessitates a multi-pronged approach to focus on identifying additional immune pathways that may be modulated to tackle cancer (Christian U. Blank, et al., *Science,* 352, 658-660 (2016)). Among these efforts, it is recognized the cyclic GMP-AMP synthase (cGAS)-STING pathway is involved in the innate response to tumor immunity in response to self, double-stranded (ds) DNA produced by dying tumor cells (S. R. Woo, et al., *Immunity.* 41, 830-842 (2014); L. Deng, et al., *Immunity.* 41, 843-852 (2014)). Upon detection of tumor-derived dsDNA, cGAS generates cyclic dinucleotides (CDNs) that bind STING and activate multifaceted tank-binding kinase 1 (TBK1)/interferon regulatory factor 3 (IRF3) and nuclear factor kappa-light-chain-enhancer of activated B cells (NF-κB), leading to the release of type I interferon (IFN) and pro-inflammatory cytokines, ultimately promoting T cell priming and recruitment (H. Ishikawa, et al., *Nature.* 461, 788-792 (2009); J. A. Carozza, et al., *Nat. Cancer.* 1, 184-196 (2020); E. N. Arwert, et al., *Nat. Cell Biol.* 2 (2020), doi:10.1038/s41556-020-0527-7.). STING agonists are being investigated in clinical trials (NCT04220866, NCT02675439, and NCT03010176), but most are based on CDNs, which exhibit poor metabolic stability, due to their negative charges and small molecular weight, and must be delivered intratumorally (IT) for as long as two years to achieve efficacy (K. E. Sivick, et al., *Cell Rep.* 25, 3074-3085.e5 (2018); L. Corrales, et al., *Cell Rep.* 11, 1018-1030 (2015)). Aside from poor patient adherence, multiple IT injections severely limit STING agonist-based CDNs to a few readily accessible tumor types and can introduce the risk of disrupting the tumor microenvironment (TME) and peritumoral vascular network, potentially inducing cancer cell extravasation and metastases (A. Marabelle, et al. *Ann. Oncol.* 29, 2163-2174 (2018); A. Huang, et al. *J. Control. Release* (2020), doi:10.1016/j.jconrel.2020.06.029; E. G. Mathenge, et al. *Neoplasia.* 16, 950-960 (2014)). Therefore, there is an urgent need for a delivery technology that could safely and noninvasively enable the systemic delivery of CDNs to deep-seated and difficult-to-permeate tumors.

Sonoporation, is a method of increasing the permeability of microvasculature by application of intraluminal microbubbles (MB) and concomitant ultrasound (US) exposure. MBs are gas-filled microspheres stabilized by a lipid, protein, or polymer shell. Due to their gas-filled, and hence compressible core, they are responsive to ultrasound pressure waves. This process of alternate growing and shrinking is called cavitation. Depending on the ultrasound intensities, cavitation can be further categorized as stable cavitation and inertial cavitation. The quantitative characterization of the sonoporation-induced drug uptake is still missing, especially in non-cerebral solid tumors. Furthermore, the understanding of sonoporation's impact on the immunoactivation and immunosuppression is particularly lacking.

In this Example, sonoporation-induced drug uptake was examined using a highly potent and clinically relevant CDN-based STING agonist, MSA-1. Since MSA-1 was previously pursued as an IT dosing regimen, a dose-escalation study of intravenously (IV) administered MSA-1 was first conducted and its dose-dependent anti-tumor efficacy and PK/PD characteristics on a syngeneic mouse model MC38 was assessed. A sub-efficacious dose of MSA-1 was then combined with FDA-approved intraluminal MB and 5-min concomitant US exposure from a commercially available diagnostic ultrasound machine (FIG. 24). Surprisingly, this 5-min sonoporation substantially elevated tumor local concentration of MSA-1 and resulted in the enhanced production of type I IFNs and pro-inflammatory cytokines TNF-α and IL-6. The percent complete regression (CR), tumor-specific growth rate, as well as percent survival were all significantly improved in the sonoporation-treated group. The improved efficacy in the sonoporation-treated group could be attributed to two distinct mechanisms, the enhanced PK, as well as the improved immunomodulation. Then, in the immunophenotyping experiment, sonoporation treatment sustained STING-mediated immune activation, while reversing some of the STING-mediated immune suppression. Lastly, in a bilateral syngeneic mouse model, it was demonstrated that sonoporation treatment resulted in complete regression, both the primary and distant tumors, in 44% of enrolled subjects, highly superior to the IT dosed group. These results show that by using the sonoporation approach, it is feasible to achieve significantly higher MSA-1 delivery to the treated tumor without any toxicity. The delivery strategy of MSA-1 in this Example can be further combined with immune regulatory checkpoint blockades to fully realize the immunomodulatory effect of sonoporation. This approach may be aligned for clinical trial via an arm in an active treatment cohort or leveraging FDA's guidance document on the expanded access to investigational drugs for treatment use to tackle some of the huge unmet needs where lack of treatment efficacy can be attributed to lack of tumor exposure, to ultimately help patients in need.

Materials and Methods

All animal studies were performed in accordance with guidelines of the Institutional Animal Care and Use Committee at Merck & Co., Inc., Kenilworth, NJ, USA, and mice were kept in a pathogen-free facility.

Treatment of MC38 Tumors

For the therapeutic study, female Balb/c mice (Jackson Laboratory) of age 6-8 weeks were subcutaneously inoculated with $5\times10^5$ [Jun, I think the captions in the paper all say $5\times10^6$ cells]MC38 cells/mouse on the right flank on day 0. On day 8, animals were dosed with PBS or MSA-1 formulated in PBS IV at 10, 3, 1, or 0.3 mg/kg or intratumorally at 20 μg. In some experiments, Imagent® microbubbles (Vesselon) and/or Mindray TE7 commercial ultrasound system (Mindray North American) were applied for indicated groups of animals. The tumor volume was measured 2 times/week and the volume was estimated with the following equation: volume=0.5×length×width$^2$. Animals were euthanized when the tumor volume reached 2000 mm$^3$ or had active ulceration.

Sonoporation

Insonation of mice was performed using a Mindray TE7 commercial ultrasound system (Mindray North America) with a P4-2s transducer fixed by clamps in a vertical position oriented in approximately a transverse plane. A latex probe cover with the tip filled with acoustic gel (Parker Laboratories) provided an approximate 2 cm soft standoff from the tumor. The fixture holding the transducer was able to be lowered using a rotary indexing mechanism to avoid putting too much pressure on the mice. Air bubbles in the probe cover gel were displaced so that there was a clear gel pathway for the ultrasound beam from the transducer face to the tumor. A 2 cm thick by 9 cm diameter ultrasound gel pad was placed underneath the mice to reduce reflections from the procedural surface. Mice were shaved over the tumor and additional gel couplant was applied. The system settings for insonation were in Contrast Mode, 2.2 MHz center frequency at a mechanical index (MI) of 0.531, and thermal index (TI) of 0.1. Total insonation time was 5 min with periodic 1100 ms ultrasound bursts of 1.304 MI administered every 10 s.

Pharmacodynamic Cytokine Analysis

For the pharmacodynamic study, mice were IV injected with MSA-1 formulated in PBS at 0.3, 1, and 3 mg/kg. In some experiments, Imagent® microbubbles (Vesselon) and/or ultrasound insonation were applied for indicated groups of animals. At predetermined time points post-injection, 400 μL blood was collected in Microtainer® Blood Collection Tubes with Lithium Heparin/PST™ Gel (Becton, Dickinson and Company) and kept on ice. The samples were centrifuged at 10,000 g for 5 min at room temperature, and 100 μL of the plasma was analyzed by TNF-α, IL-6, and type I IFN (IFN-α and IFN-0) ELISA (Meso Scale Diagnostics) following the manufacturer's instructions.

Pharmacokinetic Study

For the pharmacokinetic study, mice were intravenously injected with MSA-1 formulated in PBS at 0.3, 1, and 3 mg/kg. In some experiments, Imagent® microbubbles and/or ultrasound insonation were applied for indicated groups of animals. At predetermined time points post-injection, in addition to blood, tumors were collected and kept on dry ice. Tumor homogenates were mixed with blank plasma to matrix match the tumor to a plasma calibration curve. Plasma and mixed tumor homogenates were protein precipitated with acetonitrile containing an internal standard analog. Supernatants from the protein precipitation were diluted into the water with 0.1% formic acid. Calibrators and unknowns were measured by ion-exchange liquid chromatography-mass spectrometry. Chromatographic separation was performed on a Shimadzu Nexera UPLC with an Imtakt Unison UK-Amino (50×2 mm, 3 mm) column maintained at 45° C. with a flow rate of 0.6 mL/min. Mobile phase A consisted of 70:30:1 acetonitrile, water, 1 M ammonium acetate. Mobile phase B consisted of 70:30:2:10:0.5 acetonitrile, water, 1 M ammonium acetate, isopropanol, ammonium hydroxide. Mass spectrometry quantitation was performed on an AB Sciex 6500+.

Immunophenotyping

For analysis of immune cell population infiltration, fresh mouse tumors were enzymatically digested using the GentleMACS Mouse Tumor Dissociation kit (Miltenyi Biotec, Bergisch Gladbach, Germany). The mixture was then filtered through 70 m cell strainers to generate single-cell suspensions. The single-cell suspension from tumors was then washed and counted. Whole blood or two to three million cells from tumor were incubated with a fixable viability dye FVS780 (BD Biosciences, San Diego, CA) and then blocked with antibodies to CD16/CD32 (BD Biosciences, San Diego, CA) for 10 min on ice. After Fc-blocking, samples were stained with fluorescence-conjugated antibodies in flow cytometry staining buffer with Brilliant Stain Buffer (BD Biosciences, San Diego, CA). The surface antibody cocktail included CD45 (Clone 30-F11), CD11b (Clone M1/70), CD8 (Clone 53-6.7), CD24 (M1/69), Ly6G (Clone 1A8), F4/80 (Clone BM8), Ly6C (Clone AL-21), I-A/I-E (Clone M5/114.15.2), CD11c (Clone N418), CD3e (Clone 145-2C11), CD4 (Clone GK1.5), CD49b (Clone DX5), CD335 (Clone 29A14), CD25 (Clone PC61), PD-1

(Clone RMP1-30), and PD-L1 (Clone MIH5). After surface staining, blood samples were lysed by BD FACS™ Lysing Solution, and then intracellular staining of Ki-67 (Clone 16A8), Granzyme B (QA16A02), and FOXP3 (Clone MF-14) on both blood and tumor samples was performed using eBioscience™ Foxp3/Transcription Factor Staining Buffer Set (Thermo Fisher Scientific, Waltham, MA) according to the manufacturer's instructions. The stained samples were acquired on a BD Fortessa cytometer with DIVA software (BD Biosciences, San Diego, CA). Counting Beads (Thermo Fisher Scientific) were added to the blood samples before acquisition to enable absolute cell counts per blood volume. All the RAW data were analyzed using FCS Express (De Novo Software, Pasadena, CA) according to the following gating strategies. Gates were drawn on $CD45^+$ leukocytes by doublet exclusion (forward scatter height versus forward scatter area; side scatter height versus side scatter area) and dead cell exclusion using fixable viability dyes. Gates were then drawn on the $CD3^+$ T cell population, followed by $CD4^+$ and $CD8^+$ populations. Among $CD4^+$ T cells, $FOXP3^+CD25^+$ were Tregs. $CD3^-CD335^+CD49b^+$ gated on $CD45^+$ population defined NK cells. Granzyme B, Ki-67, and PD-1 were further gated on T or NK cells. Myeloid populations including gMDSC/neutrophils ($CD45^+$ $CD11b^+Ly6G^+$), M-MDSC ($CD45^+CD11b^+MHCII^+$ $F4/80^-$ $Ly6C^+$), macrophage ($CD45^+CD11b^+MHCII^+$ $F4/80^+$ $Ly6C^-$), DC ($CD45^+CD11c^+MHCII^+$ $CD24^+$) or mixed monocytic cells ($CD45^+CD11b^+MHCII^+$ $F4/80^-$ $Ly6C^+$) were drawn. Fluorescence minus one, unstained, and isotype controls were included for assessment of surface and intracellular proteins. The percentage of each cell subset within viable $CD45^+$ cells in the tumor and absolute cell number per L blood was calculated.

Statistical Analysis

All statistical analyses were performed using the GraphPad Prism software package (PRISM 8.1.1; GraphPad Software). Biological replicates were used in all experiments unless otherwise stated. The survival benefit was determined using a log-rank test. All experimental results were indicated as the means±SEM. One-way analysis of variance (ANOVA) was used when there were multiple comparisons. The student's t-test was used for single comparisons. The specific statistical methods are provided in the figure legends.

Results

Dose Escalation and PK/PD Study of MSA-1 in Syngeneic Mouse Model MC38 after IV Administration MSA-1 is a phosphorothioate CDN analog to cGAMP generated to improve STING agonist activity. Since MSA-1 was previously positioned as an IT dosing regimen, a dose-escalation study of IV administered MSA-1 was first conducted and its dose-dependent anti-tumor efficacy was assessed. In the MC38 syngeneic mouse model, dose ranges from 0.3 mpk to 10 mpk at either a single dose on day 1 or three doses given on days 1, 4, and 7, were administered IV (FIG. 25A). All mice administered with STING agonists showed varying degrees of response to treatment that was dose-dependent. There exists a clear dose separation: at or below 1 mpk dose, no complete regression was observed; on the contrary, at or above 3 mpk dose, a significantly high percent complete regression was achieved. Additionally, there is no clear difference in the percent complete regression and percent survival between single versus triple dosing (FIG. 25B). Percent body weight change was consistent among various groups (FIG. 25C). These results suggest that the sub-efficacious 1 mpk or 0.3 mpk single dose could be combined with the sonoporation approach.

To correlate the anti-tumor efficacy with local tumor concentration of MSA-1, the levels of MSA-1 in the tumor and plasma was measured 10 min after single IV administration of 0.3, 1, 3, and 10 mpk dose (FIGS. 26A-B). Both the plasma and tumor showed dose-dependent MSA-1 concentrations. For tumor local concentrations specifically, at 3 mpk, the efficacious dose, the concentration was 0.328 μM whereas at 1 mpk, the sub-efficacious dose, the concentration was 0.177 μM. Therefore, if sonoporation could increase the MSA-1 delivery efficiency by 85%, then a meaningful anti-tumor efficacy from a single dose of 1 mpk, a 3-fold dose reduction, could be expected. Similarly, if sonoporation could increase the MSA-1 delivery efficiency by 181%, then a meaningful anti-tumor efficacy from a single dose of 0.3 mpk, a 10-fold dose reduction, could be expected. As a direct result of the dose-dependent MSA-1 concentrations in the tumor and plasma, dose-dependent type 1 interferon and pro-inflammatory cytokine concentrations 4 hr after IV administration, both in the tumor and plasma, were observed (FIGS. 26C-E). For 1 mpk and 0.3 mpk specifically, the systemic and tumor local concentrations of the pro-inflammatory cytokines were undifferentiated, suggesting that the sub-efficacious 1 mpk or 0.3 mpk single dose could be safely combined with the sonoporation approach.

Sonoporation Significantly Improved the Anti-Tumor Efficacy of MSA-1 at 1 mpk Single Dose After establishing the baseline performance of MSA-1 in the MC38 tumor model, the anti-tumor efficacy behavior was investigated when combining MSA-1 at either 1 mpk or 0.3 mpk with sonoporation. After dosing, the mouse was immediately transferred to a treatment platform where a layer of ultrasound induction gel was applied onto the surface of the shaved tumor to enable the coupling with a P4-2s transducer covered with a 2 cm gel standoff and controlled by a Mindray TE7 ultrasound system. Throughout the ultrasound procedure, the mouse was under anesthesia. Since sonoporation is composed of two functional components, namely the microbubbles and ultrasound, the impact of each attribute was further segregated and combined them individually with 1 mpk (FIG. 27A). As expected, there is no difference between vehicle and vehicle plus sonoporation, suggesting the sonoporation process itself does not directly contribute to the tumor-killing. When comparing 0.3 mpk with 0.3 mpk plus sonoporation, no significant improvement in efficacy was observed. Surprisingly, when combined 1 mpk with sonoporation, 30% complete regression was achieved versus none in 1 mpk treated group. Sonoporation treated group also yielded significantly slower specific growth rate compared to all other control groups. For reference, three doses of IT administered MSA-1 at 1 mpk achieved 80% complete regression. When combining the individual component of the sonoporation process with 1 mpk, no significant improvement in the percent complete regression was noted. However, 1 mpk plus ultrasound did offer significantly improved percent survival compared to 1 mpk alone (FIG. 27B). Additionally, 1 mpk plus microbubbles did not differentiate itself from 1 mpk alone, both in the complete regression as well as percent survival, suggesting that, in the absence of ultrasound, microbubbles by themselves do not offer any favorable pharmacological intervention. Across all treatment groups, no abnormal body weight change was observed, highlighting that the sonoporation approach itself is safe and can be readily combined with systemically administered compounds (FIG. 27C).

Sonoporation Drastically Enhanced Tumor Local Concentration of MSA-1 and Resulted in Substantially Elevated Cytokine Production It was hypothesized that one of the two main mechanisms resulting in sonoporation-mediated MSA-1 anti-tumor efficacy enhancement is increased drug delivery into the tumors. To test this, a PK study was conducted where mice receiving 1 mpk MSA-1 or 1 mpk MSA-1 plus sonoporation were sacrificed at designated time points and both the tumor and plasma concentrations of MSA-1 were quantified. As soon as 20 min post-dosing, or 15 min post sonoporation, the median tumor local concentration of MSA-1 was increased from 0.126 μM in the MSA-1 alone group to 0.441 μM in the MSA-1 plus sonoporation group, a 6.58-fold increase (FIGS. 28A-B). 1 hr post-dosing, or 55 min post sonoporation, while all samples in the MSA-1 group fell below the level of quantification (LOQ), 3 out of the 5 samples in the MSA-1 plus sonoporation group yielded a positive value above LOQ, further supporting the hypothesis that the 5 min sonoporation process significantly enhanced the tumor local concentration of MSA-1 (FIGS. 28C-D). The improved PK profile of MSA-1 as a result of sonoporation treatment further resulted in substantially improved PD cytokine levels. 4 hr post-dosing, both TNF-α, and INF-β reported a significant increase from MSA-1 control in the plasma (FIGS. 28E-H). TNF-α, INF-α, and INF-β reported a substantial increase as compared to MSA-1 control in the tumor (FIGS. 28I-L). Due to large sample variability, even though IL-6 showed an upward trend in the sonoporation treated group, the increase in that particular cytokine was not statistically significant.

Interestingly, 1 hr post-dosing, IL-6, and TNF-α from the plasma as well as IL-6 from the tumor showed a drastic increase in the sonoporation treated group. These results collectively suggest that the 5 min sonoporation treatment significantly increased the delivery of systemically administered MSA-1 into the tumor and elicited greater STING-mediated cytokine production as compared to MSA-1 control.

Figures 29A, 29B, 29C, 29D, 29E, 29F:
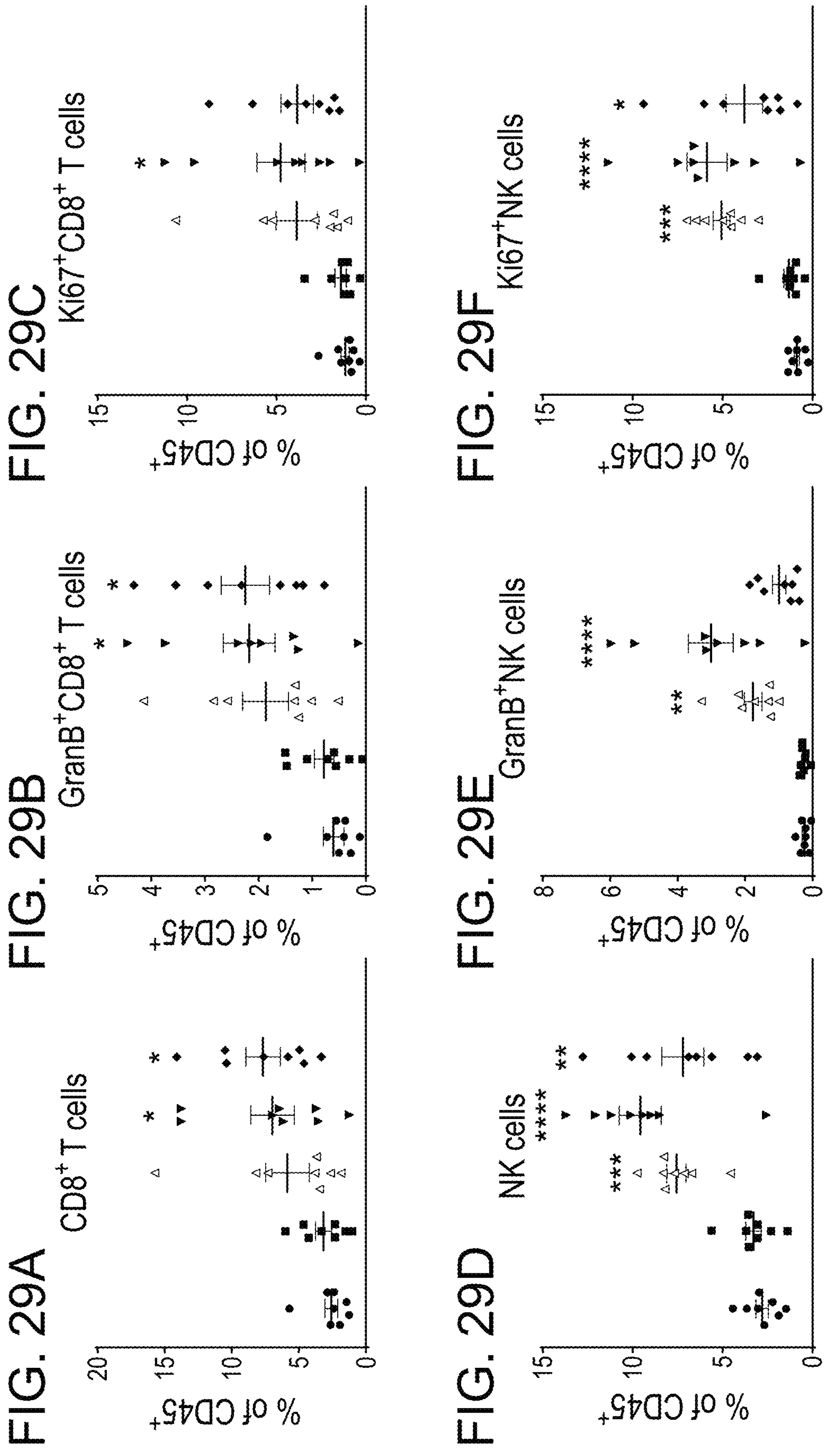
Figures 29G, 29H, 29I, 29J, 29K, 29L:
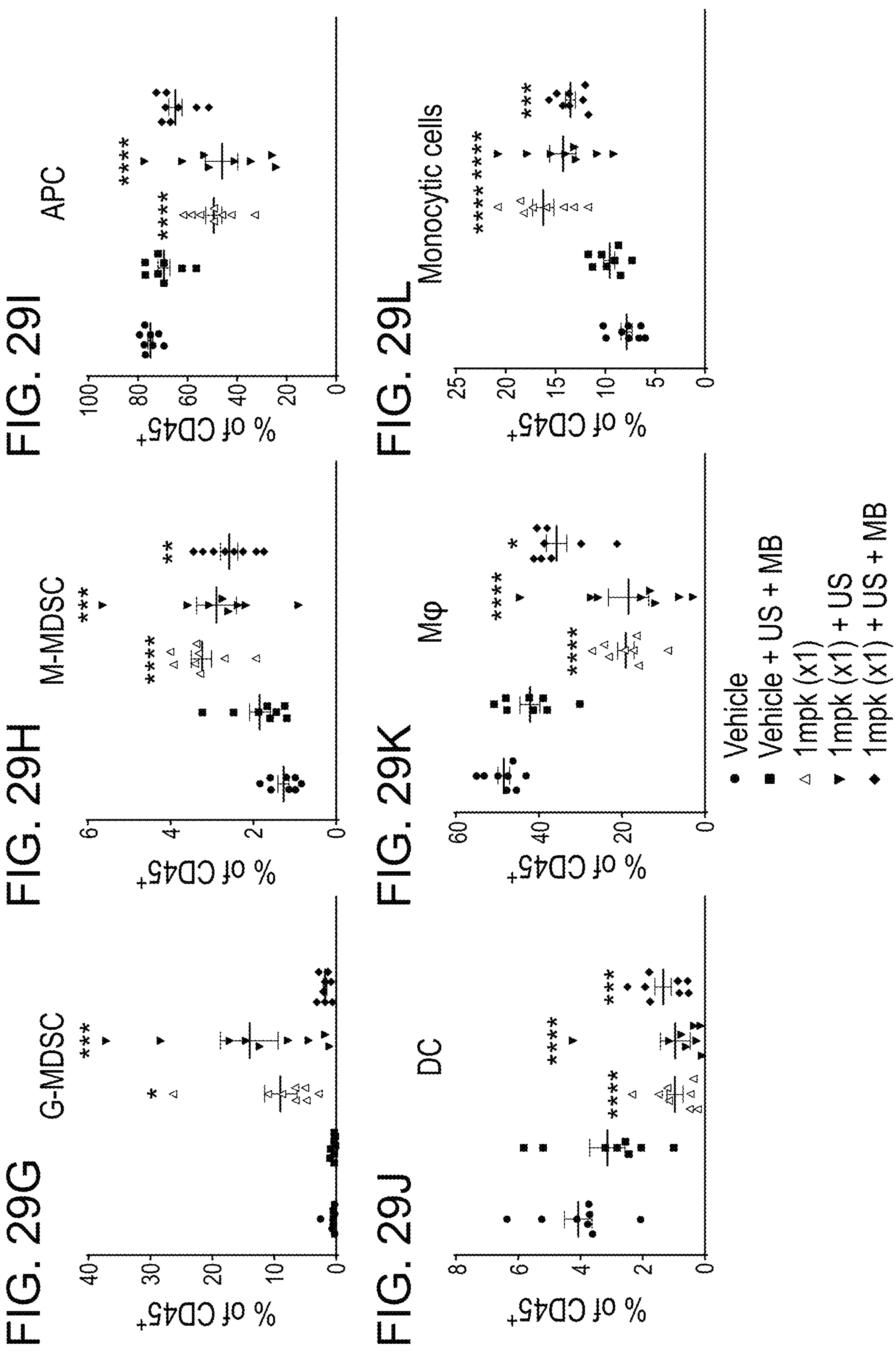

Sonoporation Sustained MSA-1's Immune Activation Mechanisms while Reversed its Immune Suppression Mechanisms In addition to the sonoporation enhanced delivery of MSA-1 into the tumor, it was also hypothesized that the 5 min sonoporation could trigger immunomodulation that could synergize with MSA-1's mechanism of action in regressing tumors. To investigate sonoporation's potential immunomodulatory effect on the tumor microenvironment (TME), the immune cell population was analyzed within the tumor five days after treatments. First, it was noticed that 1 mpk plus sonoporation treatment resulted in significantly smaller tumors, which further validates the previous findings. From the lymphoid lineage, it was observed that both ultrasound and sonoporation increased the infiltration of CD8+ and GranB+CD8+ T cells (FIGS. 29A-B). Furthermore, ultrasound alone enhanced the infiltration of highly proliferative CD8+ T cells (FIG. 29C). Additionally, ultrasound and sonoporation sustained MSA-1 mediated NK cell recruitment (FIGS. 29D-F). No noticeable trend was observed on CD4+ and Treg cells and programmed cell death protein 1 (PD-1) expression on both CD4+ and CD8+ cells was undifferentiated. These results suggest that both ultrasound and sonoporation could sustain, and enhance in some cases, MSA-1 mediated immune activation. From the myeloid lineage, however, sonoporation reversed MSA-1 mediated immune suppression. Specifically, sonoporation reduced STING associated recruitment of myeloid-derived suppressor cells (MDSC), including G-MDSC and M-MDSC (FIGS. 29G-H). Furthermore, sonoporation reversed STING associated inhibition of antigen-presenting cells (APC) recruitment, including both the dendritic cells (DC) and macrophages (MΦ) (FIGS. 29I-K). Lastly, STING-mediated recruitment of immunosuppressive monocytic cells was partially inhibited by sonoporation (FIG. 29L). It is worth noting that ultrasound alone did substantiate MSA-1 mediated immune suppression on the myeloid lineage. The immune cells were also analyzed in the plasma and no noticeable trend was observed. Collectively, these results demonstrate the favorable immune-modulatory effect that sonoporation imposes on the TME, which substantiated MSA-1 triggered immune activation while reversed MSA-1 mediated immune suppression.

MSA-1 in Combination with Sonoporation Eradicated Distantly Located Non-Ultrasound-Treated Tumors It was further hypothesized that in combination with sonoporation, 1 mpk MSA-1 could regress not only primary tumors that received direct ultrasound treatment but also distantly located tumors that did not. To test this hypothesis, mice were inoculated on both the left and right flanks with MC38 cells and only the right tumor was treated with ultrasound for 5 min after IV administration of MSA-1 and microbubbles. A control group was introduced where 1 mpk MSA-1 was IT administered to the right tumor. The growth profile of both the right (primary) and left (distant) tumors were monitored. For the primary tumors that received 1 mpk MSA-1 IV plus sonoporation, three out of the nine tumors were fully eradicated (FIG. 30A). In comparison, seven out of the nine tumors that received 1 mpk MSA-1 IT were fully regressed. No regression was observed in other groups. Surprisingly, for the distantly located tumors that did not receive ultrasound treatment, three out of the nine tumors were fully eradicated in the 1 mpk MSA-1 IV plus sonoporation group versus none in the 1 mpk MSA-1 IT treated group (FIG. 30B). No other tumor regression was noted in other treatment groups. When looking at the overall survival, 1 mpk MSA-1 plus sonoporation outperformed all other groups, even the IT treated group, and resulted in 33% complete regression.

Discussion

First-generation STING agonists, the CDN analogs of cGAMP, when administered systemically in animals, induce equipotent inflammatory cytokine productions both in tumor and normal tissues, owing to ubiquitous STING expression. Thus, CDN-based STING agonists currently undergoing clinical trials, MK-1454 and ADU-S100 for example, are dosed intratumorally which limits their application to a narrow set of tumors. To address a broad spectrum of cancers, approaches that could enable systemic administration and promote the targeted delivery to tumors are urgently needed. Various particulate-based delivery strategies have been proposed, and, despite their excellent preclinical proof-of-concept, the clinical translation foresees to be challenging due to the lack of a line of sight or perceived high chemistry, manufacturing, and control (CMC) complexity (M. Luo, et al. *Nat. Nanotechnol.* 12, 648-654 (2017); Y. Liu, et al., *Nat. Commun.* 10, 1-15 (2019); D. Shae, et al., *ACS Nano* (2020), doi:10.1021/acsnano.0c02765; F. Wang, et al., *Nat. Biomed. Eng.* (2020), doi:10.1038/s41551-020-0597-7; X. Lu, et al., *Sci. Transl. Med.* 6606, 1-17 (2020)). Platforms requiring complex and multistep synthesis can be very challenging to manufacture on a large scale, specifically, each step creates challenges in understanding the control of impurity removal, raw material quality, and the impact on the final critical quality attributes of the nano- or microconstruct drug product, making the widespread adoption or exploration of these novel delivery systems challenging.

This Example demonstrates that sonoporation, using microbubbles and non-invasive ultrasound commonly used in clinical practice, can enable the systemic administration of clinically relevant STING agonist, MSA-1, and allow MSA-1 to enter tumors in higher concentrations than their normal PK/PD characteristics provide. This is the first comprehensive study that employs an already approved microbubble and diagnostic ultrasound, in combination with a clinically relevant STING agonist to investigate quantitatively and mechanistically the impact of sonoporation in a mouse syngeneic tumor model. Unlike most of the previous preclinical studies in the field employing customized and difficult to standardize ultrasound equipment, as well as microbubbles that are made in house, in this study, FDA approved microbubbles and a commercially available diagnostic ultrasound system were used to foster better clinical translation.

Since MSA-1 was previously pursued as an IT dosing regimen, a dose-escalation study was first conducted to identify the minimally efficacious IV dose for the MC38 syngeneic mouse model. A clear separation on the tumor growth curve was noted where doses at or below 1 mpk failed to regress tumor growth whereas doses at or above 3 mpk did (FIG. 25A). Therefore, the minimal efficacious IV dose of MSA-1 for the MC38 model is determined by 3 mpk. Through PK examination, it was hypothesized that if the delivery efficiency for 1 mpk can be enhanced by 85%, improved anti-tumor efficacy can be expected from this current sub-efficacious dose (FIG. 26B). Additionally, PD cytokine profiling confirmed that doses higher than 1 mpk resulted in higher, if not equal inflammatory cytokine productions in the systemics, which could jeopardize the safety profile upon IV administration; doses at or below 1 mpk, however, resulted in equal, if not lower inflammatory cytokine productions in the systemics, suggesting these dosing regimens can be safe upon IV administration (FIGS. 26C-F). MSA-1 at both 1 mpk and 0.3 mpk was chosen to combine with the sonoporation procedure, which is comprised of two main components: an IV administration of 0.025 mL Imagent® perflexane lipid microspheres and a five min ultrasound insonation administered via a Mindray TE7 commercial ultrasound system with a P4-2s transducer. The system settings for insonation were in Contrast Mode, 2.2 MHz center frequency at a mechanical index (MI) of 0.531, and thermal index (TI) of 0.1. Total insonation time was 5 min with periodic 1100 ms ultrasound bursts of 1.304 MI administered every 10 s. In contrary to most other preclinical studies where only one MI insonation regimen was employed, we, on the other hand, incorporated two different MI insonation regimens in our 5 min treatment. At a MI of 0.531, stable cavitation was expected, whereas, at a MI of 1.304, inertial cavitation was expected. Collectively, these alternating cavitation phenomenona greatly enhanced the anti-tumor efficacy of MSA-1 at 1 mpk (FIG. 27A). Compared to all other control groups, MSA-1 at 1 mpk plus sonoporation significantly increased the number of complete regressed tumors. Furthermore, it also improved the percent survival profile at no cost of safety (FIGS. 27B-C). Intrigued by the results, it was then hypothesized that the improved anti-tumor efficacy was a result of two dominant mechanisms, namely, the improved PK/PD profile, as well as favorable immune modulation. To test the hypothesis, through the PK/PD study, it was revealed that the sonoporation procedure resulted in a significant elevation of the tumor local concentration of MSA-1 upon IV administration. Specifically, 15 min post sonoporation, we reported a 6.58-fold increase of tumor MSA-1 concentrations in the sonoporation-treated group (FIG. 28A). Additionally, 55 min post sonoporation, a meaningful increase of tumor MSA-1 concentrations was observed in the sonoporation-treated group as the control group failed to yield any value above the LOQ (FIG. 28C). This improved PK profile translated into better tumor local cytokine levels 1 hr and 4 hr post drug administration (FIGS. 28E-L). Therefore, the data from this PK/PD study demonstrated that the improved anti-tumor efficacy in the sonoporation treated group was a result of the improved PK/PD profile.

STING activation can be considered a double-edged sword, on one hand, STING facilitates anti-tumor immune response through promoting the infiltration of effector T cells and NK cells and eradication of tumor cells; on the other hand, STING activation may hamper immune response by inducing the infiltration of immune suppressive cells, such as MDSC, and enhancing the activity of indoleamine 2,3-dioxygenase (IDO), an enzyme catalyzing the transformation of tryptophan into kynurenine that hampers the antigen presenting ability of DCs. To this end, the impact of sonoporation on the immune modulation was analyzed separately. As shown in FIGS. 29A-F, STING activation in the TME can facilitate the recruitment of effector CD8+ T cells and NK cells. The impact of sonoporation on this lineage was additive as the mean percentage of some of these effector lymphocytes was trending upwards in the sonoporation treated group versus drug alone. Surprisingly, it was noted the mean percentage of all these effector populations was trending upwards in the ultrasound treated group in the absence of microbubbles. Based on the lack of anti-tumor efficacy improvement from the ultrasound treated group, such dramatic and favorable immune modulation on the lymphocyte lineage was not anticipated. It was concluded that in the absence of microbubbles, the cavitation nuclei, the degree of permeabilization enhancement across the peritumoral endothelial cells as a result of ultrasound insonation is barely marginal, thus the PK/PD profile from the ultrasound treated group should be indifferent from drug alone group. On the other hand, however, ultrasound can result in increased generation of reactive oxygen species (ROS), oxygen ions or oxygen-containing radicals for example, and altered redox status in the TME (B. Yang, et al. *Chem. Rev.* 119, 4881-4985 (2019); C. Nathan, et al., *Nat. Rev. Immunol.* 13, 349-361 (2013)). The role of oxidants in inducing local inflammation has been vigorously investigated in all manner of experimental models and ultimately, through bystander activation or by stimulation with the antigens released from inflamed tumor tissue, additional T cells and NK cells are recruited to the tumor (B. Perillo, et al., *Exp. Mol. Med.* 52, 192-203 (2020); I. S. Harris, et al, *Trends Cell Biol.* 30, 440-451 (2020)). It was also validated that STING activation could result in the increased recruitment of immunosuppressive MDSCs (H. Liang, et al., *Nat. Commun.* 8, 1-10 (2017)). Surprisingly, sonoporation treatment dampened the recruitment of both G-MDSC and M-MDSC (FIGS. 29G-H, 5L). This might be attributed to IFN's skewed impact on the monocytopoiesis and granulopoiesis process and interferon-independent activities of STING (L. H. Yamashiro, et al., *Nat. Commun.* 11, 3382 (2020)). Additionally, sonoporation treatment reversed the negative impact on the recruitment of APC from STING activation (FIGS. 29I-K). Collectively, the immunophenotyping results suggest that both ultrasound and sonoporation treatment sustained STING activation's positive impact on immune activation while only the sonoporation treatment reversed STING activation's negative impact on immune suppression.

Based on the results from the anti-tumor efficacy study and the immunophenotyping, it was then hypothesized that the improved PK/PD profile and favorable immune modulation after sonoporation treatment could ultimately regress distantly located tumors. Therefore, an abscopal study was conducted in a bilateral syngeneic mouse tumor model where only the primary tumor was treated with ultrasound immediately after IV administration of MSA-1 and microbubbles. A similar tumor growth pattern was observed on the primary tumor to the unilateral anti-tumor efficacy study where the sonoporation treated group offered better efficacy (FIG. 30A). Interestingly, the tumor growth pattern on the distant tumors suggests that sonoporation treatment could generate a systemic anti-tumor immune response and result in regressed distant tumors (FIG. 30B). In this Example, an IT dosing group was introduced at an equivalent MSA-1 dose, and, despite its excellent efficacy against the injected primary tumors, it failed to regress the distantly located untreated tumors. Therefore, it was concluded that the 5 min sonoporation on the primary tumor resulted in robust immune modulation that ultimately translated into a better abscopal effect than the IT administration at the equivalent dose.

Sonoporation has been explored across many preclinical applications but has lacked translational momentum (Y. Ho, et al. *J. Control. Release.* 323, 12-23 (2020)). Key to this next step into the clinic will be the characteristics of the microbubble employed as well as the ultrasound parameters chosen. These choices will significantly impact the adoption potential of this approach by minimizing the time of the treatment and facilitating its use in an outpatient environment. Microbubbles can be prepared in any in vitro lab with readily available ingredients. However convenient and inexpensive lab-scale microbubbles are to prepare, in order to be safely and routinely injected into patients, a wide range of risks including the potential to embolize capillaries must be considered. Only four microbubbles have been approved by the FDA to date, all for diagnostic purposes. This work has chosen to utilize Imagent® perflexane lipid microspheres that were approved by the FDA in 2002. Imagent has several characteristics that allow it to be used as an important contributor to the sonoporation process. It has a flexible monolayer lipid wall with a neutral charge and does not require polyethylene glycol (PEG) to prevent protein binding and reduce the risk of complement activation. Compared to other commercial microbubbles, it has a 0% propensity to be taken up by Kupffer cells and sequestered prematurely into the liver (K. Yanagisawa, et al. *Ultrasound Med. Biol.* 33, 318-325 (2007)). These surface characteristics of Imagent and the use of the vapor of a liquid perfluorocarbon to stabilize the microbubbles, enable the use of relatively modest mechanical indices to collapse Imagent microbubbles to selectively induce inertial cavitation in the desired tissue location. The flexible shell is efficient at absorbing ultrasound energy such that the expansion and contraction characteristics of Imagent's stable cavitation can translate ultrasound energy into biomechanical effects that temporarily permeabilize endothelial walls. Imagent microbubble size is also effective for sonoporation using commercially available broadband frequency transducers. Commercial microbubbles are all considered "polydisperse" in that there is a range of microbubble sizes centered around a median diameter. Reconstituted Imagent demonstrates a biphasic size distribution centered around both 1 micron and 4.5 microns that would all be acoustically active in stable cavitation upon exposure to typical broadband transmit pulses from modern diagnostic ultrasound systems. This also provides a larger median gas volume which has been shown to be a key dose parameter in the blood-brain barrier (BBB) opening with sonoporation (K. H. Song, et al., *Theranostics.* 7, 144-152 (2017)). Inside the microbubble, the choice of gases is a critical design feature. Imagent was engineered with the lowest solubility gas of FDA approved microbubbles—perfluorohexane. Perfluorocarbon solubility decreases significantly for every additional carbon atom (E. G. Schutt, et al., *Angew. Chemie—Int. Ed.* 42, 3218-3235 (2003)). Perfluorohexane has a water solubility 1,000 times lower than sulfur hexafluoride and 704 times lower than octafluoropropane, the gases used in other FDA approved microbubbles. This factor increases the circulation time by approximately 50% in vivo. Additionally, the Imagent vial headspace also includes nitrogen gas that, when reconstituted, osmotically equilibrates the pressures inside the microbubble with the dissolved gases in the surrounding aqueous suspending medium (e.g. blood), thereby also contributing to longer circulation time.

In Dimcevski's pioneering clinical paper, low mechanical indexes were chosen with a long insonation time of 31.5 minutes with multiple IV injections of microbubbles (G. Dimcevski, et al., *J. Control. Release.* 243, 172-181 (2016)). With a net transmit duty cycle of 0.3%, cumulative ultrasound exposure was less than 6 seconds for the entire treatment. The design goal of this Example was to reduce the insonation time to under 10 minutes with a single IV injection so as to reduce the time a technologist needs to hold the transducer in place over the tissue of interest to make it practicable for clinical adoption. By adding intermittent higher mechanical index pulses every 10 seconds, the goal was to enable both stable and inertial cavitation to enhance the permeability effect of sonoporation using Imagent. Other diagnostic clinical studies researching microbubble contrast have used MI's of greater than 1.6 without significant safety issues in multiple tissues. For a therapeutic context, especially in oncology, the 1.304 MI pulses used intermittently in this Example are expected to also yield a clinically acceptable safety profile.

Cross-examination of various STING agonists, such as an orally available non-nucleotide STING agonist MSA-2 and a non-nucleotide cGAMP mimetic SR-717, is warranted on the attributes such as efficacy, toxicity, route of administration, and patient compliance.

In summary, by combining 1 mpk MSA-1 with a 5 min sonoporation treatment from FDA approved microbubbles and a commercially available diagnostic ultrasound system, the present inventors successfully demonstrated a clinically translational approach to enable the systemic administration of a nucleotide STING agonist. Through rigorous animal testing, it was shown that the sonoporation treatment enhanced the anti-tumor efficacy of IV administered MSA-1 at 1 mpk, both in unilaterally inoculated syngeneic mouse tumor model as well as in bilaterally inoculated model. The underlying mechanisms that attributed to the efficacy improvement were two-fold: the improved PK/PD profile as a result of cavitation-mediated peritumoral endothelial permeabilization; and the positively modulated TME. This approach does not require any modification of the therapeutics and uses an optimally designed FDA approved microbubble with diagnostic ultrasound equipment that is available in many cancer centers, making the clinical translation much easier than particulate-based approaches. Additionally, the modularity of this approach, as a result of the ultrasound beam focusing, opens up opportunities for many tumors that are anatomically deeply seated and difficult to reach with intratumoral techniques. This approach can also be aligned and positioned for clinical trial via an arm in an active cancer treatment cohort.

Example 4. In Vivo Study of the Biodistribution of Encapsulated Monoclonal Antibodies Using HT29 Human Colorectal Carcinoma Xenograft Model A non-GLP study was conducted (Metis Labs, Ronkonkoma, NY, USA) using Imagent microbubbles, a human monoclonal antibody and ultrasound with a TE7 and P4-2S probe (Mindray North America, New Jersey, USA); settings used were 2.2 MHz frequency, 0.35 and 0.70 mechanical indexes (MI) during insonation, once every 10 seconds, a microbubble destruct pulse of 1.3 MI lasting 1,100 milliseconds was applied. Total insonation time of 5 minutes per animal was used. Imagent was conjugated with bevacizumab-awwb (Mvasi®, Amgen, Thousand Oaks, CA, USA) ("eBev") in HT29 human colorectal carcinoma model.

Thirty-six athymic nude mice (The Jackson Laboratory, Bar Harbor, ME, USA) were randomized into 9 groups of 4 mice and once tumor volumes reached ~200 $mm^3$, the mice were treated once on day 1. Animals were euthanized on Day 3. The bevacizumab-awwb (either eBev or free bevacizumab-awwb) dose was 100 µL of either a 25:1, 50:1, or 5:1 dilution, depending on the experimental arm, via intravenous administration (i.v.) via jugular vein catheter (Instech One Channel Mouse Button, Instech, Plymouth Meeting, PA, USA). Ultrasound treatment proceeded immediately after injection.

Group 1: vehicle.

Group 2: bevacizumab-awwb only; 25:1 dilution.

Group 3a: bevacizumab-awwb+Imagent+ultrasound (0.35 MI only); 25:1 dilution.

Group 3b: bevacizumab-awwb+Imagent+ultrasound (0.35 MI, 1.3 MI); 25:1 dilution.

Group 3c: bevacizumab-awwb+Imagent+ultrasound (0.7 MI only); 25:1 dilution.

Group 3d: bevacizumab-awwb+Imagent+ultrasound (0.7 MI, 1.3 MI); 25:1 dilution.

Group 4: bevacizumab-awwb+eBev+ultrasound (0.7 MI, 1.3 MI); 25:1 dilution.

Group 5: bevacizumab-awwb+eBev+ultrasound (0.7 MI, 1.3 MI); 50:1 dilution.

Group 6: eBev+ultrasound (0.7 MI, 1.3 MI); 5:1 dilution.

Group 1 subjects were dosed with 100 µL 0.9% Sodium Chloride as a control. Group 2 subjects were dosed with 100 µL of 25:1 dilution bevacizumab-awwb. Group 3a subjects were dosed with 100 µL of 25:1 dilution bevacizumab-awwb and 100 µL Imagent microbubbles and ultrasound at 0.35 MI. Group 3b subjects were dosed with 100 µL of 25:1 dilution bevacizumab-awwb and 100 µL Imagent microbubbles and ultrasound at 0.35 MI with intermittent 1.3 MI destruct pulses. Group 3c subjects were dosed with 100 µL of 25:1 dilution bevacizumab-awwb and 100 µL Imagent microbubbles and ultrasound at 0.70 MI. Group 3d subjects were dosed with 100 µL of 25:1 dilution bevacizumab-awwb and 100 µL Imagent microbubbles and ultrasound at 0.35 MI with intermittent 1.3 MI destruct pulses. Group 4 subjects were dosed with 100 µL of 25:1 dilution bevacizumab-awwb and 100 µL eBev (without washing infranatant) and ultrasound at 0.70 MI with intermittent 1.3 MI destruct pulses. Group 5 subjects were dosed with 100 µL of 50:1 dilution bevacizumab-awwb and 100 µL eBev (without washing infranatant) and ultrasound at 0.70 MI with intermittent 1.3 MI destruct pulses. Group 6 subjects were dosed with 100 µL of eBev (washed out infranatant) and ultrasound at 0.70 MI with intermittent 1.3 MI destruct pulses.

eBev was prepared generally using the Vial Method (as described above). A 100 mg (4 mL) vial of bevacizumab-awwb was injected into a vial of Imagent for reconstitution. After gently swirling the bevacizumab-awwb solution in the Imagent vial to mix and form the microbubbles, the Imagent vial was incubated at 40° C. for 60 minutes. In the test groups using "unwashed" eBev, the infranatant was not expressed out of the syringe containing 0.5 mL prior to administration. The eBev groups used a process to wash the excess bevacizumab-awwb not encapsulated into the carrier. The wash steps included adding 6.0 mL SWFI to a syringe containing 3.0 mL of unwashed eBev and gently rocked for ~2 minutes. The syringe was centrifuged (Allegra™6R Centrifuge, Beckman Coulter, Brea, CA, USA) at approximately 200 rpm for 40 minutes, after which the infranatant was expressed out of the syringe to leave a cream layer of eBev as the supernatant. Sterile saline (2.0 mL) was added to the supernatant in the syringe and gently mixed with the eBev for injection. A small quantity (150 µL) of the supernatant and infranatant was assayed using an ELISA kit to determine the amount of bevacizumab-awwb encapsulated in the carrier and in the infranatant.

Tumor Distribution Results

On Day 3, tumors were excised and analyzed for drug concentration. Experimental Tumors were homogenized in equal volume cold Dulbecco's Phosphate-Buffered Saline (DPBS) (mg/ml) with Protease Inhibitors. Tumors were placed in IKA TURRAX vials and homogenized on ice for 2 minutes at 1,000 rpm. After homogenization vials were placed in Sorvall 600D centrifuge and centrifuged at 1,000×g for 10 minutes at 4° C. After centrifugation, each samples supernatant was removed and placed into Beckman Coulter high speed centrifugation vials. The supernatants were centrifuged at 20,000×g for 30 minutes at 4° C. The resulting supernatants were aspirated into 5 mL Eppendorf LoBind and stored at −80° C. until use. HPLC Column: TSKgel G3SXWL—250A, 5 m, 30 cm×7.8 mm; Mobile Phase A: DPBS; Mobile Phase B: None; Column Temp: 25° C.; Loop: 2000 µL; Gradient: 0 min: 100% A, 30 min: 100% A; Flowrate: 0.6 mL/min; UV wavelength: 212 nm; Injection Volume: 500 µL; Elution Time (bevacizumab-awwb): 14-16 min.

As shown in FIG. 32A, the mean concentration of bevacizumab-awwb as measured in the tumors in the various arms ranged from 0.71 µg to 6.3 µg. Interestingly, the free bevacizumab-awwb (Group 2) concentration was approximately equal to that of Groups 3a, 3b, 3c, 3d, and 4, whereas the concentration was substantially different compared to Groups 5 and 6. The free bevacizumab-awwb and free bevacizumab-awwb co-administered with Imagent microbubbles groups were generally around 3 µg, whereas Group 5 (which had approximately 50% less bevacizumab-awwb compared to Groups 2, 3a-3d, 4) showed a mean concentration of 6.4 µg, and Group 6 (which had approximately 99% less bevacizumab-awwb compared to Groups 2, 3a-3d, 4) showed a mean tumor concentration of 0.71 µg. In a comparison between Group 5 (unwashed eBev) and Group 2 (free bevacizumab-awwb), approximately 50% less bevacizumab-awwb administered yielded 200% more bevacizumab-awwb in the tumor. Comparing Group 6 (eBev) to Group 2 (free bevacizumab-awwb), exhibited an unexpected 99% less bevacizumab-awwb administered yielded 22% of the antibody into the tumor versus free antibody.

Furthermore, when Day 3 tumor weights were compared (FIG. 32B) across the groups, Group 1 (vehicle), Groups 2, 3a-3d, 4 all exhibited approximately the same tumor weight (1.03-1.15 mg) 48 hours post-treatment, whereas Group 5 exhibited remarkably lower tumor weight (0.65 mg) and Group 6 indicated stable weight (0.79 mg) of the tumor.

Example 5. In Vivo Study for Microbubble Encapsulated Plasmids in Non-Human Primate (NHP) (Prophetic)

Imagent has the ability to serve as a non-viral delivery vector for plasmids by encapsulating/binding nucleic acid plasmids into the standard Imagent phospholipid shell and using ultrasound-directed targeting to preferentially deliver those plasmids to a specific tissue or tumor. One translational limitation of many gene expression studies is that murine models are not a reliable vehicle to predict large mammal/human success. The goal is to take large, therapeutically relevant monoclonal antibodies (pembrolizumab and ipilimumab) and fabricate plasmids that encode the light chain and heavy chain of those antibodies and deliver them, protected in circulation within Imagent, to NHP liver cells to determine if those hepatocytes can be transfected with sufficient plasmid load to express therapeutically relevant levels of antibody as measured in the blood.

Cell biomarkers and CD antigen expression cell surface markers are measured from cells recovered in blood samples to measure whether the immunogenic response of the animal to the plasmids is similar to what is documented responses from.

Plasmid Preparation.

A nucleotide sequence from the published amino acid sequence of pembrolizumab and ipilimumab was created by codon optimization. The resulting plasmids from this sequencing were then applied to A549 mammalian tumor cells to express the antibodies. The resultant incubation byproduct antibodies were purified and tested by ELISA with antibody specific reagents to confirm active pembrolizumab and ipilimumab were expressed by those cells.

Plasmid Encapsulation.

Plasmids are mixed with Imagent per optimized techniques previously documented (FIG. 20). The resultant encapsulated plasmids will be intravenously administered to Cynomolgus Monkeys at approximately 5-200 micrograms of plasmids per animal (TBD).

In Vivo Procedure.

Cynomolgus monkeys have a patch of their flanks shaved to promote ultrasound gel coupling access to the liver. Immediately upon injection of the plasmids encapsulated within Imagent, the livers are exposed to diagnostic ultrasound at approximately 2 MHz frequency, 0.5 Mechanical Index (MI) for between 5-10 minutes with periodic ultrasound pulses >0.9 MI every 10 seconds (FIG. 21)

Experimental Arms.

- Control (n=2) of naked plasmids, i.v. No ultrasound, no microbubbles
- Arm 1 (n=3). Imagent encapsulated with pembrolizumab.
- Arm 2 (n=3). Imagent encapsulated with pembrolizumab+Imagent encapsulated with ipilimumab.

Endpoints.

Serum Concentration of Pembrolizumab and Ipilimumab are measured via ELISA days 3-15, and cell biomarkers and CD antigen expression cell surface markers listed below are also measured.

| *T&B lymphocytes & NK cells biomarkers | |
|---|---|
| T cells | CD3+ |
| CD8+ lymphocytes | CD8+ |
| NK cells | CD159a+ |
| Myeloid cells | HLA-DR+CD20-CD40-CD3-CD159a- |
| B cells | CD20+ |
| CD4+ lymphocytes | CD4+ |

*Non-Human Primates Cell Surface Marker Panels, CD Marker Panels

| Panel | CD Antibodies |
|---|---|
| 1 | CD95-biot |
| 1 | CD95 |
| 1 | CD28-PE |
| 2 | CD62L-FITC |
| 2 | CD45RA-PE/Cy7 |
| 1, 2 | CD8-PEVio770 |
| 3 | ICOS-BB515 |
| 3 | CD25-BB700 |
| 3 | FOXP3-PE |
| 3 | Fixative solution |
| 4 | CD14-PE |
| 4 | CD20-PECy7 |
| 1, 2, 3, 4 | CD4-APC |
| 4, 5, 6 | CD3-AF488 |
| 5 | CD49d-PE |
| 5 | CD66-PE/Vio770 |
| 5 | CD11c-APC |
| 6 | CD16-PE/Cy7 |
| 6 | CD7-APC |
| 2, 6 | CD8-PE |
| 7 | CD69 |
| 7 | Ki-67 |

Example 6. Sonoporation to Test CRISPR/Cas9 In Vivo Gene Editing in the Rat Liver (Prophetic)

Intravenous administration of Imagent, followed by Sonoporation are performed in rats under anesthesia to ensure ease of administration and targeting.

The ability of Imagent to mediate intracellular delivery of naked DNA, mRNA or RNP's are tested in an initial pilot study. Specifically, sonoporation mediated uptake and expression of exogenous reporter constructs are tested in target organs, prior to delivery of gene editing constructs. The first session of testing focus on identifying the best format of delivery of CRISPR/Cas9 gene-editing tools (DNA, mRNA, RNP) to generate in vivo Knock-Out's (KO) (FIG. 22). An alternative sonoporation delivery system under consideration is using Adenoviral or AAV vectors encoding Cas9, gRNA and template DNA. This initial round of Sonoporation will also ensure that selected organs can reliably be imaged.

This initial pilot study should identify the most efficient format for performing the second round of CRISPR/Cas9 editing to demonstrate a Knock-In (KI). Gene products can be knocked into and expressed from a ubiquitously expressed "safe-harbor" locus such Col1A1 as Rosa26 (FIG. 23). Alternate cardiac and liver genes are also considered.

A. Route of Administration in Rats:

Rats are sedated with an injectable anesthetic, as oxygen supplementation can impact IV Imagent concentrations. Preparation of Imagent and DNA, mRNA or RNP are performed on site. Control and test mixtures are delivered in rats by tail vein injection of 400 ul and US imaged. The concentrations of DNA, mRNA and protein are measured in the final mixtures, after sonication using Qubit assays.

B. Target Organ: Imaging and Sonoporation of the Rat Liver

C. Bioactive Materials to Deliver:

Delivering naked dsDNA into cells by Sonoporation is an important demonstration that this approach can be used instead of vector mediated gene correction. An initial session is used to optimize large DNA plasmid delivery that may result in sustained gene expression. A second session is designed to compare the relative efficiency of local and intracellular delivery of 2 short-acting CRISPR/Cas9 reagents for in vivo gene editing: specifically mRNA and RNP. The third and final session utilizes the optimal combination of reagents for more complex CRISPR/Cas9 Knock-In gene-editing.

1. DNA: pCas9-Guide-EF1a Cas9 (GE100018) at 1 mg and 3 mg: This is a Large 10 Kb Plasmid with 3 Separate Mammalian Promoters.

A Cas9 cDNA is expressed from a Cytomegalovirus (CMV) promoter that can be silenced in some mammalian cells. An Elongation Factor I promoter that is robustly expressed in most tissues drives a GFP reporter. This plasmid contains a second Ubiquitin 6 (U6) promoter with a multiple cloning site, where a specific guide RNA (sgRNA) sequence can be cloned in. This all in one vector can be used for CRISPR/Cas9 gene editing, as well as testing large dsDNA delivery.

Most plasmids with a strong promoter driving EGFP expression produce peak expression between 24 to 48 hours after transfection into cells in vitro. Plasmid DNA are often silenced or lost in dividing cells. The exogenous DNA may be randomly integrated into the genome of a small proportion of dividing cells producing stable clones of cell expressing a transgene for weeks or permanently. These transgenes can also be silenced but still detectable in genomic DNA. For the purposes of this demonstration, detection of robust EGFP expression at 48 hours should be sufficient to determine whether plasmid delivery can enable CRISPR/Cas9 gene editing via Sonoporation. In many cases persistent expression of Cas9 or EGFP from a plasmid may be detected in tissues for days to weeks, after delivery. Collection and analysis of EGFP expression and CRISPR/Cas9 editing are also assessed at 1 week.

2. mRNA: Synthetic spCas9 mRNA 1 mg and 100 ug/ml of EGFP mRNA

Co-delivery of independent mRNA's encoding Cas9 and EGFP could provide an important control to demonstrate intracellular delivery.

Expression of the EGFP protein is typically seen within 4 hours, with peak intensity between 12 and 16 hours and is eliminated within 24 hours. This would also highlight that other therapeutic mRNAs can readily be delivered.

3. Ribonucleoprotein (RNP) Complexes: spCas9-GFP Recombinant Protein at 1 mg/ml Incubated with gRNA Synthetic spCas9 mRNA 1 mg and 100 ug of EGFP mRNA Uptake of synthetic RNP complexes into cultured cells is usually detectable within 0-4 hours post-transfection.

It is anticipated that delivery of Cas9 protein pre-incubated with gRNA's, as ready to edit Ribonucleoprotein complexes (RNP's) is the most-effective format for both KI and KO models. After RNP delivery, Double Strand Breaks (DSBs) are usually detectable within 24-48 hours in dividing cells. Mismatch repair of DSB's in cells often produce Insertion and Deletion mutations (INDELS) that can disrupt target genes' function. With careful gRNA design and efficient RNP delivery, cutting efficiencies, as measured buy INDEL formation can be as high as 60-80%.

D. For Knock-In Projects there are Two Main Repair Mechanisms and Donor Templates:

1. Knock-in by Homology Directed Repair (HDR) from a shorter single-stranded Oligo Donor (ssODN): These tend to be short-200 to 500 bp, as longer lengths can result in potential secondary structures.
2. Knock-in by Homologous Recombination (HR) from a longer double-stranded DNA donor (dsDNA): These dsDNA donors typically range from 3 to 5 Kb. This approach can be useful to knock in a cDNA in frame or into the 3'UTR of a Gene of Interest (GOI). Mirimus has successfully targeted human cDNA's into the 3'UTR of a rat gene of interest to create KI/KO models (Examples: CD147 and Ace2).

Inclusion of a longer dsDNA donor is a critical demonstration of Vesselon's Sonogene program, KI strategies should focus on the HR approach. While the initial study will inform the second study as to optimal format, we have proposed to use CRISPR/Cas9 RNP with co-delivery of dsDNA donor for KI's.

E. Potential Rat Models to Genetically Manipulate:

Col1A1-GFP rat model: A transgenic parental rat strain was used to make custom RNAi rat models against different genes of interest. The Col1A1-CMUTS rat strain has a landing site in this safe-harbor, for knock-in different shRNA sequences. This model could be useful for both KO and KI studies. It is predictable to disrupt this locus by CRISPR/Cas9 mediated DSB and mismatch repair resulting in an insertion or deletion (INDEL).

G. Genetic Analyses of CRISPR/Cas9 Activity:

PCR samples are analyzed to evaluate mixed tissues in CRISPR/Cas9 gene-edited mosaic founder rats to assess the relative cutting efficiencies of different gRNA's in populations of cells. Using this approach, a quantitative breakdown of the most common alleles containing KO-INDEL sequences by percentage is obtained. It is more sensitive than a semi-quantitative T7E1 assay that does not detect INDELs that are 1-2 base-pair in length. The NGS assay is sensitive enough to detect above a 1% cutting efficiency.

H. Alternatives Rat Models:

Type 1 KO: we have gRNA's validated for targeting 2 rat Complement Factor genes produced in the liver Type 2-KI: we have gRNA's and ssODN's validated for knocking in point mutations into 4 cardiac genes I. Construct Design for Custom KI-Models dsDNA construct containing both an mKate2 (red fluorescent protein) and a cDNA for a therapeutic gene of interest into the Col1A1 safe-harbor locus are synthesized. mKate2-P2A-cDNA constructs are created to have co-expression of a reporter and gene product in the same locus. After CRISPR/Cas9 mediated integration by HR, both genes should be ubiquitously expressed in the target tissues.

Strategy 1: Knock-Out by Sonoporation to Test the Delivery of CRISPR/Cas9

DNA Targeting the Col1a1 Locus

Experimental Variables and Proposed Cohorts:

Preparation of Imagent CRISPR/Cas9 Complexes of concentration of 1 and 3 mg

Proposed Cohort Size: 12 rats (with 3 back-up for tail vein injection) Control rats injected with naked complexes to determine tissue uptake without Imagent Strategy 2: Knock-Out by Sonoporation to Test the Delivery of CRISPR/Cas9 mRNA and RNP Targeting the Col1a1 Locus

Experimental Variables and Proposed Cohorts:

Preparation of Imagent CRISPR/Cas9 Complexes at a target concentration of 1 mg/ml Proposed Cohort Size: 12 rats (6 per treatment with 3 back-up for tail vein injection)

Strategy 3: KI Model for Overexpression of a Gene from the Col1a1 Locus

The rat Col1a1 locus has been widely used as a permissible site for transgene expression. This utilizes CRISPR/Cas9 in combination with CRISPR/Cas9 and gRNA to insert an expression cassette at the "safe-harbor" Col1a1 locus. The expression cassette is targeted into the Col1a1 locus by homologous recombination that occurs during the repair of the double-strand break generated by Cas9. The cDNA could be of a therapeutic gene of interest such as Factor IX expressed in the liver-Gene to be determined by Vesselon. The use of a P2A signal will enable co-expression of the cDNA and a reporter protein, such as GFP or mKate2.

Experimental Variables and Proposed Cohorts:

Preparation of Imagent CRISPR/Cas9 Complexes, with one set of CRISPR/Cas9 RNP and donor dsDNA construct (above) at 1 mg/ml Proposed Cohort Size: 6 rats (with 3 back-up for tail vein injection)

Time Point 1 to Detect Insertion into Col1A1 Locus:

1. Imagent RNP and dsDNA Construct Only (Control)—analyze at 48 hours 2-3. Imagent RNP and dsDNA Construct with Sonoporation analyze at 48 hours Time Point 2 to Detect Lasting Insertion into Col1A1 Locus:

4. Imagent RNP and dsDNA Construct Only (Control)—analyze at 1 week 5-6. Imagent RNP and dsDNA Construct with Sonoporation analyze at 1 week Control set to determine any potential cellular uptake without Sonoporation.

Example 7. In Vivo Protocol for Microbubble Encapsulated Oncolytic Virus with Pembrolizumab Gene in Humanized Mice (Prophetic)

Study Objective. Imagent has the ability to serve as a protectant and targetable delivery carrier for therapeutic viruses. As a protectant, Imagent shields the virus from any innate or adaptive immune response thereby potentially allowing multiple intravenous injections over time without the patient developing an adverse immunogenic response. Also, virus-carrying Imagent can be targeted to a specific tissue via ultrasound guidance with no need for the virus to carry a tissue specific tropism. This targeting ability also eliminates the need for clinically sub-optimal intratumoral administration. In addition, the Ad 5/3-C-RGD-D24 oncolytic virus can carry a transgene that can express biologic therapeutic agents. Two mechanisms would be simultaneously deployed: 1) replication of the OV creates oncolysis to destroy the infected tumor cells, and 2) replication of the cloned transgene will express the therapeutic agent by the tumor cells so that the tumor becomes the production line for the therapeutic biologic. This study evaluates both the tumor killing and therapeutic biologic expression of a pembrolizumab gene cloned into the Ad 5/3-C-RGD-D24 virus.

Plasmid preparation. Codon optimization was used to create a nucleotide sequence from the published amino acid sequence of pembrolizumab. The resulting plasmids from this sequencing were then applied to A549 mammalian tumor cells to express the antibodies. The resultant incubation byproduct antibodies were purified and tested by ELISA with antibody specific reagents to confirm active pembrolizumab is expressed by those cells.

Plasmid Cloning. Plasmids are cloned into the available gene locus on the Ad 5/3-C-RGD-D24 and recovered. In vitro testing on mammalian cells confirmed retained potency of the OV with the pembrolizumab gene. Once potency is confirmed, OV are amplified to sufficient concentrations for in vivo study encapsulated within Imagent.

OV Encapsulation into Imagent. The Ad 5/3 with pembro gene (OV-PG) is optimally mixed with Imagent, incubated and separated from free virus as described separately.

In Vivo Procedure. Humanized mice with a selected human tumor xenograft (TBD) have a patch of their flanks shaved over the tumor to promote ultrasound gel coupling access.

Immediately upon injection of the OV-PG/Imagent conjugate, the tumors are exposed to diagnostic ultrasound at approximately 2 MHz frequency, 0.5 Mechanical Index (MI) for between 5-10 minutes with periodic ultrasound pulses >0.9 MI every 10 seconds.

Experimental Arms.

Control 1 (n=4) OV-PG, no encapsulation. i.v., no ultrasound, no microbubbles

Control 2 (n=4) OV-PG, no encapsulation. i.v., no ultrasound, no microbubbles, sacrifice Day TBD for tumor assay and immunophenotyping Arm 1 (n=4). OV-PG/Imagent conjugate, i.v., no ultrasound Arm 2 (n=4). OV-PG/Imagent conjugate, i.v., no ultrasound, sacrifice Day TBD for tumor assay and immunophenotyping Arm 3 (n=4). OV-PG/Imagent conjugate, i.v., with ultrasound Arm 4 (n=4). OV-PG/Imagent conjugate, i.v., with ultrasound, sacrifice Day TBD for tumor assay and immunophenotyping Endpoints.

1. Measure Serum Concentration of Pembrolizumab via ELISA days 3-15 (interval TBD).
2. Measure Tumor Size every 4 days until death, animal distress, or study completion.
3. Measure Animal Weight every 4 days to monitor health or distress.
4. Sacrifice on Day TBD to Assay Tumor for Pembrolizumab concentration and Immunophenotyping tumor lymphocytes and cell surface markers (TBD)

Example 8. In Vivo Protocol for Microbubble Encapsulated Adeno-Associated Viruses (AAV)

Microbubbles in IMAGENT Vial:

The IMAGENT Package Insert specifies a range of 5.9-13.7×$10^8$ MB/mL. As a working estimate, we can assume it is 10×$10^8$ MB/mL=$10^9$ MB/mL. With a 10 mL reconstitution volume a vial of IMAGENT would produce $10^{10}$ MBs per vial.

Due to the nature of the starch/lipid microspheres in the IMAGENT vial, there is a fixed number of microbubbles, independent of the diluent volume. Therefore a smaller viral diluent volume of 4.0 mL would still produce $10^{10}$ MBs per vial.

Viral Encapsulation Preparation for AAV In Vivo Study:

AAV9 with a luciferase reporter will be used in wild type 8-10 wk male mice. This is a rapid onset, moderate-expression AAV.

Use a 4 mL viral diluent volume for each IMAGENT vial, with a 30 minute incubation period at 40° C. With this initial volume, 3 mL MB suspension can then be safely removed from the IMAGENT Vial into the syringe. One must be very careful to avoid any of the foam in the IMAGENT Vial.

Note: Please use Norm-Ject syringes that do not have the black rubber gaskets.

Take the 3 mL IMAGENT/AAV Suspension and Spin Separate it in the syringe at 2,000 RPMs for 7 minutes. Infranatant will be clear. Express out infranatant to leave the MB "cream" which will be approximately 0.30 mL. Add 4.7 mL PBS and Spin Separate it again as a wash.

Add 3 mL Complement to syringe and let incubate for 30 minutes to inactivate free virus. Spin separate and remove Complement infranatant.

Add 4.7 mL PBS for final wash. Spin Separate, removing final wash infranatant, and then add 2 mL PBS for final injectable IMAGENT/AAV suspension Preserving this $0.75\times10^{10}$ MBs in the cream and adding 2 mL PBS, the dose will be ~$0.75\times10^{10}$ MBs/2.3 mL=$3.26\times10^{9}$ MB/mL In Vivo Arms:

| ARM (n = 4) | Ultrasound | AAV Dose |
|---|---|---|
| Control (No Treatment) | None | None |
| AAV Only (No Tumor) | None | 50 μL of $2.0\times10^{11}$ AAVs |
| AAV Only (Tumor) | None | 50 μL of $2.0\times10^{11}$ AAVs |
| AAV Only (No Tumor) | None | 50 μL of $2.0\times10^{12}$ AAVs |
| AAV Only (Tumor) | None | 50 μL of $2.0\times10^{12}$ AAVs |
| IMAGENT/AAV (No Tumor) | On Liver, 10 min | 50 μL ($1.63\times10^{8}$ MB/ ~$1.63\times10^{9}$ AAVs) |
| IMAGENT/AAV (Tumor) | On Tumor, 10 min | 50 μL ($1.63\times10^{8}$ MB/ ~$1.63\times10^{9}$ AAVs) |

Use a 50 μL ($1.63\times10^{8}$ MB/~$1.63\times10^{9}$ AAVs) dose per mouse for IMAGENT/AAV suspension in a single tail vein injection. For MB doses the injection will be followed by a 50 μL PBS injection.

AAV-Alone arms (no MBs) are dosed at $2.0\times10^{11}$ AAVs in a 50 μL dose to evaluate IMAGENT/AAV uptake at 100×-1,000× less dose.

A single tail vein injection will be used for all doses. Treatment arms will inject the IMAGENT/AAV conjugate immediately followed by sonication of the liver or the tumor for 10 minutes per mouse with intermediate high MI pulses.

After Treatment Follow Up: IVIS imaging will measure total flux emittance from each animal as well as emittance from the liver ROI on Days 7, 14, 29, 56, 100 and finally at 6 months. (Reference Zincarelli C. *Molecular Therapy* vol. 16 no. 6, 1073-1080 June 2008).

Example 9. In Vivo Protocol for Microbubble Encapsulated Lipid Nanoparticles (LNP) Clinical Need Prior efforts to target nanoparticles to malignant tissues for improved diagnosis and therapy suffer from poor delivery. Only 0.7% (median) of the administered nanoparticle dose is found to be delivered to a solid tumor. Poor efficiency presents challenges in translating nanotechnology for human use with respect to manufacturing, cost, toxicity, and imaging and therapeutic efficacy.

LNP Conjugation Preparation for In Vivo Study:

LNP with a Green Fluorescent Protein mRNA reporter will be used in wild type 8-10 wk mice.

Use a 4 mL diluent LNP volume with a total of 0.08 mg mRNA in the LNPs. This 0.02 mg/mL concentration will be administered to each mouse at approximately 0.1 GFP-mRNA mg/kg, IV.

LNP diluent volume for each IMAGENT vial, with a 30 minute incubation period at 40° C. With this initial volume, 3 mL MB suspension can then be safely removed from the IMAGENT Vial into the syringe being careful to avoid any of the foam in the IMAGENT Vial.

Note: Please use Norm-Ject syringes that do not have the black rubber gaskets.

Take the 3 mL IMAGENT/LNP Suspension.

In Vivo Arms:

| ARM (n = 4) | Ultrasound |
|---|---|
| Control (No Treatment) | None |
| LNP Only, i.v. | None |
| IMAGENT/LNP , i.v. | None |
| IMAGENT/LNP , i.v. | On Liver, 10 min |
| IMAGENT/LNP, i.v. | On Tumor, 10 min |

MC38 tumor cells implanted in nude mice. Allow tumors to achieve a mean tumor size of 250 $mm^3$ prior to treatment.

A single tail vein injection will be used for all doses. Treatment arms will inject the IMAGENT/LNP conjugate immediately followed by sonication of the liver or the tumor for 10 minutes per mouse with intermediate high MI pulses.

After Treatment Follow Up:

On Day 2 after treatment, liver and tumor will be harvested from each animal for IVIS imaging. Will measure total flux emittance from each liver or tumor.

Example 10: Cryo TEM Imaging

Cryo TEM imaging of exemplary compositions was conducted to provide additional insights and data and was performed at New York University Langone Health's Cryo-Electron Microscopy Laboratory (RRID: SCR_019202) (using either Talos Artica™ or Titan Krios™ and Vitrobot™ equipment).

FIG. 43A is a general schematic of a testing protocol. Briefly, the steps for reconstitution and preparation for cryo TEM imaging as shown in FIG. 43A include injecting 4 mL of DNA plasmid into a vial of IMAGENT microbubbles and gently swirling the vial to wet the IMAGENT powder completely while avoiding the creation of large bubbles in the foam. Then after inverting the vial, 3 mL of the reconstituted IMAGENT/DNA complex are withdrawn into a syringe. The needle is removed and the syringe is placed on a spinning device for 15 minutes at 1,300 rpms to separate the microbubbles from the infranatant. The infranatant is expressed into a tube from which a sample is taken, prepared and frozen for cryo imaging. In a preferred embodiment of the present invention as shown in FIG. 43B, the carrier is an object (preferably spherical) consisting of a lipid layer.

In this example, IMAGENT was reconstituted (generally as previously described in the Vial Method above) with 4.0 mL of DNA plasmid (1 mg/mL pembrolizumab, pcDNA3.4, GenScript USA Inc., Piscataway, NJ). After phase separation of the microbubble layer and the infranatant, a small sample (<1 μL) of the microbubble cream layer was placed on a carbon grid, frozen and imaged. FIG. 43B shows a nanoscale object approximately 300-400 nm (scale bar=50 nm) in diameter. As a simple measure, histogram analysis (GIMP-2.10.30, GNU Image Manipulation Program, www.gimp.org) was performed to estimate relative brightness of the object, as a proxy for density, The relative object densities may indicate the presence of a substance (e.g., agent) encapsulated by, associated, or interacted with the carrier. 43Ba (as denoted by a square—enlarged for clarity) indicates the approximate location of a 25×25 pixel square within a liposomal object abutting a larger liposomal object. 43Bb is a 25×25 pixel square at the approximate central location of the larger object. 43Bc is a 25×25 pixel square located outside of either liposomal objects. As the sample ice thickness is approximately 116 nm, the larger object may be a compressed liposomal object with a diameter less than 300 nm, which may be either a nano scale bubble or a liposome formed from the free lipids in the IMAGENT vial. The median histogram values for 43Ba, 43Bb, and 43Bc are 0.435, 0.408, and 0.443, respectively. The approximately 8% difference in brightness between 43Bb (darker) and either 43Ba (lighter) or 43Bc (lightest) seems to indicate the presence of a substance encapsulated, associated with, or interacted with the liposomal object. As a solution of DNA plasmid was used to reconstitute IMAGENT, it is hypothesized that DNA is the substance. Other liposomal and lipid structures (not shown), including liposomes (~35-50 nm diameter), rods, or discs also may be present in the microbubble cream layer.

FIG. 44 is a cryo TEM image showing multiple liposomes present in the sample as prepared for FIG. 43, except the microbubbles were insonated using a commercial Mindray ultrasound scanner (equipment as noted in Example 1 below) to induce inertial cavitation causing implosion of the microbubbles, creating lipid (e.g., DMPC) fragments. While it is presently unknown if the liposomes 44*a* and 44*b* were formed as a result of inertial cavitation, liposomal objects may self-assemble after inertial cavitation, or upon, for example, high energy state lipids that come into contact with a solution (whether solution contains an agent or not). In this case, while some of the liposomes (e.g., 44*a*) do not appear to contain any agent inside or on the liposome, 44*b* may contain a substance such as DNA, given its histogram value of 0.404 (shown as histogram 44*b*) vs liposome 44*a* (histogram 44*a* value of 0.443). 44*c* is indicative of lipid rods (or discs) and may provide lipid structures from which to create additional liposomes.

FIG. 45 is a cryo TEM image from the same sample as in FIG. 44, but from a different carbon grid location. In FIG. 45, there is present a large unilamellar liposome that is unlike liposomes present in previous samples, i.e., this liposome 45*a* has unexpected straight (or non-curved or non-circular) edges on both the interior and exterior lipid surfaces. The straight edges may be caused by the presence of a substance at or near the lipid surface (whether interior or exterior). As indicated in FIG. 45, DNA strands are present in various locations. During the formation of the liposomes, some DNA may be encapsulated, associated with, or interacted with the liposomes.

FIG. 46 is a cryo TEM image of a sample from the same process as used for FIG. 43, except a 1 mL volume of the infranatant was additionally processed using 25 gauge, 3⅛-inch emulsifying needles (Scientific Commodities, Lake Havasu, AZ) by passing the infranatant from syringe to syringe for 10 complete cycles. FIG. 46 shows DNA strands and various liposomes 46*a* and lipid structures 46*b* and 46*c*. 46*b* appears to be either a fragmented liposome, or a liposome in the process of being formed. If 46*b* is a liposome in the process of being formed, then any agent (e.g., DNA) in the vicinity of the lipids may be encapsulated in, associated with or interacted with the liposome. 46*c* is a lipid rod (or disc). It is noted that straight edges (either interior or exterior) are again present in the image. Alternative methods used to encapsulate, associate, or interact agents with lipid structures during their formation stage may include, but are not limited to, chemical, electrostatic, mechanical (e.g, microfluidics), or physical means.

FIG. 47 is a cryo TEM image from the infranatant sample taken after separating the microbubble cream layer as described in FIG. 43. 47*a* indicates multiple unilamellar liposomes of varying diameters formed from the free or excess lipids. DNA is present as well in the image. 47*b* indicates an object of interest that appears to be a liposome in the process of forming (note: curvature of lipid rod forming what appears to be a hairpin turn). FIGS. 48A-B are additional cryo TEM images from the same sample as FIG. 47, but from alternate carbon grid locations. 48*a* indicates a unique and unexpected multilamellar (e.g., 3 lipid layers) that appears somewhat compressed (ice thickness 104 nM). During the formation of one or more liposomes, any agent adjacent to the lipid layers may be encapsulated, associated, or interacted therein or thereon. FIG. 48B shows multiple multilamellar liposomes 48Ba, including a unilamellar liposome that appears to be in the process of forming a multilamellar liposome 48Bb. There appears to be DNA encapsulated, associated, or interacted with at least some liposomes 48Ba and 48Bb. FIG. 48C shows unilamellar and multilamellar liposomes 48Ca that appear to have DNA encapsulated, associated, or interacted with the liposomes.

FIGS. 49A-B are cryo TEM images of the IMAGENT infranatant reconstituted as per manufacturer's FDA labeling and instructions, therefore without any agent. While the liposomes 49Aa formed from the DMPC free lipids in the infranatant in the image appear to possess fewer and less defined interior or exterior straight edges seen in the other images referenced above, there is a somewhat large, hexagonal liposome 49Ab with some straight edges that appears to either be multilamellar or in the process of forming a multilamellar liposome. FIG. 49B shows 2 multilamellar non-circular liposomes 49Ba and multiple lipid rods (or sheets or discs) 49Bb.

FIG. 50A is a schematic of a testing protocol.

The protocol set forth in FIG. 50A was performed using a SARS-CoV-2 vaccine (Moderna, Cambridge, MA) consisting of lipid nanoparticles and mRNA. FIGS. 50B-E are cryo TEM images of the infranatant from the reconstitution of IMAGENT with the SARS-CoV-2 vaccine (Moderna, Cambridge, MA). Briefly, the steps for reconstitution and preparation for cryo TEM imaging as shown in FIG. 50A included injecting 4 mL of the vaccine into a vial of IMAGENT microbubbles and gently swirling the vial to wet the IMAGENT powder completely while avoiding the creation of large bubbles in the foam. Then after inverting the vial, 3 mL of the reconstituted IMAGENT/LNP/mRNA complex were withdrawn into a syringe. The needle was removed and the syringe placed on a spinning device for 15 minutes at 1,300 rpms to separate the microbubbles from the infranatant. The infranatant was expressed into a tube from which a sample is taken, prepared and frozen for cryo imaging.

Figure 50B:
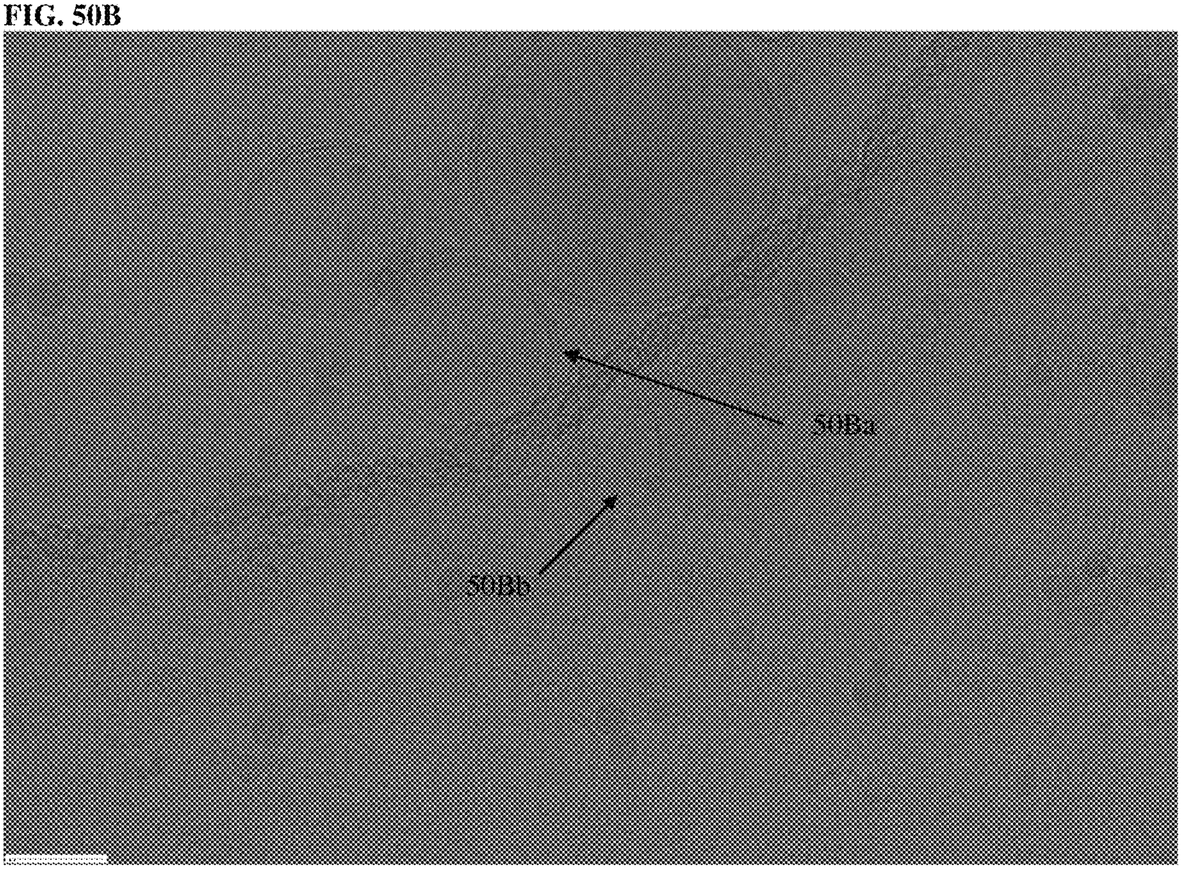
Figure 50C:
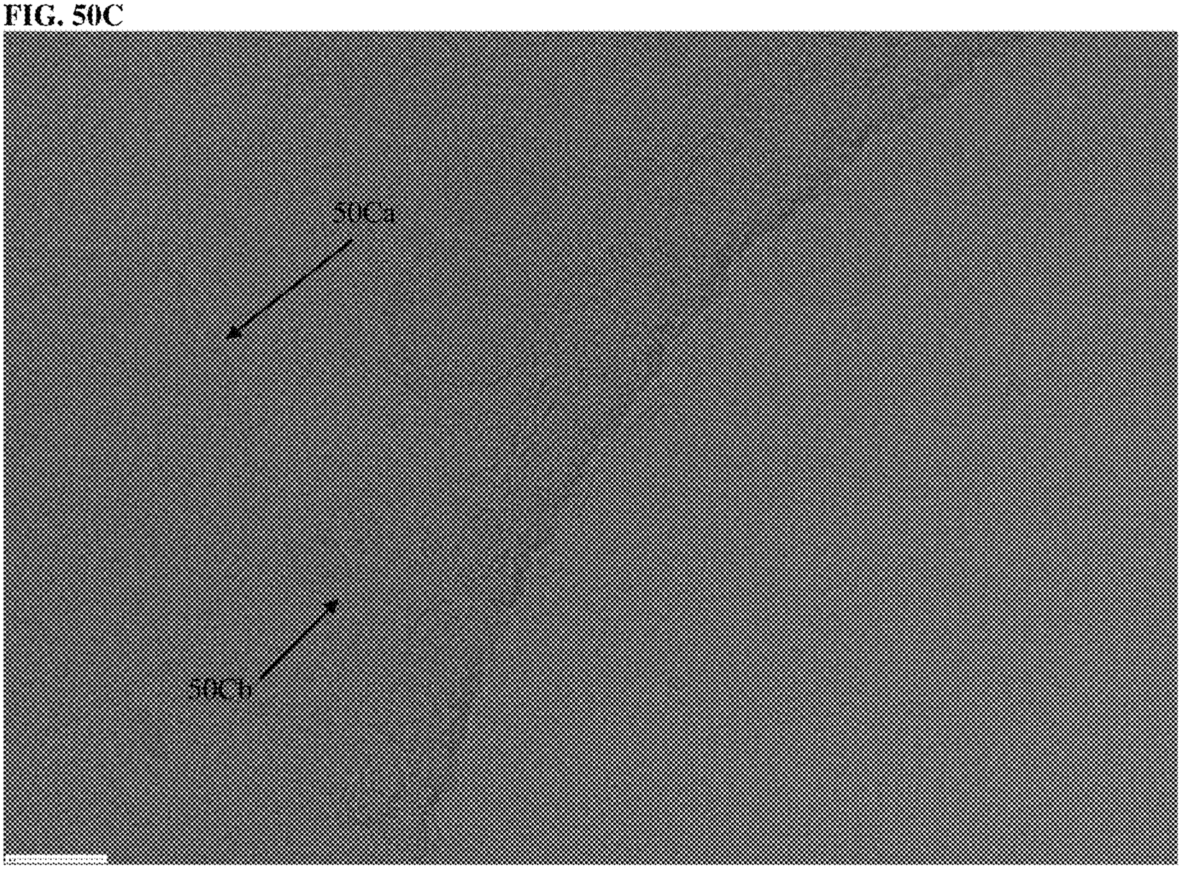
Figure 50D:
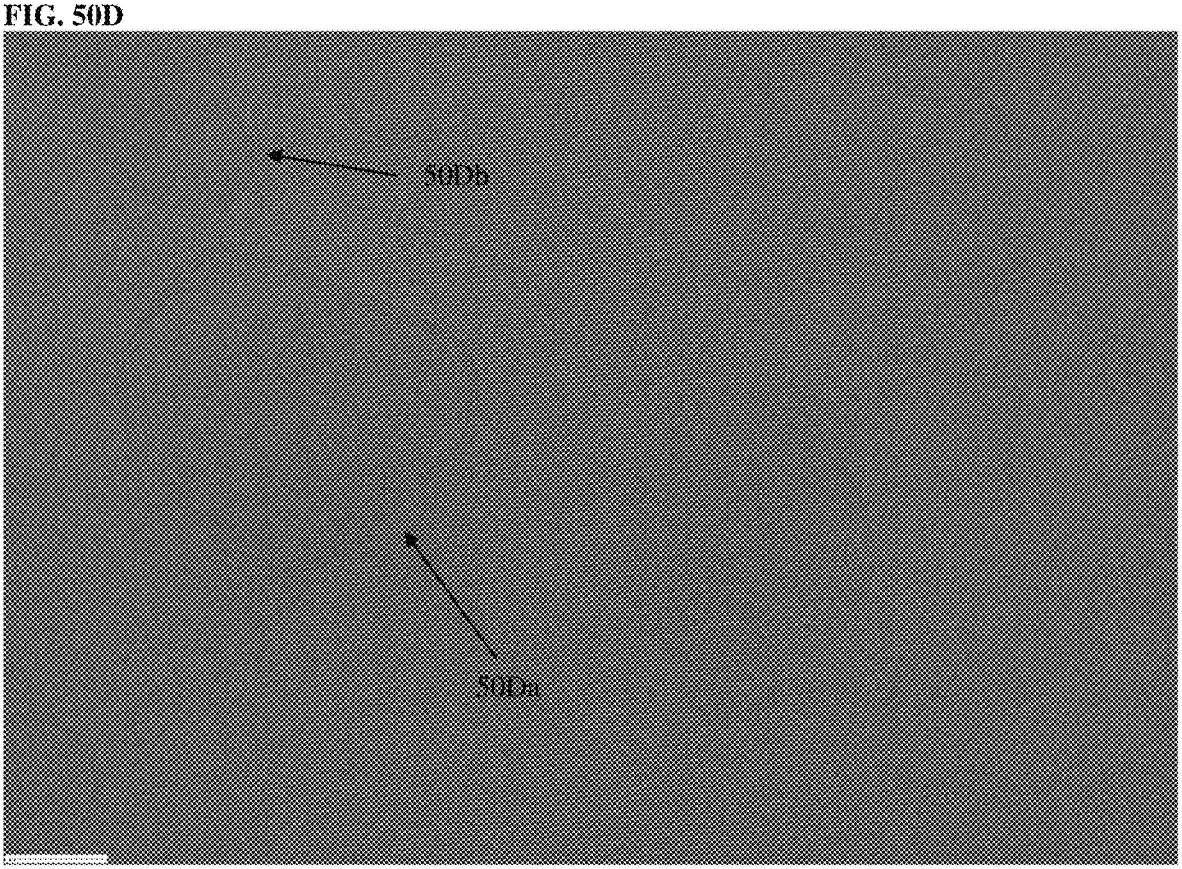
Figure 50E:
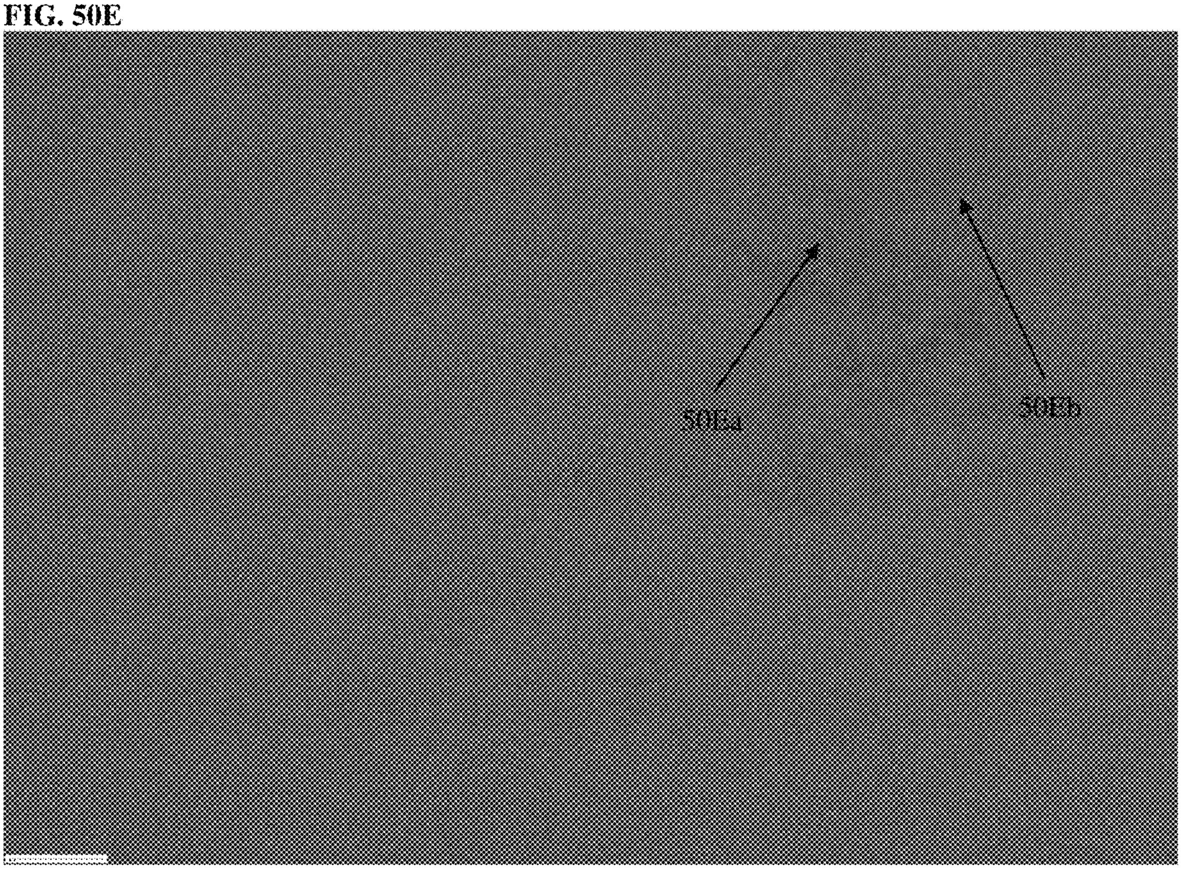

FIG. 50B shows a liposome 50Ba roughly similar in diameter to the length of the LNP 50Bb. Upon formation, assuming the liposome has a sufficient diameter, the liposome may be capable of encapsulating an LNP of a smaller diameter. FIG. 50C shows a liposome 50Ca with a greater diameter than the length of the LNP 50Cb, potentially allowing sufficient space to encapsulate at least one LNP or free agent in the vicinity. FIG. 50D shows a liposome 50Da with a greater diameter than the length of the LNP 50*db*, potentially allowing sufficient space to encapsulate at least one LNP or free agent in the vicinity. FIG. 50E shows a liposome 50Ea with a greater diameter than the length of the LNP 50Eb which happens to be within the boundary of the liposome 50Ea. While the image does not provide enough detail to confirm whether the LNP 50Eb is actually encapsulated within the liposome 50Ea, it is hypothesized that it may occur.

REFERENCES

Aliper, A M, et. al. "A role for G-CSF and GM-CSF in nonmyeloid cancers," Cancer Medicine, Vol. 3, pp. 737-746, 2014.

Bashiardes, S, et. al. "The microbiome in anti-cancer therapy." Semin Immunol, Vol. 32, pp. 74-81, 2017.

Carson, A R, et. al. "Ultrasound-targeted microbubble destruction to deliver siRNA cancer therapy." Cancer Research, Vol. 72, pp. 6191-6199, 2012.

Carstensen, E L, et. al. "Nonlinear propagation and the mechanical index scanners." American Institute of Ultrasound in Medicine Abstracts and Handouts: Workshop on Effects of Nonlinear Propagation on Output Display Indices (TI and MI), Mar. 20, 1998.

Chauhan, V P, et. al. "Delivery of molecular and nanoscale medicine to tumors: transport barriers and strategies," Annual Review of Chemical and Biomolecular Engineering, Vol. 2, pp. 281-298, 2011.

Chen, H, et. al. "The size of blood-brain barrier opening induced by focused ultrasound is dictated by the acoustic pressure," Journal of Cerebral Blood Flow & Metabolism, Vol. 7, pp. 1197-1204, 2014.

Choi, J J, et. al. "Microbubble-size dependence of focused ultrasound-induced blood-brain barrier opening in mice in vivo," IEEE Transactions on Biomedical Engineering, Vol. 57, pp, 145-154, 2010.

Cochran, M C, et. al. "Doxorubicin and paclitaxel loaded microbubbles for ultrasound triggered drug delivery," International Journal of Pharmaceutics, Vol. 414, pp. 161-170, 2011.

Den Otter, W, et. al. "Local therapy of cancer with free IL-2," Cancer Immunology Immunotherapy, Vol. 57, pp. 931-950, July 2008.

Deng Z, et al. "Reversal of multidrug resistance phenotype in human breast cancer cells using doxorubicin-liposome-microbubble complexes assisted by ultrasound," Journal of Controlled Release, Vol. 174, pp. 109-116, 2014.

Dimcevski, G, et. al. "A human clinical trial using ultrasound and microbubbles to enhance gemcitabine treatment of inoperable pancreatic cancer," Journal of Controlled Release, Vol. 243, pp. 172-181, 2016.

Dobbins, G C, et. al. "A multi targeting conditionally replicating adenovirus displays enhanced oncolysis while maintaining expression of immunotherapeutic agents," PLoS ONE, Vol. 10, 2015.

Eisenbrey, J R, et. al. "Delivery of encapsulated Doxorubicin by ultrasound-mediated size reduction of drug-loaded polymer contrast agents," IEEE Transactions on Biomedical Engineering, Vol. 57, no. 1, pp. 24-28, 2010.

Dwivedi, A, et. al. "Lymphocytes in Cellular Therapy: Functional Regulation of CAR T Cells," Frontiers in Immunology, Vol. 9, Article 3180, 2019.

Escoffre, J-M, et. al. "Doxorubicin liposome-loaded microbubbles for contrast imaging and ultrasound-triggered drug delivery," IEEE Transactions on Ultrasonics, Ferroelectrics, and Frequency Control, Vol. 60, pp. 78-87, January 2013.

Fan, C-H, et al. "Antiangiogenic-targeting drug-loaded microbubbles combined with focused ultrasound for glioma treatment," Biomaterials, Vol. 34, pp. 2146-2155, 2013.

Fan, C-H, et al. "SPIO-conjugated, doxorubicin-loaded microbubbles for concurrent MRI and focused-ultrasound enhanced brain-tumor drug delivery," Biomaterials, Vol. 34, pp. 3706-3715, 2013.

Fan, C-H, et. al. "Ultrasound/Magnetic targeting with SPIO-DOX-microbubble complex for image-guided drug delivery," Theranostics, Vol. 6, pp. 1542-1556, 2016.

Feshitan, J A, et. al. "Microbubble size isolation be differential centrifugation," Journal of Colloid and Interface Science, Vol. 329, pp. 316-324, 2009.

Gaspar, R., Coelho F., Silva, B. F. B., Lipid-Nucleic Acid Complexes: Physicochemical Aspects and Prospects for Cancer Treatment, Molecules 2020, 25(21), 5006, https://doi.org/10.3390/molecules25215006

Geller, L T, et. al. "Intratumoral bacteria may elicit chemoresistance by metabolizing anticancer agents," Molecular & Cellular Oncology, Vol. 5:1, DOI: 10.1080/23723556.2017.1405139.

Geller, L T, et. al. "Potential role of intratumoral bacteria in mediating tumor resistance to the chemotherapeutic drug gemcitabine," Science, Vol. 357, pp. 1156-1160, September 2017.

Guo, X-1, et. al. "Inhibition of autophagy enhances anticancer effects of bevacizumab in hepatocarcinoma," Journal of Molecular Medicine, Vol. 91, pp. 473-483, 2013.

Halpern, E J, et. al. "Detection of prostate carcinoma with contrast-enhanced sonography using intermittent harmonic imaging." Cancer, Vol. 104(11), pp. 2373-2383, 2005.

"Section 7—Discussion of the Mechanical Index and Other Exposure Parameters," Journal of Ultrasound in Medicine, Vol. 19, pp. 143-168, 2000.

Kang, J, et al. "Antitumor effect of docetaxel-loaded lipid microbubbles combined with ultrasound-targeted microbubble activation on VX2 rabbit liver tumors," Journal of Ultrasound in Medicine, Vol. 29, pp. 61-70, 2010.

Kuo, T-T, et. al. "Concurrent osteosarcoma theranostic strategy using contrast-enhanced ultrasound and drug-loaded bubbles," Pharmaceutics, Vol. 11, 223, 2019.

Lentacker, I, et. al. "Understanding ultrasound induced sonoporation: Definitions and underlying mechanisms," Advanced Drug Delivery Reviews, Vol. 72, pp. 49-64 (2014).

Li, P, et al. "Ultrasound triggered drug release from 10-hydroxycamptothecin-loaded phospholipid microbubbles for targeted tumor therapy in mice," Journal of Controlled Release, Vol. 162, no. 2, pp. 349-354, 2012.

Liu, H, et al. "Ultrasound-mediated destruction of LHRHa-targeted and paclitaxel-loaded lipid microbubbles induces proliferation inhibition and apoptosis in ovarian cancer cells," Molecular Pharmaceutics, Vol. 11, no. 1, pp. 40-48, 2014.

Liu, H-L, et. al. "Low-pressure pulsed focused ultrasound with microbubbles promotes an anticancer immunological response," Journal of Translational Medicine, Vol. 10 221, 2012.

Liu, H-L, et. al. "Focused Ultrasound Enhances Central Nervous System Delivery of Bevacizumab for Malignant Glioma Treatment," Radiology, Vol. 281, pp. 99-108, October 2016.

Liu, M, et. al. "The emerging role of CSCL10 in cancer (Review)," Oncology Letters, Vol. 2, pp. 583-589, July 2011.

Lunardi, S, et. al. "IP-10/CXCL10 induction in human pancreatic cancer stroma influences lymphocytes recruitment and correlates with poor survival," Oncotarget, Vol. 5, pp. 11064-11080, 2014.

Pu, C, et al. "Ultrasound-mediated destruction of LHRHa-targeted and paclitaxel-loaded lipid microbubbles for the treatment of intraperitoneal ovarian cancer xenografts," Molecular Pharmaceutics, Vol. 11, no. 1, pp. 49-58, 2014.

Ren, S T, et al. "The antitumor effect of a new docetaxel-loaded microbubble combined with low-frequency ultrasound in vitro: preparation and parameter analysis," Pharmaceutical Research, Vol. 30, no. 6, pp. 1574-1585, 2013.

Rosenberg, S A, et. al. "Durable complete responses in heavily pretreated patients with metastatic melanoma using T-cell transfer immunotherapy," Clinical Cancer Research, Vol. 17, pp. 4450-7, 2011.

Su, T, et. al. "STING activation in cancer immunotherapy," Theranostics, Vol. 9, pp. 7759-7771, October 2019.

Sun, T, et. al. "Acoustic cavitation-based monitoring of the reversibility and permeability of ultrasound-induced blood-brain barrier opening," Physics in Medicine & Biology, Vol. 60, pp 9079-9094, 2015.

Taghipour Fard Ardekani, M, et. al. "Evaluation of pre-treatment serum levels of IL-7 and GM-CSF in colorectal cancer patients," Int J Mol Cell Med, Vol. 3, pp. 27-34, 2014.

Teppo, H-R, et al. "Reactive oxygen species-mediated mechanisms of action of targeted cancer therapy," Oxidative Medicine and Cellular Longevity, Vol. 2017, Article ID 1485283, 11 pages.

Ting, C-Y, et. al. "Concurrent blood-brain barrier opening and local drug delivery using drug-carrying microbubbles and focused ultrasound for brain glioma treatment," Biomaterials, Vol. 33, pp. 704-712, 2012.

Toiyama, Y, et. al. "Evaluation of CSCL10 as a novel serum marker for predicting liver metastasis and prognosis in colorectal cancer," International Journal of Oncology, Vol. 40, pp. 560-566, 2012.

Weinberg, F, et. al. "Reactive oxygen species in the tumor microenvironment: An overview," Cancers, Vol. 11, 1191, 2019.

Xie, F, et. al. "Repeatability of the 'flash-replenishment' method in contrast-enhanced ultrasound for the quantitative assessment of hepatic microvascular perfusion," Brazilian Journal of Medical and Biological Research, Vol. 51, n. 4, e7058, 2018.

Yan, F, et. al. "Paclitaxel-liposome-microbubble complexes as ultrasound-triggered therapeutic drug delivery carriers," Journal of Controlled Release, Vol. 166, no. 3, pp. 246-255, 2013.

Zhang, L, et. al. "Multifunctional microbubbles for image-guided antivascular endothelial growth factor therapy," J Biomedical Optics, Vol. 15, pp. 030515-1-030515-3, May/June 2010.

Zhang, Y, et. al. "Docetaxel-loaded lipid microbubbles combined with ultrasound-triggered microbubble destruction for targeted tumor therapy in MHCC-H cells," OncoTargets and Therapy, Vol. 9, pp. 4763-4771, 2016.

Informal Sequence Listing

```
>SEQ ID NO: 1 Pembrolizumab heavy chain
MGWSCIILFLVATATGVHSQVQLVQSGVEVKKPGASVKVSCKASGYTFT
NYYMYWVRQAPGQGLEWMGGINPSNGGTNFNEKFKNRVTLTTDSSTTTA
YMELKSLQFDDTAVYYCARRDYRFDMGFDYWGQGTTVTVSSASTKGPSV
FPLAPCSRSTSESTAALGCLVKDYFPEPVTVSWNSGALTSGVHTFPAVL
QSSGLYSLSSVVTVPSSSLGTKTYTCNVDHKPSNTKVDKRVESKYGPPC
PPCPAPEFLGGPSVFLFPPKPKDTLMISRTPEVTCVVVDVSQEDPEVQF
NWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNV
FSCSVMHEALHNHYTQKSLSLSLGK*

>SEQ ID NO: 2 Pembrolizumab light chain
MGWSCIILFLVATATGVHSEIVLTQSPATLSLSPGERATLSCRASKGVS
TSGYSYLHWYQQKPGQAPRLLIYLASYLESGVPARFSGSGSGTDFTLTI
SSLEPEDFAVYYCQHSRDLPLTFGGGTKVEIKRTVAAPSVFIFPPSDEQ
LKSGTASVVCLLNNFYPREAKVQWKVDNALQSGNSQESVTEQDSKDSTY
SLSSTLTLSKADYEKHKVYACEVTHQGLSSPVTKSENRGEC*

>SEQ ID NO: 3 Ipilimumab heavy chain
MGWSCIILFLVATATGVHSQVQLVESGGGVVQPGRSLRLSCAASGFTFS
SYTMHWVRQAPGKGLEWVTFISYDGNNKYYADSVKGRFTISRDNSKNTL
YLQMNSLRAEDTAIYYCARTGWLGPFDYWGQGTLVTVSSASTKGPSVFP
LAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCDKTHT
CPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGN
VFSCSVMHEALHNHYTQKSLSLSPGK*

>SEQ ID NO: 4 Ipilimumab light chain
MGWSCIILFLVATATGVHSEIVLTQSPGTLSLSPGERATLSCRASQSVG
SSYLAWYQQKPGQAPRLLIYGAFSRATGIPDRFSGSGSGTDFTLTISRL
EPEDFAVYYCQQYGSSPWTFGQGTKVEIKRTVAAPSVFIFPPSDEQLKS
GTASVVCLLNNFYPREAKVQWKVDNALQSGNSQESVTEQDSKDSTYSLS
STLTLSKADYEKHKVYACEVTHQGLSSPVTKSFNRGEC*

>SEQ ID NO: 5 Pembrolizumab heavy and light chain
MGWSCIILFLVATATGVHSQVQLVQSGVEVKKPGASVKVSCKASGYTFT
NYYMYWVRQAPGQGLEWMGGINPSNGGTNFNEKFKNRVTLTTDSSTTTA
YMELKSLQFDDTAVYYCARRDYRFDMGFDYWGQGTTVTVSSASTKGPSV
FPLAPCSRSTSESTAALGCLVKDYFPEPVTVSWNSGALTSGVHTFPAVL
QSSGLYSLSSVVTVPSSSLGTKTYTCNVDHKPSNTKVDKRVESKYGPPC
PPCPAPEFLGGPSVFLFPPKPKDTLMISRTPEVTCVVVDVSQEDPEVQF
NWYVDGVEVHNAKTKPREEQFNSTYRVVSVLTVLHQDWLNGKEYKCKVS
NKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNV
FSCSVMHEALHNHYTQKSLSLSLGKGSGATNFSLLKQAGDVEENPGPMG
WSCIILFLVATATGVHSEIVLTQSPATLSLSPGERATLSCRASKGVSTS
GYSYLHWYQQKPGQAPRLLIYLASYLESGVPARFSGSGSGTDFTLTISS
LEPEDFAVYYCQHSRDLPLTFGGGTKVEIKRTVAAPSVFIFPPSDEQLK
SGTASVVCLLNNFYPREAKVQWKVDNALQSGNSQESVTEQDSKDSTYSL
SSTLTLSKADYEKHKVYACEVTHQGLSSPVTKSFNRGEC*

>SEQ ID NO: 6 Ipilimumab heavy and light chain
MGWSCIILFLVATATGVHSQVQLVESGGGVVQPGRSLRLSCAASGFTFS
SYTMHWVRQAPGKGLEWVTFISYDGNNKYYADSVKGRFTISRDNSKNTL
YLQMNSLRAEDTAIYYCARTGWLGPFDYWGQGTLVTVSSASTKGPSVFP
LAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCDKTHT
CPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGN
VFSCSVMHEALHNHYTQKSLSLSPGKRAKRGSGATNFSLLKQAGDVEEN
PGPMGWSCIILFLVATATGVHSEIVLTQSPGTLSLSPGERATLSCRASQ
SVGSSYLAWYQQKPGQAPRLLIYGAFSRATGIPDRFSGSGSGTDFTLTI
SRLEPEDFAVYYCQQYGSSPWTFGQGTKVEIKRTVAAPSVFIFPPSDEQ
LKSGTASVVCLLNNFYPREAKVQWKVDNALQSGNSQESVTEQDSKDSTY
SLSSTLTLSKADYEKHKVYACEVTHQGLSSPVTKSFNRGEC*
```

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
Sequence total quantity: 6
SEQ ID NO: 1            moltype = AA  length = 466
FEATURE                 Location/Qualifiers
REGION                  1..466
                        note = Description of Artificial Sequence: Synthetic
                         polypeptide
source                  1..466
                        mol_type = protein
                        organism = synthetic construct
SEQUENCE: 1
MGWSCIILFL VATATGVHSQ VQLVQSGVEV KKPGASVKVS CKASGYTFTN YYMYWVRQAP  60
GQGLEWMGGI NPSNGGTNFN EKFKNRVTLT TDSSTTTAYM ELKSLQFDDT AVYYCARRDY  120
RFDMGFDYWG QGTTVTVSSA STKGPSVFPL APCSRSTSES TAALGCLVKD YFPEPVTVSW  180
NSGALTSGVH TFPAVLQSSG LYSLSSVVTV PSSSLGTKTY TCNVDHKPSN TKVDKRVESK  240
YGPPCPPCPA PEFLGGPSVF LFPPKPKDTL MISRTPEVTC VVVDVSQEDP EVQFNWYVDG  300
VEVHNAKTKP REEQFNSTYR VVSVLTVLHQ DWLNGKEYKC KVSNKGLPSS IEKTISKAKG  360
QPREPQVYTL PPSQEEMTKN QVSLTCLVKG FYPSDIAVEW ESNGQPENNY KTTPPVLDSD  420
GSFFLYSRLT VDKSRWQEGN VFSCSVMHEA LHNHYTQKSL SLSLGK                466

SEQ ID NO: 2            moltype = AA  length = 237
FEATURE                 Location/Qualifiers
REGION                  1..237
                        note = Description of Artificial Sequence: Synthetic
                         polypeptide
source                  1..237
                        mol_type = protein
                        organism = synthetic construct
SEQUENCE: 2
MGWSCIILFL VATATGVHSE IVLTQSPATL SLSPGERATL SCRASKGVST SGYSYLHWYQ  60
QKPGQAPRLL IYLASYLESG VPARFSGSGS GTDFTLTISS LEPEDFAVYY CQHSRDLPLT  120
FGGGTKVEIK RTVAAPSVFI FPPSDEQLKS GTASVVCLLN NFYPREAKVQ WKVDNALQSG  180
NSQESVTEQD SKDSTYSLSS TLTLSKADYE KHKVYACEVT HQGLSSPVTK SFNRGEC     237

SEQ ID NO: 3            moltype = AA  length = 467
FEATURE                 Location/Qualifiers
REGION                  1..467
                        note = Description of Artificial Sequence: Synthetic
                         polypeptide
source                  1..467
                        mol_type = protein
                        organism = synthetic construct
SEQUENCE: 3
MGWSCIILFL VATATGVHSQ VQLVESGGGV VQPGRSLRLS CAASGFTFSS YTMHWVRQAP  60
GKGLEWVTFI SYDGNNKYYA DSVKGRFTIS RDNSKNTLYL QMNSLRAEDT AIYYCARTGW  120
LGPFDYWGQG TLVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKRVEPKSC  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSRDELTK NQVSLTCLVK GFYPSDIAVE WESNGQPENN YKTTPPVLDS  420
DGSFFLYSKL TVDKSRWQQG NVFSCSVMHE ALHNHYTQKS LSLSPGK               467

SEQ ID NO: 4            moltype = AA  length = 234
FEATURE                 Location/Qualifiers
REGION                  1..234
                        note = Description of Artificial Sequence: Synthetic
                         polypeptide
source                  1..234
                        mol_type = protein
                        organism = synthetic construct
SEQUENCE: 4
MGWSCIILFL VATATGVHSE IVLTQSPGTL SLSPGERATL SCRASQSVGS SYLAWYQQKP  60
GQAPRLLIYG AFSRATGIPD RFSGSGSGTD FTLTISRLEP EDFAVYYCQQ YGSSPWTFGQ  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 5            moltype = AA  length = 725
FEATURE                 Location/Qualifiers
REGION                  1..725
                        note = Description of Artificial Sequence: Synthetic
                         polypeptide
source                  1..725
                        mol_type = protein
                        organism = synthetic construct
SEQUENCE: 5
MGWSCIILFL VATATGVHSQ VQLVQSGVEV KKPGASVKVS CKASGYTFTN YYMYWVRQAP  60
GQGLEWMGGI NPSNGGTNFN EKFKNRVTLT TDSSTTTAYM ELKSLQFDDT AVYYCARRDY  120
RFDMGFDYWG QGTTVTVSSA STKGPSVFPL APCSRSTSES TAALGCLVKD YFPEPVTVSW  180
NSGALTSGVH TFPAVLQSSG LYSLSSVVTV PSSSLGTKTY TCNVDHKPSN TKVDKRVESK  240
```

-continued

```
YGPPCPPCPA PEFLGGPSVF LFPPKPKDTL MISRTPEVTC VVVDVSQEDP EVQFNWYVDG  300
VEVHNAKTKP REEQFNSTYR VVSVLTVLHQ DWLNGKEYKC KVSNKGLPSS IEKTISKAKG  360
QPREPQVYTL PPSQEEMTKN QVSLTCLVKG FYPSDIAVEW ESNGQPENNY KTTPPVLDSD  420
GSFFLYSRLT VDKSRWQEGN VFSCSVMHEA LHNHYTQKSL SLSLGKGSGA TNFSLLKQAG  480
DVEENPGPMG WSCIILFLVA TATGVHSEIV LTQSPATLSL SPGERATLSC RASKGVSTSG  540
YSYLHWYQQK PGQAPRLLIY LASYLESGVP ARFSGSGSGT DFTLTISSLE PEDFAVYYCQ  600
HSRDLPLTFG GGTKVEIKRT VAAPSVFIFP PSDEQLKSGT ASVVCLLNNF YPREAKVQWK  660
VDNALQSGNS QESVTEQDSK DSTYSLSSTL TLSKADYEKH KVYACEVTHQ GLSSPVTKSF  720
NRGEC                                                             725

SEQ ID NO: 6            moltype = AA  length = 727
FEATURE                 Location/Qualifiers
REGION                  1..727
                        note = Description of Artificial Sequence: Synthetic
                         polypeptide
source                  1..727
                        mol_type = protein
                        organism = synthetic construct
SEQUENCE: 6
MGWSCIILFL VATATGVHSQ VQLVESGGGV VQPGRSLRLS CAASGFTFSS YTMHWVRQAP  60
GKGLEWVTFI SYDGNNKYYA DSVKGRFTIS RDNSKNTLYL QMNSLRAEDT AIYYCARTGW  120
LGPFDYWGQG TLVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKRVEPKSC  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSRDELTK NQVSLTCLVK GFYPSDIAVE WESNGQPENN YKTTPPVLDS  420
DGSFFLYSKL TVDKSRWQQG NVFSCSVMHE ALHNHYTQKS LSLSPGKRAK RGSGATNFSL  480
LKQAGDVEEN PGPMGWSCII LFLVATATGV HSEIVLTQSP GTLSLSPGER ATLSCRASQS  540
VGSSYLAWYQ QKPGQAPRLL IYGAFSRATG IPDRFSGSGS GTDFTLTISR LEPEDFAVYY  600
CQQYGSSPWT FGQGTKVEIK RTVAAPSVFI FPPSDEQLKS GTASVVCLLN NFYPREAKVQ  660
WKVDNALQSG NSQESVTEQD SKDSTYSLSS TLTLSKADYE KHKVYACEVT HQGLSSPVTK  720
SFNRGEC                                                           727
```

We claim:

1. A composition, comprising:

(i) a plurality of microbubbles comprising: a monolayer shell comprising 1,2-dimyristoyl-sn-glycero-3-phosphocholine (DMPC), and a core comprising a perfluorocarbon gas, wherein the plurality of microbubbles is characterized by a neutral charge and a diameter of about 1 μm to about 10 μm;

(ii) a plurality of liposomes formed by self-assembly from high energy state lipids upon contact with aqueous solution, wherein the high energy state lipids comprise DMPC;

(iii) at least one therapeutic agent comprising an antibody, which is present both as free therapeutic agent, which is not associated with the plurality of microbubbles or the plurality of liposomes, and as associated therapeutic agent encapsulated within the plurality of microbubbles and the plurality of liposomes; and (iv) an aqueous solution.

2. The composition of claim 1, wherein the level of the at least one therapeutic agent in the composition is lower than the level of the therapeutic agent required to achieve a substantially equivalent therapeutic effect when administered without being associated with the plurality of microbubbles and the plurality of liposomes.

3. The composition of claim 2, wherein the substantially equivalent therapeutic effect is about 80%, about 85%, about 90%, about 91%, about 92%, about 93%, about 94%, about 95%, about 96%, about 97%, about 98%, about 99% or about 100% of the therapeutic effect of the therapeutic agent when administered without being associated with the plurality of microbubbles and the plurality of liposomes.

4. The composition of claim 1, wherein the level of the at least one therapeutic agent in the composition is about 0.001% to about 99%, about 0.001% to about 75%, about 0.001% to about 50%, about 0.005% to about 50%, about 0.005% to about 25%, or about 0.0001% to about 25% of the level of the therapeutic agent required to achieve a substantially equivalent therapeutic effect when administered without being associated with the plurality of microbubbles and the plurality of liposomes.

5. The composition of claim 1, wherein administration of the composition results in a reduced systemic toxicity, as compared to administration of a composition of the same level of therapeutic agent without being associated with the plurality of microbubbles and the plurality of liposomes, optionally wherein administration of the composition results in a reduced systemic toxicity, as compared to administration of a composition of the therapeutic agent without being associated with the plurality of microbubbles and the plurality of liposomes required to achieve a substantially equivalent therapeutic effect.

6. The composition of claim 1, further comprising a cytokine.

7. The composition of claim 6, wherein the cytokine is selected from a group consisting of IL-2, IL-7, IL-10, IL-12, IL-15, IL-18, IL-21, IL-23, IL-27, interferon, GM-CSF and TNF-alpha.

8. The composition of claim 6, wherein the cytokine is IL-2, optionally wherein the level of IL-2 associated with the plurality of microbubbles and the plurality of liposomes is about 0.01 pg/mL to about 10 pg/mL, about 10 pg/mL to about 100 pg/mL, about 100 pg/mL to about 100 ug/mL, about 100 pg/mL to about 100 ng/ml, about 100 ng/ml to about 1 μg/mL, about 1 μg/ml to about 10 μg/mL, about 10 μg/mL to about 100 μg/mL, about 200 ng/ml to about 500 ng/mL, about 500 ng/mL to about 2 μg/mL, or about 2 μg/mL to about 5 μg/mL.

9. The composition of claim 1, wherein the antibody is a monoclonal antibody.

10. The composition of claim 9, wherein the monoclonal antibody is selected from the group consisting of bevacizumab, pembrolizumab, nivolumab, cemiplimab, durvalumab, atezolizumab, avelumab, ipilimumab, rituximab, cetuximab and trastuzumab.

11. The composition of claim 10, wherein the monoclonal antibody is bevacizumab, optionally wherein the level of bevacizumab associated with the plurality of microbubbles and the plurality of liposomes is about 0.01 pg/mL to about 10 pg/mL, about 1 pg/mL to about 25 mg/mL, about 1 ng/mL to about 25 mg/mL, about 1 μg/mL to about 25 mg/mL, about 1 pg/mL to about 100 pg/mL, about 100 pg/mL to about 500 pg/mL, about 500 pg/mL to about 1 ng/ml, about 1 ng/mL to about 100 ng/mL, about 100 ng/ml to about 500 ng/ml, about 500 ng/mL to about 1 μg/mL, about 1 μg/mL to about 100 μg/mL, about 100 μg/mL to about 500 μg/mL, about 500 μg/mL to about 1 mg/mL, about 1 mg/mL to about 5 mg/mL, about 5 mg/mL to about 10 mg/mL, about 10 mg/mL to about 25 mg/mL, about 100 μg/mL to about 250 μg/mL, about 250 μg/mL to about 2.5 mg/mL, or about 2.5 mg/mL to about 10 mg/mL.

12. The composition of claim 10, wherein the monoclonal antibody is pembrolizumab, optionally wherein the level of pembrolizumab associated with the plurality of microbubbles and the plurality of liposomes is about 0.01 pg/mL to about 10 pg/mL, about 1 pg/mL to about 25 mg/mL, about 1 ng/mL to about 25 mg/mL, about 1 μg/mL to about 25 mg/mL, about 1 pg/mL to about 100 pg/mL, about 100 pg/mL to about 500 pg/mL, about 500 pg/mL to about 1 ng/ml, about 1 ng/mL to about 100 ng/mL, about 100 ng/mL to about 500 ng/ml, about 500 ng/mL to about 1 μg/mL, about 1 μg/mL to about 100 μg/mL, about 100 μg/mL to about 500 μg/mL, about 500 μg/mL to about 1 mg/mL, about 1 mg/mL to about 5 mg/mL, about 5 mg/mL to about 10 mg/mL, about 10 mg/mL to about 25 mg/mL, about 100 μg/mL to about 250 μg/mL, about 250 μg/mL to about 2.5 mg/mL, or about 2.5 mg/mL to about 10 mg/mL.

13. A method of treating a disease or condition in or delivering the at least one therapeutic agent to a subject, the method comprising administering the composition of claim 1, and applying an ultrasound energy to the subject, thereby treating the disease or condition in or delivering the at least one therapeutic agent to the subject.

14. A method of reducing tumor growth in a subject, the method comprising administering the composition of claim 1, and applying an ultrasound energy to the subject, thereby reducing tumor growth, in the subject.

15. The composition of claim 1, wherein the level of the at least one therapeutic agent in the composition is less than a maximum tolerated dose (MTD) of the at least one therapeutic agent.

16. The composition of claim 1, wherein:

(i) the core of the plurality of microbubbles further comprises nitrogen;

(ii) the high energy state lipids are characterized by lipid bonds that have been broken by high velocity, high temperature spray drying;

(iii) the monolayer shell of the plurality of microbubbles is about 3 nm thick;

(iv) the monolayer shell of the plurality of microbubbles is a malleable shell that stabilizes the core of the microbubble in vivo above a crystalline phase transition temperature of −24° C.;

and/or (v) the plurality of microbubbles is characterized by a volume weighted average diameter of 6 microns.

17. The composition of claim 16, wherein the plurality of microbubbles is characterized by a diameter distribution having multiple peaks.

18. The composition of claim 17, wherein the diameter distribution comprises a first peak corresponding to a diameter of about 1 μm, and a second peak corresponding to a diameter of about 4.5 μm to about 5 μm.

19. The composition of claim 1, wherein the plurality of microbubbles can be burst using transient inertial cavitation which minimizes the risk of longer sonication exposures at peak negative pressures that induce widespread inertial cavitation;

wherein the plurality of microbubbles can be burst using a five-minute sonication period during which transiently increasing the mechanical index of pulses above 1 MPa at minutes 1, 2, 3, and 4 ensures that all microbubbles within the field will burst due to inertial cavitation;

wherein the plurality of microbubbles can be burst using a 5-minute sonication period during which the mechanical index of pulses occur at intervals of 10 seconds, 30 seconds, 1 minute or 1.5 minutes;

wherein the plurality of microbubbles can be burst using a 10-minute sonication period during which the mechanical index of pulses occur at 2-minutes, at 4-minutes, at 6-minutes, and at 8-minutes; and/or wherein the plurality of microbubbles can be burst using insonation system settings comprising Contrast Mode, 2.2 MHz center frequency at a mechanical index (MI) of 0.531, and thermal index (TI) of 0.1, and a 5-minute total insonation time with periodic 1100 ms ultrasound bursts of 1.304 MI administered every 10 seconds.

20. The composition of claim 16, wherein the plurality of microbubbles comprise osmotically stabilized microbubbles.

21. The composition of claim 1, wherein the monolayer shell of the plurality of microbubbles further comprises a polymer, a lipid, a lipopolymer, a protein, a surfactant, or a combination thereof.

22. The composition of claim 21, wherein:

(i) the polymer comprises polyvinyl alcohol (PVA); polyethylene glycol (PEG); poly(isobutylcyanoacrylate); poly(lactic-co-glycolic acid) (PLGA); poly(allylamine hydrochloride) (PAH); or poly(styrene sulfonate) (PSS);

(ii) the lipid comprises 4-dimethylaminochalcone (DMAC); dipalmitoyl phosphatidylcholine (DPPC), 1,2-distearyol-sn-glycero-3-phosphocoline (DSPC); 1,2-distearyol-sn-glycero-3-phosphoethanolamine-N-[methoxy (polyethylene glycol) 2000] (DSPE-PEG2000); lipofectamine; a cationic lipid; or a helper lipid;

(iii) the protein comprises albumin; and/or (iv) the surfactant comprises Span 60 or Tween 80.

23. The composition of claim 1, further comprising a carrier selected from the group consisting of a lipid rod, a lipid disc, a lipid sheet, and a combination thereof.

24. The composition of claim 1, wherein the liposomes comprise multiple multilamellar liposomes.

25. The composition of claim 1, wherein the plurality of microbubbles and the plurality of liposomes are formed together in a single container from high energy state lipids comprising DMPC upon contact with aqueous solution.

26. The composition of claim 1, wherein the antibody is an immune checkpoint inhibitor (ICI).

27. The composition of claim 26, wherein an ICI may be co-administered with a carrier or may be encapsulated within a carrier in order to improve the biodistribution of the ICI within the TME or to the tumor cells.

28. The composition of claim 1, wherein the antibody is selected from the group consisting of an anti-PD-1 agent, an anti-PD-L1 agent, and an anti-CTLA-4 agent.

29. The composition of claim 1, wherein the antibody is an anti-PD-1 antibody.

30. The composition of claim 1, wherein the at least one therapeutic agent is an antibody drug conjugate.

31. The composition of claim 1, wherein the associated therapeutic agent encapsulated within the plurality of microbubbles and the plurality of liposomes is prepared without modifying the surface of the plurality of microbubbles and the plurality of liposomes.

32. The composition of claim 1, wherein administration of the composition to a subject followed by the application of an ultrasound energy increases the efficacy and/or potency of the at least one therapeutic agent.

33. The composition of claim 1, wherein administration of the composition to a subject followed by the application of an ultrasound energy increases the therapeutic index of the at least one therapeutic agent, wherein the therapeutic index is represented by $TD_{50}/ED_{50}$, wherein the $TD_{50}$ is the toxic dose of the at least one therapeutic agent at which plasma concentration causes 50% of subjects to have adverse effects, and the $ED_{50}$ is the plasma concentration of the at least one therapeutic agent which is effective in 50% of subjects.

34. The composition of claim 1, wherein administration of the composition to a subject followed by the application of an ultrasound energy:

(i) increases the therapeutic index by decreasing the plasma concentration of the at least one therapeutic agent that provides safe and effective therapy;

(ii) decreases the plasma concentration of the at least one therapeutic agent which is effective in 50% of subjects, thereby increasing the potency of the at least one therapeutic agent;

(iii) improves the pharmacokinetics (PK), pharmacodynamics (PD), or biodistribution (BD) of the at least one therapeutic agent as compared to conventional systemic administration;

(iv) improves the biodistribution of the at least one therapeutic agent to a target site is selected from the group consisting of an organ, a tissue, a cell, and a tumor site;

(v) enables the systemic delivery of the at least one therapeutic agent to deep-seated and difficult-to-permeate tumors; and/or (vi) reduces the systemic toxicity of the at least one therapeutic agent.

35. The composition of claim 34, wherein the tumor site comprises a primary or metastatic tumor, a tumor microenvironment (TME), or a tumor cell.

36. The composition of claim 1, wherein the associated therapeutic agent is bound to and encapsulated within the plurality of microbubbles and the plurality of liposomes.

* * * * *